(12) United States Patent
Noji et al.

(10) Patent No.: US 8,609,647 B2
(45) Date of Patent: Dec. 17, 2013

(54) NITROGEN-CONTAINING SPIROCYCLIC COMPOUNDS AND PHARMACEUTICAL USES THEREOF

(75) Inventors: Satoru Noji, Takatsuki (JP); Makoto Shiozaki, Takatsuki (JP); Tomoya Miura, Takatsuki (JP); Yoshinori Hara, Takatsuki (JP); Hiroshi Yamanaka, Takatsuki (JP); Katsuya Maeda, Takatsuki (JP); Akimi Hori, Takatsuki (JP); Masafumi Inoue, Takatsuki (JP); Yasunori Hase, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 416 days.

(21) Appl. No.: 12/847,025

(22) Filed: Jul. 30, 2010

(65) Prior Publication Data

US 2011/0136778 A1 Jun. 9, 2011

Related U.S. Application Data

(60) Provisional application No. 61/274,137, filed on Aug. 13, 2009.

(30) Foreign Application Priority Data

Jul. 31, 2009 (JP) ................................. 2009-179502

(51) Int. Cl.
| | |
|---|---|
| C07D 487/04 | (2006.01) |
| A61K 31/519 | (2006.01) |
| A61P 19/02 | (2006.01) |
| A61P 37/00 | (2006.01) |
| A61P 17/06 | (2006.01) |
| A61P 27/04 | (2006.01) |
| A61P 29/00 | (2006.01) |

(52) U.S. Cl.
USPC .................. 514/210.16; 514/265.1; 544/280; 544/230; 544/231; 546/16

(58) Field of Classification Search
USPC ........... 544/280, 230, 231; 514/265.1, 210.16
See application file for complete search history.

(56) References Cited

U.S. PATENT DOCUMENTS

| | | |
|---|---|---|
| 7,335,667 B2 | 2/2008 | Rodgers et al. |
| 2006/0183906 A1 | 8/2006 | Rodgers et al. |
| 2007/0208053 A1 | 9/2007 | Arnold et al. |
| 2007/0275990 A1 | 11/2007 | Ohmoto et al. |
| 2008/0261973 A1 | 10/2008 | Capraro et al. |
| 2009/0264399 A1 | 10/2009 | Inoue et al. |

FOREIGN PATENT DOCUMENTS

| | | |
|---|---|---|
| JP | 2008-069149 | 3/2008 |
| JP | 2009-519340 | 5/2009 |
| WO | WO 99/62518 | 12/1999 |
| WO | WO 99/65908 | 12/1999 |
| WO | WO 99/65909 | 12/1999 |
| WO | WO 01/42246 | 6/2001 |
| WO | WO 2005/047286 | 5/2005 |
| WO | WO 2006/069080 | 6/2006 |
| WO | WO 2006/090261 | 8/2006 |
| WO | WO 2006/127587 | 11/2006 |
| WO | WO 2007/007919 | 1/2007 |
| WO | WO 2007/070514 | 6/2007 |
| WO | WO 2007/071393 | 6/2007 |
| WO | WO2007/084667 | 7/2007 |
| WO | WO 2007/103719 | 9/2007 |
| WO | WO 2008/029237 | 3/2008 |
| WO | WO 2008/077811 | 7/2008 |
| WO | WO 2008/119792 | 10/2008 |
| WO | WO 2009/089454 | 7/2009 |
| WO | WO 2009/140320 | 11/2009 |
| WO | WO 2010/003133 | 1/2010 |
| WO | WO 2010/135650 | 11/2010 |
| WO | WO 2011/012896 | 2/2011 |
| WO | WO 2011/029043 | 3/2011 |

OTHER PUBLICATIONS

Boy et al., "Double-blind, placebo-controlled, dose-escalation study to evaluate the pharmacologic effect of CP-690,550 in patients with psoriasis" J Invest Dermatol., 129(9):2299-302 (2009).

Campbell et al., "The myeloproliferative disorders" N. Engl J Med., 355(23):2452-66 (2006).

(Continued)

Primary Examiner — Susanna Moore
(74) Attorney, Agent, or Firm — Fish & Richardson P.C.

(57) ABSTRACT

A compound of the following general formula [I]:

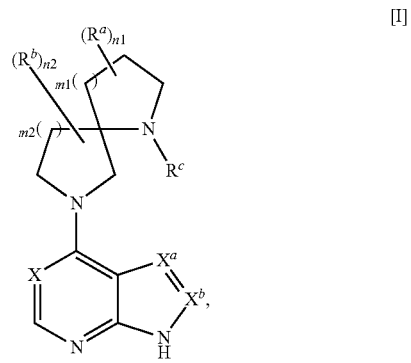

wherein each symbol has the same meaning as defined herein, or a pharmaceutically acceptable salt thereof, or a solvate thereof, and a pharmaceutical use of the same in treating organ transplant rejection, graft versus host reaction after transplantation, autoimmune disease, allergic disease and chronic myeloproliferative disease.

95 Claims, No Drawings

(56) References Cited

OTHER PUBLICATIONS

Changelian et al., "Prevention of organ allograft rejection by a specific Janus kinase 3 inhibitor" Science, 302(5646):875-78 (2003).
International Search Report from PCT/JP2010/062873, Nov. 2, 2010.
Jiang et al., "Examining the chirality, conformation and selective kinase inhibition of 3-((3R,4R)-4-methyl-3-(methyl(7H-pyrrolo[2,3-d]pyrimidin-4-yl)amino)piperidin-1-yl)-3-oxopropanenitrile (CP-690,550)" J Med Chem., 51(24):8012-18 (2008).
Kremer et al., "The safety and efficacy of a JAK inhibitor in patients with active rheumatoid arthritis: Results of a double-blind, placebo-controlled phase IIa trial of three dosage levels of CP-690,550 versus placebo" Arthritis Rheum., 60(7):1895-905 (2009).
Kudlacz et al., "The JAK-3 inhibitor CP-690550 is a potent anti-inflammatory agent in a murine model of pulmonary eosinophilia" Eur J Pharmacol., 582(1-3):154-61 (2008).
O'Shea et al., "A new modality for immunosuppression: targeting the JAK/STAT pathway" Nat Rev Drug Discov., 3(7):555-64 (2004).
Papageorgiou et al., "Is JAK3 a new drug target for immunomodulation-based therapies?" Trends Pharmacol Sci., 25(11):558-62 (2004).
Pesu et al., "Jak3, severe combined immunodeficiency, and a new class of immunosuppressive drugs" Immunol Rev., 203:127-42 (2005).
Quintás-Cardama et al., "Preclinical characterization of the selective JAK1/2 inhibitor INCB018424: therapeutic implications for the treatment of myeloproliferative neoplasms" Blood, 115(15):3109-17 (2010).
Supplementary European Search Report and European Search Opinion for EP Application No. 10804531.1 dated Nov. 15, 2012.

NITROGEN-CONTAINING SPIROCYCLIC COMPOUNDS AND PHARMACEUTICAL USES THEREOF

CROSS REFERENCE TO RELATED APPLICATIONS

This application claims the benefit of priority of U.S. provisional application Ser. No. 61/274,137, filed Aug. 13, 2009, and Japanese application serial number 2009-179502, filed Jul. 31, 2009. The disclosures of the prior applications are considered part of (and are incorporated by reference in) the disclosure of this application.

TECHNICAL FIELD

The present invention relates to a novel nitrogen-containing spiro cyclic compound and a pharmaceutical use thereof. Specifically, the present invention relates to an inhibitor of Janus kinase 3, referred to as JAK3 hereinafter, a compound for prevention or treatment of organ transplant rejection, graft versus host reaction after transplantation, autoimmune disease and allergic disease, and a pharmaceutical use of the same.

The present invention also relates to an inhibitor of Janus kinase 2, referred to as JAK2 hereinafter, a compound for prevention or treatment of chronic myeloproliferative disease, and a pharmaceutical use of the same.

BACKGROUND ART

JAK3 is a member of Janus family which belongs to protein kinases. Other members of this family are expressed in various tissues, while JAK3 is expressed only in hematopoietic cells.

This limiting expression is involved in an important role of JAK3 by a non-covalent association of JAK3 with γ-chains common to multiply-linked receptors including IL-2, IL-4, IL-7, IL-9, IL-15 and IL-21 in the receptor-mediated signal transduction.

Significantly reduced JAK3 protein levels or gene defects in common γ-chains are found in Severe Combined Immunodeficiency, referred to as SCID hereinafter, patient population. That indicates that an immunosuppression is produced by blocking JAK3-mediated signaling pathway.

It has been reported in animal experiments that JAK3 plays an important role in maturity of NK cells, B-lymphocytes and T-lymphocytes and is essentially required for the maintenance of T cell functions.

It has been also reported that a JAK3 inhibitor CP-690,550 ((3R,4R)-3-[4-methyl-3-[N-methyl-N-(7H-pyrrolo[2,3-d]pyrimidin-4-yl)amino]piperidin-1-yl]-3-oxopropionitrile) improves rheumatoid arthritis and psoriasis conditions, and shows rejection-suppression effects in simian renal transplantation model and airway inflammation-suppression effects in mouse asthma model.

In view of the above knowledge, it is believed that a regulation of an immune activity by JAK3 inhibitors is useful for the prevention or treatment of organ transplant rejection, graft versus host reaction after transplantation, autoimmune disease and allergic disease.

On the other hand, it has been indicated that an inhibition of JAK2 is useful for patients suffering from a chronic myeloproliferative disease. The chronic myeloproliferative disease includes polycythemia vera, primary myelofibrosis, essential thrombocythemia, chronic myelocytic leukemia, chronic myelomonocytic leukemia, chronic eosinophilic leukemia, chronic neutrophilic leukemia, systemic mastocytosis.

It is believed that the chronic myeloproliferative disease may be caused by acquired cell mutations in hematopoietic stem cells, and it has been reported that a large majority of polycythemia vera's patients as well as a significant number of primary myelofibrosis's and essential thrombocythemia's patients have gain-of-function mutations of JAK2. It has been also reported that an inhibition of a JAK2V617F kinase by low-molecular inhibitors causes an inhibition of proliferation of hematopoietic cells.

In view of the above knowledge, it is believed that a regulation of proliferation of hematopoietic cells by JAK2 inhibitors is useful for the prevention or treatment of chronic myeloproliferative diseases.

Four types of members of a Janus kinase, referred to as JAK hereinafter, family are known including Janus kinase 1, referred to as JAK1 hereinafter, JAK2, JAK3, and tyrosine kinase 2, referred to as Tyk2 hereinafter, and it is believed that a JAK1 inhibitor and a Tyk2 inhibitor are also useful for the prevention or treatment of varieties of diseases similar to a JAK3 inhibitor.

DISCLOSURE OF INVENTION

Problems to be Resolved by the Invention

According to extensive studies for the purpose of developing a novel therapeutic or preventive agent for organ transplant rejection, graft versus host reaction after transplantation, autoimmune disease and allergic disease alternative to conventional one, the inventors have found novel nitrogen-containing spiro cyclic compounds with JAK3 inhibitory effect and achieved the present invention.

The present inventors have also found novel nitrogen-containing spiro cyclic compounds with JAK2 inhibitory effect and achieved the present invention.

Means of Solving the Problems

Specifically, the present invention is as follows.

[1] A compound of the following general formula [I]:

[Chemical Formula 1]

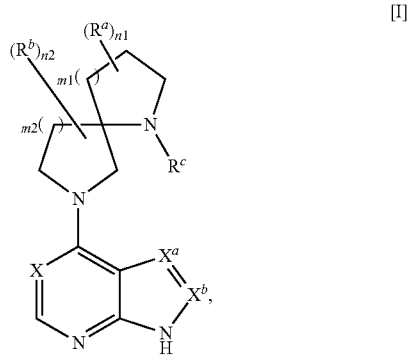

wherein $R^a$ is the same or different and each:
(1) $C_{1-6}$ alkyl, or
(2) halogen atom,
n1 is an integer selected from 0 to 4,
$R^b$ is the same or different and each:
(1) $C_{1-6}$ alkyl, or
(2) halogen atom,
n2 is an integer selected from 0 to 4,
m1 is an integer selected from 0 to 3,
m2 is an integer selected from 1 to 4,
$X^a=X^b$ is:
(1) CH=CH,
(2) N=CH, or
(3) CH=N,
X is:
(1) nitrogen atom, or
(2) C—$R^d$ wherein $R^d$ is hydrogen atom or halogen atom,
$R^c$ is a group selected from the following (1) to (6):
(1) hydrogen atom,
(2) $C_{1-6}$ alkyl optionally substituted by the same or different 1 to 5 substituents selected from the following Group A,
(3) —C(=O)—$R^{c1}$,
(4) —C(=O)—O—$R^{c2}$,
(5) —C(=O)—$NR^{c3}R^{c4}$
in which $R^{c1}$, $R^{c2}$, $R^{c3}$ and $R^{c4}$ are the same or different and each:
(i) hydrogen atom, or
(ii) $C_{1-6}$ alkyl optionally substituted by the same or different 1 to 5 substituents selected from the following Group A, or
(6) a group of formula:

[Chemical Formula 2]

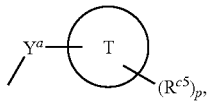

in which $Y^a$ is a group selected from the following (i) to (iii):
(i) $C_{1-6}$ alkylene,
(ii) —C(=O)—, or
(iii) —C(=O)—O—,
Ring T is:
(i) $C_{6-10}$ aryl,
(ii) $C_{3-10}$ cycloalkyl, or
(iii) saturated monoheterocyclyl wherein the saturated monoheterocyclyl comprises 1 to 4 heteroatoms selected from nitrogen atom, oxygen atom or sulfur atom as well as carbon atoms and the number of the constituent ring atoms is 3 to 7,
$R^{c5}$ is the same or different and each:
(i) cyano, or
(ii) nitro,
p is an integer selected from 0 to 4,
Group A is the group consisting of:
(a) hydroxyl,
(b) $C_{1-6}$ alkoxy,
(c) cyano,
(d) $C_{1-6}$ alkoxycarbonyl,
(e) $C_{1-6}$ alkylcarbonyloxy, and
(f) $C_{2-6}$ alkenyloxy, or a pharmaceutically acceptable salt thereof, or a solvate thereof.
[2] The compound of [1], wherein, in the general formula [I],
n1 is an integer selected from 0 to 2,
n2 is an integer selected from 0 to 2,
m1 is an integer selected from 0 to 3,
m2 is an integer selected from 1 to 3,
X is:
(1) nitrogen atom, or
(2) C—$R^d$ wherein $R^d$ is halogen atom,
$R^c$ is a group selected from the following (1) to (6):
(1) hydrogen atom,
(2) $C_{1-6}$ alkyl substituted by one substituent selected from the following Group A,
(3) —C(=O)—$R^{c1}$,
(4) —C(=O)—O—$R^{c2}$,
(5) —C(=O)—$NR^{c3}R^{c4}$
in which $R^{c1}$ is $C_{1-6}$ alkyl optionally substituted by one substituent selected from the following Group A,
$R^{c2}$ is $C_{1-6}$ alkyl,
$R^{c3}$ is $C_{1-6}$ alkyl optionally substituted by one substituent selected from the following Group A,
$R^{c4}$ is
(i) hydrogen atom, or
(ii) $C_{1-6}$ alkyl, or
(6) a group of formula:

[Chemical Formula 3]

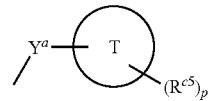

in which $Y^a$ is a group selected from the following (i) to (iii):
(i) $C_{1-6}$ alkylene,
(ii) —C(=O)—, or
(iii) —C(=O)—O—,
Ring T is:
(i) phenyl,
(ii) $C_{3-6}$ cycloalkyl, or
(iii) pyrrolidinyl,
$R^{c5}$ is
(i) cyano, or
(ii) nitro,
p is an integer selected from 0 or 1,
Group A is the group consisting of:
(a) hydroxyl,
(b) $C_{1-6}$ alkoxy,
(c) cyano,
(d) $C_{1-6}$ alkoxycarbonyl,
(e) $C_{1-6}$ alkylcarbonyloxy, and
(f) $C_{2-6}$ alkenyloxy, or a pharmaceutically acceptable salt thereof, or a solvate thereof.
[3] The compound of either one of [1] or [2], wherein m1 is an integer of 0 or 1 and m2 is an integer of 1 or 2, or a pharmaceutically acceptable salt thereof, or a solvate thereof.
[4] The compound of [3], wherein a combination of (m1,m2) is (1,2), which is a compound of the general formula [II]:

[Chemical Formula 4]

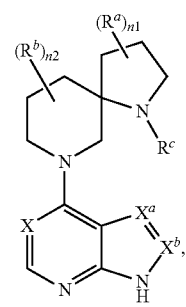

wherein each symbol has the same meaning as defined in [1], or a pharmaceutically acceptable salt thereof, or a solvate thereof.

[5] The compound of [3], wherein a combination of (m1,m2) is (0,2), which is a compound of the general formula [III]:

[Chemical Formula 5]

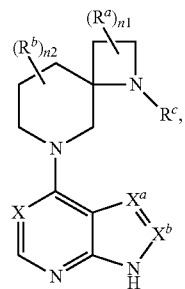

[III]

wherein each symbol has the same meaning as defined in [1], or a pharmaceutically acceptable salt thereof, or a solvate thereof.

[6] The compound of [3], wherein a combination of (m1,m2) is (0,1), which is a compound of the general formula [IV]:

[Chemical Formula 6]

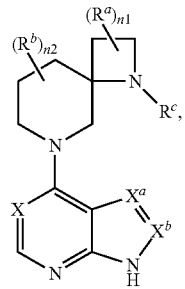

[IV]

wherein each symbol has the same meaning as defined in [1], or a pharmaceutically acceptable salt thereof, or a solvate thereof.

[7] The compound of either one of [1] or [2], wherein a combination of (m1,m2) is selected from (0,3), (2,1), (2,2) or (3,2), or a pharmaceutically acceptable salt thereof, or a solvate thereof.

[8] The compound of any one of [1] to [7], wherein $X^a=X^b$ is CH=CH and X is nitrogen atom, or a pharmaceutically acceptable salt thereof, or a solvate thereof.

[9] The compound of either one of [1] or [2], wherein a combination of (n1,n2) is (0,0), or a pharmaceutically acceptable salt thereof, or a solvate thereof.

[10] The compound of either one of [1] or [2], wherein a combination of (n1,n2) is (1,0), or a pharmaceutically acceptable salt thereof, or a solvate thereof.

[11] The compound of either one of [1] or [2], wherein a combination of (n1,n2) is (0,1), or a pharmaceutically acceptable salt thereof, or a solvate thereof.

[12] The compound of either one of [1] or [2], wherein a combination of (n1,n2) is (2,0), or a pharmaceutically acceptable salt thereof, or a solvate thereof.

[13] The compound of either one of [1] or [2], wherein a combination of (n1,n2) is (0,2), or a pharmaceutically acceptable salt thereof, or a solvate thereof.

[14] The compound of either one of [10] or [12], wherein $R^a$ is methyl or fluorine atom, or a pharmaceutically acceptable salt thereof, or a solvate thereof.

[15] The compound of any one of [1] to [14], wherein $R^c$ is —C(=O)—$R^{c1}$, or a pharmaceutically acceptable salt thereof, or a solvate thereof.

[16] The compound of [15], wherein $R^{c1}$ is $C_{1-6}$ alkyl substituted by one hydroxyl or cyano group, or a pharmaceutically acceptable salt thereof, or a solvate thereof.

[17] The compound of any one of [1] to [14], wherein $R^c$ is —C(=O)—$NR^{c3}R^{c4}$, or a pharmaceutically acceptable salt thereof, or a solvate thereof.

[18] The compound of [17], wherein $R^{c3}$ is $C_{1-6}$ alkyl substituted by one cyano group, and $R^{c4}$ is hydrogen, or a pharmaceutically acceptable salt thereof, or a solvate thereof.

[19] The compound of [1] selected from the following chemical structural formula:

[Chemical Formula 7]

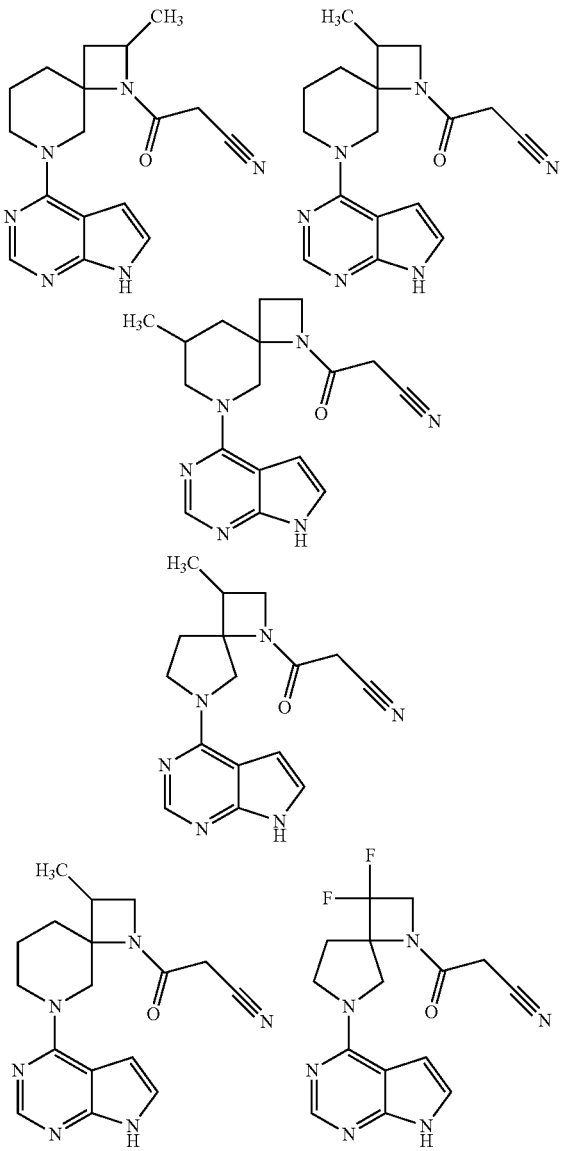

-continued
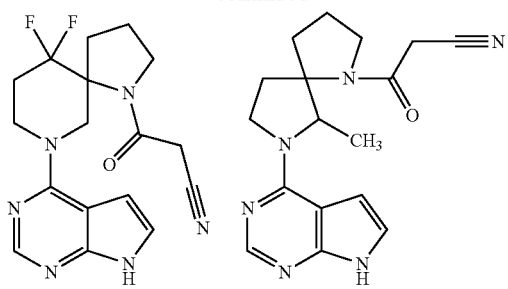
[Chemical Formula 8]
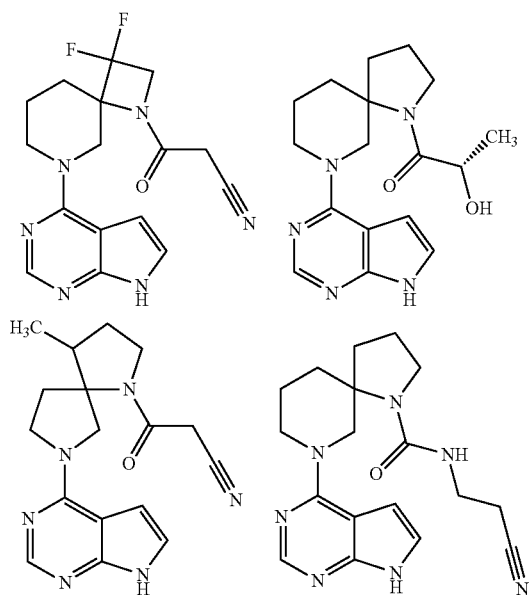
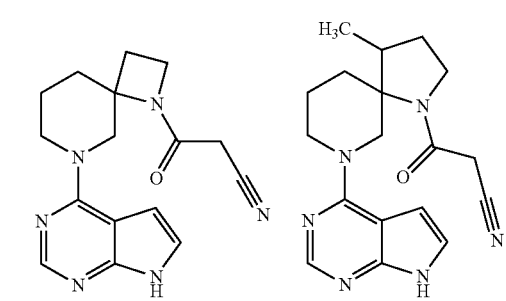
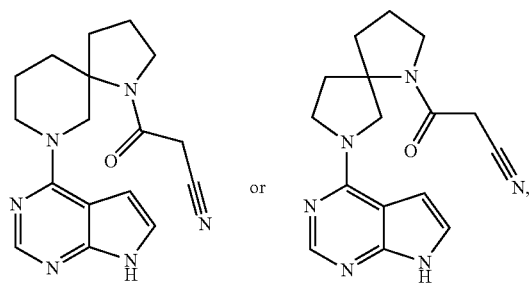
or a pharmaceutically acceptable salt thereof, or a solvate thereof.
[20] The compound of [1] selected from the following chemical structural formula:
[Chemical Formula 9]
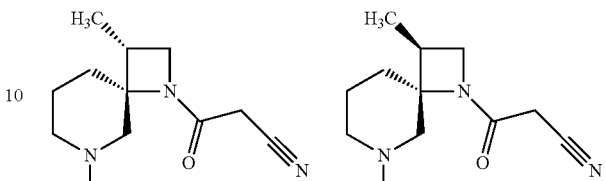
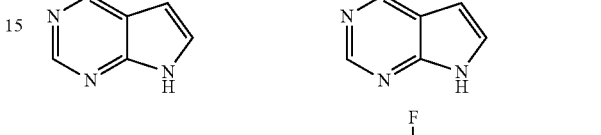
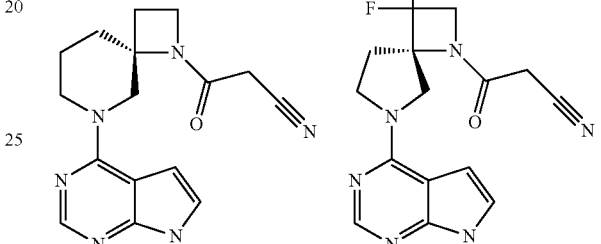
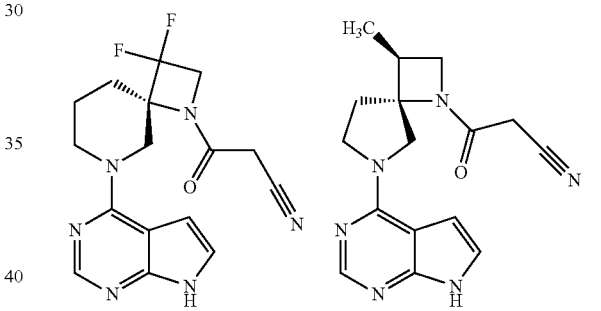
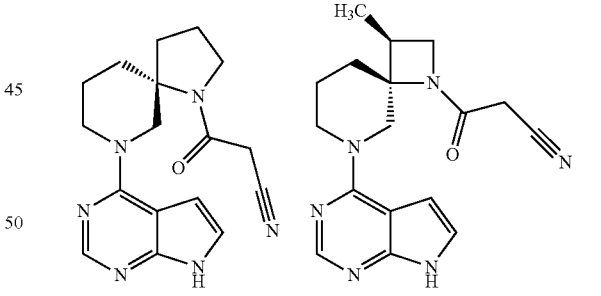
[Chemical Formula 10]
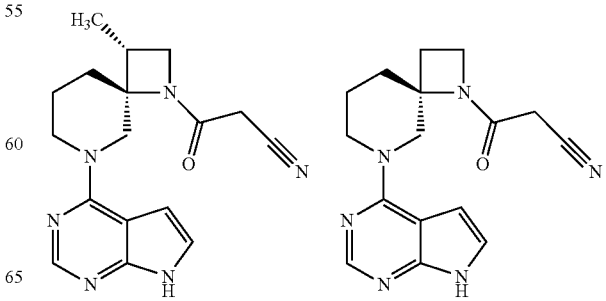

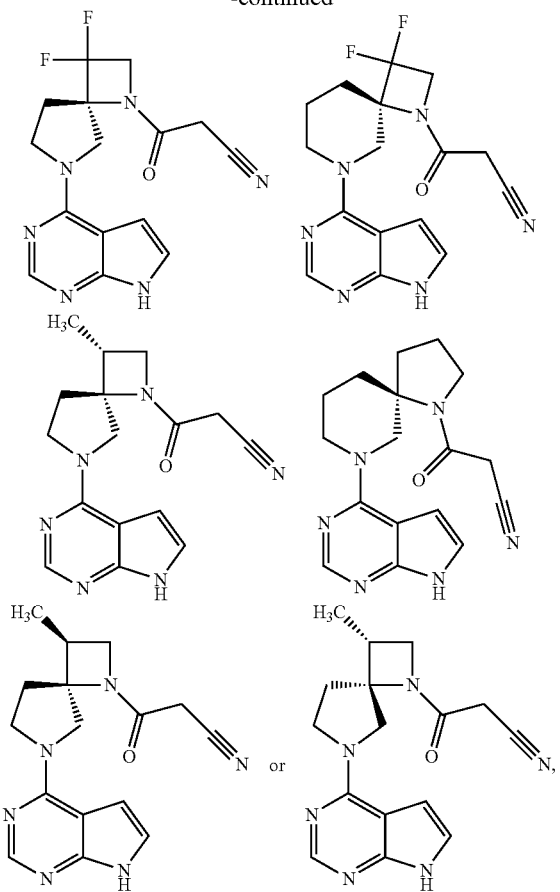

or a pharmaceutically acceptable salt thereof, or a solvate thereof.

[21] A pharmaceutical composition, comprising the compound of any one of [1] to [20] or a pharmaceutically acceptable salt thereof, or a solvate thereof, and a pharmaceutically acceptable carrier.

[22] A Janus kinase inhibitor, comprising the compound of any one of [1] to [20] or a pharmaceutically acceptable salt thereof, or a solvate thereof.

[23] The Janus kinase inhibitor of [22], wherein the Janus kinase is Janus kinase 3.

[24] The Janus kinase inhibitor of [22], wherein the Janus kinase is Janus kinase 2.

[25] A therapeutic or preventive agent for a disease selected from the group consisting of organ transplant rejection, graft versus host reaction after transplantation, autoimmune disease, allergic disease and chronic myeloproliferative disease, comprising the compound of any one of [1] to [20] or a pharmaceutically acceptable salt thereof, or a solvate thereof.

[26] A therapeutic or preventive agent for rheumatoid arthritis, comprising the compound of any one of [1] to [20] or a pharmaceutically acceptable salt thereof, or a solvate thereof.

[27] A therapeutic or preventive agent for psoriasis, comprising the compound of any one of [1] to [20] or a pharmaceutically acceptable salt thereof, or a solvate thereof.

[28] A method for inhibiting Janus kinase, comprising administering to a mammal a pharmaceutically effective amount of the compound of any one of [1] to [20] or a pharmaceutically acceptable salt thereof, or a solvate thereof.

[29] The method of [28], wherein the Janus kinase is Janus kinase 3.

[30] The method of [28], wherein the Janus kinase is Janus kinase 2.

[31] A method for treating or preventing a disease selected from the group consisting of organ transplant rejection, graft versus host reaction after transplantation, autoimmune disease, allergic diseases and chronic myeloproliferative disease, comprising administering to a mammal a pharmaceutically effective amount of the compound of any one of [1] to [20] or a pharmaceutically acceptable salt thereof, or a solvate thereof.

[32] A method for treating or preventing rheumatoid arthritis, comprising administering to a mammal a pharmaceutically effective amount of the compound of any one of [1] to [20] or a pharmaceutically acceptable salt thereof, or a solvate thereof.

[33] A method for treating or preventing psoriasis, comprising administering to a mammal a pharmaceutically effective amount of the compound of any one of [1] to [20] or a pharmaceutically acceptable salt thereof, or a solvate thereof.

[34] Use of the compound of any one of [1] to [20] or a pharmaceutically acceptable salt thereof, or a solvate thereof in the manufacture of a Janus kinase inhibitor.

[35] The use of [34], wherein the Janus kinase is Janus kinase 3.

[36] The use of [34], wherein the Janus kinase is Janus kinase 2.

[37] Use of the compound of any one of [1] to [20] or a pharmaceutically acceptable salt thereof, or a solvate thereof in the manufacture of a medicament for treating or preventing a disease selected from the group consisting of organ transplant rejection, graft versus host reaction after transplantation, autoimmune disease, allergic diseases and chronic myeloproliferative disease.

[38] Use of the compound of any one of [1] to [20] or a pharmaceutically acceptable salt thereof, or a solvate thereof in the manufacture of a medicament for treating or preventing rheumatoid arthritis.

[39] Use of the compound of any one of [1] to [20] or a pharmaceutically acceptable salt thereof, or a solvate thereof in the manufacture of a medicament for treating or preventing psoriasis.

[40] A commercial kit, comprising (a) a pharmaceutical composition comprising as the active ingredient the compound of any one of [1] to [20] or a pharmaceutically acceptable salt thereof, or a solvate thereof; and (b) a drug package insert of the pharmaceutical composition which indicates that the pharmaceutical composition may be used or should be used for the treatment or prevention of rheumatoid arthritis or psoriasis.

[41] A commercial package, comprising (a) a pharmaceutical composition comprising as the active ingredient the compound of any one of [1] to [20] or a pharmaceutically acceptable salt thereof, or a solvate thereof; and (b) a drug package insert of the pharmaceutical composition which indicates that the pharmaceutical composition may be used or should be used for the treatment or prevention of rheumatoid arthritis or psoriasis.

Effect of Invention

The inventive nitrogen-containing spiro cyclic compound of the present application is effective as a therapeutic or preventive agent for organ transplant rejection, graft versus host reaction after transplantation, autoimmune disease and allergic disease, etc. due to its JAK3 activity-inhibition effect.

Moreover, the inventive nitrogen-containing spiro cyclic compound of the present application is effective as a therapeutic or preventive agent for chronic myeloproliferative disease due to its JAK2 activity-inhibition effect.

BEST MODE FOR CARRYING OUT THE INVENTION

Terms and phrases used herein are defined as below.

The phrase "optionally substituted" includes both cases that substitutable positions are substituted and are not substituted (unsubstituted) in the subject group. The term "unsubstituted" refers to such a case that all substitutable positions are substituted by hydrogen atom in the subject group.

For example, "$C_{1-6}$ alkyl optionally substituted by the same or different 1 to 5 substituents selected from Group A" includes both cases that substitutable positions of $C_{1-6}$ alkyl are substituted by the same or different 1 to 5 substituents selected from Group A and not substituted (unsubstituted).

The phrase "halogen atom" includes fluorine atom, chlorine atom, bromine atom or iodine atom, preferably fluorine atom or chlorine atom.

The phrase "$C_{1-6}$ alkyl" refers to $C_{1-6}$ straight- or branched-chain saturated hydrocarbon, e.g. methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, preferably methyl, ethyl, propyl, isopropyl, etc.

The phrase "$C_{2-6}$ alkenyl" refers to $C_{2-6}$ straight- or branched-chain unsaturated hydrocarbon containing one or more double bonds, e.g. vinyl, 1-methylvinyl, 1-propenyl, allyl, methylpropenyl (including 1-methyl-1-propenyl, 2-methyl-1-propenyl, etc.), 1-butenyl, 2-butenyl, 3-butenyl, methylbutenyl (including 1-methyl-1-butenyl, 2-methyl-1-butenyl, 3-methyl-1-butenyl, etc.), pentenyl, methylpentenyl, hexenyl, preferably vinyl, 1-methylvinyl, 1-propenyl, methylpropenyl, etc.

The phrase "$C_{1-6}$ alkylene" refers to a divalent group derived from straight-chain $C_{1-6}$ alkyl as defined above, e.g. methylene, ethylene, trimethylene, tetramethylene, pentamethylene, hexamethylene, preferably methylene, ethylene, etc.

The phrase "$C_{6-10}$ aryl" refers to $C_{6-10}$ aromatic hydrocarbon, e.g. phenyl, 1-naphthyl, 2-naphthyl, preferably phenyl.

The phrase "$C_{3-10}$ cycloalkyl" refers to $C_{3-10}$ monocyclic saturated hydrocarbon, e.g. cyclopropyl, cyclobutyl, cyclopentyl, cyclohexyl, cycloheptyl, cyclooctyl, preferably $C_{3-6}$ cycloalkyl (including cyclopropyl, cyclobutyl, cyclopentyl, cyclohexyl, etc.).

The phrase "saturated monoheterocyclyl" wherein the saturated monoheterocyclyl comprises 1 to 4 heteroatoms selected from nitrogen atom, oxygen atom or sulfur atom as well as carbon atoms and the number of the constituent ring atoms is 3 to 7 includes oxyranyl, thiolanyl, aziridinyl, azetidinyl, oxetanyl, pyrrolidinyl, pyrrolidino (including 1-pyrrolidinyl), tetrahydrofuranyl, tetrahydrothienyl, oxazolinyl, oxazolidinyl, isoxazolinyl, isoxazolidinyl, thiazolinyl, thiazolidinyl, isothiazolinyl, isothiazolidinyl, imidazolinyl, imidazolidinyl, pyrazolinyl, pyrazolidinyl, piperidinyl, piperidino (including 1-piperidinyl), morpholinyl, morpholino (including 4-morpholinyl), thiomorpholinyl, thiomorpholino (including 4-thiomorpholinyl), piperazinyl, piperazino (including 1-piperazinyl), hexahydro-1,3-oxazinyl, homomorpholine, homopiperazine, etc.

The phrase "$C_{1-6}$ alkoxy" refers to $C_{1-6}$ straight- or branched-chain alkoxy, particularly methoxy, ethoxy, propoxy, isopropoxy, butoxy, isobutoxy, s-butoxy, t-butoxy, pentyloxy, isopentyloxy, 2-methylbutoxy, neopentyloxy, 1-ethylpropoxy, hexyloxy, etc.

The phrase "$C_{1-6}$ alkoxycarbonyl" refers to a group wherein $C_{1-6}$ straight- or branched-chain alkoxy binds to carbonyl, particularly methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentyloxycarbonyl, isopentyloxycarbonyl, 2-methylbutoxycarbonyl, neopentyloxycarbonyl, 1-ethylpropoxycarbonyl, hexyloxycarbonyl, 4-methylpentyloxycarbonyl, etc.

The phrase "$C_{1-6}$ alkylcarbonyloxy" refers to a group wherein a "group wherein $C_{1-6}$ alkyl binds to carbonyl" binds to oxy, particularly acetyloxy, propionyloxy, butyryloxy, isobutyryloxy, etc.

The phrase "$C_{2-6}$ alkenyloxy" refers to a group wherein "$C_{2-6}$ alkenyl" binds to oxy, particularly allyloxy, 1-butenyloxy, etc.

Preferable embodiments for each group in a compound of the general formula [I], which is also referred to as the present compound hereinafter, are illustrated as below.

Preferable embodiments of $R^a$ include:
(1) methyl, or
(2) fluorine atom, etc.

Preferable embodiments of n1 include an integer of 0, 1 or 2.

Preferable embodiments of $R^b$ include:
(1) methyl, or
(2) fluorine atom, etc.

Preferable embodiments of n2 include an integer of 0, 1 or 2.

Preferable embodiments of m1 include an integer selected from 0 to 3.

Preferable embodiments of m2 include an integer of 1, 2 or 3.

A combination of (m1,m2) includes (0,1), (0,2), (0,3), (1,1), (1,2), (2,1), (2,2) or (3,2).

Preferably, $R^a$ and $R^b$ may be substituted on carbon atoms constituting each spirocycle of the general formula [I] except for a spiro carbon, and carbon atoms which are not substituted by $R^a$ or $R^b$ are saturated by hydrogen atoms. In case that n1 is 2 or above, $R^a$ may be the same or different and each, and substituted on the same or different positions. Further, in case that n2 is 2 or above, $R^b$ may be the same or different and each, and substituted on the same or different positions.

$X^a=X^b$ is:
(1) CH=CH,
(2) N=CH, or
(3) CH=N,
preferably (1) CH=CH.

Preferable embodiments of X are:
(1) nitrogen atom, or
(2) C—Cl,
more preferably (1) nitrogen atom.

Preferable embodiments of $R^c$ include hydrogen atom, cyanoethyl, acetyl, benzyl, cyanomethylcarbonyl, propenyloxyethylcarbonyl, 2-propanylcarbonyl, ethylcarbonyl, methoxycarbonyl, (S)-hydroxyethylcarbonyl, hydroxymethylcarbonyl, 1-hydroxyethylcarbonyl, acetoxymethylcarbonyl, (S)-acetoxyethylcarbonyl, methoxymethylcarbonyl, methoxyethylcarbonyl, (S)-methoxyethylcarbonyl, (R)-methoxyethylcarbonyl, 3-cyanopyrrolidinylcarbonyl, 3-cyanophenylcarbonyl, 4-cyanophenylcarbonyl, methoxycarbonylethylcarbonyl, p-nitrophenoxycarbonyl, 1-cyanomethylcyclopropanylcarbonyl, t-butoxycarbonyl, N-ethylcarbamoyl, N-cyanomethylcarbamoyl, N-cyanoethylcarbamoyl, N,N-methylcyanomethylcarbamoyl, N,N-methylcyanoethylcarbamoyl, N-propanylcarbamoyl, preferably cyanomethylcarbonyl, hydroxymethylcarbonyl or cyanoethylcarbamoyl.

Preferable embodiments of a compound of the general formula [I] include compounds of the following formulae:

[Chemical Formula 11]

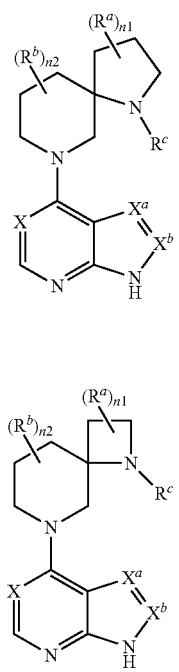

[II]

[III]

[IV]

A compound of the general formula [II] includes preferably a compound of the general formula [II-A], [II-B] or [II-C].

[Chemical Formula 12]

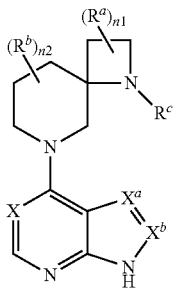

[II-A]

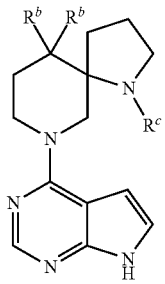

[II-B]

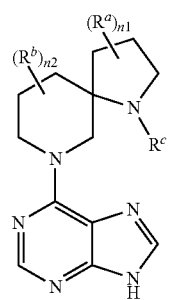

[II-C]

A compound of the general formula [III] includes preferably a compound of the general formula [III-A], [III-B] or [III-C].

[Chemical Formula 13]

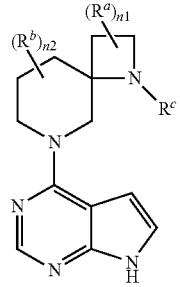

[III-A]

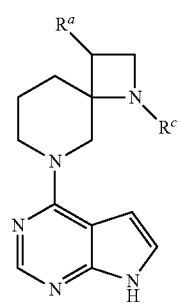

[III-B]

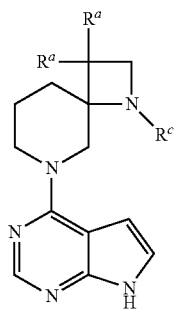
[III-C]

A compound of the general formula [IV] includes preferably a compound of the general formula [IV-A], [IV-B] or [IV-C].

[Chemical Formula 14]

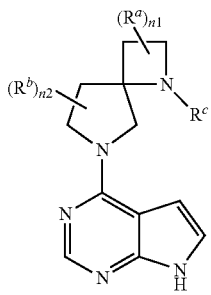
[IV-A]

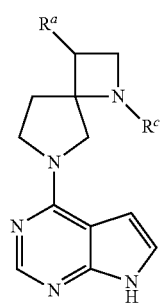
[IV-B]

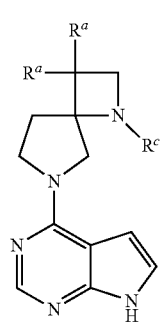
[IV-C]

Another preferable embodiment of a compound of the general formula [I] includes compounds of the following formula:

[Chemical Formula 15]

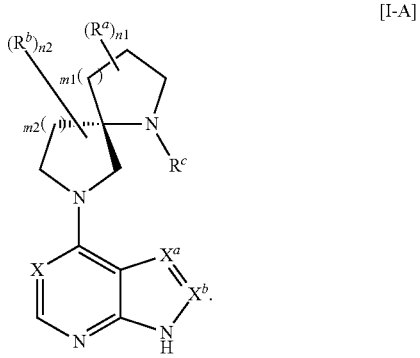
[I-A]

Another preferable embodiment of a compound of the general formula [I] has JAK1 and/or JAK2 and/or Tyk2 inhibitory effects as well as JAK3 inhibitory effect. More preferably, a compound of the general formula [I] has all of JAK1, JAK2, JAK3 and Tyk2 inhibitory effects.

The "pharmaceutically acceptable salt" of a compound of the general formula [I], which is also referred to as the present compound hereinafter, may be any atoxic salts of the present compound and includes a salt with an inorganic acid, an organic acid, an inorganic base, an organic base, an amino acid, etc.

The salt with an inorganic acid includes a salt with hydrochloric acid, nitric acid, sulfuric acid, phosphoric acid, hydrobromic acid, etc.

The salt with an organic acid includes a salt with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, etc.

The salt with an inorganic base includes sodium salt, potassium salt, calcium salt, magnesium salt, ammonium salt, etc.

The salt with an organic base includes a salt with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine, etc.

The salt with an amino acid includes a salt with lysine, arginine, aspartic acid, glutamic acid, etc.

According to known methods, each salt may be obtained by reacting a compound of the general formula [I] with an inorganic base, an organic base, an inorganic acid, an organic acid or an amino acid.

The "solvate" refers to a material wherein solvent molecules coordinate with a compound of the general formula [I] or a pharmaceutically acceptable salt thereof, and includes hydrate. A preferable solvate is a pharmaceutically acceptable solvate including 1 hydrate, 1/2 hydrate or 2 hydrate of a compound of the general formula [I], 1 hydrate of sodium salt of a compound of the general formula [I], 1 methanolate, 1 ethanolate or 1 acetonitrilate of a compound of the general formula [I], 2/3 ethanolate of 2 hydrochloride of a compound of the general formula [I], etc. More preferable solvate is 1 hydrate of a compound of the general formula [I]. According to known methods, a solvate thereof may be obtained.

A compound of the general formula [I] also exists as various "isomers". For example, a geometric isomer thereof includes E- and Z-isomers. In case that any asymmetric carbon atoms exist, a stereoisomer based on such carbon atoms includes enantiomers and diastereomers. In case that any chiral axes exist, a stereoisomer based on such axes exists. A tautomer may exist as the case may be. Therefore, the scope of the present invention encompasses all these isomers and a mixture thereof.

A compound of the general formula [I] may be also labelled by isotopes (e.g., $^3$H, $^{14}$C, $^{35}$S, etc.).

A preferable compound of the general formula [I] or a pharmaceutically acceptable salt thereof, or a solvate thereof is substantially-purified compound of the general formula [I] or a pharmaceutically acceptable salt thereof, or a solvate thereof. More preferable one is a compound of the general formula [I] or a pharmaceutically acceptable salt thereof, or a solvate thereof which is purified in the purity of 80% or above.

In the present invention, a prodrug of a compound of the general formula [I] may be also a useful drug. The "prodrug" refers to a derivative of the present compound with chemically or metabolically decomposable functional groups which is administered in vivo, followed by converting into a corresponding parent compound by hydrolysis, solvolysis or physiological decomposition to show original drug efficacies, and includes any composites with noncovalent bonds and salts thereof. The prodrug is utilized to improve absorption in oral administration or to target at its target site, for example. Modification sites for the prodrug formation include any reactive functional groups of the present compound including hydroxyl, carboxyl, amino, thiol, etc.

A modified group for hydroxyl includes acetyl, propionyl, isobutyryl, pivaloyl, palmitoyl, benzoyl, 4-methylbenzoyl, dimethylcarbamoyl, dimethylaminomethylcarbonyl, sulfo, alanyl, fumaryl, or sodium-saltified 3-carboxybenzoyl or 2-carboxyethylcarbonyl, etc.

A modified group for carboxyl includes methyl, ethyl, propyl, isopropyl, butyl, isobutyl, tert-butyl, pivaloyloxymethyl, carboxymethyl, dimethylaminomethyl, 1-(acetyloxy)ethyl, 1-(ethoxycarbonyloxy)ethyl, 1-(isopropyloxycarbonyloxy)ethyl, 1-(cyclohexyloxycarbonyloxy)ethyl, (5-methyl-2-oxo-1,3-dioxol-4-yl)methyl, benzyl, phenyl, o-tolyl, morpholinoethyl, N,N-diethylcarbamoylmethyl, phthalidyl, etc.

A modified group for amino includes tert-butyl, docosanoyl, pivaloylmethyloxy, alanyl, hexylcarbamoyl, pentylcarbamoyl, 3-methylthio-1-(acetylamino)propylcarbonyl, 1-sulfo-1-(3-ethoxy-4-hydroxyphenyl)methyl, (5-methyl-2-oxo-1,3-dioxol-4-yl)methyl, (5-methyl-2-oxo-1,3-dioxol-4-yl)methoxycarbonyl, tetrahydrofuranyl, pyrrolidylmethyl, etc.

The "pharmaceutical composition" includes an oral preparation such as tablet, capsule, granule, powder, lozenge, syrup, emulsion, suspension, or a parenteral preparation such as external preparation, suppository, injection, drop, nasal drug, pulmonary drug.

The pharmaceutical composition of the present invention may be prepared by properly mixing a compound of the general formula [I] or a pharmaceutically acceptable salt thereof, or a solvate thereof with at least one or more types of pharmaceutically acceptable carriers in appropriate amounts according to known methods in the medicinal preparation field. A content of a compound of the general formula [I] or a pharmaceutically acceptable salt thereof, or a solvate thereof in the pharmaceutical composition depends on its dosage forms, dosage amounts, etc., and for example, is 0.1 to 100% by weight of the composition.

The "pharmaceutically acceptable carrier" includes various conventional organic or inorganic carriers for pharmaceutical materials, e.g., excipient, disintegrant, binder, fluidizer, lubricant for solid preparations, or solvent medium, solubilizing agent, suspending agent, tonicity agent, buffer, soothing agent for liquid preparations. Further, an additive including a preserving agent, an antioxidant agent, a colorant, a sweetening agent may be used, if needed.

The "excipient" includes lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic, etc.

The "disintegrant" includes carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose, etc.

The "binder" includes hydroxypropylcellulose, hydroxypropylmethylcellulose, povidone, crystalline cellulose, sucrose, dextrin, starch, gelatin, carmellose sodium, gum arabic, etc.

The "fluidizer" includes light anhydrous silicic acid, magnesium stearate, etc.

The "lubricant" includes magnesium stearate, calcium stearate, talc, etc.

The "solvent medium" includes purified water, ethanol, propylene glycol, macrogol, sesame oil, corn oil, olive oil, etc.

The "solubilizing agent" includes propylene glycol, D-mannitol, benzyl benzoate, ethanol, triethanolamine, sodium carbonate, sodium citrate, etc.

The "suspending agent" includes benzalkonium chloride, carmellose, hydroxypropylcellulose, propylene glycol, povidone, methylcellulose, glyceryl monostearate, etc.

The "tonicity agent" includes glucose, D-sorbitol, sodium chloride, D-mannitol, etc.

The "buffer" includes sodium hydrogen phosphate, sodium acetate, sodium carbonate, sodium citrate, etc.

The "soothing agent" includes benzyl alcohol, etc.

The "preserving agent" includes ethyl paraoxybenzoate, chlorobutanol, benzyl alcohol, sodium dehydroacetate, sorbic acid, etc.

The "antioxidant agent" includes sodium sulfite, ascorbic acid, etc.

The "colorant" includes food dye (e.g., Food Red No. 2 or 3, Food Yellow No. 4 or 5, etc.), β-carotene, etc.

The "sweetening agent" includes saccharin sodium, dipotassium glycyrrhizinate, aspartame, etc.

The pharmaceutical composition of the present invention may be orally or parenterally (e.g., locally, rectally, intravenously, etc.) administered to a mammal except human beings (e.g., mice, rats, hamsters, guinea pigs, rabbits, cats, dogs, pigs, cows, horses, sheep, monkeys, etc.) as well as human beings. A dose of said pharmaceutical composition depends on administration subjects, diseases, conditions, dosage forms, administration routes, and the dose in case of orally administering to adult patients (body weight: about 60 kg) who are suffering from organ transplant rejection, graft versus host reaction after transplantation, autoimmune disease or allergic disease, etc. is usually in the range from about 1 mg to 1 g per day with comprising the present compound as the active ingredient. The dose may be administered at a time or in several divided doses.

19

The compound of the general formula [I] or a pharmaceutically acceptable salt thereof, or a solvate thereof may be used as the active ingredient of a therapeutic or preventive agent for the following diseases due to its JAK3 inhibitory activity:

(a) organ transplant rejection, or graft versus host reaction after transplantation;

(b) autoimmune diseases including rheumatoid arthritis, psoriasis, psoriatic arthritis, multiple sclerosis, ulcerative colitis, Crohn's disease, systemic lupus erythematosus, type I diabetes, myasthenia gravis, Castleman's disease, juvenile idiopathic arthritis, dry eye; and (c) allergic diseases including asthma, atopic dermatitis, rhinitis.

Preferably, a compound of the general formula [I] or a pharmaceutically acceptable salt thereof, or a solvate thereof may be used as the active ingredient of a therapeutic or preventive agent for rheumatoid arthritis or psoriasis.

Moreover, a compound of the general formula [I] or a pharmaceutically acceptable salt thereof, or a solvate thereof may be used as the active ingredient of a therapeutic or preventive agent for chronic myeloproliferative diseases including polycythemia vera, primary myelofibrosis, essential thrombocythemia, etc. due to its JAK2 inhibitory activity.

The phrase "JAK inhibitory" refers to inhibiting functions of JAK to disappear or reduce its activity, and inhibiting any functions of JAK family. A preferable "JAK inhibitory" is "human JAK inhibitory".

A preferable "JAK inhibitor" is "human JAK inhibitor".

The phrase "JAK3 inhibitory" refers to inhibiting functions of JAK3 to disappear or reduce its activity. For example, it refers to inhibiting functions of JAK3 under the conditions of test examples as described hereinbelow. A preferable "JAK3 inhibitory" is "human JAK3 inhibitory".

A preferable "JAK3 inhibitor" is "human JAK3 inhibitor".

The phrase "JAK2 inhibitory" refers to inhibiting functions of JAK2 to disappear or reduce its activity. For example, it refers to inhibiting functions of JAK2 under the conditions of test examples as described hereinbelow. A preferable "JAK2 inhibitory" is "human JAK2 inhibitory".

A preferable "JAK2 inhibitor" is "human JAK2 inhibitor".

As an example, a method for preparing compounds for working the present invention is illustrated as follows, and the method for preparing the present compound is not intended to be limited thereto.

Unless otherwise specified, effective preparation methods may be carried out by introducing any protecting groups to any functional groups, if needed, and then deprotecting such groups at a later step; treating any functional groups in the forms of their precursors in each step and converting such precursors into the corresponding desirable functional groups at an appropriate step; or interchanging each order of process and step.

In each step, each aftertreatment of reaction may be carried out in a conventional manner, and an isolation and purification process may be optionally selected from the conventional method including crystallization, recrystallization, distillation, separation, silica gel chromatography, preparative HPLC, or a combination thereof. The room temperature refers to 1° C. to 40° C.

20

General Preparation Method 1

General Preparation Method of Compound [I]

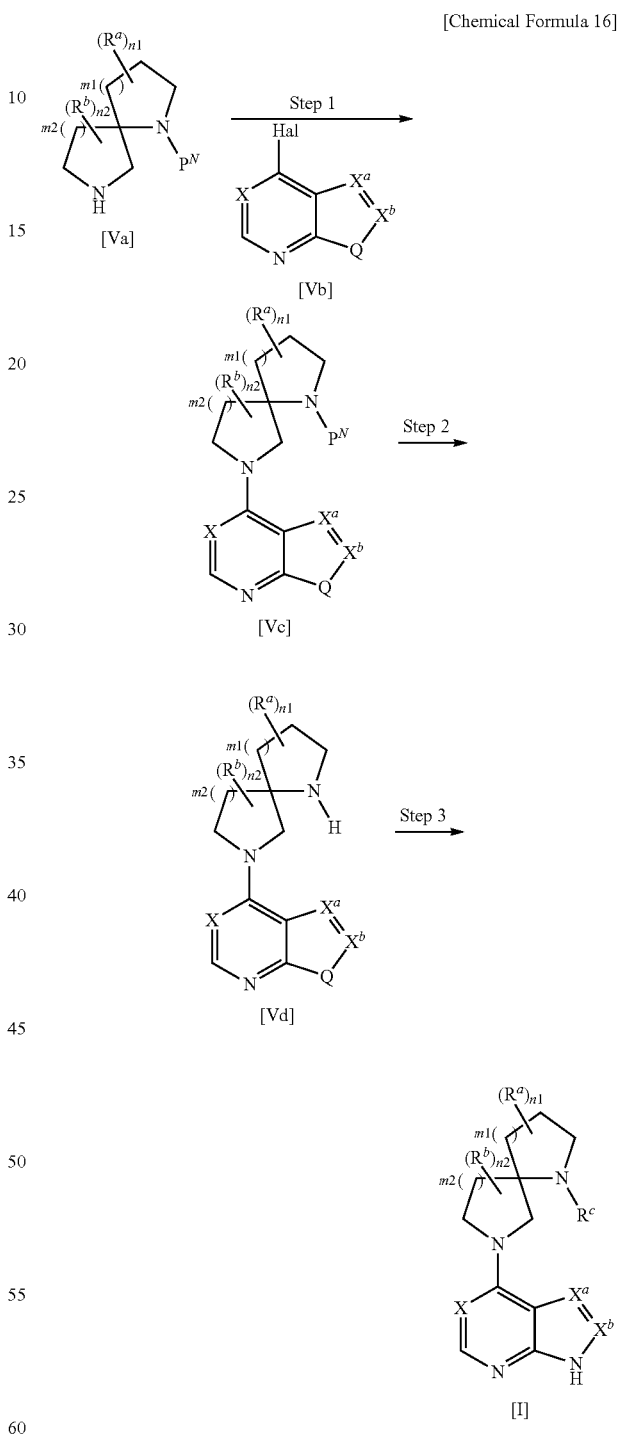

[Chemical Formula 16]

[In the above scheme, $P^N$ is a protecting group of amine, preferably tert-butoxycarbonyl, benzyl, p-methoxybenzyl, benzyloxycarbonyl; Q is N (nitrogen atom) substituted by a protecting group, or NH; Hal is a halogen atom; $R^a$, $R^b$, n1, n2, $X^a$, $X^b$, X, m1, m2 and $R^c$ have the same meanings as defined in the above formula [I].]

(Step 1)

Compound [Va] may be reacted with Compound [Vb] in a solvent in the presence of a base to give Compound [Vc].

The solvent used in the reaction includes an ester solvent such as ethyl acetate; a ketone solvent such as acetone; an amide solvent such as N,N-dimethylformamide; an alcohol solvent such as ethanol; an ether solvent such as dioxane; a hydrocarbon solvent such as toluene; a halogenated hydrocarbon solvent such as chloroform; water, and may be used alone or in a combination of 2 or more of them. A preferable solvent in the reaction is water.

The base used in the reaction includes triethylamine, N,N-diisopropylethylamine, pyridine, 4-dimethylaminopyridine, N-methylmorpholine, lithium hydroxide, sodium hydroxide, potassium hydroxide, sodium carbonate, potassium carbonate, sodium bicarbonate, preferably potassium carbonate.

The reaction temperature is usually room temperature to 110° C., preferably about 80° C. to 110° C.

The reaction time is usually about 30 minutes to 3 days, preferably about 3 hours to 1 day.

(Step 2)

Compound [Vd] may be obtained by removing $P^N$ of Compound [Vc] in a conventional manner of amine-deprotection reaction. The deprotection reaction may be carried out by known methods depending on selected protecting groups.

For example, Compound [Vc] wherein $P^N$ is tert-butoxycarbonyl may be treated in a single or mixed solvent of chloroform, dioxane, ethyl acetate, ethanol, methanol, water, etc. with an acid including hydrochloric acid, trifluoroacetic acid.

For example, Compound [Vc] wherein $P^N$ is benzyl or benzyloxycarbonyl may be hydrogenated in a single or mixed solvent of chloroform, tetrahydrofuran, dioxane, ethyl acetate, ethanol, methanol, etc. in the presence of a catalyst including palladium carbon, palladium hydroxide.

(Step 3)

Compound [Vd] may be introduced $R^c$ in a solvent to give Compound [I].

For example, Compound [Vd] may be reacted with 1-cyanoacetyl-3,5-dimethylpyrazole in a solvent in the presence of a base to give Compound [I] wherein $R^c$ is cyanoacetyl. The solvent used in the reaction includes an ester solvent such as ethyl acetate; a ketone solvent such as acetone; an amide solvent such as N,N-dimethylformamide; an alcohol solvent such as ethanol; an ether solvent such as dioxane; a hydrocarbon solvent such as toluene; a halogenated hydrocarbon solvent such as chloroform, and may be used alone or in a combination of 2 or more of them. A preferable solvent in the reaction is dioxane. The base used in the reaction includes triethylamine, pyridine, 4-dimethylaminopyridine, N-methylmorpholine, N,N-diisopropylethylamine, preferably N,N-diisopropylethylamine. The reaction temperature is usually room temperature to 110° C., preferably about 80° C. to 110° C. The reaction time is usually about 30 minutes to 1 day, preferably about 2 to 4 hours.

For example, Compound [Vd] may be reacted with a carboxylic acid compound in a conventional amidation reaction in a solvent in the presence of a condensing agent and a base to give Compound [I] wherein $R^c$ is acyl. The solvent used in the reaction includes an amide solvent such as N,N-dimethylformamide; a halogenated hydrocarbon solvent such as chloroform, and may be used alone or in a combination of 2 or more of them. A preferable solvent in the reaction is an ether solvent such as tetrahydrofuran or dioxane. The condensing agent used in the reaction includes water-soluble carbodiimide (e.g., 1-ethyl-3-(3'-dimethylaminopropyl)carbodiimide hydrochloride), N,N'-dicyclohexylcarbodiimide, diphenylphosphoryl azide, carbonyldiimidazole. To the reaction mixture may be added 1-hydroxy-1H-benzotriazole, 4-dimethylaminopyridine, if needed. A preferable condensing agent in the reaction is carbonyldiimidazole.

In the above amidation reaction, the carboxylic acid compound may be also pre-converted into a corresponding acid chloride or mixed acid anhydride, and then reacted with Compound [Vd] to give Compound [I].

For example, Compound [Vd] may be reacted with acrylonitrile in the presence of a base including triethylamine, pyridine, N,N-diisopropylethylamine, 1,8-diazabicyclo[5.4.0]undec-7-ene in an amide solvent including N,N-dimethylformamide, N,N-dimethylacetamide, or acetonitrile to give Compound [I] wherein $R^c$ is propylnitrile.

For example, Compound [Vd] may be reacted with alkyl chloroformate, etc. by a conventional synthesis of carbamate to give Compound [I] wherein $R^c$ is alkoxycarbonyl.

For example, Compound [Vd] may be reacted with alkyl isocyanate, etc. by a conventional synthesis of urea to give Compound [I] wherein $R^c$ is alkylaminocarbonyl.

In the above urea synthesis, the alkylamine compound may be also reacted with 4-nitrophenyl chloroformate to give alkyl carbamic acid 4-nitrophenyl ester which may be sequentially reacted with Compound [Vd] to give Compound [I].

A conventional deprotection of amine in Compound [Vd] wherein N of Q is substituted by a protecting group may be optionally carried out after or before introducing $R^c$. The deprotection may be carried out by known methods depending on selected protecting groups.

For example, the deprotection in which a protecting group is p-toluenesulfonyl may be carried out by treating with an alkali including sodium hydroxide, potassium hydroxide, cesium carbonate in a single or mixed solvent of an ether solvent such as tetrahydrofuran or dioxane; an alcohol solvent such as ethanol or methanol; water, etc.

For example, the deprotection in which a protecting group is p-methoxybenzyl may be carried out by treating with an acid such as hydrochloric acid, trifluoroacetic acid in a single or mixed solvent of an ether solvent such as anisole; a halogenated hydrocarbon solvent such as chloroform; an ester solvent such as ethyl acetate; an ether solvent such as dioxane; an alcohol solvent such as ethanol or methanol; water, etc.

As an example, some synthetic methods of Compound [Va] in General Preparation Method 1 are illustrated in the following General Preparation Methods 2 to 4.

In the following General Preparation Methods 2 to 4, Compounds [VIi] and [VIo] correspond to Compound [Va].

General Preparation Method 2

[Chemical Formula 17]

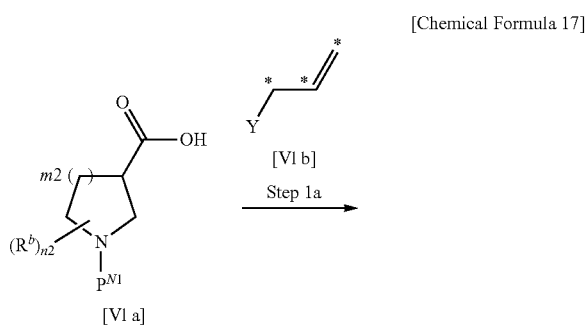

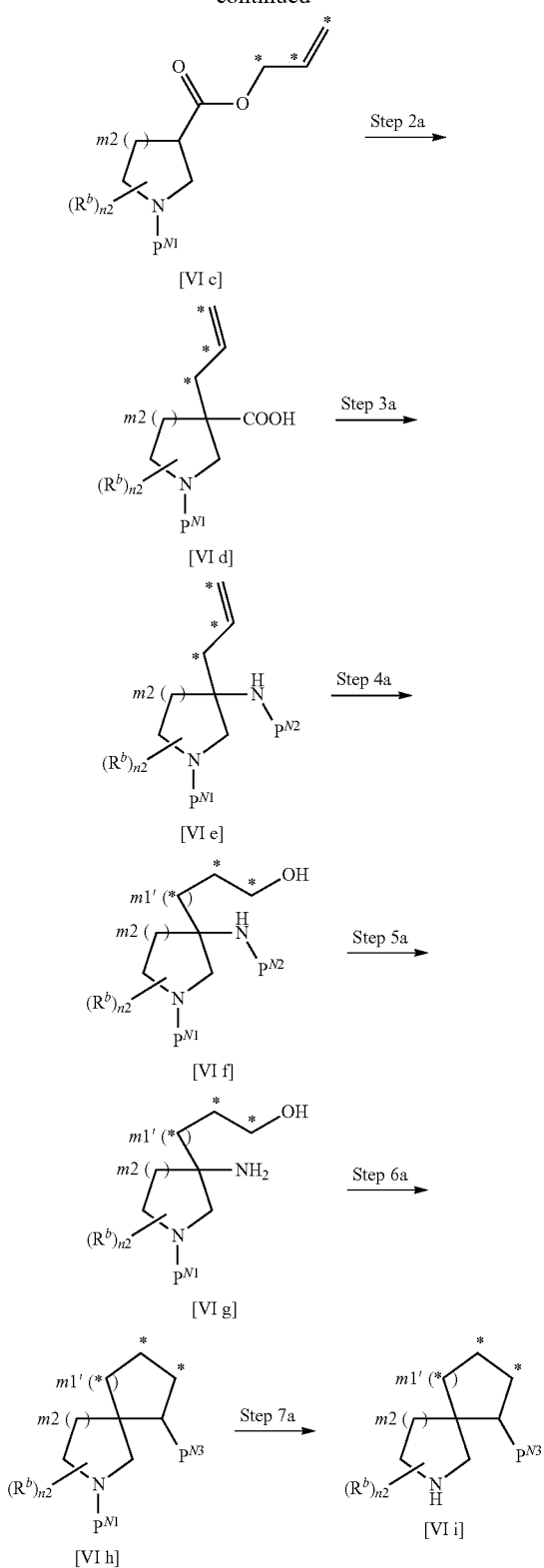

[In the above scheme, $P^{N1}$, $P^{N2}$ and $P^{N3}$ are a protecting group of amine, preferably tert-butoxycarbonyl, benzyl, benzyloxycarbonyl; Y is hydroxyl, or a leaving group including chlorine atom, bromine atom, iodine atom, mesyloxy, tosyloxy; m1' is 0 or 1; carbon atoms with * may be substituted by $R^a$ so as to be chemically acceptable; $R^a$, $R^b$, n1, n2 and m2 have the same meanings as defined in the above formula [I].]

(Step 1a)

Compound [VIa] may be conventionally esterified with Compound [VIb] in a solvent to give Compound [VIc]. For example, Compound [VIa] may be reacted with Compound [VIb] wherein Y is hydroxyl in a solvent in the presence of a condensing agent and a base.

The solvent used in the reaction includes an amide solvent such as N,N-dimethylformamide; an ether solvent such as tetrahydrofuran; a halogenated hydrocarbon solvent such as chloroform, and may be used alone or in a combination of 2 or more of them. A preferable solvent in the reaction is a halogenated hydrocarbon solvent such as chloroform.

A preferable condensing agent used in the reaction is water-soluble carbodiimide (e.g., 1-ethyl-3-(3'-dimethylaminopropyl)carbodiimide hydrochloride), etc.

A preferable base used in the reaction is an organic base such as 4-dimethylaminopyridine, etc.

A preferable reaction temperature is room temperature.

The reaction time is usually about 30 minutes to 1 day, preferably about 2 to 6 hours.

For example, Compound [VIa] may be also reacted with Compound [VIb] wherein Y is a leaving group in a solvent in the presence of a base.

The leaving group includes chlorine atom, bromine atom, iodine atom, mesyloxy and tosyloxy, preferably bromine atom.

The solvent used in the reaction includes an amide solvent such as N,N-dimethylformamide; an ether solvent such as dioxane; a hydrocarbon solvent such as toluene, and may be used alone or in a combination of 2 or more of them. A preferable solvent in the reaction is N,N-dimethylformamide.

The base used in the reaction includes an inorganic base such as sodium carbonate, potassium carbonate, sodium phosphate, potassium phosphate, sodium bicarbonate, preferably potassium carbonate.

The reaction temperature is usually room temperature to 120° C., preferably room temperature to 60° C.

The reaction time is usually about 30 minutes to 1 day, preferably about 2 to 6 hours.

(Step 2a)

Compound [VIc] may be treated by a conventional Claisen rearrangement in a solvent in the presence of a base to give Compound [VId].

A preferable solvent used in the reaction is tetrahydrofuran.

The base used in the reaction includes a base such as lithium diisopropylamide, lithium hexamethyl disilazide, potassium hexamethyl disilazide, sodium hexamethyl disilazide, sodium hydride, potassium tert-butoxide, preferably lithium hexamethyl disilazide.

A preferable reaction temperature is about −80° C. to 0° C.

The reaction time is usually about 30 minutes to 1 day, preferably about 2 to 4 hours.

(Step 3a)

The carboxylic acid moiety of Compound [VId] may be converted into a carbamate in a solvent to give Compound [VIe]. The conversion includes a conventional Curtius rearrangement.

A preferable reagent used in the reaction is diphenylphosphoryl azide.

The solvent used in the reaction includes an amide solvent such as N,N-dimethylformamide; an alcohol solvent such as benzyl alcohol; an ether solvent such as dioxane; a hydrocarbon solvent such as toluene, and may be used alone or in a combination of 2 or more of them. A preferable solvent in the reaction is a mixed solution of toluene and benzyl alcohol.

A preferable base used in the reaction is triethylamine.

The reaction temperature is usually room temperature to 110° C., preferably about 80° C. to 110° C.

The reaction time is usually about 30 minutes to 2 days, preferably about 2 hours to 1 day.

An additive including 4-dimethylaminopyridine may be used, if needed.

(Step 4a)

The olefin moiety of Compound [VIe] may be converted into hydroxyl to give Compound [VIf]. The conversion is illustrated in the following Step 4a-1 or 2, as an example.

(Step 4a-1)

Compound [VIe] may be treated in a solvent by an ozone oxidation, followed by a reduction to give Compound [VIf]. The ozone oxidation may be carried out according to a conventional method.

A preferable solvent used in the ozone oxidation is a mixed solution of chloroform and methanol.

The reaction temperature in the ozone oxidation is usually about −100° C. to 0° C., preferably about −80° C. to −60° C.

The reaction time in the ozone oxidation is usually about 5 minutes to 6 hours, preferably about 15 minutes to 3 hours.

A preferable reagent used in the reduction is sodium borohydride.

The reaction temperature in the reduction is usually about −100° C. to room temperature, preferably about −20° C. to 0° C.

The reaction time in the reduction is usually about 30 minutes to 6 hours, preferably about 1 to 3 hours.

(Step 4a-2)

Compound [VIe] may be treated in a solvent by a hydroboration, followed by an oxidation to give Compound [VIf].

The reagent used in the hydroboration includes borane-pyridine complex, borane-dimethyl sulfide complex, 9-borabicyclo[3.3.1]nonane, or a solution of borane-tetrahydrofuran complex in tetrahydrofuran, preferably a solution of borane-tetrahydrofuran complex in tetrahydrofuran.

A preferable solvent used in the hydroboration is tetrahydrofuran.

The reaction temperature in the hydroboration is usually about −20° C. to room temperature, preferably 0° C.

A preferable reaction time in the hydroboration is about 1 to 4 hours.

The reagent used in the oxidation includes hydrogen peroxide or sodium peroxoborate monohydrate, preferably sodium peroxoborate monohydrate.

The reaction temperature in the oxidation is usually about 0° C. to room temperature, preferably room temperature.

A preferable reaction time in the oxidation is about 1 hour to 1 day.

(Step 5a)

$P^{N2}$ among $P^{N1}$ and $P^{N2}$ may be selectively removed from Compound [VIf] by a conventional amine deprotection in the similar manner to the above Step 2 of General Preparation Method 1 to give Compound [VIg]. The deprotection may be carried out by known methods depending on selected protecting groups.

(Step 6a)

Compound [VIg] may be treated in a solvent by a cyclization, followed by an introduction of $P^{N3}$ to give Compound [VIh]. The cyclization may be carried out by introducing a leaving group into hydroxyl of Compound [VIg] in a solvent in the presence of a base. As an example, Step 6a-1 or 2 is illustrated as below.

(Step 6a-1)

Compound [VIg] may be reacted with carbon tetrabromide and triphenylphosphine (or alternatively methanesulfonyl chloride in place of the two reagents) in a solvent in the presence of a base to achieve an introduction of a leaving group and a cyclization in one step.

A preferable solvent used in the reaction is dichloromethane.

A preferable base used in the reaction is triethylamine.

A preferable reaction temperature is 0° C. to room temperature.

The reaction time is usually about 10 minutes to 24 hours, preferably about 30 minutes to 12 hours.

(Step 6a-2)

The introduction of a leaving group and the cyclization may be divided in two steps.

A preferable reagent used in the introduction of a leaving group is methanesulfonyl chloride.

A preferable solvent used in the introduction of a leaving group is chloroform.

A preferable base used in the introduction of a leaving group is triethylamine.

The reaction temperature of the introduction of a leaving group is usually about 0° C. to room temperature, preferably 0° C.

A preferable reaction time of the introduction of a leaving group is about 30 minutes to 2 hours.

A preferable solvent used in the cyclization is N,N-dimethylformamide.

A preferable base used in the cyclization is sodium hydride.

The reaction temperature of the cyclization is usually about 0° C. to room temperature, preferably 0° C.

A preferable reaction time of the cyclization is about 10 minutes to 2 hours.

The cyclized compound may be introduced $P^{N3}$ by a conventional amine protection to give Compound [VIh]. The amine protection may be carried out by known methods depending on selected protecting groups.

For example, a compound wherein $P^{N3}$ is benzyloxycarbonyl may be obtained by treating with benzyl chloroformate in a halogenated hydrocarbon solvent such as chloroform, dichloromethane in the presence of an organic base such as triethylamine.

Step 5a may be abbreviated, and then, Step 6a-2 may be carried out.

(Step 7a)

$P^{N1}$ among $P^{N1}$ and $P^{N3}$ may be selectively removed from Compound [VIh] by a conventional amine deprotection in the similar manner to the above Step 2 of General Preparation Method 1 to give Compound [VIi]. The deprotection may be carried out by known methods depending on selected protecting groups.

Either Compound [Va], [Vc], [Vd] or [I] in General Preparation Method 1 or Compounds [VId] to [VIi] in General Preparation Method 2 may be optically resolved to give an optically-active compound.

The optical resolution includes a method wherein racemic Compound [VId] and an optically-active amine compound are mixed in a solvent, followed by crystallizing as a single diastereomeric salt. The resulting diastereomeric salt may be desalted in a conventional manner to give optically-active Compound [VId]. (+)- or (−)-Isomer of Compound [VId] may be prepared by adopting an appropriate optically-active amine compound.

The optically-active amine compound includes (S)-(−)-2-amino-3-phenylpropan-1-ol, (R)-(+)-2-amino-3-phenylpropan-1-ol, (S)-(−)-1-(1-naphthyl)ethylamine, (R)-(+)-1-(1-naphthyl)ethylamine, (S)-(+)-2-amino-2-phenyl-ethanol, (R)-(−)-2-amino-2-phenyl-ethanol.

The solvent includes a ketone solvent such as acetone, methyl ethyl ketone, methyl isobutyl ketone; an ester solvent such as methyl acetate, ethyl acetate, isopropyl acetate, isobutyl acetate; an ether solvent such as isopropyl ether, 1,2-dimethoxyethane; an alcohol solvent such as methanol, ethanol, isopropanol; water, and may be used alone or in a combination of 2 or more of them. A preferable solvent includes isopropyl acetate, isopropanol or 1,2-dimethoxyethane.

Additionally, a conventional method for enhancing the optical purity may be optionally carried out. For example, a recrystallization may be repeated.

An alternative method for the optical resolution includes a method wherein racemic Compound [I] is treated by a chiral stationary-phase column to separate desirable optically-active Compound [I] from another isomer thereof.

General Preparation Method 3

[Chemical Formula 18]

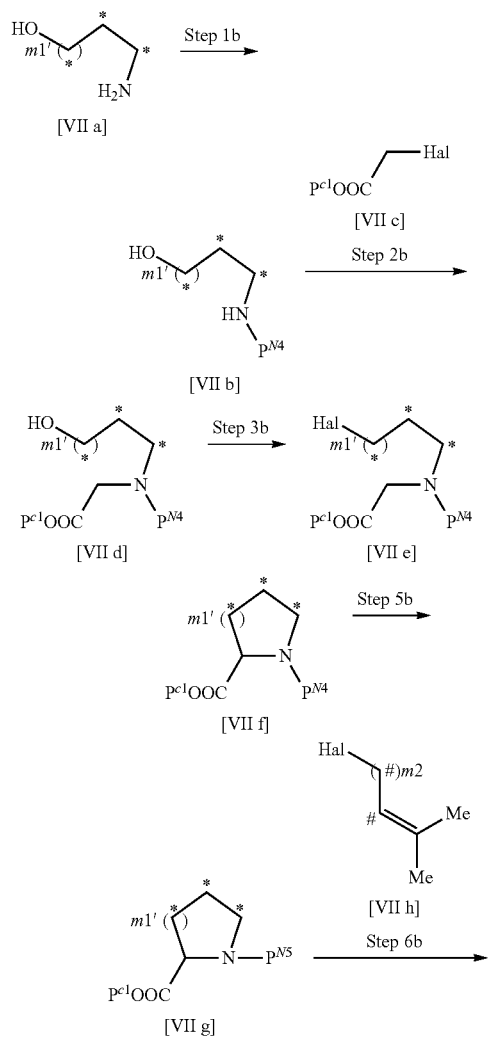

[Chemical Formula 19]

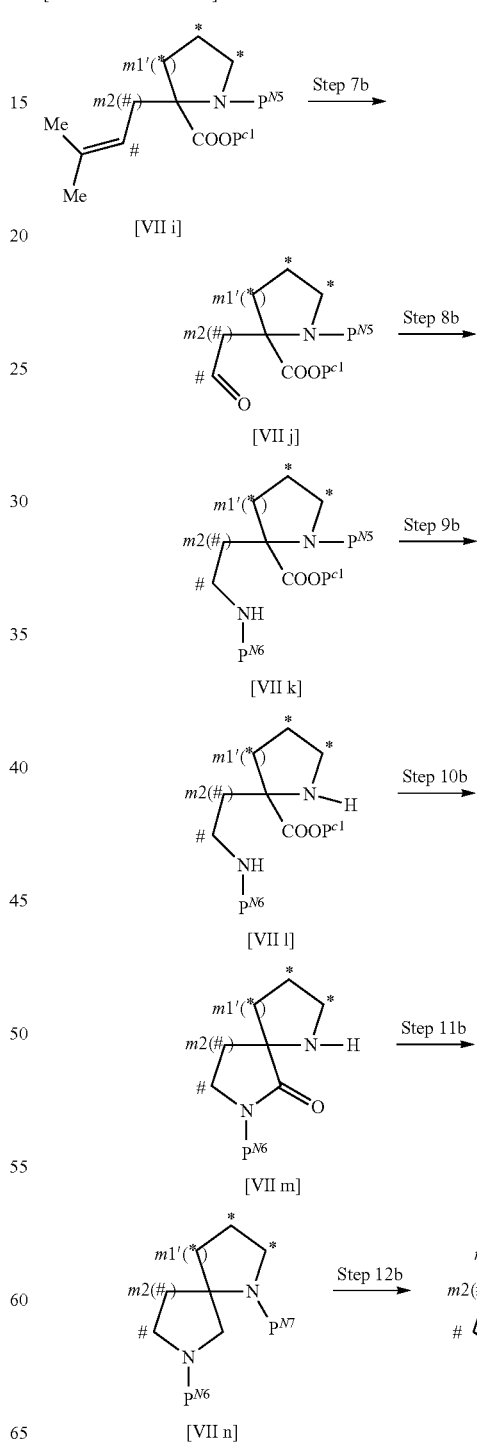

[In the above scheme, $P^{N4}$, $P^{N5}$, $P^{N6}$ and $P^{N7}$ are a protecting group of amine, preferably benzyl, tert-butoxycarbonyl or benzyloxycarbonyl; $P^{C1}$ is a protecting group of carboxylic acid, preferably tert-butyl ester, methyl ester or ethyl ester; Hal is a halogen atom; m1' is 0 or 1; carbon atoms with * may be substituted by $R^a$ so as to be chemically acceptable; carbon atoms with # may be substituted by $R^b$ so as to be chemically acceptable; $R^a$, $R^b$, n1, n2 and m2 have the same meanings as defined in the above formula [I].]

(Step 1b)

Compound [VIIa] may be introduced $P^{N4}$ by a conventional amine protection to give Compound [VIIb]. The amine protection may be carried out by known methods depending on selected protecting groups.

For example, in case that $P^{N4}$ is benzyl, the protection may be carried out by hydrogenating with benzaldehyde in an alcohol solvent such as methanol, ethanol in the presence of a palladium catalyst such as palladium carbon.

(Step 2b)

Compound [VIIb] may be reacted with Compound [VIIc] in a solvent in the presence of a base to give Compound [VIId].

A preferable solvent used in the reaction is N,N-dimethylformamide.

A preferable base used in the reaction is potassium carbonate.

The reaction temperature is usually room temperature to 120° C., preferably room temperature to 60° C.

The reaction time is usually about 30 minutes to 2 days, preferably about 6 hours to 1 day.

(Step 3b)

Compound [VIId] may be halogenated in a solvent in a conventional manner, followed by a rearrangement to give Compound [VIIe].

A preferable reagent used in the halogenation is thionyl chloride.

A preferable solvent used in the halogenation is chloroform.

A preferable reaction temperature of the halogenation is room temperature to 60° C.

The reaction time of the halogenation is usually about 30 minutes to 1 day, preferably about 1 to 6 hours.

The rearrangement is illustrated in the following Step 3b2. Specifically, Compound [VIIe2] obtained in the halogenation may be rearranged in a solvent to give Compound [VIIe3].

[Chemical Formula 20]

A preferable solvent used in the rearrangement is N,N-dimethylformamide.

A preferable reaction temperature of the rearrangement is about 60° C. to 100° C.

A preferable reaction time of the rearrangement is about 30 minutes to 3 days.

(Step 4b)

Compound [VIIe] may be intramolecularly cyclized in a solvent in the presence of a base to give Compound [VIIf].

A preferable base used in the reaction is lithium hexamethyl disilazide.

A preferable solvent used in the reaction is a mixed solution of tetrahydrofuran and hexamethyl phosphoramide.

The reaction temperature is usually about −100° C. to 0° C., preferably about −80° C. to 0° C.

The reaction time is usually about 30 minutes to 6 hours, preferably about 1 to 2 hours.

(Step 5b)

$P^{N4}$ of Compound [VIIf] may be converted into $P^{N5}$ to give Compound [VIIg].

The removal of $P^{N4}$ may be carried out by a conventional amine deprotection in the similar manner to the above General Preparation Method 1 Step 2. The deprotection may be carried out by known methods depending on selected protecting groups.

The introduction of $P^{N5}$ may be carried out by a conventional amine protection in the similar manner to the above General Preparation Method 3 Step 1b. The amine protection may be carried out by known methods depending on selected protecting groups.

For example, in case that $P^{N4}$ of Compound [VIIf] is benzyl and $P^{N5}$ of Compound [VIIg] is tert-butoxycarbonyl, $P^{N4}$ may be converted into $P^{N5}$ in one step by hydrogenating Compound [VIIf] with di-tert-butyl dicarbonate in a mixed solvent of tetrahydrofuran and methanol in the presence of a catalyst such as palladium carbon or palladium hydroxide.

(Step 6b)

Compound [VIIg] may be reacted with Compound [VIIh] in a solvent in the presence of a base to give Compound [VIIi].

A preferable base used in the reaction is lithium hexamethyl disilazide.

A preferable solvent used in the reaction is tetrahydrofuran.

The reaction temperature is usually about −80° C. to room temperature, preferably about −80° C. to 0° C.

The reaction time is usually about 30 minutes to 3 hours, preferably about 30 minutes to 1 hour.

(Step 7b)

The olefin moiety of Compound [VIIi] may be oxidatively cleaved in a solvent to give Compound [VIIj].

The oxidative cleavage includes an ozone oxidation by a reductive treatment.

A preferable solvent used in the reaction is a mixed solution of chloroform and methanol.

The reaction temperature is usually about −100° C. to 0° C., preferably about −80° C. to 0° C.

The reaction time is usually about 5 minutes to 6 hours, preferably about 30 minutes to 2 hours.

The reagent used as the reducing agent includes dimethyl sulfide or triphenylphosphine, preferably triphenylphosphine.

(Step 8b)

Compound [VIIj] may be reductively aminated in a solvent to give Compound [VIIk].

A preferable amine used in the reaction is benzylamine.

A preferable solvent used in the reaction is tetrahydrofuran.

A preferable reaction temperature is room temperature.

A preferable reaction time is about 12 hours to 1 day.

A preferable reagent used as the reducing agent is sodium triacetoxyborohydride.

(Step 9b)

Compound [VIIk] may be treated by simultaneous removal of $P^{C1}$ and $P^{N5}$ in conventional carboxylic acid deprotection and amine deprotection to give Compound [VIII]. The deprotection may be carried out by known methods depending on selected protecting groups.

For example, Compound [VIIk] wherein $P^{C1}$ is tert-butyl ester and $P^{N5}$ is tert-butoxycarbonyl may be treated in a single or a mixed solvent of anisole, chloroform, ethyl acetate, dioxane, water, etc. by an acid such as hydrochloric acid, trifluoroacetic acid.

(Step 10b)

Compound [VIII] may be intramolecularly cyclized in a solvent to give Compound [VIIm]. The cyclization includes a conventional amidation in the presence of a condensing agent and a base.

A preferable condensing agent used in the reaction is O-(7-azabenzotriazol-1-yl)-N,N,N',N'-tetramethyluronium hexafluorophosphate.

A preferable base used in the reaction is diisopropylethylamine.

A preferable solvent used in the reaction is chloroform.

A preferable reaction temperature is room temperature.

The reaction time is usually about 30 minutes to 1 day, preferably about 1 to 6 hours.

As an alternative cyclization, Compound [VIIk] wherein $P^{C1}$ is ethyl ester or methyl ester may be selectively removed $P^{N5}$ by a conventional amine deprotection with remaining $P^{C1}$, followed by a cyclization with 2M aqueous sodium hydroxide solution in an alcohol solvent such as ethanol at room temperature to give Compound [VIIm].

(Step 11b)

The amide moiety of Compound [VIIm] may be reduced to an amine in a solvent, followed by an introduction of $P^{N7}$ by a conventional amine protection to give Compound [VIIn].

A preferable reducing agent used in the reduction is a mixture of lithium aluminum hydride and concentrated sulfuric acid. A preferable usage of concentrated sulfuric acid is 0.5 moles to 1 mole of lithium aluminum hydride.

A preferable solvent used in the reduction is tetrahydrofuran.

The reaction temperature of the reduction is usually about 0° C. to room temperature, preferably 0° C.

The reaction time of the reduction is usually about 30 minutes to 3 hours, preferably about 1 to 2 hours.

The amine protection may be carried out by known methods depending on selected protecting groups in the similar manner to the above General Preparation Method 3 Step 1b. For example, in case that $P^{N7}$ is tert-butoxycarbonyl, Compound [VIIm] may be reacted with di-tert-butyl dicarbonate in tetrahydrofuran.

(Step 12b)

$P^{N6}$ among $P^{N6}$ and $P^{N7}$ of Compound [VIIn] may be selectively removed by a conventional amine deprotection in the similar manner to the above General Preparation Method 1 Step 2 to give Compound [VIIo]. The deprotection may be carried out by known methods depending on selected protecting groups.

General Preparation Method 4

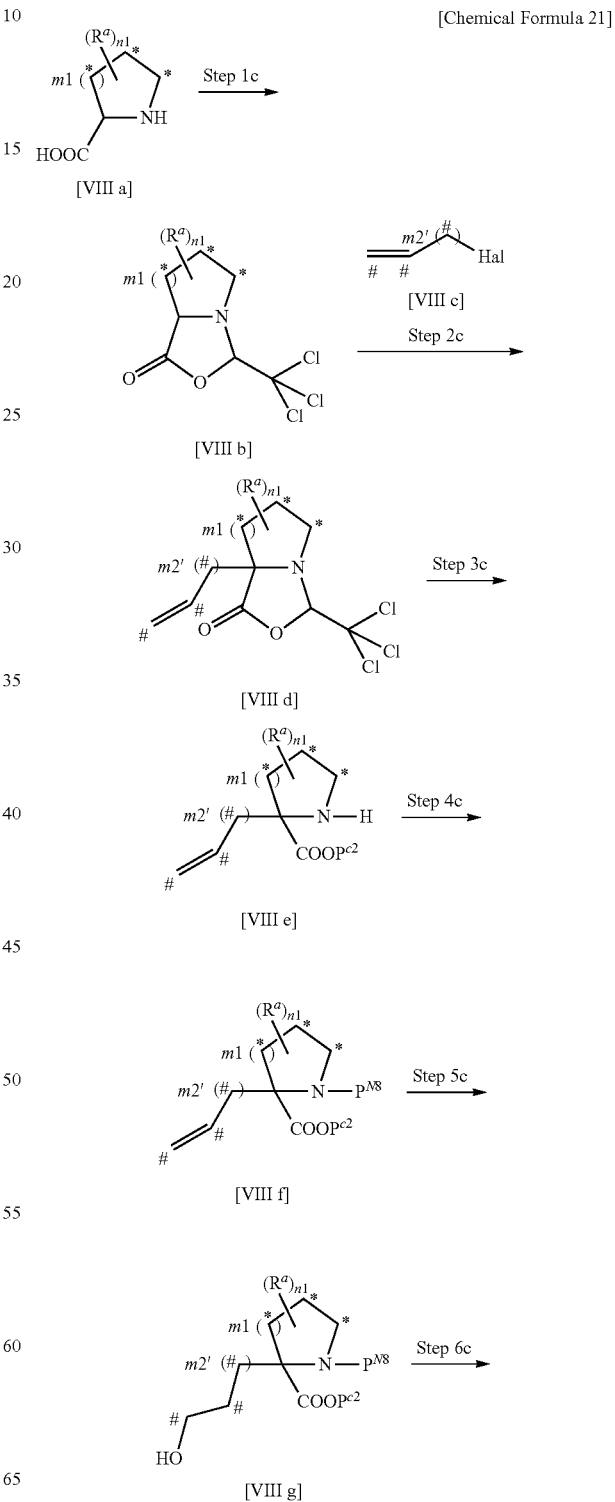

[Chemical Formula 21]

[VIII h] → Steps 8 to 12b → [VIII o]

[In the above scheme, $P^{N8}$ is a protecting group of amine, preferably tert-butoxycarbonyl; $P^{C2}$ is a protecting group of carboxylic acid, preferably tert-butyl ester; Hal is a halogen atom; m2' is 1 or 2; carbon atoms of * may be optionally substituted by $R^a$ so as to be chemically acceptable; carbon atoms of # may be optionally substituted by $R^b$ so as to be chemically acceptable; $R^a$, $R^b$, n1, n2 and m1 have the same meanings as defined in the above formula [I].]

(Step 1c)

Compound [VIIIa] may be reacted with trichloroethanal in a solvent to give Compound [VIIIb].

A preferable solvent used in the reaction is acetonitrile.

A preferable reaction temperature is room temperature.

The reaction time is usually about 30 minutes to 3 days, preferably about 6 hours to 1 day.

(Step 2c)

Compound [VIIIb] may be reacted with Compound [VIIIc] in a solvent in the presence of a base to give Compound [VIIId].

A preferable solvent used in the reaction is tetrahydrofuran.

A preferable base used in the reaction is lithium diisopropylamide.

The reaction temperature is usually about −80° C. to room temperature, preferably about −80° C. to 0° C.

The reaction time is usually about 30 minutes to 1 day, preferably about 1 to 3 hours.

(Step 3c)

Compound [VIIId] may be treated by solvolysis under an acidic condition in an alcohol solvent to give Compound [VIIIe].

A preferable solvent used in the reaction is methanol.

A preferable acid used in the reaction is concentrated sulfuric acid. A preferable usage of concentrated sulfuric acid is 0.1 to 3 moles to 1 mole of Compound [VIIId].

A preferable reaction temperature is room temperature to 65° C.

The reaction time is usually about 30 minutes to 3 days, preferably about 6 hours to 1 day.

(Step 4c)

Compound [VIIIe] may be introduced $P^{N8}$ by a conventional amine protection in the similar manner to the above General Preparation Method 3 Step 1b to give Compound [VIIIf]. The amine protection may be carried out by known methods depending on selected protecting groups. For example, in case that $P^{N8}$ is tert-butoxycarbonyl, Compound [VIIIe] may be reacted with di-tert-butyl dicarbonate in tetrahydrofuran.

(Step 5c)

Compound [VIIIf] may be treated in a solvent by a hydroboration, followed by an oxidation to give Compound [VIIIg] in the similar manner to General Preparation Method 2 Step 4a-2.

(Step 6c)

Compound [VIIIg] may be oxidized in a solvent to give Compound [VIIIh].

The reagent used in the reaction includes sulfur trioxide-pyridine complex or Dess-Martin periodinane, preferably Dess-Martin periodinane.

A preferable solvent used in the reaction is chloroform.

A preferable reaction temperature is about 0° C. to room temperature.

The reaction time is usually about 30 minutes to 1 day, preferably about 2 to 6 hours.

Bases including sodium bicarbonate as an additive may be optionally added.

The resulting Compound [VIIIh] may be reacted in the similar manner to General Preparation Method 3 Step 8b or later to give an amine compound corresponding to Compound [VIIo].

EXAMPLES

Next, the preparations of the present compounds are specifically illustrated by Examples. However, the present invention is not intended to be limited thereto.

Stereochemistries in chemical structures of the compounds are abbreviated in the Examples.

Measurement apparatuses and conditions used in the Examples are as follows.

HPLC Analysis Condition 1

Preparation method for solution A: Sodium dihydrogen phosphate dihydrate (23.4 g) was dissolved in water (3000 mL) to be adjusted to pH 2.1 by using phosphoric acid (10.2 mL).

Measurement instrument: HPLC system SHIMADZU CORPORATION High Performance Liquid Chromatograph Prominence Column: DAICEL CHIRALPAK AD-3R 4.6 mmϕ×150 mm Column temperature: 40° C.

Mobile phase: (solution A) 100 mM phosphate (sodium) buffer (pH 2.1), (solution B) methanol Solution A:Solution B=30:70 (constantly 20-minute sending).

Sending rates of solutions: 0.5 ml/min

Detection: UV (220 nm)

Preparation 1

Synthesis of Compound 1

[Chemical Formula 22]

(1) Piperidine-1,3-dicarboxylic acid 3-((E)-but-2-enyl)ester 1-tert-butyl ester

[Chemical Formula 23]

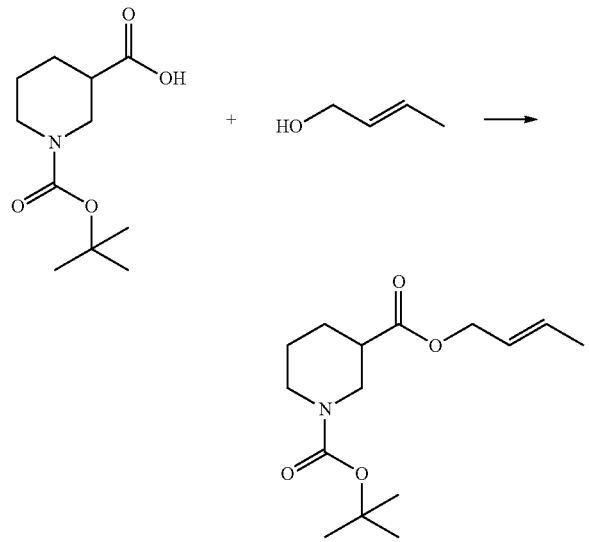

To a solution of 1-(tert-butoxycarbonyl)-3-piperidine carboxylic acid (50.0 g) and 1-ethyl-3-(3-dimethylaminopropyl)-carbodiimide (45.8 g) in chloroform (500 ml) was added 4-dimethylaminopyridine (29.3 g), and the mixture was stirred for 50 minutes. To the mixture was added (E)-but-2-en-1-ol (22.1 ml), and the mixture was stirred at room temperature for 1.5 hours. To the reaction mixture was added 10% aqueous potassium bisulfate solution (500 ml), and the mixture was extracted with chloroform. The separated organic layer was sequentially washed with saturated aqueous sodium bicarbonate solution (400 ml) and saturated aqueous sodium chloride solution (350 ml). The separated aqueous layer was extracted with chloroform (300 ml) again. The combined organic layer was dried over anhydrous sodium sulfate, and concentrated under reduced pressure. The resulting residue was purified by silica gel column chromatography (eluent: n-hexane/ethyl acetate=7/1) to give the titled compound (57.1 g).

$^1$H-NMR (CDCl$_3$) δ: 5.84-5.73 (1H, m), 5.62-5.52 (1H, m), 4.51 (2H, d, J=6.4 Hz), 4.37-4.00 (1H, m), 3.95-3.88 (1H, m), 3.19-2.87 (1H, m), 2.84-2.76 (1H, m), 2.48-2.40 (1H, m), 2.08-2.01 (1H, m), 1.74-1.66 (5H, m), 1.63-1.55 (1H, m), 1.46 (9H, s).

(2) 3-(1-Methyl-allyl)-piperidine-1,3-dicarboxylic acid 1-tert-butyl ester

[Chemical Formula 24]

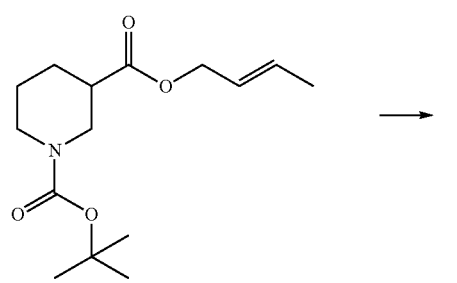

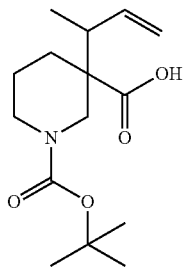

To a solution of piperidine-1,3-dicarboxylic acid 3-((E)-but-2-enyl)ester 1-tert-butyl ester (105.7 g) in tetrahydrofuran (1000 ml) cooled to −68° C. was added lithium hexamethyl disilazide (1.1M tetrahydrofuran solution, 411 ml). The reaction mixture was warmed to 0° C. over 20 minutes, stirred at the same temperature for additional 30 minutes, and then cooled to −68° C. again. To the mixture was added trimethylsilyl chloride (56.6 ml). The reaction mixture was warmed to room temperature over 2 hours, and stirred at the same temperature for additional 2 hours. After ice-cooling, to the mixture were sequentially added water (1000 ml) and 2M aqueous sodium hydroxide solution (136 ml), and the mixture was washed with n-hexane (1000 ml). The separated aqueous layer was acidified by 2M aqueous hydrochloric acid solution, and then extracted with ethyl acetate (800 ml). The organic layer was sequentially washed with water (700 ml) and saturated aqueous sodium chloride solution (400 ml), and the separated aqueous layer was extracted with ethyl acetate (600 ml) again. The combined organic layer was dried over anhydrous sodium sulfate, and concentrated under reduced pressure. The resulting residue was slurry-washed with n-hexane/ethyl acetate solution (6/1, 700 ml) to give the titled compound (59.8 g). The filtrate was concentrated under reduced pressure, and the resulting residue was slurry-washed with n-hexane/ethyl acetate solution (4/1, 200 ml) again to give a solid (14.4 g). The solid was slurry-washed with n-hexane/ethyl acetate solution (5/1, 100 ml) again to give the titled compound (11.9 g). The resultant was combined to give the titled compound (71.7 g).

$^1$H-NMR (CDCl$_3$) δ: 5.80-5.71 (1H, m), 5.09-5.07 (1H, m), 5.06-5.03 (1H, m), 4.32-4.20 (1H, m), 3.90-3.83 (1H, m), 2.87-2.74 (2H, m), 2.39-2.31 (1H, m), 2.19-2.11 (1H, m), 1.64-1.55 (2H, m), 1.51-1.44 (1H, m), 1.45 (9H, s), 1.07 (3H, d, J=7.1 Hz).

(3) Optically-Active Compound of 3-(1-methylallyl)piperidine-1,3-dicarboxylic acid 1-tert-butyl ester

[Chemical Formula 25]

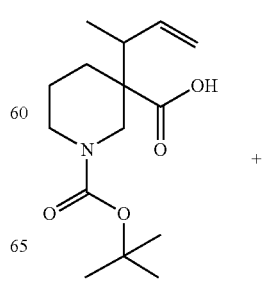

+

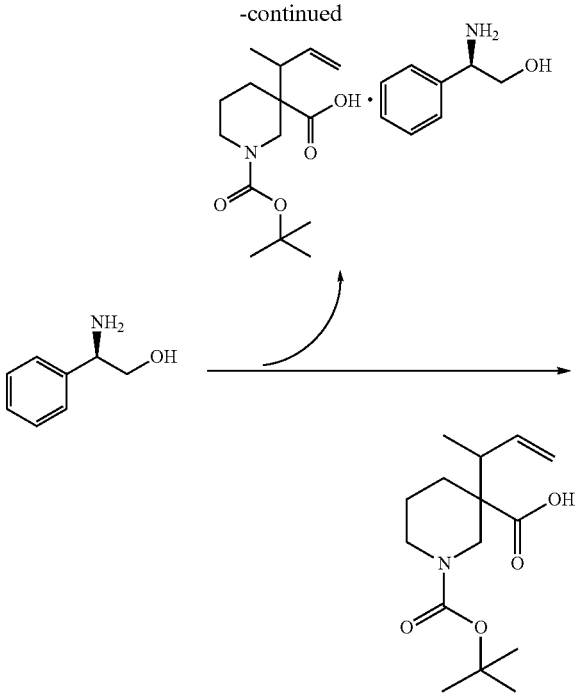

(3)-(1) Seed Crystal of a Salt of an Optically-Active Compound of 3-(1-methyl-allyl)-piperidine-1,3-dicarboxylic acid 1-tert-butyl ester with (R)-(−)-2-amino-2-phenyl-ethanol

[Chemical Formula 26]

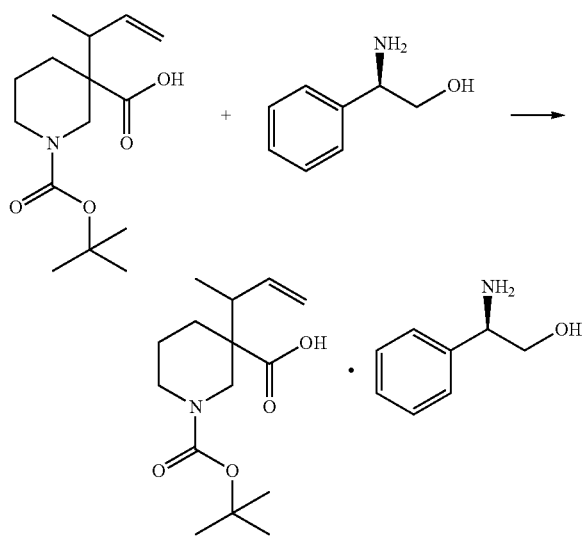

3-(1-Methylallyl)piperidine-1,3-dicarboxylic acid 1-tert-butyl ester (2.0 g), isopropyl acetate (10 ml) and isopropanol (10 ml) were mixed to dissolve. To the mixture was added (R)-(−)-2-amino-2-phenyl-ethanol (484 mg), and the mixture was stirred at room temperature for 24 hours. The slurry mixture was filtered, and the resulting solid was washed with isopropyl acetate (6 ml) and dried under reduced pressure to give the titled compound (735 mg).

(3)-(2) Salt of an Optically-Active Compound of 3-(1-methylallyl)piperidine-1,3-dicarboxylic acid 1-tert-butyl ester with (R)-(−)-2-amino-2-phenyl-ethanol 3-(1-Methylallyl)piperidine-1,3-dicarboxylic acid 1-tert-butyl ester (106.6 g), (R)-(−)-2-amino-2-phenyl-ethanol (31.0 g), isopropyl acetate (480 ml) and isopropanol (480 ml) were mixed to dissolve at room temperature. To the mixture solution was added the seed crystal obtained in (3)-(1), and the mixture was stirred for 16 hours. The slurry mixture was filtered to give the titled compound (47.0 g). An analysis of the resulting solid by HPLC analysis condition 1 showed that an isomer with shorter retention times was a main product.

An isomer with shorter retention times (retention time 6.48 minutes)

An isomer with longer retention times (retention time 10.70 minutes)

(3)-(3) Optically-Active Compound of 3-(1-methylallyl)piperidine-1,3-dicarboxylic acid 1-tert-butyl ester Recovered from the Filtrate of (3)-(2)

The filtrate of (3)-(2) was concentrated under reduced pressure, and the resulting residue was mixed with ethyl acetate (500 ml) and water (500 ml). The mixture was acidified by the addition of potassium bisulfate. The separated organic layer was washed with saturated aqueous sodium chloride solution and concentrated under reduced pressure. To the residue was added isopropanol, and the mixture was concentrated under reduced pressure to give the titled compound (75.0 g).

$^1$H-NMR (CDCl$_3$) δ: 5.80-5.71 (1H, m), 5.09-5.07 (1H, m), 5.06-5.03 (1H, m), 4.32-4.20 (1H, m), 3.90-3.83 (1H, m), 2.87-2.74 (2H, m), 2.39-2.31 (1H, m), 2.19-2.11 (1H, m), 1.64-1.55 (2H, m), 1.51-1.44 (1H, m), 1.45 (9H, s), 1.07 (3H, d, J=7.1 Hz).

(4) Salt of an Optically-Active Compound of 3-(1-methylallyl)piperidine-1,3-dicarboxylic acid 1-tert-butyl ester with (S)-(+)-2-amino-2-phenyl-ethanol

[Chemical Formula 27]

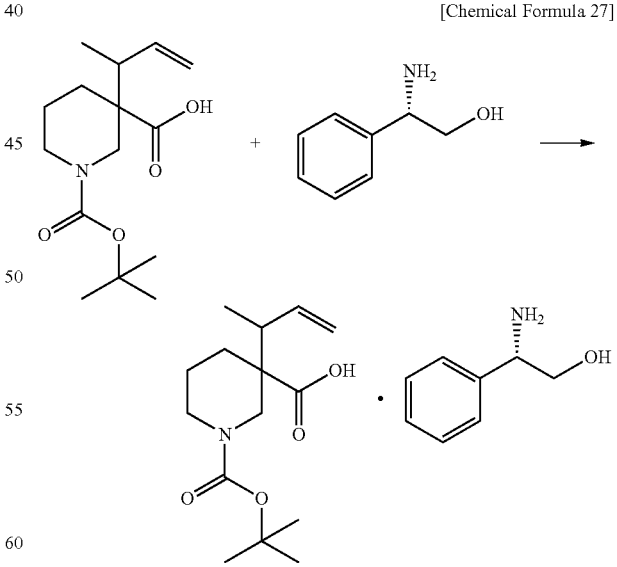

The resulting residue (75.0 g) obtained in (3)-(3), (S)-(+)-2-amino-2-phenyl-ethanol (31.0 g), isopropyl acetate (335 ml) and isopropanol (306 ml) were mixed to dissolve at room temperature. To a mixed solution was added the seed crystal obtained in (3)-(1), and the mixture was stirred for 17.5 hours.

The slurry mixture was filtered, and the resulting solid was washed with isopropyl acetate (150 ml) to give the titled compound (54.2 g). An analysis of the solid by HPLC analysis condition 1 showed that an isomer with longer retention times was a main product.

An isomer with shorter retention times (retention time 6.48 minutes)

An isomer with longer retention times (retention time 10.70 minutes)

(5) Optically-Active Compound of 3-(1-methylallyl)piperidine-1,3-dicarboxylic acid 1-tert-butyl ester

[Chemical Formula 28]

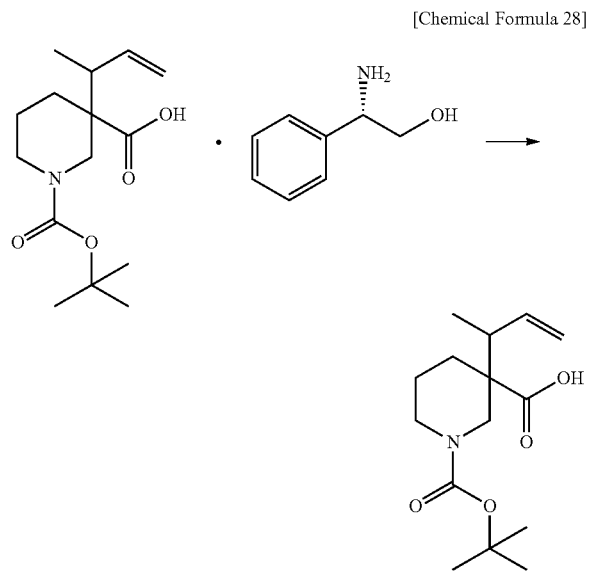

To an optically-active compound of 3-(1-methylallyl)piperidine-1,3-dicarboxylic acid 1-tert-butyl ester and salt of (S)-(+)-2-amino-2-phenyl-ethanol (52.7 g) were added to mix ethyl acetate (264 ml) and water (264 ml), and the mixture was acidified by the addition of potassium bisulfate. The separated organic layer was washed with saturated aqueous sodium chloride solution, dried over anhydrous sodium sulfate, and concentrated under reduced pressure to give the titled compound (36.0 g). The crude product was partially used in the next step without further purification.

$^1$H-NMR (CDCl$_3$) δ: 5.80-5.71 (1H, m), 5.09-5.07 (1H, m), 5.06-5.03 (1H, m), 4.32-4.20 (1H, m), 3.90-3.83 (1H, m), 2.87-2.74 (2H, m), 2.39-2.31 (1H, m), 2.19-2.11 (1H, m), 1.64-1.55 (2H, m), 1.51-1.44 (1H, m), 1.45 (9H, s), 1.07 (3H, d, J=7.1 Hz).

(6) Optically-Active Compound of 3-benzyloxycarbonylamino-3-(1-methylallyl)piperidine-1-carboxylic acid tert-butyl ester

[Chemical Formula 29]

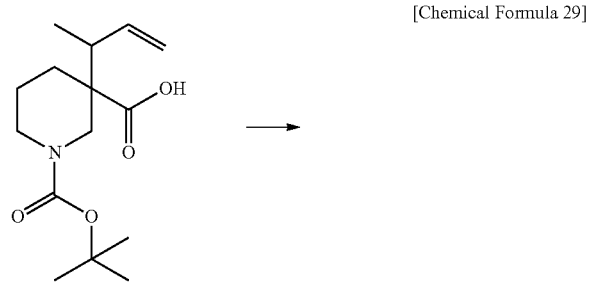

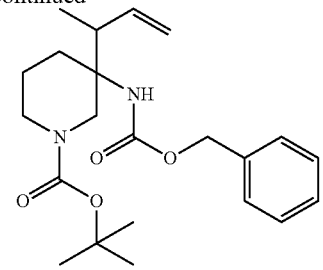

To a refluxed solution of an optically-active compound of 3-(1-methylallyl)piperidine-1,3-dicarboxylic acid 1-tert-butyl ester (9.0 g) and triethylamine (8.9 ml) in toluene (90 ml) was added dropwise diphenylphosphoryl azide (8.9 ml) over 25 minutes. The reaction mixture was stirred for 2.5 hours at the same temperature, and then thereto were added benzyl alcohol (10 ml) and 4-dimethylaminopyridine (771 mg). The mixture was stirred for 33 hours with refluxing, followed by cooled to room temperature, and acidified by the addition of 10% aqueous potassium bisulfate solution. The mixture was extracted with ethyl acetate, and the organic layer was washed with saturated aqueous sodium chloride solution and concentrated under reduced pressure. The resulting residue was purified by silica gel column chromatography (eluent: chloroform/acetone=20/1). The fractions which could not be isolated or purified were concentrated under reduced pressure, and the resulting residue was purified by silica gel column chromatography (eluent: chloroform/acetone=20/1) again. The purified fractions are combined to be concentrated under reduced pressure to give the titled compound (11.0 g).

$^1$H-NMR (CDCl$_3$) δ: 7.37-7.29 (5H, m), 5.80-5.70 (1H, m), 5.36-5.17 (0.5H, m), 5.12-4.99 (4H, m), 4.96-4.74 (0.5H, m), 4.08-3.92 (2H, m), 2.98-2.33 (4H, m), 1.64-1.38 (4H, m), 1.44 (9H, s), 1.03 (3H, d, J=7.0 Hz).

(7) Optically-Active Compound of 3-benzyloxycarbonylamino-3-(2-hydroxy-1-methylethyl)piperidine-1-carboxylic acid tert-butyl ester

[Chemical Formula 30]

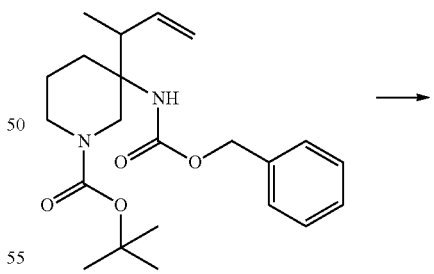

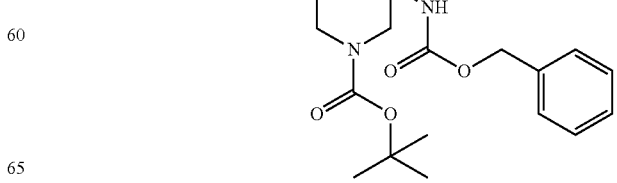

A solution of an optically-active compound of 3-benzyloxycarbonylamino-3-(1-methylallyl)piperidine-1-carboxylic acid 1-tert-butyl ester (25.5 g) in chloroform/methanol (250 ml/250 ml) cooled to −78° C. was flowed ozone air for 30 minutes. To the reaction mixture was added sodium borohydride (7.5 g) in small batches, and the mixture was warmed to room temperature. To the mixture was added 5% aqueous sodium bicarbonate solution (250 ml), and the mixture was extracted with chloroform (125 ml). The separated aqueous layer was extracted with chloroform (125 ml) again. The combined organic layer was sequentially washed with a mixed aqueous solution of sodium bicarbonate/sodium thiosulfate (12.5 g/25.0 g, 275 ml), water (125 ml) and 10% aqueous sodium chloride solution (125 ml), dried over anhydrous magnesium sulfate, and concentrated under reduced pressure. The resulting residue was purified by silica gel column chromatography (eluent: n-hexane/ethyl acetate=1/0 to 2/3) to give the titled compound (21.9 g).

$^1$H-NMR (CDCl$_3$) δ: 7.37-7.29 (5H, m), 5.54-5.15 (1H, m), 5.06 (1H, d, J=12.4 Hz), 5.02 (1H, d, J=12.4 Hz), 4.03-3.93 (1H, m), 3.84-3.64 (3H, m), 3.27-2.84 (2H, m), 2.16-1.86 (2H, m), 1.66-1.59 (2H, m), 1.52-1.45 (1H, m), 1.44 (9H, s), 1.04 (3H, d, J=7.1 Hz).

(8) Optically-Active Compound of 3-amino-3-(2-hydroxy-1-methylethyl)piperidine-1-carboxylic acid tert-butyl ester

[Chemical Formula 31]

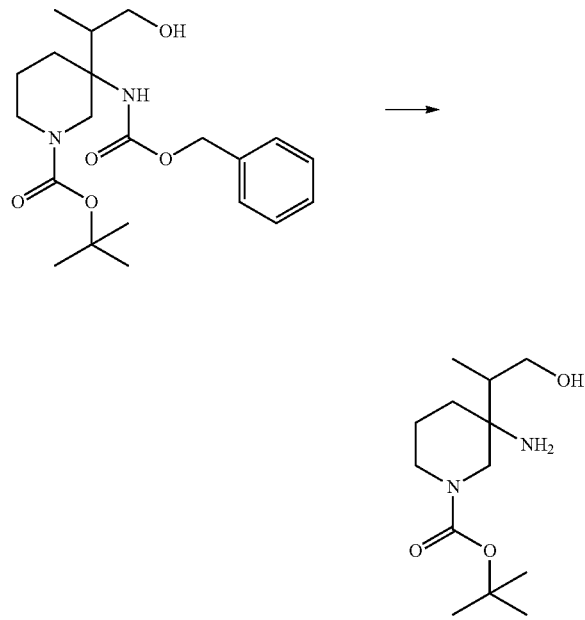

To a solution of an optically-active compound of 3-benzyloxycarbonylamino-3-(2-hydroxy-1-methylethyl)piperidine-1-carboxylic acid tert-butyl ester (21.0 g) in methanol (400 ml) was added 10% palladium carbon (2.1 g), and the mixture was hydrogenated at room temperature under ordinary pressure for 90 minutes. The mixture was filtered through Celite, and the filtrate was concentrated under reduced pressure to give the titled compound (13.8 g).

$^1$H-NMR (CDCl$_3$) δ: 3.96-3.87 (1H, m), 3.86-3.77 (1H, m), 3.74-3.65 (1H, m), 3.63-3.58 (1H, m), 3.09-2.91 (1H, m), 2.87-2.77 (1H, m), 1.70-1.43 (5H, m), 1.46 (9H, s), 0.96 (3H, d, J=6.9 Hz).

(9) Optically-Active Compound of 3-methyl-1,6-diazaspiro[3,5]nonane-1,6-dicarboxylic acid 1-benzyl ester 6-tert-butyl ester

[Chemical Formula 32]

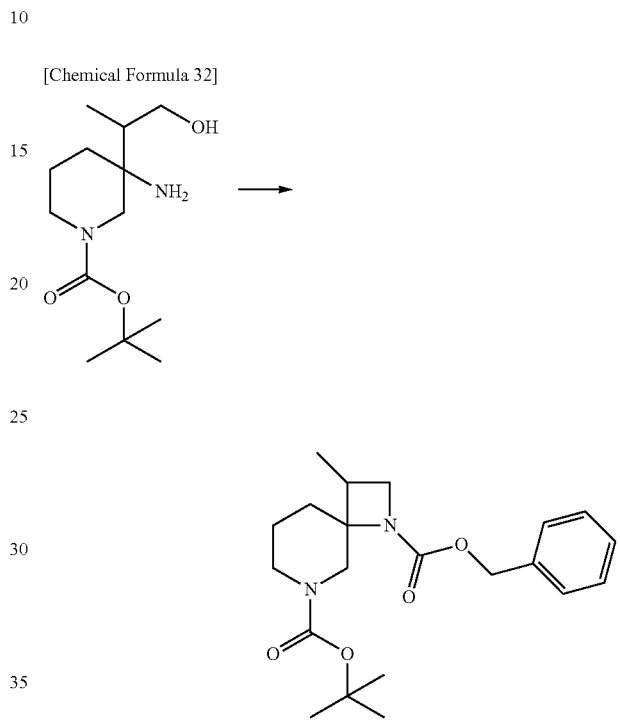

To a solution of an optically-active compound of 3-amino-3-(2-hydroxy-1-methylethyl)piperidine-1-carboxylic acid tert-butyl ester (12.9 g), triphenylphosphine (20.3 g) and triethylamine (21.6 ml) in dichloromethane (400 ml) cooled to 0° C. was added carbon tetrabromide (25.9 g) in small batches. The reaction mixture was stirred at room temperature for 1 hour, and the mixture was cooled to 4° C. Then, thereto were added triethylamine (10.8 ml) and benzyl chloroformate (10.3 ml), and the mixture was stirred at room temperature for 40 minutes. To the mixture was added 5% aqueous sodium bicarbonate solution (125 ml), and the mixture was extracted with chloroform (125 ml). The separated aqueous layer was extracted with chloroform (125 ml) again. The combined organic layer was washed with water (125 ml), 10% aqueous sodium chloride solution (125 ml), dried over anhydrous magnesium sulfate, and concentrated under reduced pressure. The resulting residue was purified by silica gel column chromatography (eluent: n-hexane/ethyl acetate=1/0 to 7/3) to give the titled compound (12.4 g).

$^1$H-NMR (CDCl$_3$) δ: 7.39-7.29 (5H, m), 5.17-5.00 (2H, m), 4.32-3.81 (3H, m), 3.48-3.02 (2H, m), 2.80-2.41 (2H, m), 2.24-2.14 (1H, m), 2.11-2.04 (0.5H, m), 1.97-1.88 (0.5H, m), 1.70-1.39 (2H, m), 1.57 (9H, s), 1.18 (3H, d, J=7.1 Hz).

(10) Optically-Active Compound of 3-methyl-1,6-diazaspiro[3,5]nonane-1-carboxylic acid 1-benzyl ester

[Chemical Formula 33]

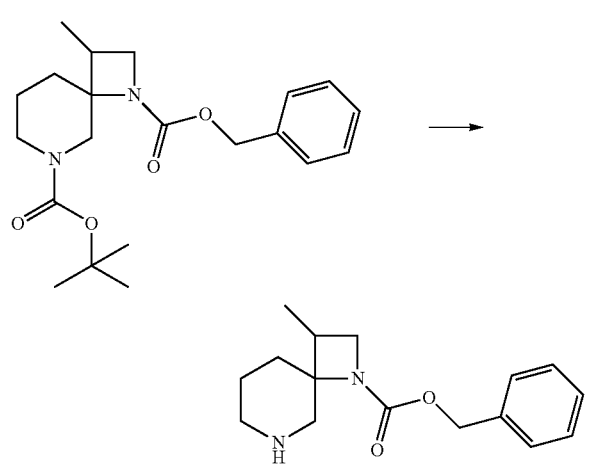

To a solution of an optically-active compound of 3-methyl-1,6-diazaspiro[3,5]nonane-1,6-dicarboxylic acid 1-benzyl ester 6-tert-butyl ester (5.54 g) in chloroform (83 ml) cooled to 4° C. was added a solution of trifluoroacetic acid/chloroform (28 ml/55 ml), and the mixture was warmed to room temperature and stirred for additional 2 hours. The reaction mixture was cooled to 4° C., and thereto was added 4M aqueous sodium hydroxide solution (90 ml). The mixture was basified to be pH 9 to 10, and extracted with chloroform/methanol (4/1, 60 ml×2) twice. The combined organic layer was sequentially washed with 5% aqueous sodium bicarbonate solution, 10% aqueous sodium chloride solution, dried over anhydrous magnesium sulfate, and concentrated under reduced pressure. The resulting residue was purified by silica gel column chromatography (eluent: chloroform/methanol/28% ammonia water=90/10/1) to give the titled compound (2.20 g).

$^1$H-NMR (CDCl$_3$) δ: 7.40-7.29 (5H, m), 5.18-5.03 (2H, m), 4.02-3.94 (1H, m), 3.41-3.26 (1.5H, m), 3.15-3.08 (0.5H, m), 2.97-2.72 (2.5H, m), 2.51-2.34 (1.5H, m), 2.24-2.13 (0.5H, m), 2.06-1.58 (3.5H, m), 1.53-1.35 (1H, m), 1.30-1.15 (3H, m).

(11) Optically-Active Compound of 3-methyl-6-(7H-pyrrolo[2,3-d]pyrimidin-4-yl)-1,6-diazaspiro[3.5]nonane-1-carboxylic acid benzyl ester

[Chemical Formula 34]

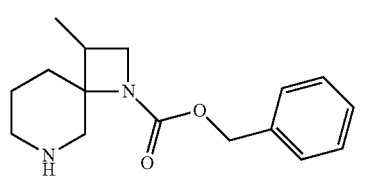

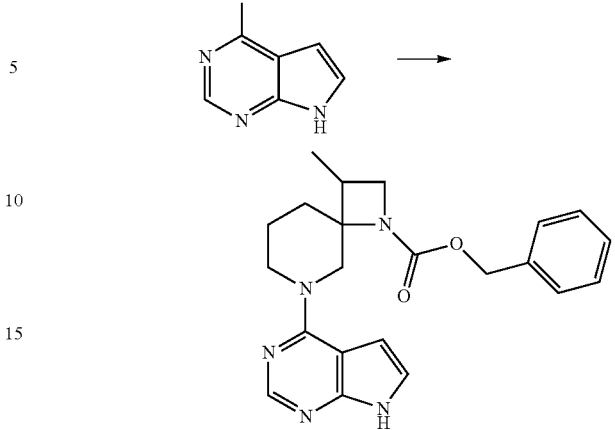

An optically-active compound of 3-methyl-1,6-diazaspiro[3,5]nonane-1-carboxylic acid 1-benzyl ester (2.20 g) was mixed with 4-chloro-7H-pyrrolo[2,3-d]pyrimidine (1.17 g), potassium carbonate (3.17 g) and water (12 ml), and the mixture was stirred for 4 hours with refluxing. The mixture was cooled to room temperature, and extracted with chloroform twice. The combined organic layer was washed with water, 10% aqueous sodium chloride solution, dried over anhydrous magnesium sulfate, and concentrated under reduced pressure. The resulting residue was purified by silica gel column chromatography (eluent: chloroform/ethyl acetate=1/0 to 1/3, followed by chloroform/methanol=95/5) to give the titled compound (2.84 g).

$^1$H-NMR (CDCl$_3$) δ: 10.40-10.30 (1H, m), 8.32 (1H, s), 7.40-7.30 (5H, m), 7.11-7.08 (1H, m), 6.57-6.51 (1H, m), 5.17-5.07 (2H, m), 5.04-4.89 (1H, m), 4.72-4.61 (1H, m), 4.14-4.07 (1H, m), 3.74-3.68 (0.5H, m), 3.57-3.51 (0.5H, m), 3.39-3.32 (1H, m), 3.15-2.96 (1H, m), 2.57-2.47 (1H, m), 2.44-2.32 (0.5H, m), 2.23-2.08 (1.5H, m), 1.92-1.80 (1H, m), 1.72-1.59 (1H, m), 1.14-1.06 (3H, m).

(12) Optically-Active Compound of 4-(3-methyl-1,6-diazaspiro[3.5]non-6-yl)-7H-pyrrolo[2,3-d]pyrimidine

[Chemical Formula 35]

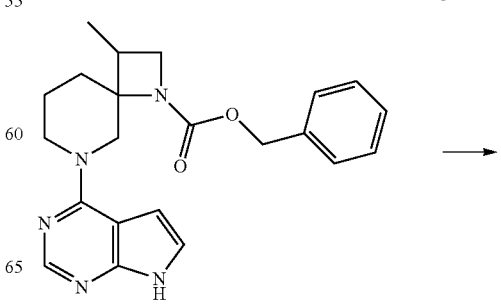

-continued

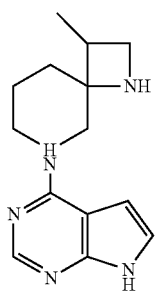

To a solution of an optically-active compound of 3-methyl-6-(7H-pyrrolo[2,3-d]pyrimidin-4-yl)-1,6-diazaspiro[3.5]nonane-1-carboxylic acid benzyl ester (2.84 g) in methanol/tetrahydrofuran (14 ml/14 ml) was added 10% palladium carbon (568 mg), and the mixture was hydrogenated under 4 atmospheres. The mixture was filtered through Celite, and the filtrate was concentrated under reduced pressure. The resulting residue was slurry-washed with toluene/tetrahydrofuran (95/5, 9 ml) to give the titled compound (1.74 g).

$^1$H-NMR (CDCl$_3$) δ: 10.63 (1H, br s), 8.32 (1H, s), 7.08 (1H, d, J=3.5 Hz), 6.54 (1H, d, J=3.5 Hz), 4.45 (1H, d, J=13.0 Hz), 4.21-4.14 (1H, m), 3.85-3.79 (1H, m), 3.57 (1H, d, J=13.0 Hz), 3.55-3.47 (1H, m), 3.08-3.01 (1H, m), 2.48-2.38 (1H, m), 2.03 (1H, br s), 1.98-1.88 (1H, m), 1.84-1.68 (3H, m), 1.19 (3H, d, J=7.3 Hz).

(13) Optically-Active Compound of 3-[3-methyl-6-(7H-pyrrolo[2,3-d]pyrimidin-4-yl)-1,6-diazaspiro[3.5]non-1-yl]-3-oxopropionitrile

[Chemical Formula 36]

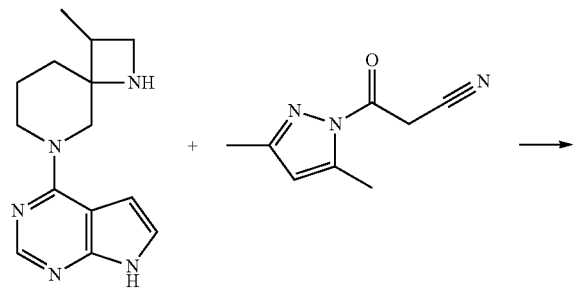

An optically-active compound of 4-(3-methyl-1,6-diazaspiro[3.5]non-6-yl)-7H-pyrrolo[2,3-d]pyrimidine (1.8 g) was mixed with 1-cyanoacetyl-3,5-dimethylpyrazole (2.3 g), N,N-diisopropylethylamine (2.4 ml) and 1,4-dioxane (18 ml), and the mixture was stirred at 100° C. for 3 hours. The mixture was cooled to room temperature. Then, thereto were added water and saturated aqueous sodium chloride solution, and the mixture was extracted with ethyl acetate. The separated aqueous layer was extracted with chloroform, and the combined organic layer was concentrated under reduced pressure. The resulting residue was purified by silica gel column chromatography (eluent: chloroform/ethyl acetate=1/1, followed by chloroform/methanol=20/1 to 10/1). The resulting residue was purified by silica gel column chromatography (eluent: chloroform/acetone=10/1 to 1/1) again. The resulting residue was purified by silica gel column chromatography (eluent: chloroform/methanol=20/1 to 10/1) again to give the titled compound (1.8 g).

$^1$H-NMR (DMSO-D$_6$) δ: 11.71 (1H, br s), 8.12 (1H, s), 7.20 (1H, dd, J=3.5, 2.4 Hz), 6.65 (1H, dd, J=3.6, 1.9 Hz), 4.93-4.88 (1H, m), 4.64-4.58 (1H, m), 4.24-4.18 (1H, m), 3.67 (2H, s), 3.61 (1H, d, J=12.8 Hz), 3.46-3.41 (1H, m), 3.03-2.95 (1H, m), 2.42-2.35 (1H, m), 2.34-2.25 (1H, m), 2.15-2.08 (1H, m), 1.83-1.77 (1H, m), 1.57-1.43 (1H, m), 1.01 (3H, d, J=7.1 Hz).

[α]$_D$=+168.10° (25° C., c=1.05, methanol)

Preparation 2

Synthesis of Compound 2

[Chemical Formula 37]

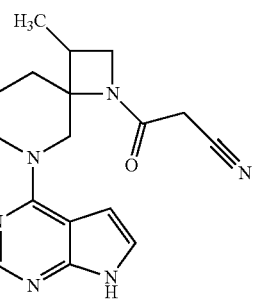

(1) Piperidine-1,3-dicarboxylic acid 3-((Z)-but-2-enyl)ester 1-tert-butyl ester

[Chemical Formula 38]

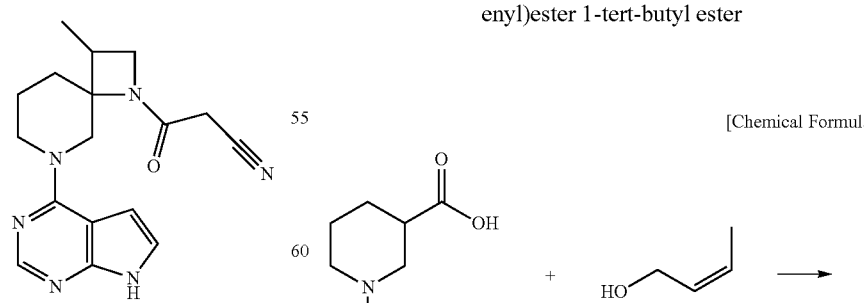

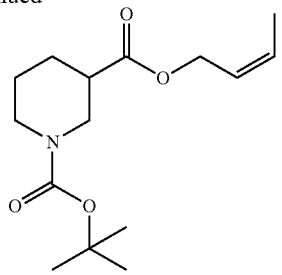

To a solution of 1-(t-butoxycarbonyl)-3-piperidinecarboxylic acid (60.0 g) and 1-ethyl-3-(3-dimethylaminopropyl)-carbodiimide (55.2 g) in chloroform (600 ml) was added 4-dimethylaminopyridine (35.2 g), and the mixture was stirred for 70 minutes. To the mixture was added (Z)-but-2-en-1-ol (26.8 ml), and the mixture was stirred at room temperature for 14 hours. To the reaction mixture were added water (300 ml) and saturated aqueous sodium chloride solution (100 ml), and the mixture was extracted with chloroform. The separated organic layer was concentrated under reduced pressure, and to the resulting residue were added ethyl acetate and n-hexane. The mixture was sequentially washed with 3.5% aqueous potassium bisulfate solution three times and saturated aqueous sodium chloride solution twice. To the separated organic layer was added silica gel (200 ml), and the mixture was stirred and filtered through Celite. The filtrate was concentrated under reduced pressure, and the resulting residue was purified by silica gel column chromatography (eluent: n-hexane/ethyl acetate=9/1) to give the titled compound (68.3 g).

$^{1}$H-NMR (DMSO-D$_6$) δ: 5.74-5.65 (1H, m), 5.55-5.47 (1H, m), 4.61 (2H, d, J=6.8 Hz), 4.05-3.75 (1H, m), 3.70-3.53 (1H, m), 2.96-2.86 (2H, m), 2.46-2.39 (1H, m), 1.92-1.84 (1H, m), 1.69-1.51 (6H, m), 1.39 (9H, s).

(2) 3-(1-Methyl-allyl)-piperidine-1,3-dicarboxylic acid 1-tert-butyl ester

[Chemical Formula 39]

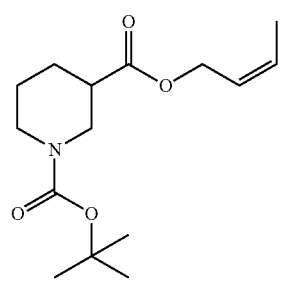

→

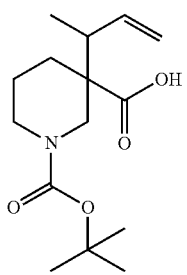

To a solution of piperidine-1,3-dicarboxylic acid 3-((Z)-but-2-enyl)ester 1-tert-butyl ester (68.3 g) in tetrahydrofuran (700 ml) cooled to −74° C. was added lithium hexamethyl disilazide (1.6M tetrahydrofuran solution, 166 ml). The reaction mixture was warmed to 0° C. over 35 minutes, stirred at the same temperature for additional 25 minutes, and cooled to −74° C. again. To the mixture was added trimethylsilyl chloride (39.6 ml). The reaction mixture was warmed to room temperature over 70 minutes, and stirred at the same temperature for additional 4 hours. To the mixture were sequentially added water (600 ml), 2M aqueous sodium hydroxide solution (70 ml), and the mixture was washed with n-hexane (600 ml). The separated aqueous layer was acidified by 2M aqueous hydrochloric acid solution, followed by extracted with ethyl acetate (300 ml, 200 ml, 150 ml) three times. The combined organic layer was washed with saturated aqueous sodium chloride solution, dried over anhydrous sodium sulfate, and concentrated under reduced pressure. The resulting residue was slurry-washed with n-hexane/ethyl acetate solution (10/1) to give the titled compound (42.5 g).

$^{1}$H-NMR (CDCl$_3$) δ: 5.83-5.72 (1H, m), 5.09-5.06 (1H, m), 5.05-5.02 (1H, m), 4.33-3.90 (1H, m), 3.73-3.63 (1H, m), 3.31-2.73 (2H, m), 2.43-2.34 (1H, m), 2.07-1.97 (1H, m), 1.64-1.56 (2H, m), 1.54-1.42 (1H, m), 1.45 (9H, s), 1.05 (3H, d, J=7.3 Hz).

(3) Salt of an Optically-Active Compound of 3-(1-methyl-allyl)-piperidine-1,3-dicarboxylic acid 1-tert-butyl ester and (S)-(+)-2-amino-2-phenyl-ethanol

[Chemical Formula 40]

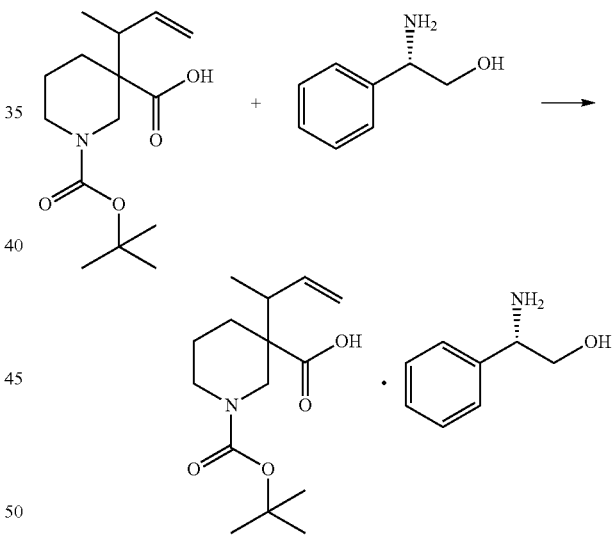

To a solution of 3-(1-methylallyl)piperidine-1,3-dicarboxylic acid 1-tert-butyl ester (3.00 g) in 1,2-dimethoxyethane (30 ml) was added (S)-(+)-2-amino-2-phenyl-ethanol (800 mg), and the mixture was stirred at room temperature overnight. The slurry mixture was filtered to give a solid (1.8 g). To the solid was added 1,2-dimethoxyethane (45 ml), and the mixture was dissolved at 80° C. The mixture was slurry-washed at room temperature for 4 hours to give the titled compound (1.46 g). An analysis by HPLC analysis condition 1 showed that an isomer with longer retention times was a main product.

An isomer with shorter retention times (retention time 6.73 minutes)

An isomer with longer retention times (retention time 13.70 minutes)

(4) Optically-Active Compound of 3-(1-methylallyl)piperidine-1,3-dicarboxylic acid 1-tert-butyl ester

[Chemical Formula 41]

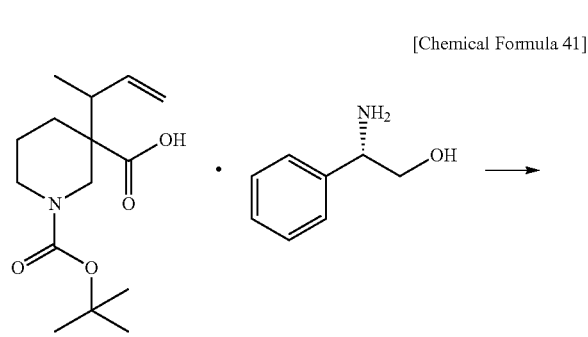

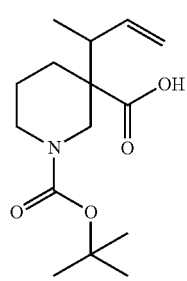

To a salt of an optically-active compound of 3-(1-methylallyl)piperidine-1,3-dicarboxylic acid 1-tert-butyl ester and (S)-(+)-2-amino-2-phenyl-ethanol (1.5 g) were added ethyl acetate (15 ml) and water (15 ml), and the mixture was acidified by the addition of potassium bisulfate (567 mg). The separated aqueous layer was extracted with ethyl acetate twice, and the combined organic layer was washed with 10% aqueous potassium bisulfate solution twice and water once, dried over anhydrous magnesium sulfate, and concentrated under reduced pressure to give the titled compound (1.02 g).

$^1$H-NMR (CDCl$_3$) δ: 5.83-5.72 (1H, m), 5.09-5.06 (1H, m), 5.05-5.02 (1H, m), 4.33-3.90 (1H, m), 3.73-3.63 (1H, m), 3.31-2.73 (2H, m), 2.43-2.34 (1H, m), 2.07-1.97 (1H, m), 1.64-1.56 (2H, m), 1.54-1.42 (1H, m), 1.45 (9H, s), 1.05 (3H, d, J=7.3 Hz).

(5) Optically-Active Compound of 3-benzyloxycarbonylamino-3-(1-methylallyl)piperidine-1-carboxylic acid tert-butyl ester

[Chemical Formula 42]

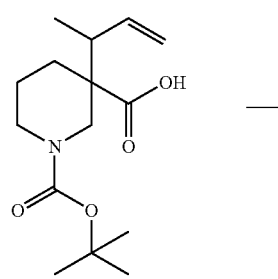

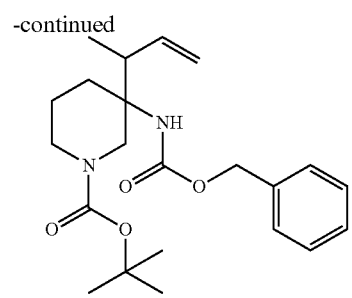

To a solution of an optically-active compound of 3-(1-methylallyl)piperidine-1,3-dicarboxylic acid 1-tert-butyl ester (1.02 g) and triethylamine (967 µl) in toluene (10 ml) heated to 90° C. was added dropwise diphenylphosphoryl azide (1.1 ml). The reaction mixture was stirred at the same temperature for 1 hour, and then thereto were added benzyl alcohol (718 µl) and 4-dimethylaminopyridine (127 mg). The mixture was stirred with refluxing overnight, then cooled to room temperature, and thereto were added water and ethyl acetate. The separated aqueous layer was extracted with ethyl acetate twice, and the combined organic layer was washed with water twice and saturated aqueous sodium chloride solution once, dried over anhydrous magnesium sulfate, and concentrated under reduced pressure. The resulting residue was purified by silica gel column chromatography (eluent: chloroform/acetone=50/1). The resulting residue was purified by silica gel column chromatography (eluent: n-hexane/ethyl acetate=20/1 to 4/1) to give the titled compound (845 mg).

$^1$H-NMR (DMSO-D$_6$) δ: 7.39-7.28 (5H, m), 6.91-6.72 (1H, m), 5.88-5.76 (1H, m), 5.18-4.84 (4H, m), 4.41-4.26 (1H, m), 3.88-3.61 (1H, m), 3.07-2.54 (2H, m), 1.99-1.43 (3H, m), 1.35 (10H, s), 0.92-0.85 (3H, m).

(6) Optically-Active Compound of 3-benzyloxycarbonylamino-3-(2-hydroxy-1-methylethyl)piperidine-1-carboxylic acid tert-butyl ester

[Chemical Formula 43]

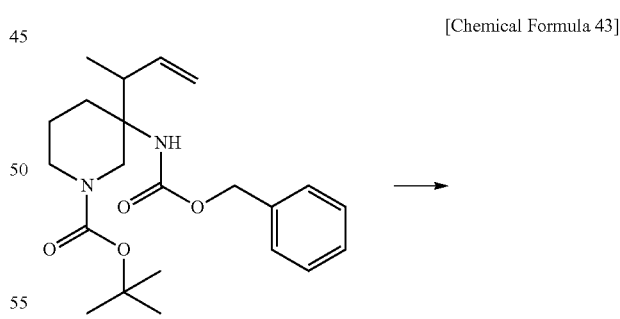

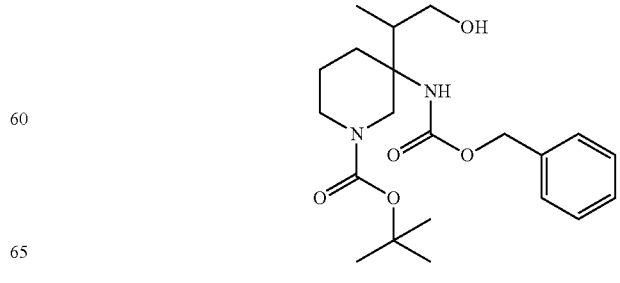

A solution of an optically-active compound of 3-benzyloxycarbonylamino-3-(1-methylallyl)piperidine-1-carboxylic acid 1-tert-butyl ester (815 mg) in chloroform/methanol (6.6 ml/6.6 ml) cooled to −78° C. was flowed ozone air for 30 minutes. To the reaction mixture was added sodium borohydride (318 mg) in small batches, and then the mixture was warmed to room temperature over 40 minutes. To the mixture was added saturated aqueous sodium bicarbonate solution, and the mixture was extracted with chloroform twice. The combined organic layer was washed with aqueous sodium bicarbonate solution, dried over anhydrous magnesium sulfate, and concentrated under reduced pressure. The resulting residue was purified by silica gel column chromatography (eluent: n-hexane/ethyl acetate=3/2 to 0/1) to give the titled compound (406 mg).

$^1$H-NMR (DMSO-D$_6$) δ: 7.39-7.27 (5H, m), 6.74-6.55 (1H, m), 5.17-4.83 (2H, m), 4.53-4.41 (1H, m), 4.32-3.93 (2H, m), 3.76-3.47 (2H, m), 3.26-3.00 (2H, m), 2.95-2.68 (1H, m), 2.30-2.00 (1H, m), 1.83-1.66 (1H, m), 1.64-1.44 (2H, m), 1.36 (9H, s), 0.92-0.77 (3H, m).

(7) Optically-Active Compound of 3-amino-3-(2-hydroxy-1-methylethyl)piperidine-1-carboxylic acid tert-butyl ester

[Chemical Formula 44]

To a solution of an optically-active compound of 3-benzyloxycarbonylamino-3-(2-hydroxy-1-methylethyl)piperidine-1-carboxylic acid tert-butyl ester (374 mg) in methanol (6 ml) was added 10% palladium carbon (38 mg), and the mixture was hydrogenated at room temperature under ordinary pressure for 14 hours. The mixture was filtered through Celite, and the filtrate was concentrated under reduced pressure to give the titled compound (269 mg).

$^1$H-NMR (DMSO-D$_6$) δ: 4.83 (1H, br s), 3.51-2.74 (4H, m), 1.79-1.25 (7H, m), 1.38 (9H, s), 0.92 (3H, d, J=6.9 Hz).

(8) Optically-Active Compound of 3-methyl-1,6-diazaspiro[3,5]nonane-1,6-dicarboxylic acid 1-benzyl ester 6-tert-butyl ester

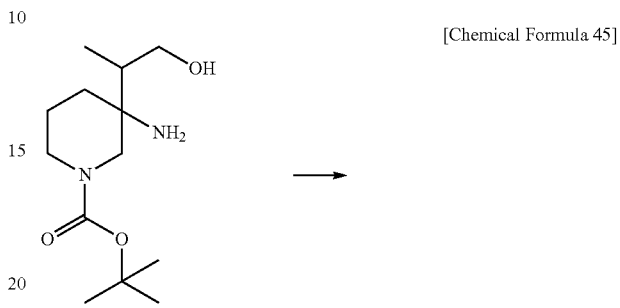

[Chemical Formula 45]

To a solution of an optically-active compound of 3-amino-3-(2-hydroxy-1-methylethyl)piperidine-1-carboxylic acid tert-butyl ester (258 mg), triphenylphosphine (472 mg) and triethylamine (502 μl) in dichloromethane (7.7 ml) cooled to 0° C. was added carbon tetrabromide (596 mg). The reaction mixture was stirred at room temperature for 2.5 hours and cooled to 4° C. Then, thereto were added triethylamine (279 μl) and benzyl chloroformate (267 μl), and the mixture was stirred for 40 minutes. To the mixture was added water, and the mixture was extracted with ethyl acetate. The separated organic layer was sequentially washed with saturated aqueous sodium bicarbonate solution and saturated aqueous sodium chloride solution, and dried over anhydrous sodium sulfate and concentrated under reduced pressure. The resulting residue was purified by silica gel column chromatography (eluent: n-hexane/ethyl acetate=20/1 to 2/1) to give the titled compound (85 mg).

$^1$H-NMR (DMSO-D$_6$) δ: 7.40-7.29 (5H, m), 5.07-4.98 (2H, m), 4.20-4.11 (1H, m), 3.99-3.83 (2H, m), 3.39-3.20 (1H, m), 3.13-2.83 (1H, m), 2.58-2.45 (1H, m), 2.44-2.32 (1H, m), 2.16-2.07 (0.5H, m), 2.01-1.82 (1.5H, m), 1.68-1.58 (1H, m), 1.39 (9H, s), 1.37-1.28 (1H, m), 1.14-1.03 (3H, m).

(9) Optically-Active Compound of 3-methyl-1,6-diazaspiro[3,5]nonane-1-carboxylic acid 1-benzyl ester

[Chemical Formula 46]

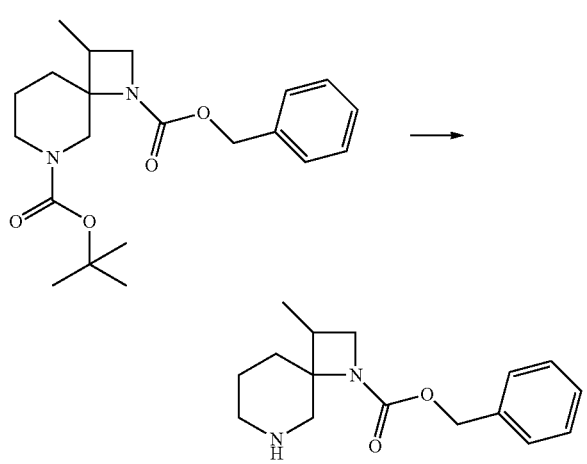

To a solution of an optically-active compound of 3-methyl-1,6-diazaspiro[3,5]nonane-1,6-dicarboxylic acid 1-benzyl ester 6-tert-butyl ester (78 mg) in chloroform (2 ml) cooled to 4° C. was added trifluoroacetic acid (0.4 ml), and the mixture was warmed to room temperature and stirred for additional 1 hour. The reaction mixture was basified by the addition of 1M aqueous sodium hydroxide solution, and extracted with chloroform. The separated organic layer was washed with saturated aqueous sodium chloride solution, dried over anhydrous sodium sulfate and concentrated under reduced pressure to give the titled compound (108 mg).

$^1$H-NMR (DMSO-D$_6$) δ: 7.42-7.31 (5.0H, m), 5.20-4.99 (2.0H, m), 4.05-3.88 (1.0H, m), 3.64-3.55 (1.0H, m), 3.43-3.37 (0.5H, m), 3.35-3.26 (0.5H, m), 3.22-2.89 (3.0H, m), 2.39-2.29 (1.0H, m), 2.22-2.13 (0.5H, m), 2.07-1.49 (4.0H, m), 1.29-1.22 (0.5H, m), 1.15 (1.5H, d, J=6.9 Hz), 1.01-0.91 (0.5H, m).

(10) Optically-Active Compound of 3-methyl-6-(7H-pyrrolo[2,3-d]pyrimidin-4-yl)-1,6-diazaspiro[3.5]nonane-1-carboxylic acid benzyl ester

[Chemical Formula 47]

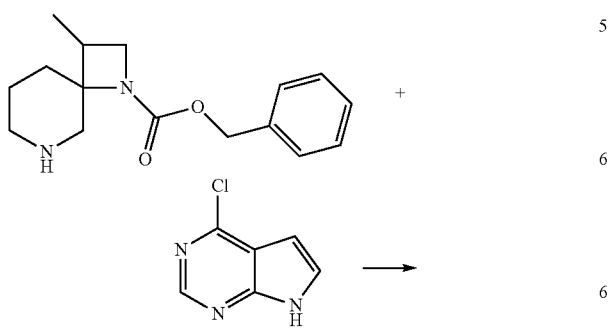

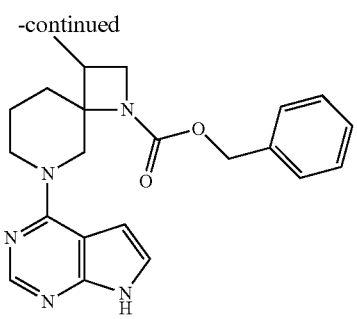

An optically-active compound of 3-methyl-1,6-diazaspiro[3,5]nonane-1-carboxylic acid 1-benzyl ester (108 mg) was mixed with 4-chloro-7H-pyrrolo[2,3-d]pyrimidine (32 mg), potassium carbonate (86 mg) and water (2.1 ml), and stirred overnight with refluxing. The mixture was cooled to room temperature, and extracted with chloroform. The separated organic layer was washed with saturated aqueous sodium chloride solution, dried over anhydrous sodium sulfate and concentrated under reduced pressure. The resulting residue was purified by silica gel column chromatography (eluent: n-hexane/ethyl acetate=2/1 to 0/1, followed by chloroform/methanol=9/1) to give the titled compound (48 mg).

$^1$H-NMR (DMSO-D$_6$) δ: 11.69 (1.0H, br s), 8.15 (1.0H, s), 7.41-7.27 (5.0H, m), 7.18 (1.0H, dd, J=3.4, 2.6 Hz), 6.64-6.59 (1.0H, m), 5.09-4.92 (3.5H, m), 4.63-4.55 (1.0H, m), 4.01-3.85 (1.0H, m), 3.45-3.39 (0.5H, m), 3.35-3.27 (0.5H, m), 3.25-3.20 (0.5H, m), 2.99-2.84 (1.0H, m), 2.46-2.38 (1.0H, m), 2.35-2.25 (0.5H, m), 2.20-2.10 (0.5H, m), 2.03-1.95 (1.0H, m), 1.88-1.79 (1.0H, m), 1.66-1.52 (1.0H, m), 0.93 (3.0H, d, J=6.9 Hz).

(11) Optically-Active Compound of 4-(3-methyl-1,6-diazaspiro[3.5]non-6-yl)-7H-pyrrolo[2,3-d]pyrimidine

[Chemical Formula 48]

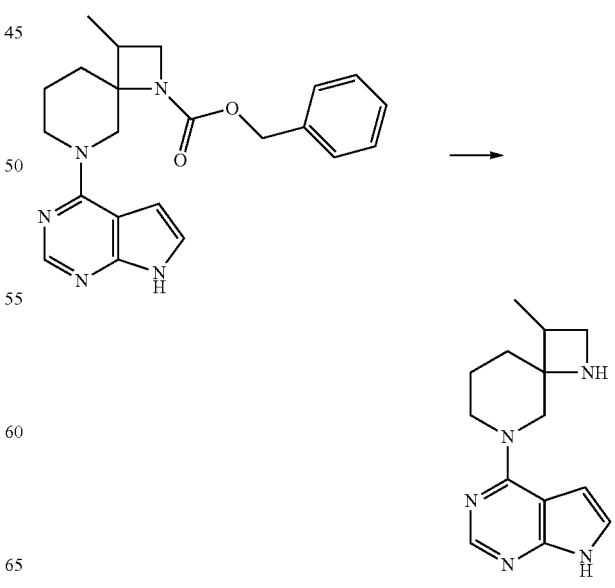

To a solution of an optically-active compound of 3-methyl-6-(7H-pyrrolo[2,3-d]pyrimidin-4-yl)-1,6-diazaspiro[3.5]nonane-1-carboxylic acid benzyl ester (46 mg) in methanol/tetrahydrofuran (1.8 ml/1.8 ml) was added 10% palladium carbon (15 mg), and the mixture was hydrogenated under 4 atmospheres for 14 hours. The mixture was filtered through Celite, and the filtrate was concentrated under reduced pressure to give the titled compound (27 mg).

$^1$H-NMR (DMSO-D$_6$) δ: 11.73 (1H, br s), 8.17 (1H, s), 7.21 (1H, dd, J=3.3, 2.0 Hz), 6.64-6.61 (1H, m), 4.35 (0.5H, br s), 4.09 (0.5H, br s), 4.03 (1H, d, J=13.5 Hz), 3.97 (1H, d, J=13.2 Hz), 3.83-3.70 (2H, m), 3.47-3.40 (1H, m), 3.23-3.18 (1H, m), 2.48-2.43 (1H, m), 1.97-1.83 (2H, m), 1.77-1.57 (2H, m), 1.04 (3H, d, J=7.3 Hz).

(12) Optically-Active Compound of 3-[3-methyl-6-(7H-pyrrolo[2,3-d]pyrimidin-4-yl)-1,6-diazaspiro[3.5]non-1-yl]-3-oxopropionitrile

[Chemical Formula 49]

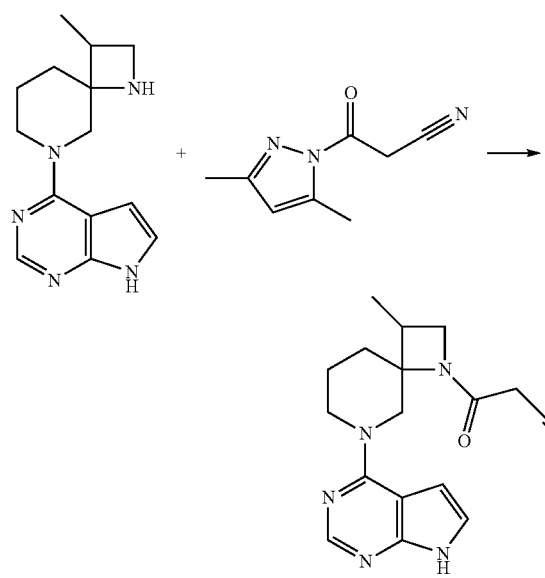

An optically-active compound of 4-(3-methyl-1,6-diazaspiro[3.5]non-6-yl)-7H-pyrrolo[2,3-d]pyrimidine (25 mg) was mixed with 1-cyanoacetyl-3,5-dimethylpyrazole (32 mg) and 1,4-dioxane (750 μl), and the mixture was stirred at 100° C. for 3.5 hours. The mixture was cooled to room temperature. Thereto were added water and saturated aqueous sodium bicarbonate solution, and the mixture was extracted with ethyl acetate. The separated aqueous layer was extracted with ethyl acetate five times, and the combined organic layer was washed with water and concentrated under reduced pressure. The resulting residue was purified by silica-gel thin layer chromatography (eluent: chloroform/methanol=9/1). The resulting residue was purified by silica-gel thin layer chromatography (eluent: ethyl acetate/methanol=93/7) again. The resulting solid (8.0 mg) was slurry-washed with n-hexane/ethyl acetate solution to give the titled compound (6.7 mg).

$^1$H-NMR (DMSO-D6) δ: 11.70 (1H, br s), 8.14 (1H, s), 7.19 (1H, dd, J=3.5, 2.4 Hz), 6.64 (1H, dd, J=3.6, 1.9 Hz), 5.03-4.96 (1H, m), 4.66-4.59 (1H, m), 4.11-4.06 (1H, m), 3.70 (1H, d, J=18.7 Hz), 3.65 (1H, d, J=18.7 Hz), 3.60-3.55 (1H, m), 3.45 (1H, d, J=13.0 Hz), 2.97-2.89 (1H, m), 2.46-2.41 (1H, m), 2.40-2.34 (1H, m), 2.00-1.94 (1H, m), 1.88-1.80 (1H, m), 1.64-1.51 (1H, m), 0.91 (3H, d, J=7.1 Hz).

[α]D=+202.79° (25° C., c=1.04, methanol)

Preparation 3

Synthesis of Compound 3

[Chemical Formula 50]

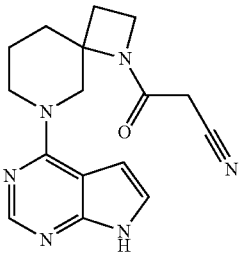 [SMILES: N#CCC(=O)N1CCC12CCCN(c1ncnc3[nH]ccc13)C2]

(1) Piperidine-1,3-dicarboxylic acid 3-allyl ester 1-tert-butyl ester

[Chemical Formula 51]

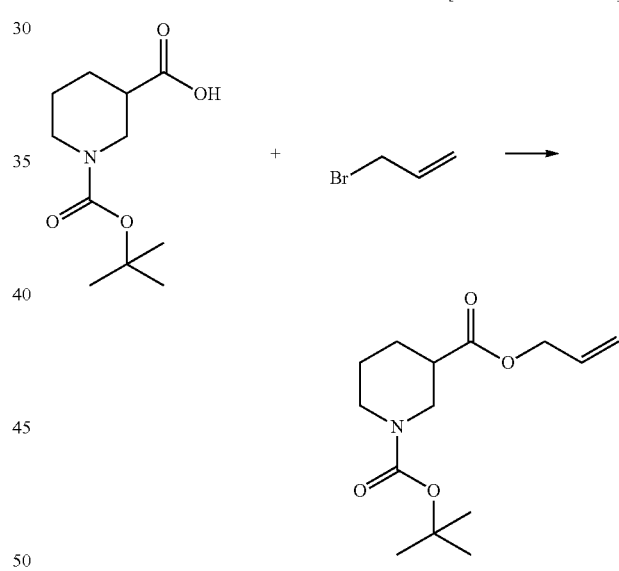

To a solution of 1-(tert-butoxycarbonyl)-3-piperidinecarboxylic acid (50.0 g) in N,N-dimethylformamide (500 ml) were added potassium carbonate (60.3 g) and allyl bromide (28.3 ml), and the mixture was stirred at room temperature for 3 hours. To the reaction mixture was added water (600 ml), and the mixture was extracted with ethyl acetate (600 ml). The organic layer was sequentially washed with water (600 ml) and saturated aqueous sodium chloride solution (400 ml). The separated aqueous layer was extracted with ethyl acetate (300 ml) again. The combined organic layer was dried over anhydrous sodium sulfate, and concentrated under reduced pressure. To a solution of the resulting residue in n-hexane/ethyl acetate (4/1, 400 ml) was added silica gel (70 g), and the mixture was stirred at room temperature. The mixture was filtered, and the filtrate was concentrated under reduced pressure to give the titled compound (62.5 g).

¹H-NMR (CDCl₃) δ: 5.97-5.85 (1H, m), 5.36-5.20 (2H, m), 4.63-4.55 (2H, m), 4.34-4.01 (1H, m), 3.97-3.86 (1H, m), 3.16-2.88 (1H, m), 2.86-2.77 (1H, m), 2.53-2.43 (1H, m), 2.11-2.02 (1H, m), 1.75-1.57 (2H, m), 1.52-1.39 (1H, m), 1.46 (9H, s).

(2) 3-Allylpiperidine-1,3-dicarboxylic acid 1-tert-butyl ester

[Chemical Formula 52]

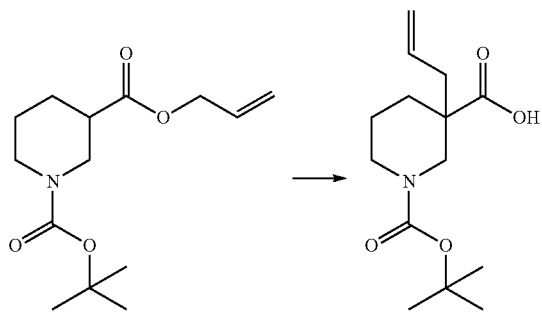

To a solution of piperidine-1,3-dicarboxylic acid 3-allyl ester 1-tert-butyl ester (62.5 g) in tetrahydrofuran (625 ml)

[Chemical Formula 53]

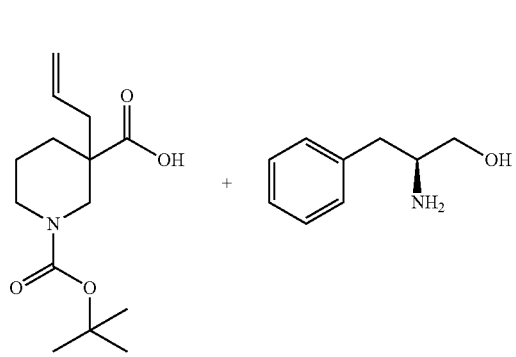

cooled to −72° C. was added lithium hexamethyl disilazide (1.6M tetrahydrofuran solution, 160 ml). The mixture was stirred at the same temperature for 30 minutes, and then the reaction mixture was warmed to 0° C. over 12 minutes and cooled to −67° C. again. To the mixture was added trimethylsilyl chloride (35.2 ml). The reaction mixture was warmed to 2.5° C. over 1 hour, and stirred at the same temperature for additional 2 hours. To the mixture were sequentially added methanol (250 ml) and 1M aqueous sodium hydroxide solution (250 ml), and the mixture was washed with n-hexane (940 ml). The separated aqueous layer was washed with n-hexane (250 ml) again. The separated aqueous layer was acidified by 1M hydrochloric acid water, and then extracted with ethyl acetate (800 ml). The organic layer was sequentially washed with water (800 ml) and saturated aqueous sodium chloride solution (400 ml), and the separated aqueous layer was extracted with ethyl acetate (500 ml) again. The combined organic layer was dried over anhydrous sodium sulfate, and concentrated under reduced pressure. The resulting residue was slurry-washed with n-hexane/ethyl acetate (10/1, 660 ml) to give the titled compound (53.4 g).

¹H-NMR (CDCl₃) δ: 5.81-5.69 (1H, m), 5.14-5.06 (2H, m), 3.93-3.78 (1H, m), 3.54-3.45 (1H, m), 3.29-3.14 (2H, m), 2.43-2.34 (1H, m), 2.29-2.21 (1H, m), 2.07-1.98 (1H, m), 1.65-1.49 (3H, m), 1.45 (9H, s).

(3) Optically-Active Compound of 3-allylpiperidine-1,3-dicarboxylic acid 1-tert-butyl ester (3)-(1) Seed Crystal of a Salt of an Optically-Active Compound of 3-allylpiperidine-1,3-dicarboxylic acid 1-tert-butyl ester with (S)-(−)-2-amino-3-phenyl-1-propanol 3-Allylpiperidine-1,3-dicarboxylic acid 1-tert-butyl ester (3.0 g) was mixed with isopropyl acetate (30 ml), and the mixture was heated to 80° C. to dissolve. To the mixture was added (S)-(−)-2-amino-3-phenyl-1-propanol (1.01 g), and the mixture was stirred at room temperature for 21 hours. The slurry mixture was filtered, and the resulting solid was washed with isopropyl acetate (8 ml) and dried under reduced pressure to give the titled compound (1.5 g). The filtrate was concentrated under reduced pressure and used in (4)-(1).

(3)-(2) Salt of an Optically-Active Compound of 3-allylpiperidine-1,3-dicarboxylic acid 1-tert-butyl ester with (S)-(−)-2-amino-3-phenyl-1-propanol

[Chemical Formula 54]

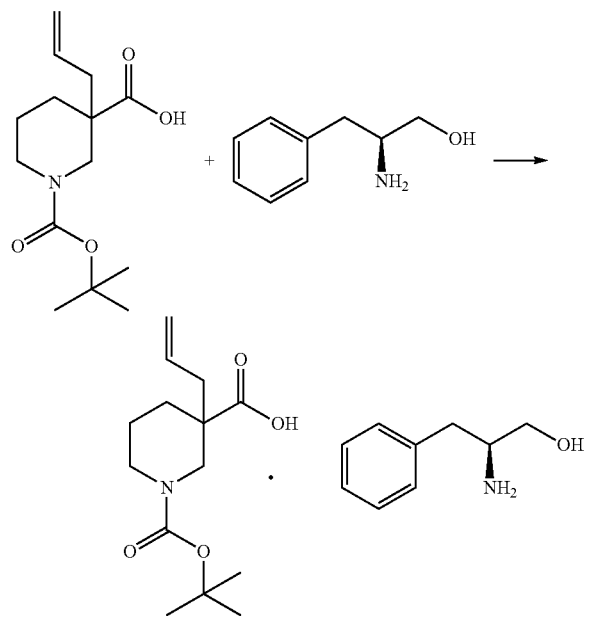

To a solution of 3-allylpiperidine-1,3-dicarboxylic acid 1-tert-butyl ester (73.3 g) in isopropyl acetate (733 ml) heated to 80° C. was added (S)-(−)-2-amino-3-phenyl-1-propanol (24.7 g). The mixed solution was cooled to room temperature. Then, thereto was added the seed crystal obtained in (3)-(1), and the mixture was stirred overnight. The slurry mixture was filtered, and the resulting solid was washed with isopropyl acetate (210 ml) to give the titled compound (37.4 g). An analysis by HPLC analysis condition 1 showed that an isomer with shorter retention times was a main product.

An isomer with shorter retention times (retention time 6.01 minutes)

An isomer with longer retention times (retention time 8.94 minutes)

(3)-(3) Optically-Active Compound of 3-allylpiperidine-1,3-dicarboxylic acid 1-tert-butyl ester from the filtrate of (3)-(2)

The filtrate of (3)-(2) was combined with the wash solution. Thereto was added aqueous potassium bisulfate solution (22.2 g/365 ml), and the mixture was stirred. The separated organic layer was sequentially washed with 10% aqueous potassium bisulfate solution, water and saturated aqueous sodium chloride solution, and concentrated under reduced pressure to give the titled compound (49 g).

$^1$H-NMR (CDCl$_3$) δ: 5.81-5.69 (1H, m), 5.14-5.06 (2H, m), 3.93-3.78 (1H, m), 3.54-3.45 (1H, m), 3.29-3.14 (2H, m), 2.43-2.34 (1M, m), 2.29-2.21 (1H, m), 2.07-1.98 (1H, m), 1.65-1.49 (3H, m), 1.45 (9H, s)

(4) Salt of an Optically-Active Compound of 3-allylpiperidine-1,3-dicarboxylic acid 1-tert-butyl ester with (R)-(+)-2-amino-3-phenyl-1-propanol

[Chemical Formula 55]

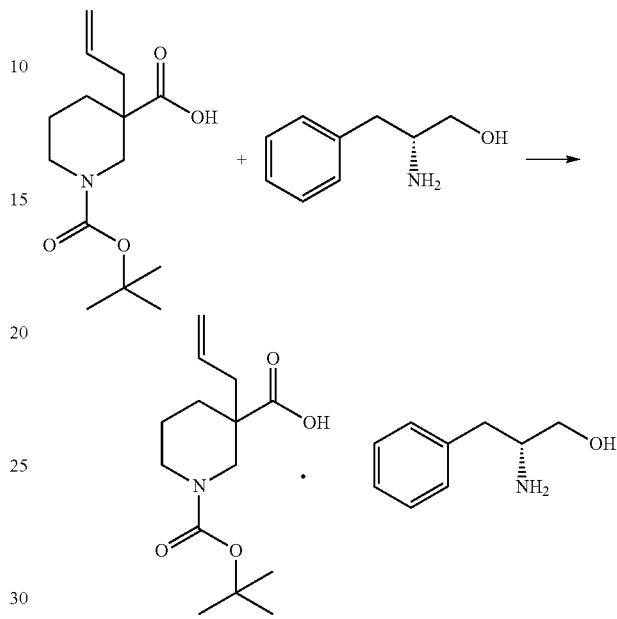

(4)-(1) Seed Crystal of a Salt of an Optically-Active Compound of 3-allylpiperidine-1,3-dicarboxylic acid 1-tert-butyl ester with (R)-(+)-2-amino-3-phenyl-1-propanol To the residue (2.74 g) obtained from the filtrate of (3)-(1) were added ethyl acetate (14 ml) and water (14 ml), and the mixture was cooled to 0° C. Then, thereto was added potassium bisulfate (494 mg). The mixture was stirred at room temperature for 30 minutes, and then extracted with ethyl acetate. The organic layer was sequentially washed with 10% aqueous potassium bisulfate solution, water (twice) and saturated aqueous sodium chloride solution, dried over anhydrous magnesium sulfate and concentrated under reduced pressure. The resulting residue (1.94 g) was mixed with isopropyl acetate (20 ml), and the mixture was heated to 80° C. to dissolve. To the mixture was added (R)-(+)-2-amino-3-phenyl-1-propanol (925 mg), and the mixture was stirred at room temperature for 19.5 hours. The slurry mixture was filtered, and the resulting solid was dried under reduced pressure to give the titled compound (1.85 g).

(4)-(2) Salt of an Optically-Active Compound of 3-allylpiperidine-1,3-dicarboxylic acid 1-tert-butyl ester with (R)-(+)-2-amino-3-phenyl-1-propanol The residue (49 g) obtained in (3)-(3) and isopropyl acetate (490 ml) were combined, and the mixture was heated to 80° C. to dissolve. To the mixture was added (R)-(+)-2-amino-3-phenyl-1-propanol (23.7 g), and the mixture was cooled to room temperature. Then, thereto was added the seed crystal obtained in (4)-(1), and the mixture was stirred overnight. The slurry mixture was filtered and washed with isopropyl acetate (150 ml) to give the titled compound (52 g). An analysis by HPLC analysis condition 1 showed that an isomer with longer retention times was a main product.

An isomer with shorter retention times (retention time 6.01 minutes)

An isomer with longer retention times (retention time 8.94 minutes)

(5) Optically-Active Compound of 3-allylpiperidine-1,3-dicarboxylic acid 1-tert-butyl ester

[Chemical Formula 56]

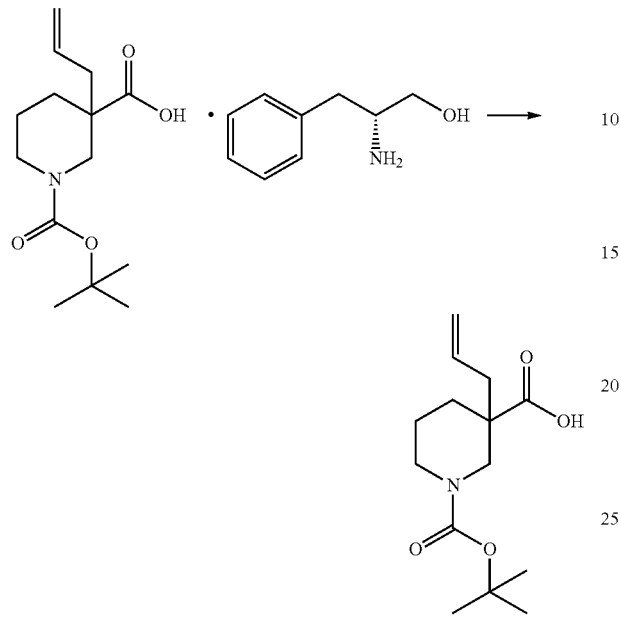

To a salt of an optically-active compound of 3-allylpiperidine-1,3-dicarboxylic acid 1-tert-butyl ester with (R)-(+)-2-amino-3-phenyl-1-propanol (52 g) obtained in (4)-(2) were added ethyl acetate (260 ml) and aqueous potassium bisulfate solution (20.2 g/260 ml), and the mixture was stirred. The separated organic layer was sequentially washed with 10% aqueous potassium bisulfate solution, water and saturated aqueous sodium chloride solution. The separated aqueous layer was extracted with ethyl acetate (130 ml) again, and sequentially washed with water and saturated aqueous sodium chloride solution. The combined organic layer was concentrated under reduced pressure to give the titled compound (32.2 g).

$^1$H-NMR (CDCl$_3$) δ: 5.81-5.69 (1H, m), 5.14-5.06 (2H, m), 3.93-3.78 (1H, m), 3.54-3.45 (1H, m), 3.29-3.14 (2H, m), 2.43-2.34 (1H, m), 2.29-2.21 (1H, m), 2.07-1.98 (1H, m), 1.65-1.49 (3H, m), 1.45 (9H, s).

(6) Optically-Active Compound of 3-allyl-3-benzyloxycarbonylaminopiperidine-1-carboxylic acid tert-butyl ester

[Chemical Formula 57]

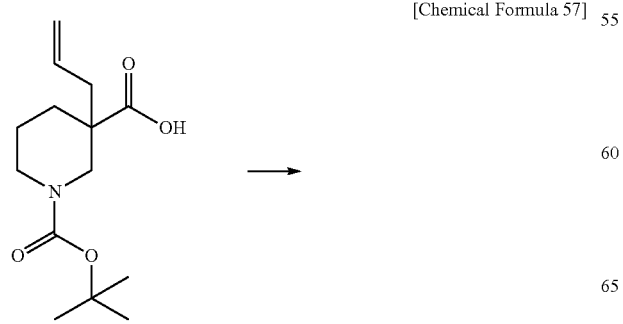

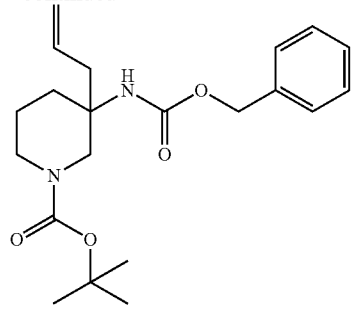

To a solution of an optically-active compound of 3-allylpiperidine-1,3-dicarboxylic acid 1-tert-butyl ester (32.2 g) and triethylamine (33.2 ml) in toluene (320 ml) heated to 80° C. was added dropwise diphenylphosphoryl azide (33.4 ml) over 50 minutes. The reaction mixture was stirred at the same temperature for 2 hours and cooled to room temperature. To the mixture were added benzyl alcohol (24.6 ml) and 4-dimethylaminopyridine (2.9 g). The mixture was stirred at 100° C. for 21 hours and cooled to room temperature. Then, thereto were added ethanol (200 ml) and water (200 ml), and the mixture was extracted with n-hexane (200 ml). The separated organic layer was sequentially washed with saturated aqueous ammonium chloride solution (200 ml) and saturated aqueous sodium chloride solution (150 ml), and concentrated under reduced pressure. The resulting residue was purified by silica gel column chromatography (eluent: n-hexane/ethyl acetate=1/0 to 6/1) to give the titled compound (39.4 g).

$^1$H-NMR (DMSO-D$_6$) δ: 7.39-7.27 (5H, m), 6.90-6.68 (1H, m), 5.75-5.63 (1H, m), 5.13-4.85 (4H, m), 4.07-3.94 (0.5H, m), 3.63-3.47 (1H, m), 3.39-3.12 (1H, m), 3.11-2.88 (1.5H, m), 2.79-2.54 (1H, m), 2.28-2.01 (1H, m), 1.79-1.66 (1H, m), 1.63-1.45 (3H, m), 1.36 (9H, s).

(7) Optically-Active Compound of 3-benzyloxycarbonylamino-3-(2-hydroxyethyl)piperidine-1-carboxylic acid tert-butyl ester

[Chemical Formula 58]

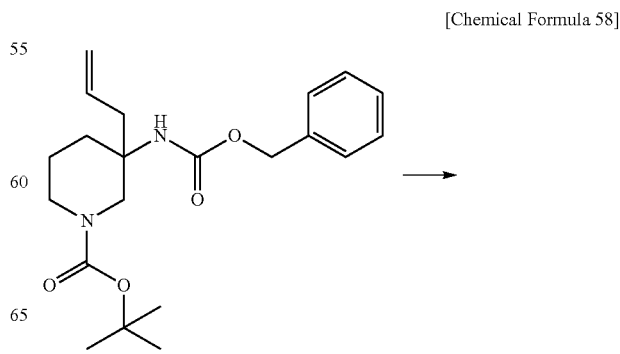

-continued

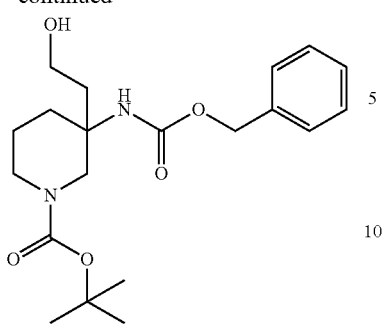

A solution of an optically-active compound 3-allyl-3-benzyloxycarbonylaminopiperidine-1-carboxylic acid tert-butyl ester (39.4 g) in chloroform/methanol (493 ml/493 ml) cooled to −78° C. was flowed ozone air for 1 hour. To the reaction mixture was added sodium borohydride (19.9 g) in small batches, and the mixture was warmed to 4° C. over 50 minutes. To the mixture were added saturated aqueous sodium bicarbonate solution (200 ml) and water (400 ml), and the mixture was extracted with chloroform (200 ml). The separated aqueous layer was extracted with chloroform (300 ml) again, and the combined organic layer was concentrated under reduced pressure. The resulting residue was slurry-washed with n-hexane/ethyl acetate (1/1, 394 ml) solution to give a solid (23.5 g). The filtrate was concentrated under reduced pressure, and the resulting residue was slurry-washed with n-hexane/ethyl acetate (1/1) solution again to give a solid (2.4 g). Then, the filtrate was concentrated under reduced pressure, and the resulting residue was purified by silica gel column chromatography (eluent: n-hexane/ethyl acetate=1/1 to 0/1) to give a solid (1.5 g). The solids were combined to give the titled compound (27.4 g).

$^1$H-NMR (DMSO-D$_6$) δ: 7.39-7.26 (5H, m), 6.90-6.62 (1H, m), 5.12-4.87 (2H, m), 4.36 (1H, t, J=4.9 Hz), 4.00-2.96 (6H, m), 2.15-1.72 (2H, m), 1.72-1.46 (2H, m), 1.46-1.17 (2H, m), 1.36 (9H, s).

(8) Optically-Active Compound of 3-amino-3-(2-hydroxyethyl)piperidine-1-carboxylic acid tert-butyl ester

[Chemical Formula 59]

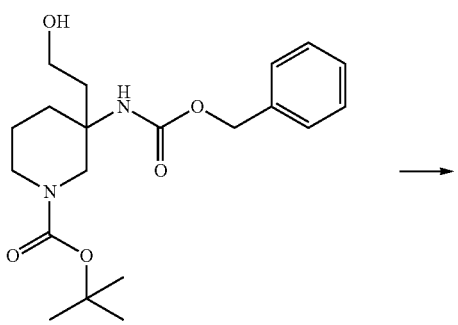

-continued

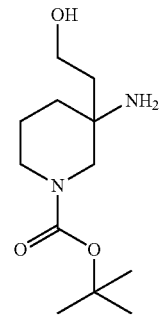

To a solution of an optically-active compound of 3-benzyloxycarbonylamino-3-(2-hydroxyethyl)piperidine-1-carboxylic acid tert-butyl ester (27.2 g) in methanol (544 ml) was added 10% palladium carbon (2.7 g), and the mixture was hydrogenated under ordinary pressure for 5 hours. The mixture was filtered through Celite, and the filtrate was concentrated under reduced pressure to give the titled compound (17.2 g).

$^1$H-NMR (DMSO-D$_6$) δ: 3.58-3.53 (2H, m), 3.43-2.85 (5H, m), 1.63-1.24 (6H, m), 1.39 (9H, s).

(9) Optically-Active Compound of 1,6-diazaspiro[3,5]-nonane-1,6-dicarboxylic acid 1-benzyl ester 6-tert-butyl ester

[Chemical Formula 60]

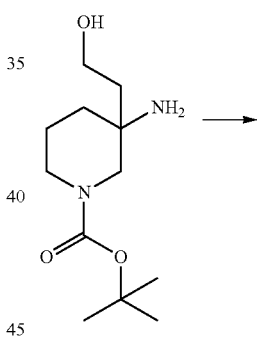

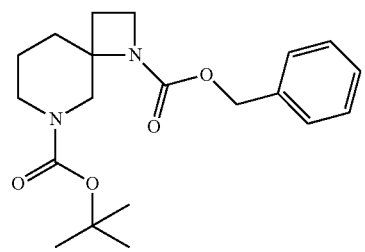

To a solution of an optically-active compound of 3-amino-3-(2-hydroxyethyl)piperidine-1-carboxylic acid tert-butyl ester (6.46 g), triphenylphosphine (12.5 g) and triethylamine (13.3 ml) in dichloromethane (226 ml) cooled to 0° C. was added carbon tetrabromide (15.8 g). The reaction mixture was stirred at room temperature for 40 minutes and cooled to 0° C. again. Then, thereto were added triethylamine (5.5 ml) and benzyl chloroformate (4.9 ml), and the mixture was stirred for 3.5 hours at room temperature. To the mixture was added water (200 ml), and the mixture was extracted with chloroform (100 ml). The organic layer was washed with saturated aqueous sodium chloride solution, and concentrated under reduced pressure. The resulting residue was purified by silica gel column chromatography (eluent: n-hexane/ethyl acetate=5/1) to give the titled compound (5.35 g).

$^1$H-NMR (DMSO-D$_6$) δ: 7.40-7.29 (5H, m), 5.07-4.98 (2H, m), 4.10-3.96 (1H, m), 3.91-3.69 (3H, m), 2.64-2.53 (1H, m), 2.13-1.83 (4H, m), 1.66-1.54 (1H, m), 1.43-1.27 (2H, m), 1.39 (9H, s).

(10) Optically-Active Compound of 1,6-diazaspiro[3.5]nonane-1-carboxylic acid benzyl ester

[Chemical Formula 61]

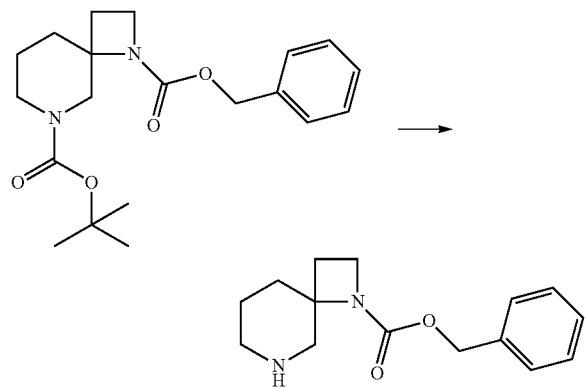

To a solution of an optically-active compound of 1,6-diazaspiro[3,5]-nonane-1,6-dicarboxylic acid 1-benzyl ester 6-tert-butyl ester (5.35 g) in chloroform (134 ml) cooled to 0° C. was added trifluoroacetic acid (27 ml), and the mixture was stirred for 30 minutes, warmed to room temperature and stirred for additional 30 minutes. The reaction mixture was cooled to 0° C., and thereto was added 4M aqueous sodium hydroxide solution (91 ml). The aqueous layer was extracted with chloroform (100 ml, 50 ml) twice, and the combined organic layer was washed with saturated aqueous sodium chloride solution and concentrated under reduced pressure. The resulting residue was purified by silica gel column chromatography (eluent: chloroform/methanol=20/1 to 4/1) to give the titled compound (2.37 g).

$^1$H-NMR (DMSO-D$_6$) δ: 7.41-7.28 (5H, m), 5.09-4.96 (2H, m), 3.83-3.76 (1H, m), 3.73-3.66 (1H, m), 2.94-2.69 (3H, m), 2.38-2.15 (2H, m), 2.12-1.77 (4H, m), 1.58-1.45 (1H, m), 1.38-1.26 (1H, m).

(11) Optically-Active Compound of 6-(7H-pyrrolo[2,3-d]pyrimidin-4-yl)-1,6-diazaspiro[3.5]nonane-1-carboxylic acid benzyl ester

[Chemical Formula 62]

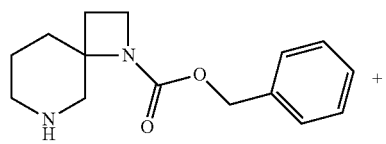 +

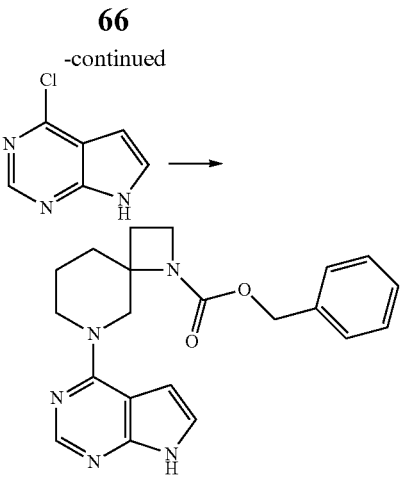

An optically-active compound of 1,6-diazaspiro[3.5]nonane-1-carboxylic acid benzyl ester (2.37 g) was mixed with 4-chloro-7H-pyrrolo[2,3-d]pyrimidine (1.4 g), potassium carbonate (3.8 g) and water (71 ml), and heated to 100° C. to stir for 3 hours. The mixture was cooled to room temperature. Then, thereto was added water and the mixture was extracted with ethyl acetate. The organic layer was washed with saturated aqueous sodium chloride solution and concentrated under reduced pressure. The resulting residue was slurry-washed with n-hexane/ethyl acetate (1/1) solution to give the titled compound (2.55 g).

$^1$H-NMR (DMSO-D$_6$) δ: 11.72 (1H, s), 8.13 (1H, s), 7.41-7.28 (5H, m), 7.19 (1H, dd, J=3.5, 2.6 Hz), 6.64-6.60 (1H, m), 5.13-5.02 (2H, m), 4.96-4.89 (1H, m), 4.64-4.56 (1H, m), 3.98-3.70 (2H, m), 3.46-3.28 (1H, m), 3.01-2.82 (1H, m), 2.31-2.22 (0.5H, m), 2.16-2.06 (0.5H, m), 2.03-1.90 (3H, m), 1.83-1.75 (1H, m), 1.61-1.47 (1H, m).

(12) Optically-Active Compound of 4-(1,6-diazaspiro[3.5]non-6-yl)-7H-pyrrolo[2,3-d]pyrimidine

[Chemical Formula 63]

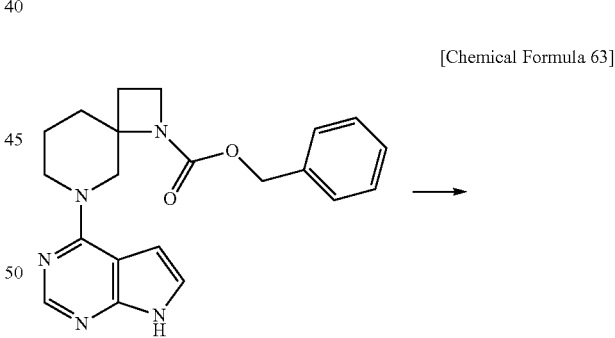

To a solution of an optically-active compound of 6-(7H-pyrrolo[2,3-d]pyrimidin-4-yl)-1,6-diazaspiro[3.5]nonane-1-carboxylic acid benzyl ester (2.55 g) in methanol/tetrahydrofuran (51 ml/51 ml) was added 20% palladium carbon (510 mg), and the mixture was hydrogenated under 4 atmospheres for 5 hours. The mixture was filtered through Celite, and the filtrate was concentrated under reduced pressure. The resulting residue was slurry-washed with diisopropyl ether (30 ml) to give the titled compound (1.55 g).

$^1$H-NMR (DMSO-D$_6$) δ: 11.68 (1H, br s), 8.12 (1H, s), 7.18 (1H, d, J=2.6 Hz), 6.61 (1H, d, J=3.2 Hz), 4.18 (1H, d, J=12.8 Hz), 4.00-3.93 (1H, m), 3.59 (1H, d, J=12.8 Hz), 3.54-3.47 (1H, m), 3.42-3.16 (3H, m), 2.03-1.82 (3H, m), 1.72-1.62 (2H, m), 1.57-1.46 (1H, m).

(13) Optically-Active Compound of 3-oxo-3-[6-(7H-pyrrolo[2,3-d]pyrimidin-4-yl)-1,6-diazaspiro[3.5]non-1-yl]-propionitrile

[Chemical Formula 64]

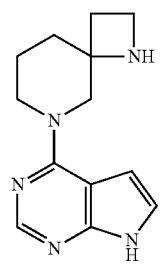
+
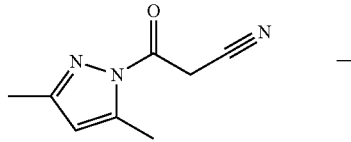
→
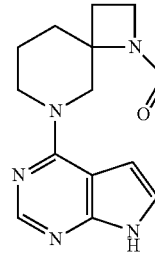

An optically-active compound of 4-(1,6-diazaspiro[3.5]non-6-yl)-7H-pyrrolo[2,3-d]pyrimidine (1.55 g) was mixed with 1-cyanoacetyl-3,5-dimethylpyrazole (1.56 g), N,N-diisopropylethylamine (1.66 ml) and 1,4-dioxane (31 ml), and the mixture was heated to 100° C. to stir for 2 hours. The mixture was cooled to room temperature. Then, thereto was added saturated aqueous sodium bicarbonate solution, and the mixture was extracted with ethyl acetate. The organic layer was washed with saturated aqueous sodium chloride solution, and concentrated under reduced pressure. The resulting residue was purified by silica gel column chromatography (eluent: ethyl acetate/methanol=20/1 to 9/1) to give the titled compound (1.50 g).

1H-NMR (DMSO-D6) δ: 11.73 (1H, br s), 8.13 (1H, s), 7.22-7.18 (1H, m), 6.67-6.63 (1H, m), 4.96 (1H, d, J=12.6 Hz), 4.68-4.60 (1H, m), 4.11-4.03 (1H, m), 4.01-3.93 (1H, m), 3.71 (2H, s), 3.53 (1H, d, J=12.6 Hz), 2.98-2.88 (1H, m), 2.40-2.30 (1H, m), 2.03-1.90 (3H, m), 1.83-1.75 (1H, m), 1.59-1.45 (1H, m).

[α]D=+210.00° (25° C., c=1.01, methanol)

Preparation 4

Synthesis of Compound 4

[Chemical Formula 65]

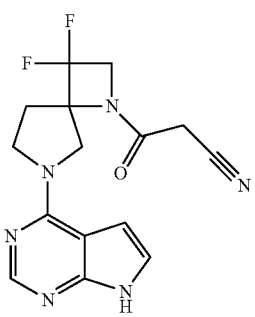

(1) Pyrrolidine-1,3-dicarboxylic acid 1-tert-butyl ester 3-(3,3-difluoroallyl)ester

[Chemical Formula 66]

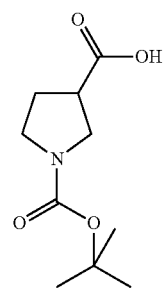 + 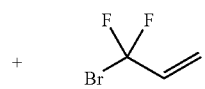 →

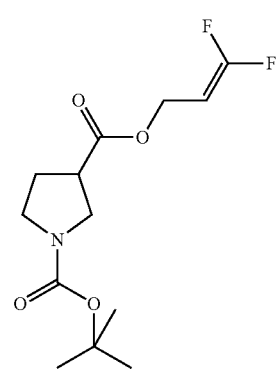

To a solution of pyrrolidine-1,3-dicarboxylic acid-1-tert-butyl ester (3.40 g) in N,N-dimethylformamide (34 ml) were added potassium carbonate (4.37 g) and 3-bromo-3,3-difluoropropene (1.93 ml), and the mixture was stirred at 60° C. for 6 hours. To the reaction mixture was added water, and the mixture was extracted with ethyl acetate. The organic layer was dried over anhydrous sodium sulfate, and concentrated under reduced pressure. The resulting residue was purified by silica gel column chromatography (eluent: n-hexane/ethyl acetate=5/1) to give the titled compound (3.73 g).

¹H-NMR (CDCl₃) δ: 4.64-4.48 (3H, m), 3.67-3.42 (3H, m), 3.41-3.29 (1H, m), 3.10-2.98 (1H, m), 2.18-2.04 (2H, m), 1.46 (9H, s).

(2) 3-(1,1-Difluoroallyl)pyrrolidine-1,3-dicarboxylic acid 1-tert-butyl ester

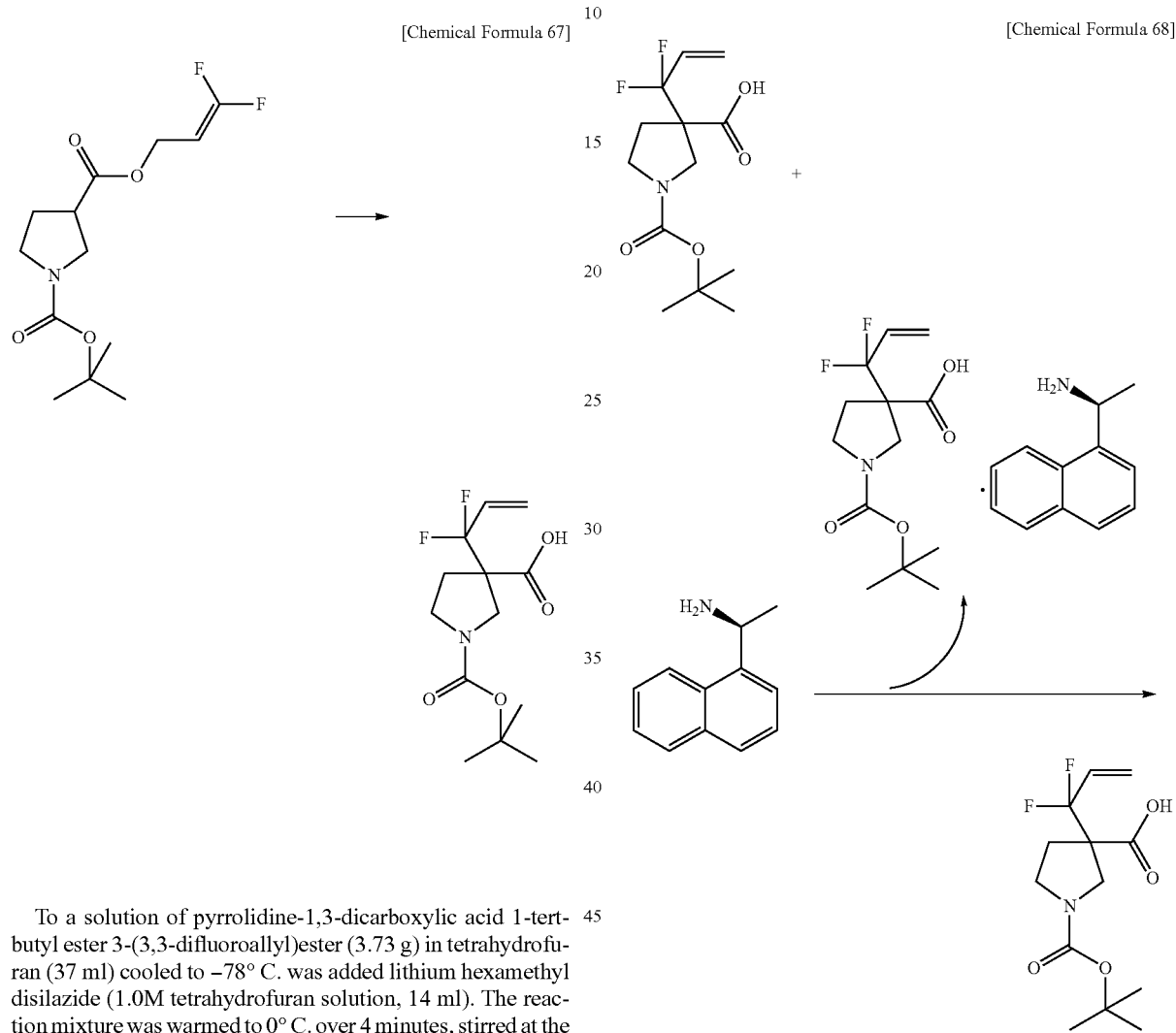

To a solution of pyrrolidine-1,3-dicarboxylic acid 1-tert-butyl ester 3-(3,3-difluoroallyl)ester (3.73 g) in tetrahydrofuran (37 ml) cooled to −78° C. was added lithium hexamethyl disilazide (1.0M tetrahydrofuran solution, 14 ml). The reaction mixture was warmed to 0° C. over 4 minutes, stirred at the same temperature for additional 14 minutes, and then cooled to −78° C. again. To the mixture was added trimethylsilyl chloride (2.0 ml). The reaction mixture was warmed to room temperature, and stirred at the same temperature for additional 3 hours. The mixture was basified by the addition of water, followed by 2M aqueous sodium hydroxide solution to pH 8 to 9, and washed with n-hexane/diethylether (4/3). To the separated organic layer was added n-hexane, and the mixture was extracted with 2M aqueous sodium hydroxide solution. The combined aqueous layer was washed with n-hexane/diethylether (4/3) 7 times, acidified by 10% aqueous citric acid solution, and extracted with ethyl acetate. The organic layer was concentrated under reduced pressure, and the resulting residue was slurry-washed with n-hexane/ethyl acetate (5/1) solution to give the titled compound (2.00 g).

¹H-NMR (DMSO-D₆) δ: 13.47 (1H, br s), 6.23-6.09 (1H, m), 5.71-5.64 (1H, m), 5.63-5.58 (1H, m), 3.79-3.72 (1H, m), 3.47-3.28 (2H, m), 3.26-3.15 (1H, m), 2.36-2.25 (1H, m), 2.21-2.06 (1H, m), 1.39 (9H, s).

(3) Optically-Active Compound of 3-(1,1-difluoroallyl)pyrrolidine-1,3-dicarboxylic acid 1-tert-butyl ester An optically-active compound of 3-(1,1-difluoroallyl)pyrrolidine-1,3-dicarboxylic acid 1-tert-butyl ester (1.5 g), (S)-(−)-1-(1-naphthyl)ethylamine (826 μl) and isopropyl acetate (15 ml) were combined, and the mixture was stirred at room temperature for 21 hours. The slurry mixture was filtered to remove a solid. The filtrate was concentrated under reduced pressure, and the resulting residue was mixed with ethyl acetate (20 ml) and 10% aqueous potassium bisulfate solution (20 ml). The mixture was stirred at 0° C. for 1 hour. The separated organic layer was sequentially washed with water and saturated aqueous sodium chloride solution, dried over anhydrous magnesium sulfate, and concentrated with under reduced pressure to give the titled compound (869 mg).

¹H-NMR (DMSO-D₆) δ: 13.47 (1H, br s), 6.23-6.09 (1H, m), 5.71-5.64 (1H, m), 5.63-5.58 (1H, m), 3.79-3.72 (1H, m), 3.47-3.28 (2H, m), 3.26-3.15 (1H, m), 2.36-2.25 (1H, m), 2.21-2.06 (1H, m), 1.39 (9H, s).

(4) Salt of an Optically-Active Compound of 3-(1,1-difluoroallyl)pyrrolidine-1,3-dicarboxylic acid 1-tert-butyl ester with (R)-(+)-1-(1-naphthyl)ethylamine

[Chemical Formula 69]

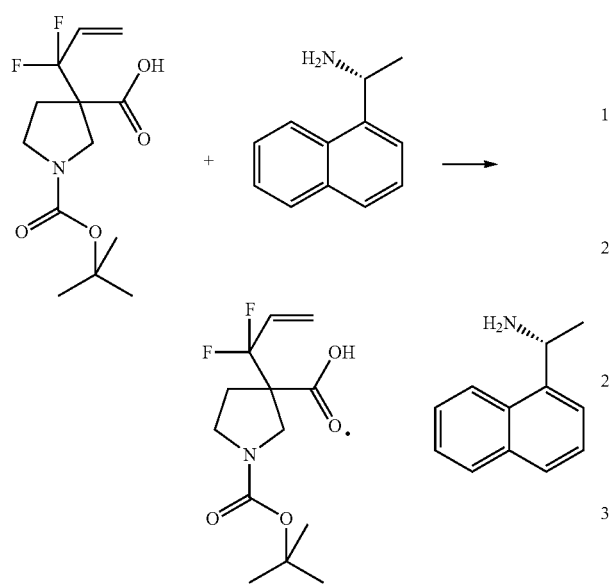

The residue (869 mg) obtained in (3) was mixed with (R)-(+)-1-(1-naphthyl)ethylamine (263 μl) and isopropyl acetate (13 ml), and the mixture was stirred at room temperature overnight. The slurry mixture was filtered, and the resulting solid was washed with isopropyl acetate (3 ml) to give the titled compound (754 mg). Analysis of the solid by HPLC analysis condition 1 showed that an isomer with longer retention times was a main product.

An isomer with shorter retention times (retention time 5.32 minutes)

An isomer with longer retention times (retention time 7.01 minutes)

(5) Optically-Active Compound of 3-(1,1-difluoroallyl)pyrrolidine-1,3-dicarboxylic acid 1-tert-butyl ester

[Chemical Formula 70]

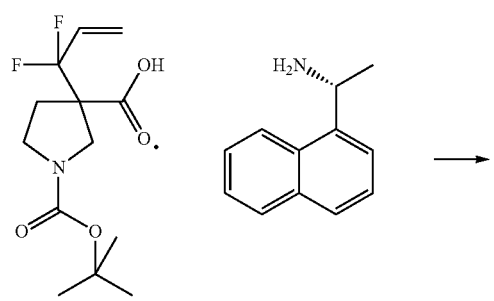

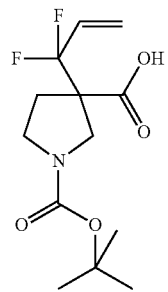

A salt of an optically-active compound of 3-(1,1-difluoroallyl)pyrrolidine-1,3-dicarboxylic acid 1-tert-butyl ester with (R)-(+)-1-(1-naphthyl)ethylamine (741 mg) was mixed with ethyl acetate (7.4 ml) and water (3.7 ml), and the mixture was acidified by the addition of potassium bisulfate (261 mg). The separated organic layer was washed with saturated aqueous sodium chloride solution, and concentrated under reduced pressure to give the titled compound (457 mg).

$^1$H-NMR (DMSO-D$_6$) δ: 13.47 (1H, br s), 6.23-6.09 (1H, m), 5.71-5.64 (1H, m), 5.63-5.58 (1H, m), 3.79-3.72 (1H, m), 3.47-3.28 (2H, m), 3.26-3.15 (1H, m), 2.36-2.25 (1H, m), 2.21-2.06 (1H, m), 1.39 (9H, s).

(6) Optically-Active Compound of 3-benzyloxycarbonylamino-3-(1,1-difluoroallyl)pyrrolidine-1-carboxylic acid tert-butyl ester

[Chemical Formula 71]

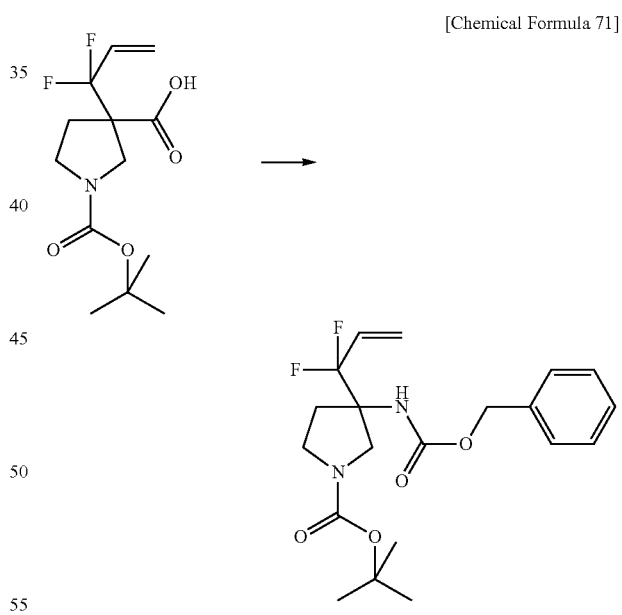

To a solution of an optically-active compound of 3-(1,1-difluoroallyl)pyrrolidine-1,3-dicarboxylic acid 1-tert-butyl ester (10.6 g) and triethylamine (10.2 ml) in toluene (106 ml) heated to 100° C. was added dropwise diphenylphosphoryl azide (10.2 ml). The reaction mixture was stirred at 100° C. for 50 minutes, and then thereto were added benzyl alcohol (5.6 ml) and 4-dimethylaminopyridine (0.89 g). The mixture was stirred at 100° C. for 16.5 hours, and then cooled to room temperature. Then, thereto was added 5% aqueous potassium bisulfate solution, and the mixture was extracted with toluene. The organic layer was sequentially washed with 1M aqueous sodium hydroxide solution and saturated aqueous sodium chloride solution, dried over anhydrous sodium sulfate and concentrated under reduced pressure. The resulting residue was purified by silica gel column chromatography (eluent: n-hexane/chloroform/ethyl acetate=5/4/1 to 4/4/1) to give the titled compound (15.5 g).

$^1$H-NMR (CDCl$_3$) δ: 7.40-7.30 (5.0H, m), 6.04-5.89 (1.0H, m), 5.76-5.68 (1.0H, m), 5.56-5.49 (1.0H, m), 5.07 (2.0H, s), 4.90-4.83 (1.0H, m), 3.85-3.79 (0.5H, m), 3.74-3.40 (3.5H, m), 2.90-2.76 (0.5H, m), 2.63-2.49 (0.5H, m), 2.27-2.18 (1.0H, m), 1.46 (9.0H, s).

(7) Optically-Active Compound of 3-benzyloxycarbonylamino-3-(1,1-difluoro-2-hydroxyethyl)pyrrolidine-1-carboxylic acid tert-butyl ester

[Chemical Formula 72]

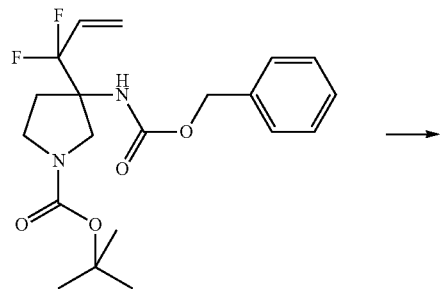

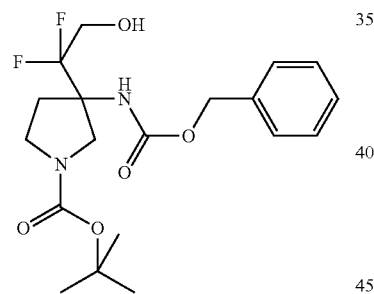

A solution of an optically-active compound of 3-benzyloxycarbonylamino-3-(1,1-difluoroallyl)pyrrolidine-1-carboxylic acid tert-butyl ester (15.5 g) in chloroform/methanol (154 ml/154 ml) cooled to −78° C. was flowed ozone air for 30 minutes. To the reaction mixture was added sodium borohydride (4.14 g) in small batches, and then the mixture was warmed to 0° C. and stirred at the same temperature for additional 4 hours. To the mixture were added saturated aqueous sodium bicarbonate solution and saturated aqueous sodium chloride solution, and the mixture was extracted with chloroform. The separated aqueous layer was extracted with ethyl acetate. The combined organic layer was dried over anhydrous sodium sulfate, and concentrated under reduced pressure. The resulting residue was purified by silica gel column chromatography (eluent: n-hexane/ethyl acetate=3/1). The fractions which could not be separated and isolated were concentrated under reduced pressure, and the resulting residue was purified by silica gel column chromatography (eluent: n-hexane/chloroform/ethyl acetate=5/4/1) again. The purified fractions were combined and concentrated under reduced pressure to give the titled compound (12.8 g).

$^1$H-NMR (CDCl$_3$) δ: 7.42-7.32 (5.0H, m), 5.15-5.07 (2.0H, m), 5.04-4.93 (1.0H, m), 4.02-3.49 (6.0H, m), 3.43-3.30 (1.0H, m), 2.67-2.57 (0.4H, m), 2.45-2.28 (1.6H, m), 1.46 (9.0H, s).

(8) Optically-Active Compound of 3-benzyloxycarbonylamino-3-(1,1-difluoro-2-methanesulfonyloxyethyl)pyrrolidine-1-carboxylic acid tert-butyl ester

[Chemical Formula 73]

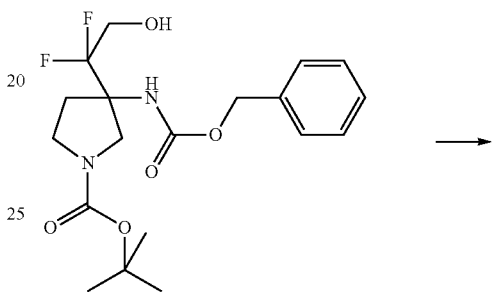

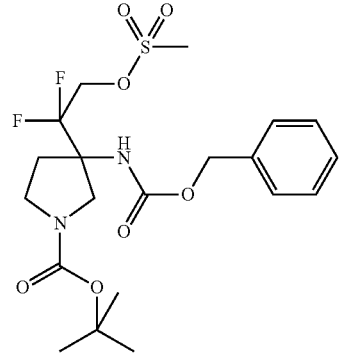

To a solution of an optically-active compound of 3-benzyloxycarbonylamino-3-(1,1-difluoro-2-hydroxyethyl)pyrrolidine-1-carboxylic acid tert-butyl ester (471 mg) and triethylamine (328 µl) in chloroform (4.7 ml) cooled to 0° C. was added methanesulfonyl chloride (118 µl), and the mixture was stirred for 50 minutes. To the mixture was added 5% aqueous potassium bisulfate solution, and the mixture was extracted with ethyl acetate. The organic layer was sequentially washed with 1M aqueous sodium hydroxide solution and saturated aqueous sodium chloride solution, dried over anhydrous sodium sulfate and concentrated under reduced pressure to give the titled compound (565 mg).

$^1$H-NMR (CDCl$_3$) δ: 7.41-7.33 (5H, m), 5.10 (2H, s), 4.94-4.86 (1H, m), 4.57-4.48 (2H, m), 3.92-3.84 (0.5H, m), 3.80-3.52 (2.5H, m), 3.47-3.33 (1H, m), 3.09 (3H, s), 2.83-2.74 (0.5H, m), 2.61-2.52 (0.5H, m), 2.31-2.21 (1H, m), 1.47 (9H, s).

(9) Optically-Active Compound of 3,3-difluoro-1,6-diazaspiro[3,4]octane-1,6-dicarboxylic acid 1-benzyl ester 6-tert-butyl ester

[Chemical Formula 74]

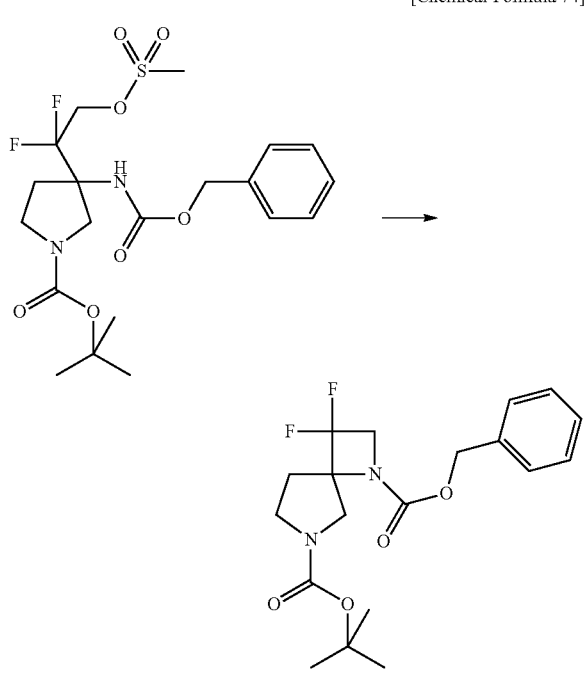

To a solution of an optically-active compound of 3-benzyloxycarbonylamino-3-(1,1-difluoro-2-methanesulfonyloxy-ethyl)pyrrolidine-1-carboxylic acid tert-butyl ester (565 mg) in N,N-dimethylformamide (17 ml) cooled to 0° C. was added sodium hydride (71 mg, with 40% mineral oil), and the mixture was stirred at the same temperature for 1 hour. To the reaction mixture was added water, and the mixture was extracted with ethyl acetate. The organic layer was washed with saturated aqueous sodium chloride solution, dried over anhydrous sodium sulfate and concentrated under reduced pressure to give the titled compound (397 mg).

$^1$H-NMR (CDCl$_3$) δ: 7.41-7.31 (5H, m), 5.25-5.06 (2H, m), 4.27-4.17 (2H, m), 3.96-3.82 (1H, m), 3.79-3.49 (2H, m), 3.41-3.27 (1H, m), 2.65-2.41 (0.5H, m), 2.38-2.17 (1.5H, m), 1.50-1.44 (9H, m).

(10) Optically-Active Compound of 3,3-difluoro-1,6-diazaspiro[3,4]octane-6-carboxylic acid tert-butyl ester

[Chemical Formula 75]

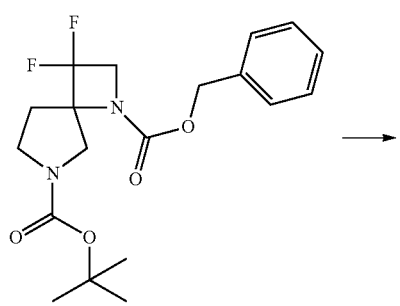

→

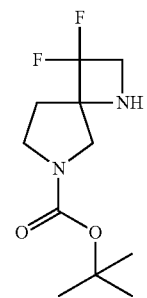

To a solution of an optically-active compound of 3,3-difluoro-1,6-diazaspiro[3,4]octane-1,6-dicarboxylic acid 1-benzyl ester 6-tert-butyl ester (397 mg) in methanol/tetrahydrofuran (3.2 ml/3.2 ml) was added 10% palladium carbon (79 mg), and the mixture was hydrogenated at room temperature under ordinary pressure for 14 hours. The mixture was filtered through Celite, and the filtrate was concentrated under reduced pressure. The resulting residue was purified by silica gel column chromatography (eluent: chloroform/acetone=4/1 to 2/1). The fractions which could not be separated and isolated were concentrated under reduced pressure, and the resulting residue was purified by silica gel column chromatography (eluent: chloroform/acetone=2/1 to 1/1) again. The purified fractions were combined and concentrated under reduced pressure to give the titled compound (211 mg).

$^1$H-NMR (CDCl$_3$) δ: 3.96-3.74 (3H, m), 3.55-3.37 (2H, m), 3.35-3.25 (1H, m), 2.45-2.35 (1H, m), 2.00-1.88 (1H, m), 1.73-1.56 (1H, m), 1.46 (9H, s).

(11) 3,3-Difluoro-1,6-diazaspiro[3,4]octane 2 hydrochloride

[Chemical Formula 76]

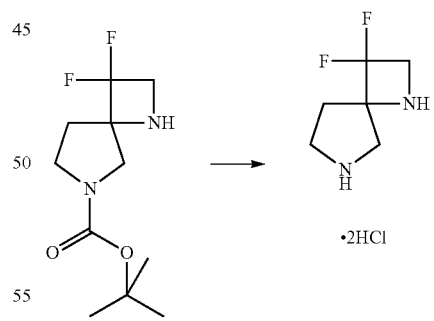

To an optically-active compound of 3,3-difluoro-1,6-diazaspiro[3,4]octane-6-carboxylic acid tert-butyl ester (211 mg) were added 4M hydrochloric acid-1,4-dioxane (2.1 ml) and 2M hydrochloric acid-methanol (2.1 ml), and the mixture was stirred at room temperature for 45 minutes. To the reaction mixture was added ethyl acetate, and the mixture was filtered to give the titled compound (163 mg).

$^1$H-NMR (DMSO-D$_6$) δ: 9.80-9.42 (2H, m), 4.58-3.83 (7H, m), 3.47-3.33 (2H, m), 2.82-2.72 (1H, m).

(12) Optically-Active Compound of 4-(3,3-difluoro-1,6-diazaspiro[3,4]oct-6-yl)-7H-pyrrolo[2,3-d]pyrimidine

[Chemical Formula 77]

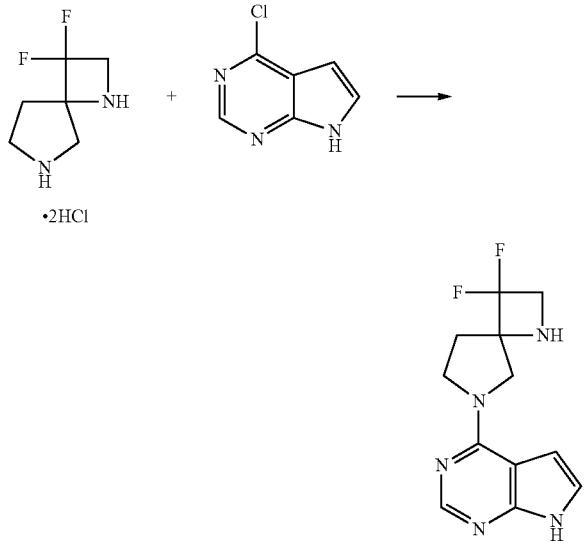

An optically-active compound of 3,3-difluoro-1,6-diazaspiro[3,4]octane 2 hydrochloride (163 mg) was mixed with 4-chloro-7H-pyrrolo[2,3-d]pyrimidine (113 mg), potassium carbonate (509 mg) and water (2.8 ml), and the mixture was stirred for 16.5 hours with refluxing. The mixture was cooled to room temperature. Thereto was added water, and the mixture was filtered to give a solid (126 mg). The filtrate was extracted with ethyl acetate/methanol 4 times and chloroform/methanol twice. The combined organic layer was dried over anhydrous sodium sulfate and concentrated under reduced pressure. The resulting residue was combined with the solid and purified by silica gel column chromatography (eluent: chloroform/methanol=92/8 to 85/15) to give the titled compound (170 mg).

$^1$H-NMR (DMSO-D$_6$) δ: 11.63 (1H, br s), 8.10 (1H, s), 7.14 (1H, dd, J=3.6, 2.4 Hz), 6.57 (1H, dd, J=3.6, 2.0 Hz), 4.15 (1H, d, J=11.7 Hz), 3.92-3.65 (5H, m), 3.35-3.22 (1H, m), 2.47-2.39 (1H, m), 2.17-2.07 (1H, m).

(13) Optically-Active Compound of 3-[3,3-difluoro-6-(7H-pyrrolo[2,3-d]pyrimidin-4-yl)-1,6-diazaspiro[3.4]oct-1-yl]-3-oxopropionitrile

[Chemical Formula 78]

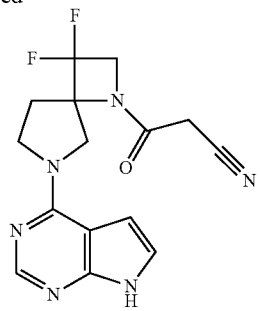

An optically-active compound of 4-(3,3-difluoro-1,6-diazaspiro[3,4]oct-6-yl)-7H-pyrrolo[2,3-d]pyrimidine (170 mg) was mixed with 1-cyanoacetyl-3,5-dimethylpyrazole (209 mg), N,N-diisopropylethylamine (117 μl) and 1,4-dioxane (3.4 ml), and the mixture was stirred at 100° C. for 75 minutes. The mixture was cooled to room temperature. Thereto was added saturated aqueous sodium bicarbonate solution, and the mixture was extracted with ethyl acetate. The separated aqueous layer was extracted with ethyl acetate twice again. The combined organic layer was washed with saturated aqueous sodium chloride solution, dried over anhydrous sodium sulfate and concentrated under reduced pressure. The resulting residue was purified by silica gel column chromatography (eluent: chloroform/ethyl acetate=2/1, followed by chloroform/methanol=92/8 to 3/1). The mixture was concentrated under reduced pressure, and the resulting residue was slurry-washed with a mixed solvent of n-heptane/ethanol (3/1) to give the titled compound (177 mg).

$^1$H-NMR (DMSO-D$_6$) δ: 11.68 (1H, br s), 8.11 (1H, s), 7.17-7.14 (1H, m), 6.58 (1H, dd, J=3.3, 1.8 Hz), 4.66-4.58 (2H, m), 4.24-4.13 (2H, m), 4.12-4.02 (1H, m), 3.89-3.78 (3H, m), 2.68-2.58 (1H, m), 2.56-2.45 (1H, m).

[α]D=+46.67° (25° C., c=0.54, methanol)

Preparation 5

Synthesis of Compound 5

[Chemical Formula 79]

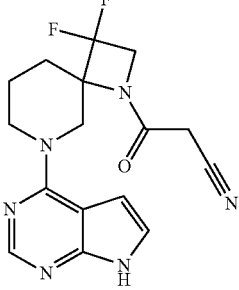

(1) Piperidine-1,3-dicarboxylic acid 1-tert-butyl ester 3-(3,3-difluoro-allyl)ester

[Chemical Formula 80]

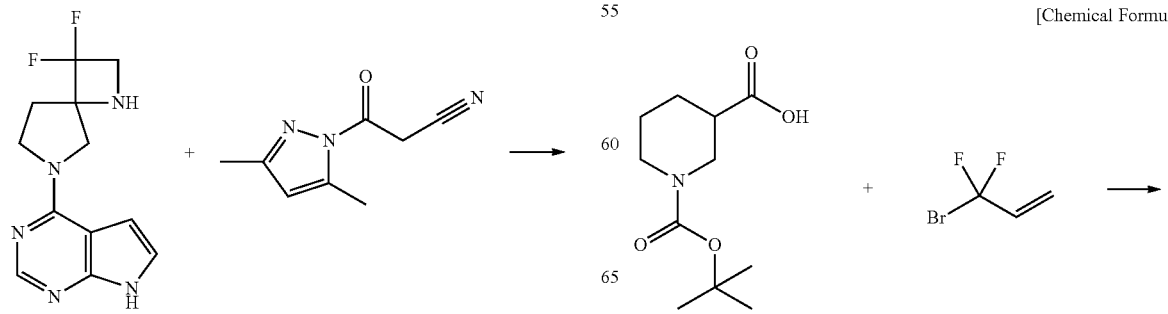

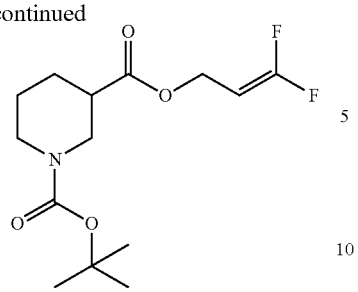

To a solution of piperidine-1,3-dicarboxylic acid 1-tert-butyl ester (30.0 g) in N,N-dimethylformamide (300 ml) were added potassium carbonate (36.2 g) and 3-bromo-3,3-difluoropropene (16 ml), and the mixture was stirred at 60° C. for 4.5 hours. To the reaction mixture was added water, and the mixture was extracted with n-hexane/ethyl acetate (1/1) solution. The organic layer was dried over anhydrous sodium sulfate, and concentrated under reduced pressure. The resulting residue was purified by silica gel column chromatography (eluent: n-hexane/ethyl acetate=10/1) to give the titled compound (33.5 g).
$^1$H-NMR (CDCl$_3$) δ: 4.62-4.46 (3H, m), 4.34-3.98 (1H, m), 3.95-3.80 (1H, m), 3.18-2.89 (1H, m), 2.87-2.77 (1H, m), 2.50-2.40 (1H, m), 2.08-1.98 (1H, m), 1.75-1.55 (2H, m), 1.52-1.41 (1H, m), 1.46 (9H, s).

(2) 3-(1,1-Difluoro-allyl)-piperidine-1,3-dicarboxylic acid 1-tert-butyl ester

[Chemical Formula 81]

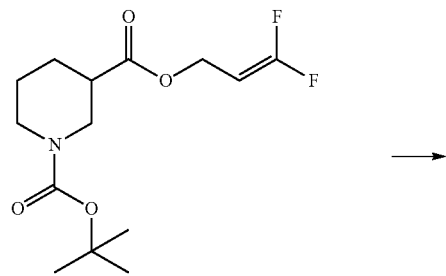

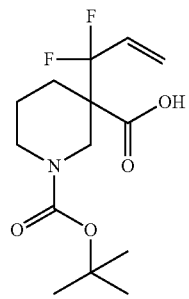

To a solution of piperidine-1,3-dicarboxylic acid 1-tert-butyl ester 3-(3,3-difluoro-allyl)ester (28.5 g) in tetrahydrofuran (285 ml) cooled to −78° C. was added lithium hexamethyl disilazide (1.1M tetrahydrofuran solution, 110 ml). The reaction mixture was warmed to −2° C. over 6 minutes, stirred at the same temperature for additional 15 minutes, and then cooled to −78° C. again. To the mixture was added trimethylsilyl chloride (19 ml). The reaction mixture was warmed to room temperature, and stirred at the same temperature for additional 30 minutes. The mixture was basified by the addition of water (300 ml), followed by 2M aqueous sodium hydroxide solution (60 ml), and washed with n-hexane (450 ml). The separated organic layer was extracted with 2M aqueous sodium hydroxide solution 3 times. The combined aqueous layer was acidified by 10% aqueous citric acid solution and extracted with ethyl acetate. The organic layer was concentrated under reduced pressure, and the resulting residue was slurry-washed with n-hexane/ethyl acetate (5/1) solution to give the titled compound (23.9 g).
$^1$H-NMR (CDCl$_3$) δ: 6.05-5.89 (1H, m), 5.72-5.65 (1H, m), 5.56-5.52 (1H, m), 4.67 (1H, d, J=13.7 Hz), 4.12-4.02 (1H, m), 3.46 (1H, br s), 2.92 (1H, d, J=13.7 Hz), 2.70-2.61 (1H, m), 2.37-2.30 (1H, m), 1.71-1.54 (3H, m), 1.45 (9H, s).

(3) Optically-Active Compound of 3-(1,1-difluoro-allyl)-piperidine-1,3-dicarboxylic acid 1-tert-butyl ester

[Chemical Formula 82]

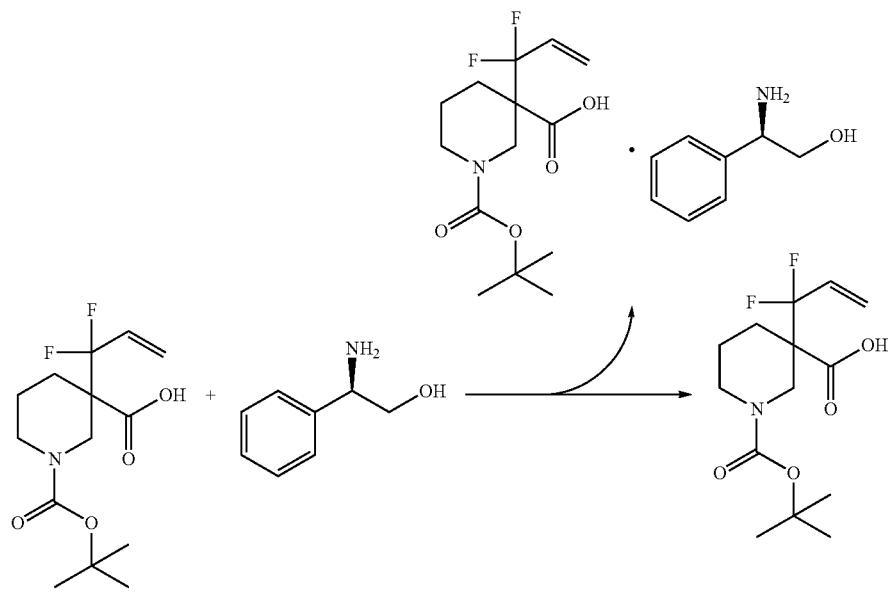

An optically-active compound of 3-(1,1-difluoro-allyl)-piperidine-1,3-dicarboxylic acid 1-tert-butyl ester (26.9 g), (R)-(−)-2-amino-2-phenyl-ethanol (6.6 g) and isopropanol (270 ml) were mixed, and the mixture was stirred at room temperature overnight. The slurry mixture was filtered to remove a solid. The filtrate was concentrated under reduced pressure, and the resulting residue was mixed with ethyl acetate (97 ml) and 25% aqueous potassium bisulfate solution (97 ml), and the mixture was stirred for 25 minutes. The separated organic layer was sequentially washed with 5% aqueous potassium bisulfate solution and saturated aqueous sodium chloride solution, dried over anhydrous sodium sulfate and concentrated under reduced pressure to give the titled compound (16.2 g).

$^1$H-NMR (CDCl$_3$) δ: 6.05-5.89 (1H, m), 5.72-5.65 (1H, m), 5.56-5.52 (1H, m), 4.67 (1H, d, J=13.7 Hz), 4.12-4.02 (1H, m), 3.46 (1H, br s), 2.92 (1H, d, J=13.7 Hz), 2.70-2.61 (1H, m), 2.37-2.30 (1H, m), 1.71-1.54 (3H, m), 1.45 (9H, s).

(4) Salt of an Optically-Active Compound of 3-(1,1-difluoro-allyl)-piperidine-1,3-dicarboxylic acid 1-tert-butyl ester with (S)-(+)-2-amino-2-phenyl-ethanol

[Chemical Formula 83]

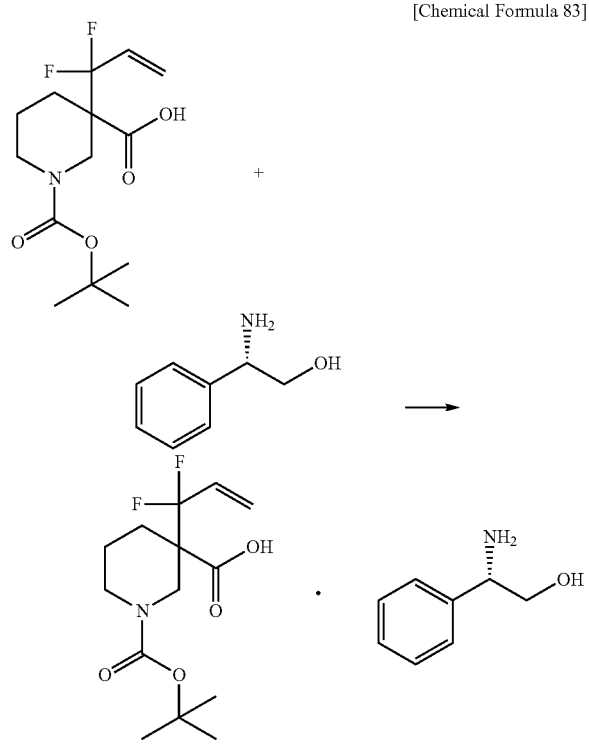

The residue (16.2 g) obtained in (3) was mixed with (S)-(+)-2-amino-2-phenyl-ethanol (6.6 g) and isopropanol (162 ml), and the mixture was stirred at room temperature for 20 hours. The slurry mixture was filtered, and the resulting solid was washed with isopropanol (80 ml) to give a solid (17.8 g). The solid was mixed with isopropanol (305 ml), and stirred at 105° C. for 20 minutes and at room temperature for 19 hours. The slurry mixture was filtered, and the resulting solid was washed with isopropanol (90 ml) to give the titled compound (16.0 g). An analysis by HPLC analysis condition 1 showed that an isomer with longer retention times was a main product.

An isomer with shorter retention times (retention time 5.41 minutes)

An isomer with longer retention times (retention time 12.47 minutes)

(5) Optically-Active Compound of 3-(1,1-difluoro-allyl)-piperidine-1,3-dicarboxylic acid 1-tert-butyl ester

[Chemical Formula 84]

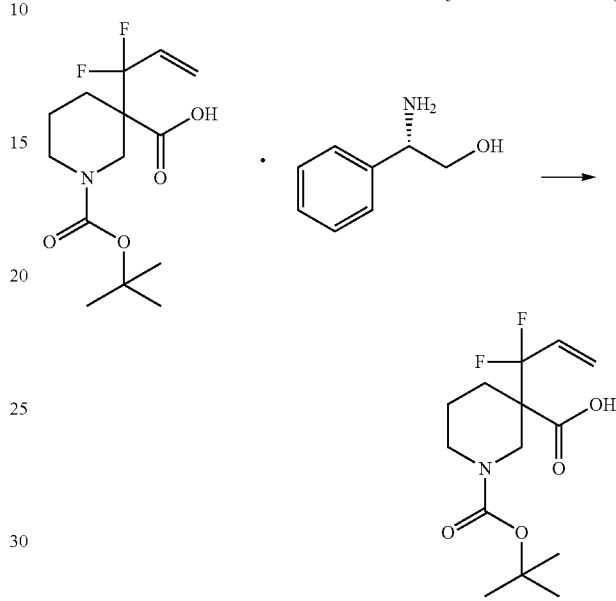

To a salt of an optically-active compound of 3-(1,1-difluoro-allyl)-piperidine-1,3-dicarboxylic acid 1-tert-butyl ester with (S)-(+)-2-amino-2-phenyl-ethanol (17.8 g) were added ethyl acetate (89 ml) and 25% aqueous potassium bisulfate solution (89 ml), and the mixture was stirred for 15 minutes. The separated organic layer was sequentially washed with 5% aqueous potassium bisulfate solution (89 ml) and saturated aqueous sodium chloride solution, dried over anhydrous sodium sulfate and concentrated under reduced pressure to give the titled compound (12.3 g).

$^1$H-NMR (CDCl$_3$) δ: 6.05-5.89 (1H, m), 5.72-5.65 (1H, m), 5.56-5.52 (1H, m), 4.67 (1H, d, J=13.7 Hz), 4.12-4.02 (1H, m), 3.46 (1H, br s), 2.92 (1H, d, J=13.7 Hz), 2.70-2.61 (1H, m), 2.37-2.30 (1H, m), 1.71-1.54 (3H, m), 1.45 (9H, s).

(6) Optically-Active Compound of 3-benzyloxycarbonylamino-3-(1,1-difluoro-allyl)-piperidine-1-carboxylic acid tert-butyl ester

[Chemical Formula 85]

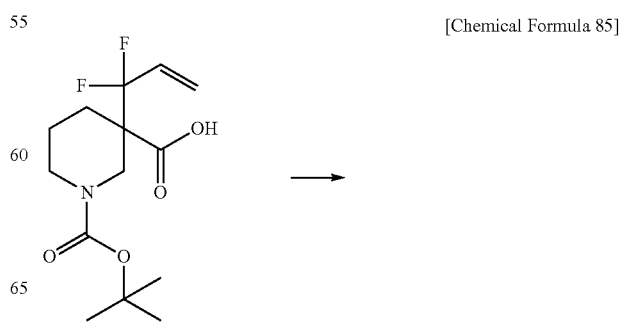

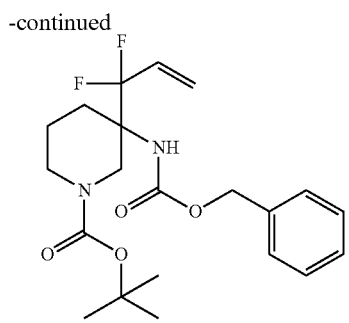

To a solution of an optically-active compound of 3-(1,1-difluoro-allyl)-piperidine-1,3-dicarboxylic acid 1-tert-butyl ester (12.3 g) and triethylamine (11.2 ml) in toluene (123 ml) heated to 100° C. was added dropwise diphenylphosphoryl azide (11.2 ml). The reaction mixture was stirred at 100° C. for 25 minutes, and then thereto were added benzyl alcohol (6.2 ml) and 4-dimethylaminopyridine (0.98 g). The mixture was stirred at 100° C. overnight, and then cooled to room temperature and concentrated under reduced pressure. The resulting residue was purified by silica gel column chromatography (eluent: n-hexane/ethyl acetate=9/1 to 85/15) to give the titled compound (15.1 g).

$^1$H-NMR (CDCl$_3$) δ: 7.38-7.28 (5H, m), 6.07-5.92 (1H, m), 5.71-5.62 (1H, m), 5.53-5.48 (1H, m), 5.36 (0.5H, br s), 5.09-4.97 (2H, m), 4.89 (0.5H, br s), 4.28-3.98 (2H, m), 3.16-2.61 (3H, m), 1.64-1.52 (3H, m), 1.49-1.36 (9H, m).

(7) Optically-Active Compound of 3-benzyloxycarbonylamino-3-(1,1-difluoro-2-hydroxy-ethyl)-piperidine-1-carboxylic acid tert-butyl ester

[Chemical Formula 86]

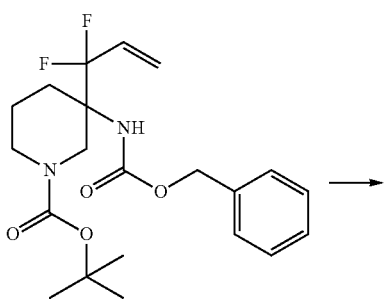

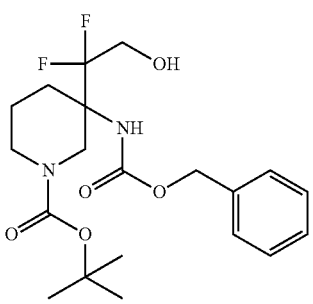

A solution of an optically-active compound of 3-benzyloxycarbonylamino-3-(1,1-difluoro-allyl)-piperidine-1-carboxylic acid tert-butyl ester (15.1 g) in chloroform/methanol (150 ml/150 ml) cooled to −78° C. was flowed ozone air for 30 minutes. To the reaction mixture was added sodium borohydride (4.2 g) in small batches, and then the mixture was warmed to 0° C. and stirred at the same temperature for additional 50 minutes. To the mixture were added saturated aqueous sodium bicarbonate solution and saturated aqueous sodium chloride solution, and the mixture was extracted with chloroform. The separated aqueous layer was extracted with ethyl acetate. The combined organic layer was dried over anhydrous sodium sulfate, and concentrated under reduced pressure. The resulting residue was purified by silica gel column chromatography (eluent: n-hexane/ethyl acetate=3/1 to 2/1) to give the titled compound (13.6 g).

$^1$H-NMR (CDCl$_3$) δ: 7.38-7.29 (5H, m), 5.78 (1H, br s), 5.15-4.99 (2H, m), 4.42-3.97 (2H, m), 3.95-3.75 (2H, m), 3.55-3.44 (1H, m), 3.15-2.60 (3H, m), 1.79-1.67 (1H, m), 1.55-1.50 (1H, m), 1.42 (9H, s).

(8) Optically-Active Compound of 3-benzyloxycarbonylamino-3-(1,1-difluoro-2-methanesulfonyloxy-ethyl)-piperidine-1-carboxylic acid tert-butyl ester

[Chemical Formula 87]

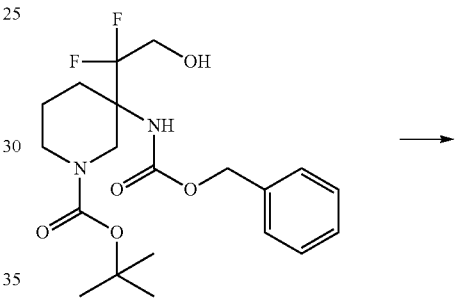

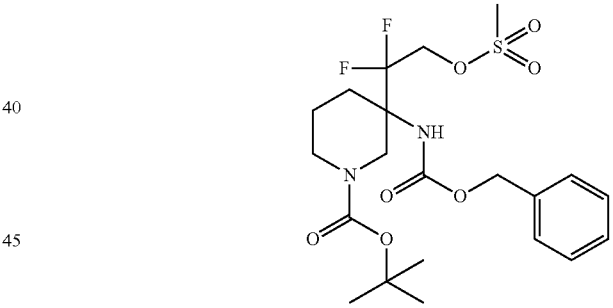

To a solution of an optically-active compound of 3-benzyloxycarbonylamino-3-(1,1-difluoro-2-hydroxy-ethyl)-piperidine-1-carboxylic acid tert-butyl ester (13.6 g) and triethylamine (11.4 ml) in chloroform (136 ml) cooled to 0° C. was added methanesulfonyl chloride (7.8 ml), and the mixture was stirred for 50 minutes. To the mixture was added 5% aqueous potassium bisulfate solution, and the mixture was extracted with ethyl acetate. The separated organic layer was sequentially washed with 4M aqueous sodium hydroxide solution twice and saturated aqueous sodium chloride solution once, dried over anhydrous sodium sulfate, and concentrated under reduced pressure to give the titled compound (17.1 g).

$^1$H-NMR (CDCl$_3$) δ: 7.39-7.29 (5H, m), 5.65 (1H, br s), 5.15-4.97 (2H, m), 4.65-4.51 (2H, m), 4.39-3.98 (2H, m), 3.15-2.62 (3H, m), 3.07 (3H, s), 1.70-1.53 (3H, m), 1.43 (9H, s).

(9) Optically-Active Compound of 3,3-difluoro-1,6-diaza-spiro[3.5]nonane-1,6-dicarboxylic acid 1-benzyl ester 6-tert-butyl ester

[Chemical Formula 88]

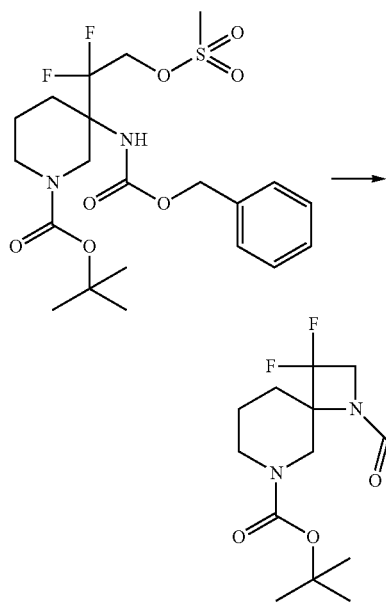

To a suspension of sodium hydride (1.7 g, with 40% mineral oil) in N,N-dimethylformamide (428 ml) cooled to 0° C. was added a solution of an optically-active compound of 3-benzyloxycarbonylamino-3-(1,1-difluoro-2-methanesulfonyloxy-ethyl)-piperidine-1-carboxylic acid tert-butyl ester (17.1 g) in N,N-dimethylformamide (86 ml), and the mixture was stirred at the same temperature for 15 minutes. To the reaction mixture was added water, and the mixture was extracted with ethyl acetate. The separated organic layer was sequentially washed with water and saturated aqueous sodium chloride solution, dried over anhydrous sodium sulfate and concentrated under reduced pressure. The resulting residue was purified by silica gel column chromatography (eluent: n-hexane/ethyl acetate=5/1) to give the titled compound (12.6 g).

$^1$H-NMR (CDCl$_3$) δ: 7.41-7.30 (5H, m), 5.21-5.02 (2H, m), 4.56-4.31 (1H, m), 4.25-4.14 (2H, m), 4.13-3.89 (1H, m), 3.41-2.98 (1H, m), 2.80-2.41 (1H, m), 2.33-2.12 (1H, m), 2.03-1.87 (1H, m), 1.80-1.67 (1H, m), 1.65-1.52 (2H, m), 1.45 (9H, s).

(10) Optically-Active Compound of 3,3-difluoro-1,6-diaza-spiro[3.5]nonane-1-carboxylic acid benzyl ester 1 hydrochloride

[Chemical Formula 89]

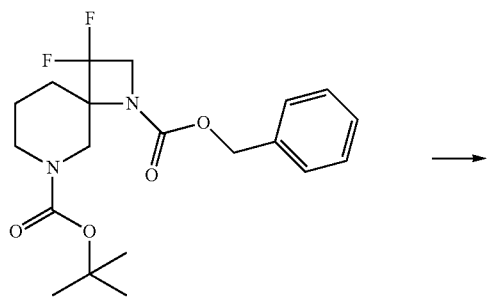

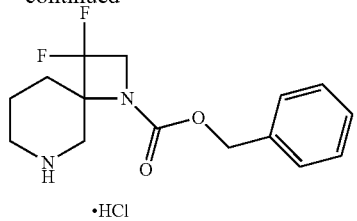

To an optically-active compound of 3,3-difluoro-1,6-diaza-spiro[3.5]nonane-1,6-dicarboxylic acid 1-benzyl ester 6-tert-butyl ester (12.6 g) was added 4M hydrochloric acid-1,4-dioxane (126 ml), and the mixture was stirred at room temperature for 30 minutes. The mixture was concentrated under reduced pressure, and thereto was added toluene. The mixture was concentrated under reduced pressure again to give the titled compound (11.2 g).

$^1$H-NMR (CDCl$_3$) δ: 11.56 (1H, br s), 8.65 (1H, br s), 7.43-7.32 (5H, m), 5.13 (2H, s), 4.43-4.20 (2H, m), 3.82-3.72 (1H, m), 3.54-3.35 (2H, m), 3.28-3.14 (1H, m), 2.34-1.91 (4H, m).

(11) Optically-Active Compound of 3,3-difluoro-6-(7H-pyrrolo[2,3-d]pyrimidin-4-yl)-1,6-diaza-spiro[3.5]nonane-1-carboxylic acid benzyl ester

[Chemical Formula 90]

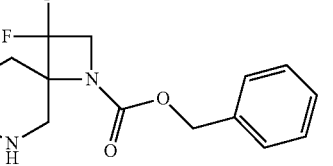

An optically-active compound of 3,3-difluoro-1,6-diaza-spiro[3.5]nonane-1-carboxylic acid benzyl ester 1 hydrochloride (11.2 g) was mixed with 4-chloro-7H-pyrrolo[2,3-d]pyrimidine (4.2 g), potassium carbonate (18.7 g) and water (104 ml), and the mixture was stirred for 16.5 hours with refluxing. The mixture was cooled to room temperature, and thereto were added ethyl acetate and water. The mixture was filtered, and the filtrate was separated and the resulting organic layer was washed with saturated aqueous sodium chloride solution, dried over anhydrous sodium sulfate and concentrated under reduced pressure. The resulting residue was purified by silica gel column chromatography (eluent: chloroform/acetone=3/1). The resulting residue was purified by silica gel column chromatography (eluent: chloroform/acetone=2/1) again to give the titled compound (12.0 g).

$^{1}$H-NMR (CDCl$_{3}$) δ: 10.22 (1H, br s), 8.37 (1H, s), 7.42-7.31 (5H, m), 7.10 (1H, dd, J=3.3, 2.2 Hz), 6.56-6.51 (1H, m), 5.25-5.06 (3H, m), 4.77-4.62 (1H, m), 4.34-4.18 (2H, m), 3.75-3.43 (1H, m), 3.14-2.94 (1H, m), 2.52-2.38 (0.5H, m), 2.36-2.27 (1H, m), 2.23-2.11 (0.5H, m), 2.04-1.91 (1H, m), 1.90-1.77 (1H, m).

(12) Optically-Active Compound of 4-(3,3-difluoro-1,6-diaza-spiro[3.5]non-6-yl)-7H-pyrrolo[2,3-d]pyrimidine

[Chemical Formula 91]

To a solution of an optically-active compound of 3,3-difluoro-6-(7H-pyrrolo[2,3-d]pyrimidin-4-yl)-1,6-diaza-spiro[3.5]nonane-1-carboxylic acid benzyl ester (12.0 g) in methanol/tetrahydrofuran (120 ml/120 ml) was added 10% palladium carbon (2.4 g), and the mixture was hydrogenated at room temperature under 4 atmospheres for 21 hours. The mixture was filtered through Celite, and the filtrate was concentrated under reduced pressure. The resulting residue was slurry-purified by a mixed solvent of n-hexane/ethyl acetate (2/1) to give the titled compound (6.6 g).

$^{1}$H-NMR (CDCl$_{3}$) δ: 10.04 (1H, br s), 8.32 (1H, s), 7.10 (1H, d, J=3.5 Hz), 6.53 (1H, d, J=3.7 Hz), 4.60 (1H, d, J=13.7 Hz), 4.20-4.13 (1H, m), 4.08-3.97 (1H, m), 3.92-3.81 (1H, m), 3.76 (1H, d, J=13.7 Hz), 3.64-3.55 (1H, m), 2.08-1.78 (5H, m).

(13) Optically-Active Compound of 3-[3,3-difluoro-6-(7H-pyrrolo[2,3-d]pyrimidin-4-yl)-1,6-diaza-spiro[3.5] non-1-yl]-3-oxo-propionitrile

[Chemical Formula 92]

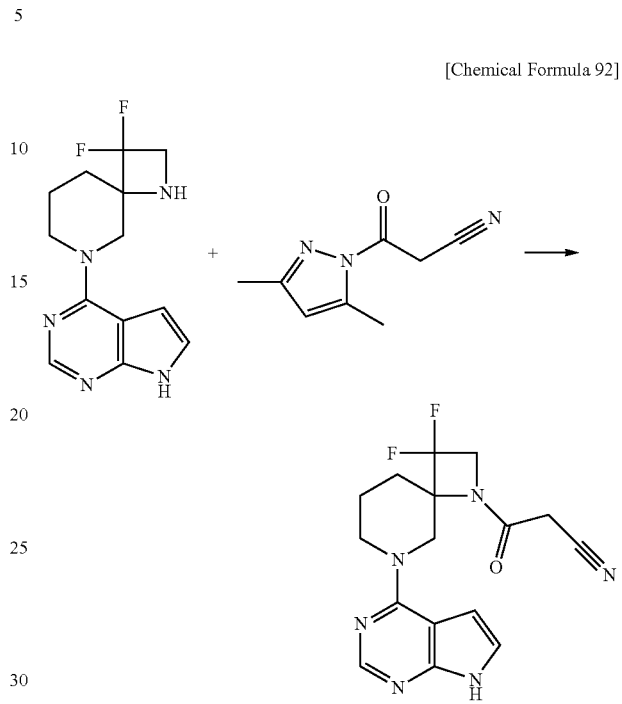

An optically-active compound of 4-(3,3-difluoro-1,6-diaza-spiro[3.5]non-6-yl)-7H-pyrrolo[2,3-d]pyrimidine (6.6 g) was mixed with 1-cyanoacetyl-3,5-dimethylpyrazole (7.7 g), N,N-diisopropylethylamine (4.3 ml) and 1,4-dioxane (132 ml), and the mixture was stirred at 100° C. for 2 hours. The mixture was cooled to room temperature. Then, thereto was added water, and the mixture was extracted with ethyl acetate. The separated aqueous layer was further extracted with ethyl acetate 5 times. The combined organic layer was sequentially washed with saturated aqueous sodium bicarbonate solution and saturated aqueous sodium chloride solution, dried over anhydrous sodium sulfate and concentrated under reduced pressure. The resulting residue was purified by silica gel column chromatography (eluent: chloroform/acetone=3/2 to 2/3). To the resulting residue was added n-heptane, and the mixture was concentrated under reduced pressure. To the resulting residue was added diethylether, and the mixture was slurry-washed and filtered to give a solid (7.5 g). The filtrate was concentrated under reduced pressure. To the resulting residue was added diethylether, and the mixture was slurry-washed to give a solid (0.2 g). The combined solid was purified by silica gel column chromatography (eluent: chloroform/methanol=97/3 to 9/1). To the resulting solid was added ethanol, and the mixture was concentrated under reduced pressure to give the titled compound (7.1 g).

$^{1}$H-NMR (DMSO-D6) δ: 11.74 (1H, br s), 8.15 (1H, s), 7.22-7.19 (1H, m), 6.65-6.62 (1H, m), 5.13-5.07 (1H, m), 4.69-4.46 (3H, m), 3.83 (1H, d, J=18.8 Hz), 3.77 (1H, d, J=19.2 Hz), 3.61-3.55 (1H, m), 2.99-2.91 (1H, m), 2.39-2.29 (1H, m), 2.26-2.19 (1H, m), 1.99-1.91 (1H, m), 1.63-1.48 (1H, m).

[α]D=+139.52° (25° C., c=1.04, methanol)

Preparation 6

Synthesis of Compound 6

[Chemical Formula 93]

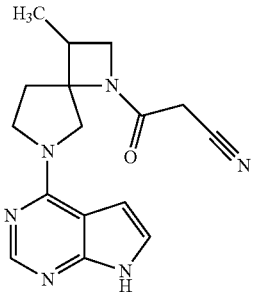

(1) Optically-Active Compound of 2-benzylaminopropan-1-ol

[Chemical Formula 94]

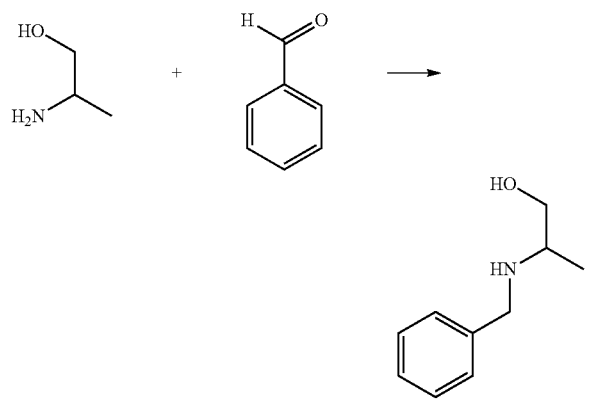

To a solution of (S)-(+)-2-aminopropan-1-ol (50.0 g) and benzaldehyde (74 ml) in ethanol (500 ml) was added 5% palladium carbon (5.0 g), and the mixture was hydrogenated at room temperature under ordinary pressure for 8 hours. The reaction mixture was filtered through Celite, and concentrated under reduced pressure to give the titled compound (111.2 g).

$^1$H-NMR (DMSO-D$_6$) δ: 7.34-7.27 (4H, m), 7.23-7.18 (1H, m), 4.53-4.47 (1H, m), 3.76 (1H, d, J=13.5 Hz), 3.66 (1H, d, J=13.5 Hz), 3.29-3.24 (2H, m), 2.65-2.55 (1H, m), 1.99 (1H, br s), 0.93 (3H, d, J=6.4 Hz).

(2) Optically-Active Compound of [benzyl-(2-hydroxy-1-methylethyl)-amino]acetic acid tert-butyl ester

[Chemical Formula 95]

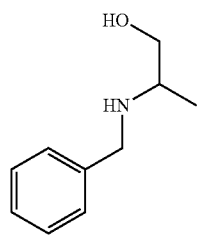

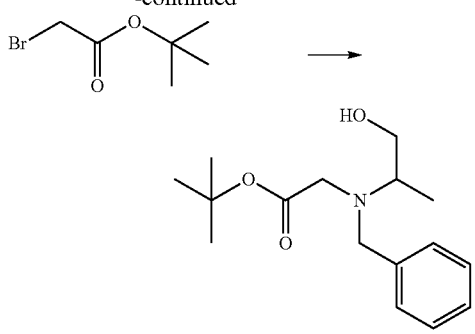

To a mixture of an optically-active compound of 2-benzylaminopropan-1-ol (111.2 g), potassium carbonate (111.6 g) and N,N-dimethylformamide (556 ml) cooled to 0° C. was added dropwise bromoacetic acid tert-butyl ester (109 ml) over 20 minutes, and the mixture was stirred at room temperature for 19.5 hours. The mixture was acidified by the addition of 2M aqueous hydrochloric acid solution and 6M aqueous hydrochloric acid solution to pH 2, and washed with toluene (1000 ml). The separated organic layer was extracted with 0.1M aqueous hydrochloric acid solution (300 ml). The combined aqueous layer was adjusted to pH 10 by 4M aqueous sodium hydroxide solution, and extracted with ethyl acetate (700 ml). The organic layer was sequentially washed with water (900 ml) and saturated aqueous sodium chloride solution (500 ml). The separated aqueous layer was extracted with ethyl acetate (400 ml) again. The combined organic layer was dried over anhydrous sodium sulfate, and concentrated under reduced pressure to give the titled compound (160.0 g).

$^1$H-NMR (DMSO-D$_6$) δ: 7.37-7.26 (4H, m), 7.24-7.19 (1H, m), 4.26 (1H, dd, J=6.9, 3.9 Hz), 3.76 (1H, d, J=14.1 Hz), 3.68 (1H, d, J=13.9 Hz), 3.45-3.39 (1H, m), 3.29-3.20 (1H, m), 3.24 (1H, d, J=17.2 Hz), 3.13 (1H, d, J=17.0 Hz), 2.84-2.74 (1H, m), 1.37 (9H, s), 0.96 (3H, d, J=6.8 Hz).

(3) Optically-Active Compound of [benzyl(2-chloropropyl)-amino]acetic acid tert-butyl ester

[Chemical Formula 96]

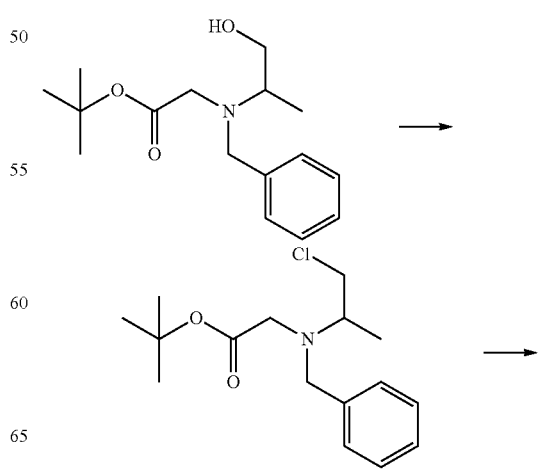

(3)-(1) Optically-Active Compound of [benzyl-(2-chloro-1-methylethyl)-amino]acetic acid tert-butyl ester

[Chemical Formula 97]

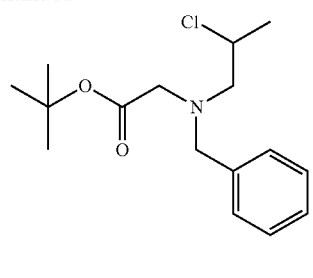

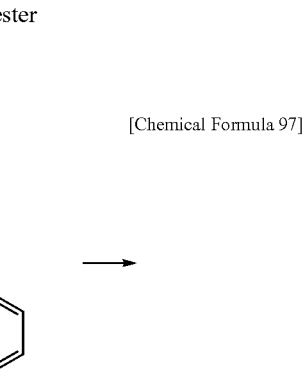

To a solution of an optically-active compound of [benzyl-(2-hydroxy-1-methylethyl)-amino]acetic acid tert-butyl ester (160.0 g) in chloroform (640 ml) cooled to 0° C. was added dropwise thionyl chloride (50.0 ml), and the mixture was stirred at 60° C. for 2 hours. The reaction mixture was cooled to 0° C. Then, thereto were added saturated aqueous sodium bicarbonate solution (1000 ml) and chloroform (100 ml), and the mixture was stirred. The separated organic layer was washed with saturated aqueous sodium chloride solution (500 ml), and the aqueous layer was extracted with chloroform (450 ml) again. The combined organic layer was dried over anhydrous sodium sulfate and concentrated under reduced pressure to give the titled compound (172.9 g).

$^1$H-NMR (CDCl$_3$) δ: 7.40-7.22 (5H, m), 4.05-3.97 (0.4H, m), 3.93-3.81 (2H, m), 3.70-3.65 (0.6H, m), 3.44-3.38 (0.6H, m), 3.29 (0.8H, s), 3.27 (1.2H, d, J=2.4 Hz), 3.24-3.15 (0.6H, m), 3.05-2.99 (0.4H, m), 2.94-2.88 (0.4H, m), 1.50 (1.2H, d, J=6.4 Hz), 1.48 (3.6H, s), 1.45 (5.4H, s), 1.23 (1.8H, d, J=6.8 Hz).

(3)-(2) Optically-Active Compound of [benzyl-(2-chloropropyl)-amino]acetic acid tert-butyl ester

[Chemical Formula 98]

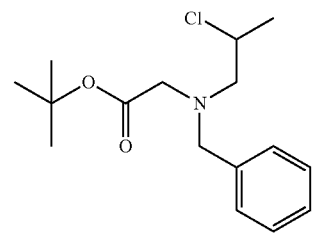

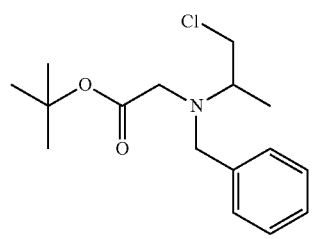

An optically-active compound of [benzyl-(2-chloro-1-methylethyl)-amino]acetic acid tert-butyl ester (172.9 g) was dissolved in N,N-dimethylformamide (520 ml), and stirred at 80° C. for 140 minutes. The reaction mixture was cooled to 0° C. Then, thereto was added water (1200 ml), and the mixture was extracted with n-hexane/ethyl acetate (2/1, 1000 ml). The organic layer was sequentially washed with water (700 ml) and saturated aqueous sodium chloride solution (400 ml), and the separated aqueous layer was extracted with n-hexane/ethyl acetate (2/1, 600 ml) again. The combined organic layer was concentrated under reduced pressure, and the resulting residue was purified by silica gel column chromatography (eluent: n-hexane/ethyl acetate=50/1 to 40/1) to give the titled compound (127.0 g).

$^1$H-NMR (CDCl$_3$) δ: 7.37-7.29 (4H, m), 7.28-7.23 (1H, m), 4.05-3.97 (1H, m), 3.91 (1H, d, J=13.5 Hz), 3.86 (1H, d, J=13.7 Hz), 3.29 (2H, s), 3.03 (1H, J=13.9, 6.6 Hz), 2.91 (1H, dd, J=13.9, 6.8 Hz), 1.50 (3H, d, J=6.4 Hz), 1.48 (9H, s).

(4) Optically-Active Compound of 1-benzyl-3-methylazetidine-2-carboxylic acid tert-butyl ester

[Chemical Formula 99]

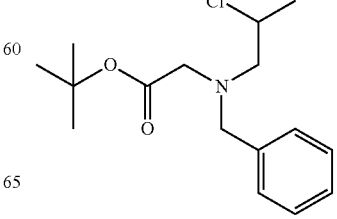

-continued

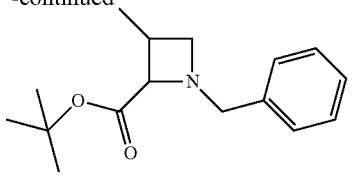

To a solution of an optically-active compound of [benzyl-(2-chloropropyl)-amino]acetic acid tert-butyl ester (60.0 g) and hexamethyl phosphoramide (36.0 ml) in tetrahydrofuran (360 ml) cooled to −72° C. was added dropwise lithium hexamethyl disilazide (1.0M tetrahydrofuran solution, 242 ml) over 18 minutes, and the mixture was warmed to 0° C. over 80 minutes. To the reaction mixture were sequentially added saturated aqueous ammonium chloride solution (300 ml) and water (400 ml), and the mixture was extracted with ethyl acetate (500 ml). The organic layer was sequentially washed with water (700 ml) and saturated aqueous sodium chloride solution (500 ml), and the separated aqueous layer was extracted with ethyl acetate (300 ml) again. The combined organic layer was dried over anhydrous sodium sulfate, and concentrated under reduced pressure. The resulting residue was purified by silica gel column chromatography (eluent: n-hexane/ethyl acetate=50/1 to 4/1) to give the titled compound (50.9 g).

$^1$H-NMR (CDCl$_3$) δ: 7.34-7.21 (5H, m), 3.75 (1H, d, J=12.6 Hz), 3.70-3.67 (1H, m), 3.58 (1H, d, J=12.6 Hz), 3.05-3.01 (1H, m), 2.99-2.95 (1H, m), 2.70-2.59 (1H, m), 1.41 (9H, s), 1.24 (3H, d, J=7.1 Hz).

(5) Optically-Active Compound of 3-methylazetidine-1,2-dicarboxylic acid di-tert-butyl ester

[Chemical Formula 100]

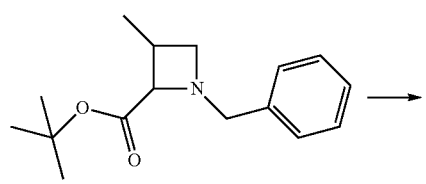

To a solution of an optically-active compound of 1-benzyl-3-methylazetidine-2-carboxylic acid tert-butyl ester (43.5 g) and di-tert-butyl dicarbonate (38.2 g) in tetrahydrofuran/methanol (130 ml/130 ml) was added 20% palladium hydroxide carbon (3.5 g), and the mixture was hydrogenated under 4 atmospheres for 2 hours. The mixture was filtered through Celite, and the filtrate was concentrated under reduced pressure to give the titled compound (48.0 g).

$^1$H-NMR (DMSO-D$_6$) δ: 4.44 (1H, d, J=8.8 Hz), 3.99-3.77 (1H, m), 3.45-3.37 (1H, m), 3.00-2.88 (1H, m), 1.45 (9H, s), 1.40-1.30 (9H, m), 1.02 (3H, d, J=7.2 Hz).

(6) Optically-Active Compound of 3-methyl-2-(3-methyl-but-2-enyl)-azetidine-1,2-dicarboxylic acid di-tert-butyl ester

[Chemical Formula 101]

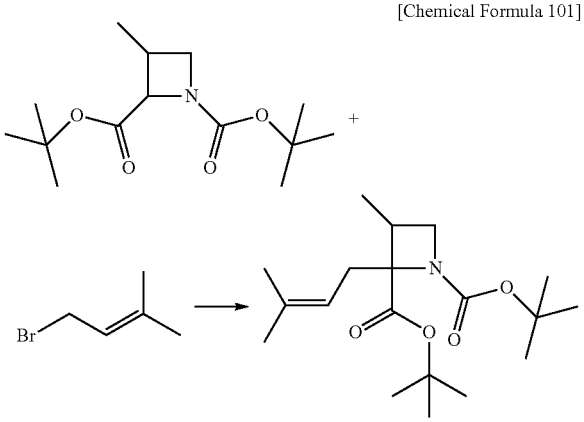

To a solution of an optically-active compound of 3-methylazetidine-1,2-dicarboxylic acid di-tert-butyl ester (48.0 g) and 1-bromo-3-methyl-2-butene (25.4 ml) in tetrahydrofuran (380 ml) cooled to −69° C. was added lithium hexamethyl disilazide (1.0M tetrahydrofuran solution, 200 ml). The reaction mixture was warmed to −20° C. over 40 minutes, and stirred at the same temperature for additional 20 minutes. To the reaction mixture were sequentially added saturated aqueous ammonium chloride solution (200 ml) and water (300 ml), and the mixture was extracted with n-hexane/ethyl acetate (1/1, 500 ml). The separated organic layer was sequentially washed with water (200 ml) and saturated aqueous sodium chloride solution (200 ml), dried over anhydrous magnesium sulfate and concentrated under reduced pressure. The resulting residue was purified by silica gel column chromatography (eluent: n-hexane/ethyl acetate=15/1 to 8/1) to give the titled compound (44.5 g).

$^1$H-NMR (CDCl$_3$) δ: 5.29-5.21 (1H, m), 3.77-3.72 (1H, m), 3.49-3.44 (1H, m), 2.73-2.52 (3H, m), 1.76-1.74 (3H, m), 1.66-1.65 (3H, m), 1.51 (9H, s), 1.43 (9H, s), 1.05 (3H, d, J=7.3 Hz).

(7) Optically-Active Compound of 3-methyl-2-(2-oxoethyl)azetidine-1,2-dicarboxylic acid di-tert-butyl ester

[Chemical Formula 102]

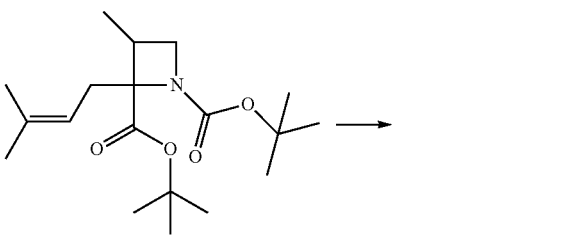

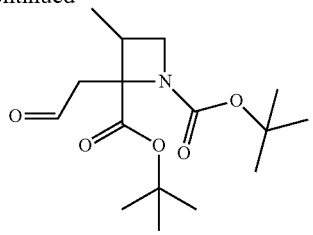

A solution of an optically-active compound of 3-methyl-2-(3-methyl-but-2-enyl)-azetidine-1,2-dicarboxylic acid di-tert-butyl ester (44.5 g) in chloroform/methanol (310 ml/310 ml) cooled to −70° C. was flowed ozone air for 1 hour. To the reaction mixture was added a solution of triphenylphosphine (44.7 g) in chloroform (45 ml) in small batches, and the mixture was warmed to room temperature. To the mixture were added saturated aqueous sodium thiosulfate solution (200 ml) and water (300 ml), and the mixture was extracted with chloroform (500 ml). The separated organic layer was washed with saturated aqueous sodium chloride solution, dried over anhydrous magnesium sulfate and concentrated under reduced pressure to give the titled compound (95.0 g), which was used in the next step without further purification.

$^1$H-NMR (DMSO-D$_6$) δ: 9.65 (1H, t, J=2.6 Hz), 3.79-3.74 (1H, m), 3.45-3.40 (1H, m), 2.99-2.80 (3H, m), 1.46 (9H, s), 1.34 (9H, s), 1.06 (3H, d, J=7.2 Hz).

(8) Optically-Active Compound of 2-(2-benzylaminoethyl)-3-methylazetidine-1,2-dicarboxylic acid di-tert-butyl ester

[Chemical Formula 103]

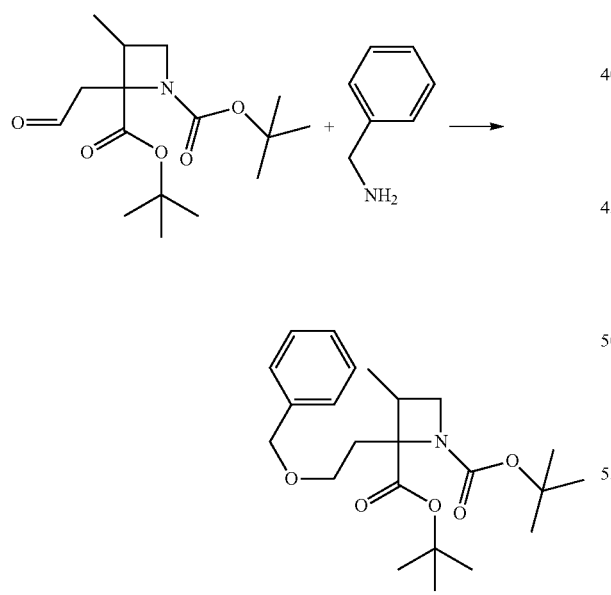

To a solution of the residue (95.0 g) obtained in (7) in tetrahydrofuran (300 ml) was added benzylamine (34 ml) at room temperature, and the mixture was stirred for 2 hours. The mixture was cooled to 0° C. Then, thereto was added sodium triacetoxyborohydride (83.3 g), and the mixture was stirred at room temperature for 1.5 hours. To the reaction mixture was added water (300 ml), and the mixture was extracted with n-hexane/ethyl acetate (1/3, 600 ml). The separated organic layer was washed with water (300 ml) and saturated aqueous sodium chloride solution (200 ml), and then extracted with 5% aqueous citric acid solution (300 ml, 200 ml) twice and 10% aqueous citric acid solution (250 ml×3) 3 times. The combined aqueous layer was basified by 4M aqueous sodium hydroxide solution to pH 10 and extracted with chloroform (300 ml). The organic layer was washed with saturated aqueous sodium chloride solution (200 ml), dried over anhydrous magnesium sulfate and concentrated under reduced pressure to give the titled compound (46.9 g).

$^1$H-NMR (DMSO-D$_6$) δ: 7.34-7.26 (4H, m), 7.22-7.17 (1H, m), 3.74-3.65 (2H, m), 3.61 (1H, t, J=7.8 Hz), 3.28 (1H, t, J=7.5 Hz), 2.76-2.66 (2H, m), 2.57-2.45 (1H, m), 2.15 (1H, br s), 2.05-1.89 (2H, m), 1.42 (9H, s), 1.27 (9H, s), 0.96 (3H, d, J=7.1 Hz).

(9) Optically-Active Compound of 2-(2-benzylaminoethyl)-3-methylazetidine-2-dicarboxylic acid 2 hydrochloride

[Chemical Formula 104]

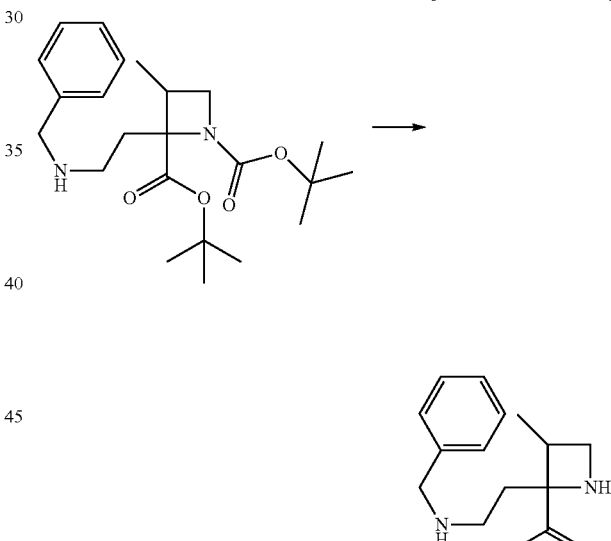

An optically-active compound of 2-(2-benzylaminoethyl)-3-methylazetidine-1,2-dicarboxylic acid di-tert-butyl ester (46.5 g) was mixed with 4M hydrochloric acid-1,4-dioxane (230 ml) and water (4.1 ml), and the mixture was stirred at 80° C. for 2 hours. The mixture was concentrated under reduced pressure, azeotroped with toluene, and then slurry-washed with n-hexane/ethyl acetate (1/1, 440 ml) to give the titled compound (30.1 g).

$^1$H-NMR (DMSO-D$_6$) δ: 10.24 (1H, br s), 9.64 (2H, br s), 8.90 (1H, br s), 7.58-7.53 (2H, m), 7.47-7.41 (3H, m), 4.21-

4.10 (2H, m), 4.02-3.94 (1H, m), 3.46-3.37 (1H, m), 3.20-3.10 (1H, m), 2.99-2.85 (2H, m), 2.69-2.54 (2H, m), 1.10 (3H, d, J=7.2 Hz).

(10) Optically-Active Compound of 6-benzyl-3-methyl-1,6-diazaspiro[3.4]octan-5-one

[Chemical Formula 105]

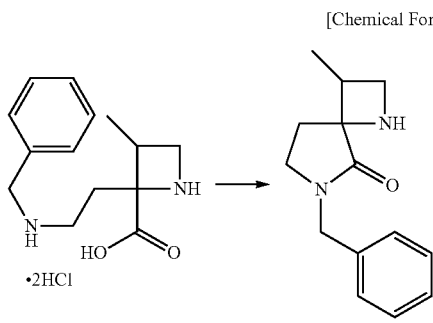

To a solution of an optically-active compound of 2-(2-benzylaminoethyl)-3-methylazetidine-2-dicarboxylic acid 2 hydrochloride (29.1 g) and N,N-diisopropylethylamine (65 ml) in chloroform (290 ml) was added O-(7-azabenzotriazol-1-yl)-N,N,N',N'-tetramethyluronium hexafluorophosphate (41.3 g) at room temperature, and the mixture was stirred for 4 hours. To the reaction mixture were added saturated aqueous sodium bicarbonate solution (200 ml) and water (100 ml), and the mixture was extracted with chloroform (200 ml). The organic layer was washed with saturated aqueous sodium chloride solution, dried over anhydrous magnesium sulfate and concentrated under reduced pressure. The resulting residue was purified by silica gel column chromatography (eluent: chloroform/methanol=20/1 to 10/1) to give the titled compound (21.3 g).

$^1$H-NMR (DMSO-D$_6$) δ: 7.38-7.31 (2H, m), 7.30-7.22 (3H, m), 4.52 (1H, d, J=14.8 Hz), 4.29 (1H, d, J=14.8 Hz), 3.35-3.27 (2H, m), 3.22-3.17 (1H, m), 3.05 (2H, dd, J=9.5, 4.0 Hz), 2.77-2.66 (1H, m), 2.16-2.10 (1H, m), 1.96-1.87 (1H, m), 0.94 (3H, d, J=7.1 Hz).

(11) Optically-Active Compound of 6-benzyl-3-methyl-1,6-diazaspiro[3.4]octane-1-carboxylic acid tert-butyl ester

[Chemiical Formula 106]

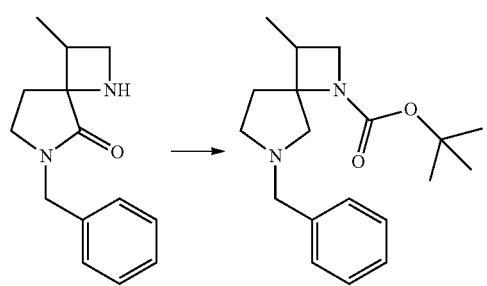

To a suspension of lithium aluminum hydride (6.8 g) in tetrahydrofuran (300 ml) was slowly added dropwise concentrated sulfuric acid (4.8 ml) under ice-cooling, and the mixture was stirred for 30 minutes. To the mixture was added dropwise a solution of an optically-active compound of 6-benzyl-3-methyl-1,6-diazaspiro[3.4]octan-5-one (21.3 g) in tetrahydrofuran (100 ml), and the mixture was stirred at the same temperature for additional 45 minutes. To the reaction mixture were sequentially added water (7.0 ml), 4M aqueous sodium hydroxide solution (7.0 ml) and water (14.0 ml), and the mixture was directly stirred for 30 minutes. To the mixture were added anhydrous magnesium sulfate and ethyl acetate (100 ml), and the mixture was stirred, and then filtered through Celite. To the filtrate was added di-tert-butyl dicarbonate (23.4 g) at room temperature, and the mixture was stirred for 3 hours. The mixture was concentrated under reduced pressure until reduced by half and washed with saturated aqueous ammonium chloride solution (200 ml×2) twice. To the separated organic layer was added n-hexane (200 ml), and the mixture was extracted with 10% aqueous citric acid solution 5 times. The separated aqueous layer was basified by 4M aqueous sodium hydroxide solution and extracted with chloroform. The organic layer was washed with saturated aqueous sodium chloride solution (200 ml), dried over anhydrous magnesium sulfate and concentrated under reduced pressure. The resulting residue was purified by silica gel column chromatography (eluent: chloroform/methanol=40/1 to 20/1) to give the titled compound (15.6 g).

$^1$H-NMR (DMSO-D$_6$) δ: 7.34-7.27 (4H, m), 7.26-7.21 (1H, m), 3.84-3.69 (1H, m), 3.62-3.47 (2H, m), 3.19-3.05 (1H, m), 3.02-2.92 (1H, m), 2.76-2.69 (1H, m), 2.47-2.24 (4H, m), 1.95-1.77 (1H, m), 1.36 (9H, s), 1.03 (3H, d, J=7.0 Hz).

(12) Optically-Active Compound of 3-methyl-1,6-diazaspiro[3.4]octane-1-carboxylic acid tert-butyl ester

[Chemical Formula 107]

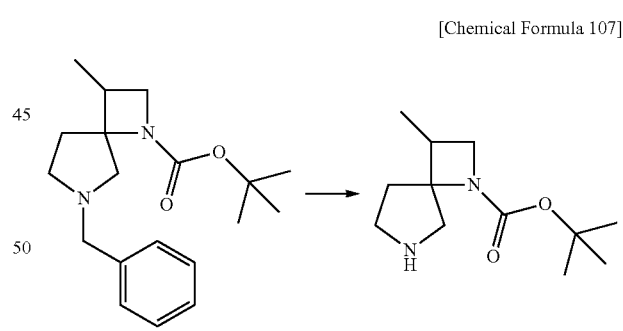

To a solution of an optically-active compound of 6-benzyl-3-methyl-1,6-diazaspiro[3.4]octane-1-carboxylic acid tert-butyl ester (10.0 g) in tetrahydrofuran/methanol (50 ml/50 ml) was added 20% palladium hydroxide carbon (2.0 g), and the mixture was hydrogenated under 4 atmospheres for 24 hours. The mixture was filtered through Celite, and the filtrate was concentrated under reduced pressure to give the titled compound (7.3 g).

$^1$H-NMR (DMSO-D$_6$) δ: 3.88-3.71 (1H, m), 3.44-3.06 (2H, m), 3.02-2.64 (4H, m), 2.55-2.38 (1H, m), 2.31-2.15 (1H, m), 1.81-1.72 (1H, m), 1.37 (9H, s), 1.07 (3H, d, J=7.0 Hz).

(13) Optically-Active Compound of 3-methyl-6-(7H-pyrrolo[2,3-d]pyrimidin-4-yl)-1,6-diazaspiro[3.4]octane-1-carboxylic acid tert-butyl ester

[Chemical Formula 108]

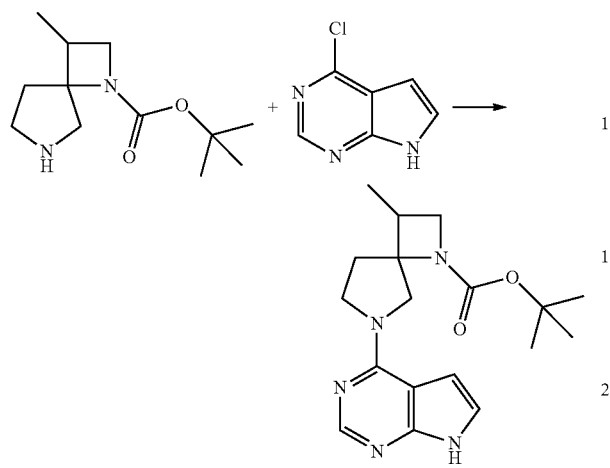

An optically-active compound of 3-methyl-1,6-diazaspiro[3.4]octane-1-carboxylic acid tert-butyl ester (6.9 g) was mixed with 4-chloro-7H-pyrrolo[2,3-d]pyrimidine (4.3 g), potassium carbonate (7.7 g) and water (65 ml), and stirred for 4 hours with refluxing. The mixture was cooled to room temperature, and thereto was added water (60 ml). The mixture was extracted with chloroform/methanol (10/1, 120 ml). The organic layer was sequentially washed with water, saturated aqueous ammonium chloride solution and saturated aqueous sodium chloride solution, and dried over anhydrous sodium sulfate. To the mixture was added silica gel (4 g), and the mixture was stirred for 10 minutes, filtered through Celite and concentrated under reduced pressure. The resulting residue was purified by silica gel column chromatography (eluent: chloroform/ethyl acetate=1/1, followed by chloroform/methanol=50/1 to 20/1) to give the titled compound (10.0 g).

$^1$H-NMR (DMSO-D$_6$) δ: 11.59 (1H, br s), 8.09 (1H, s), 7.12-7.09 (1H, m), 6.64-6.59 (1H, m), 4.09-3.66 (5H, m), 3.39-3.21 (1H, m), 2.64-2.44 (2H, m), 2.27-2.06 (1H, m), 1.36 (3H, s), 1.21 (6H, s), 1.11 (3H, d, J=6.5 Hz).

(14) Optically-Active Compound of 4-(3-methyl-1,6-diazaspiro[3.4]oct-6-yl)-7H-pyrrolo[2,3-d]pyrimidine 2 hydrochloride

[Chemical Formula 109]

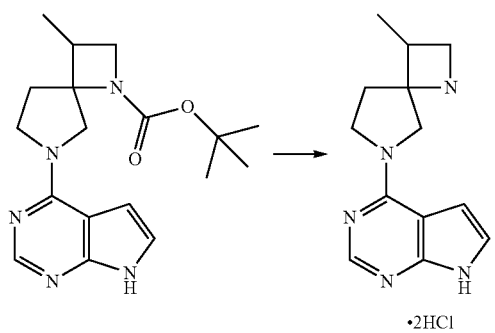

An optically-active compound of 3-methyl-6-(7H-pyrrolo[2,3-d]pyrimidin-4-yl)-1,6-diazaspiro[3.4]octane-1-carboxylic acid tert-butyl ester (9.5 g) was mixed with 4M hydrochloric acid-1,4-dioxane (50 ml), chloroform (50 ml) and methanol (100 ml), and the mixture was stirred at 60° C. for 30 minutes. The mixture was concentrated under reduced pressure, and azeotroped with toluene to give the titled compound (9.3 g).

$^1$H-NMR (DMSO-D$_6$) δ: 12.91 (1H, br s), 9.97-9.64 (2H, m), 8.45-8.35 (1H, m), 7.58-7.47 (1H, m), 7.04-6.92 (1H, m), 4.99-4.65 (1H, m), 4.32-3.21 (7H, m), 3.04-2.90 (1H, m), 2.46-2.31 (1H, m), 1.27 (3H, d, J=6.0 Hz).

(15) Optically-Active Compound of 3-[3-methyl-6-(7H-pyrrolo[2,3-d]pyrimidin-4-yl)-1,6-diazaspiro[3.4]oct-1-yl]-3-oxopropionitrile

[Chemical Formula 110]

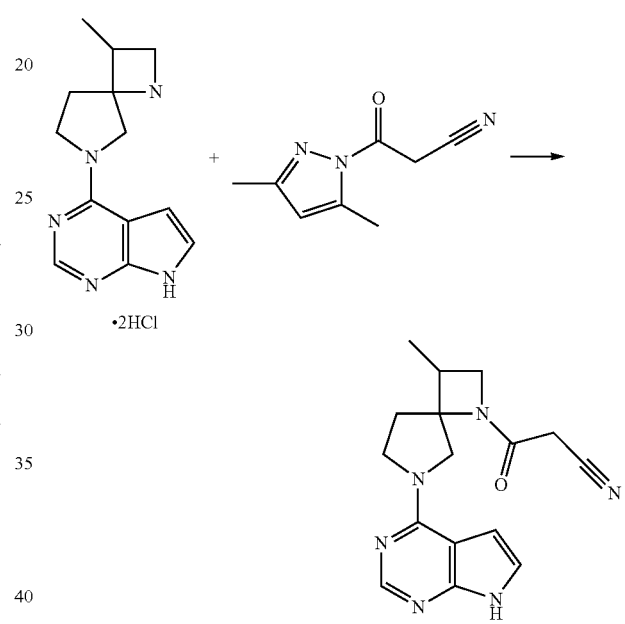

An optically-active compound of 4-(3-methyl-1,6-diazaspiro[3.4]oct-6-yl)-7H-pyrrolo[2,3-d]pyrimidine 2 hydrochloride (8.8 g) was mixed with 1-cyanoacetyl-3,5-dimethylpyrazole (6.8 g), N,N-diisopropylethylamine (20 ml) and 1,4-dioxane (100 ml), and the mixture was stirred at 100° C. for 1 hour. The mixture was cooled to room temperature, and thereto was added saturated aqueous sodium bicarbonate solution. The mixture was extracted with chloroform/methanol (10/1). The separated organic layer was washed with saturated aqueous sodium chloride solution, dried over anhydrous magnesium sulfate and concentrated under reduced pressure. The resulting residue was purified by silica gel column chromatography (eluent: chloroform/methanol=30/1 to 9/1), and concentrated under reduced pressure. The resulting residue was slurry-washed with n-heptane/ethanol (2/1, 90 ml) to give a solid (7.3 g). The solid was slurry-washed with n-heptane/ethanol (5/1, 90 ml) again to give Crystal 1 of the titled compound (6.1 g).

$^1$H-NMR (DMSO-D$_6$) δ: 11.60 (1H, br s), 8.08 (1H, s), 7.11 (1H, dd, J=3.5, 2.4 Hz), 6.58 (1H, dd, J=3.4, 1.9 Hz), 4.18-4.14 (1H, m), 4.09-3.93 (3H, m), 3.84-3.73 (1H, m), 3.71 (1H, d, J=19.0 Hz), 3.66 (1H, d, J=18.7 Hz), 3.58 (1H, dd, J=8.2, 6.0 Hz), 2.70-2.58 (2H, m), 2.24-2.12 (1H, m), 1.12 (3H, d, J=7.1 Hz).

[α]$_D$=+47.09° (25° C., c=0.55, methanol)

To the resulting Crystal 1 (2.6 g) was added 1-butanol (39 ml), and the mixture was heated at 100° C. and stirred. After the complete dissolution of solids, the solution was cooled to room temperature by 10° C. per 30 minutes, and further stirred at room temperature overnight. The generated crystals were filtered, washed with 1-butanol (6.2 ml) and dried under reduced pressure to give Crystal 2 of the titled compound (2.1 g).

Preparation 7

Synthesis of Compound 7

[Chemical Formula 111]

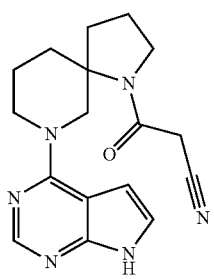

(1) Optically-Active Compound of 3-trichloromethyltetrahydropyrrolo[1,2-c]oxazol-1-one

[Chemical Formula 112]

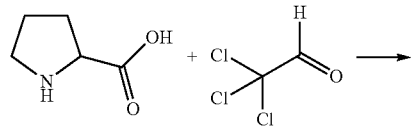

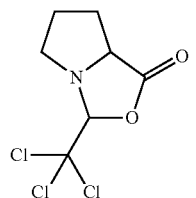

To a solution of D-proline (100.0 g) in acetonitrile (400 ml) was added dropwise chloral (169 ml) at room temperature, and the mixture was stirred for 18 hours. The mixture was filtered, and the filtrate was concentrated under reduced pressure. To the resulting residue was added water, and the mixture was extracted with chloroform. The separated organic layer was dried over anhydrous magnesium sulfate, and concentrated under reduced pressure. The resulting residue was slurry-washed with n-hexane/ethyl acetate (20/1, 900 ml) to give the titled compound (159.7 g).

$^1$H-NMR (DMSO-D$_6$) δ: 5.83 (1H, s), 4.10 (1H, dd, J=9.0, 4.2 Hz), 3.34-3.27 (1H, m), 3.20-3.13 (1H, m), 2.19-2.07 (1H, m), 1.98-1.90 (1H, m), 1.83-1.73 (1H, m), 1.67-1.55 (1H, m).

(2) Optically-Active Compound of 7a-allyl-3-trichloromethyltetrahydropyrrolo[1,2-c]oxazol-1-one

[Chemical Formula 113]

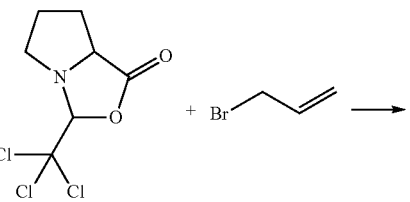

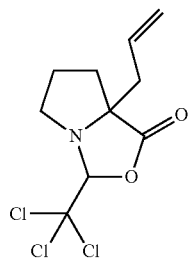

To a solution of diisopropylamine (60 ml) in tetrahydrofuran (160 ml) was added dropwise n-butyllithium (2.64M hexane solution, 161 ml) over 20 minutes under ice-cooling, and the mixture was directly stirred for 40 minutes. To the mixture cooled to −68° C. was added dropwise a solution of 3-trichloromethyltetrahydropyrrolo[1,2-c]oxazol-1-one (80.0 g) in tetrahydrofuran (640 ml) over 30 minutes, and the mixture was directly stirred for 20 minutes. To the mixture was added allyl bromide (57 ml), and the mixture was directly stirred for 1 hour. To the reaction mixture was added saturated aqueous ammonium chloride solution (1000 ml), and the mixture was extracted with ethyl acetate (800 ml). The separated organic layer was washed with water (800 ml) and saturated aqueous sodium chloride solution (500 ml). The separated aqueous layer was extracted with ethyl acetate (400 ml, 500 ml) twice. The combined organic layer was dried over anhydrous magnesium sulfate, and concentrated under reduced pressure to give the titled compound (86.1 g).

$^1$H-NMR (CDCl$_3$) δ: 5.96-5.84 (1H, m), 5.22-5.21 (1H, m), 5.20-5.16 (1H, m), 5.00-4.98 (1H, m), 3.26-3.15 (2H, m), 2.67-2.53 (2H, m), 2.19-2.11 (1H, m), 2.08-1.98 (1H, m), 1.95-1.85 (1H, m), 1.72-1.61 (1H, m).

(3) Optically-Active Compound of 2-allylpyrrolidine-1,2-dicarboxylic acid 1-tert-butyl ester 2-methyl ester

[Chemical Formula 114]

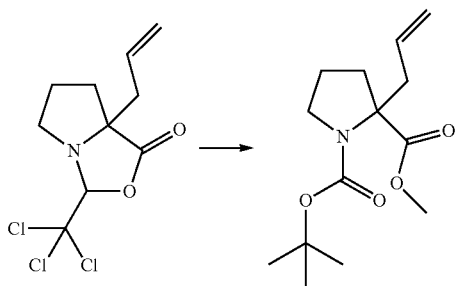

To a solution of 7a-allyl-3-trichloromethyltetrahydropyrrolo[1,2-c]oxazol-1-one (86.1 g) in methanol (430 ml) cooled to 0° C. was added dropwise concentrated sulfuric acid (43 ml), and then the mixture was stirred for 13.5 hours with refluxing. The mixture was cooled to room temperature and concentrated under reduced pressure. Then, to the resulting residue was added ethyl acetate (500 ml), and the mixture was extracted with water (500 ml). The separated organic layer was extracted with water (300 ml) again. The combined aqueous layer was neutralized by 4M aqueous sodium hydroxide solution to pH 7.5. To the mixture was added sodium bicarbonate (55 g), followed by a solution of di-tert-butyl dicarbonate (85.7 g) in tetrahydrofuran (430 ml) at room temperature, and the mixture was stirred overnight. To the mixture was added ethyl acetate (800 ml), and the mixture was extracted. The separated organic layer was sequentially washed with water (1000 ml) and saturated aqueous sodium chloride solution (500 ml). The separated aqueous layer was extracted with ethyl acetate (400 ml) again. The combined organic layer was dried over anhydrous sodium sulfate, and concentrated under reduced pressure. The resulting residue was purified by silica gel column chromatography (eluent: n-hexane/ethyl acetate=30/1 to 10/1) to give the titled compound (61.2 g).

¹H-NMR (CDCl₃) δ: 5.82-5.70 (1.0H, m), 5.16-5.14 (1.0H, m), 5.13-5.09 (1.0H, m), 3.73-3.66 (0.7H, m), 3.72 (3.0H, s), 3.63-3.56 (0.3H, m), 3.42-3.31 (1.0H, m), 3.14-3.07 (0.3H, m), 2.96-2.89 (0.7H, m), 2.65-2.57 (1.0H, m), 2.17-1.98 (2.0H, m), 1.94-1.75 (2.0H, m), 1.46 (3.0H, s), 1.43 (6.0H, s).

(4) Optically-Active Compound of 2-(3-hydroxypropyl)pyrrolidine-1,2-dicarboxylic acid 1-tert-butyl ester 2-methyl ester

[Chemical Formula 115]

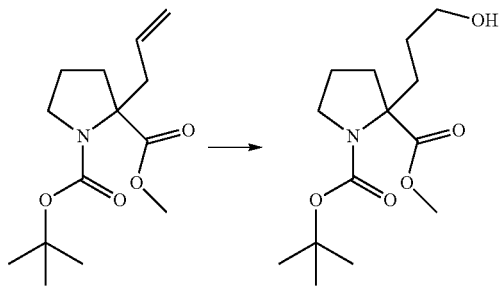

To a solution of 2-allylpyrrolidine-1,2-dicarboxylic acid 1-tert-butyl ester 2-methyl ester (25.0 g) in tetrahydrofuran (125 ml) cooled to 0° C. was added dropwise borane-tetrahydrofuran complex (1.0M tetrahydrofuran solution, 105 ml) over 30 minutes, and the mixture was stirred at the same temperature for 2.5 hours. To the reaction mixture was added dropwise additional borane-tetrahydrofuran complex (1.0M tetrahydrofuran solution, 11 ml), and the mixture was stirred at the same temperature for 50 minutes. To the reaction mixture was added dropwise water (180 ml) over 30 minutes and added sodium peroxoborate 1 hydrate (12.0 g) in small batches. The mixture was warmed to room temperature and stirred overnight, and then thereto was added water (500 ml). The mixture was extracted with ethyl acetate (600 ml). The separated organic layer was washed with 20% aqueous sodium thiosulfate solution (600 ml) and saturated aqueous sodium chloride solution. The separated aqueous layer was extracted with ethyl acetate (300 ml, 200 ml) twice. The combined organic layer was dried over anhydrous sodium sulfate, and concentrated under reduced pressure. The resulting residue was purified by silica gel column chromatography (eluent: n-hexane/ethyl acetate=2/1 to 1/1) to give the titled compound (17.4 g).

¹H-NMR (CDCl₃) δ: 3.77-3.59 (2H, m), 3.71 (3H, s), 3.47-3.36 (1H, m), 2.37-1.76 (7H, m), 1.68-1.50 (3H, m), 1.45 (4H, s), 1.41 (5H, s).

(5) Optically-Active Compound of 2-(3-oxopropyl)pyrrolidine-1,2-dicarboxylic acid 1-tert-butyl ester 2-methyl ester

[Chemical Formula 116]

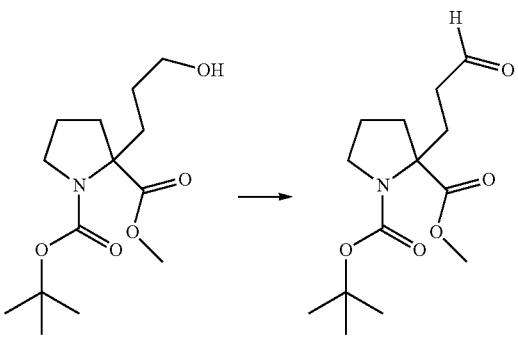

To a suspension of 2-(3-hydroxypropyl)pyrrolidine-1,2-dicarboxylic acid 1-tert-butyl ester 2-methyl ester (17.4 g) and sodium bicarbonate (12.7 g) in chloroform (175 ml) cooled to 0° C. was added Dess-Martin periodinane (28.3 g). The reaction mixture was warmed to room temperature and stirred for 1.5 hours. To the reaction mixture was added additional Dess-Martin periodinane (1.0 g), and the mixture was stirred for 50 minutes. To the reaction mixture cooled to 0° C. was added additional Dess-Martin periodinane (15 g), and the mixture was stirred for 2 hours. To the mixture were added 20% sodium thiosulfate (250 ml) and saturated aqueous sodium bicarbonate solution (250 ml), and the mixture was stirred at room temperature for 20 minutes. The mixture was extracted with chloroform (200 ml×2) twice, and the combined organic layer was dried over anhydrous sodium sulfate and concentrated under reduced pressure. The resulting residue was purified by silica gel column chromatography (eluent: n-hexane/ethyl acetate=4/1 to 3/2) to give the titled compound (5.68 g).

¹H-NMR (CDCl₃) δ: 9.78-9.76 (0.5H, m), 9.70-9.68 (0.5H, m), 3.76-3.69 (3.5H, m), 3.61-3.52 (0.5H, m), 3.44-3.32 (1.0H, m), 2.68-2.40 (3.0H, m), 2.29-2.06 (2.0H, m), 2.03-1.76 (3.0H, m), 1.44 (4.0H, s), 1.41 (5.0H, s).

(6) Optically-Active Compound of 2-(3-benzylaminopropyl)pyrrolidine-1,2-dicarboxylic acid 1-tert-butyl ester 2-methyl ester

[Chemical Formula 117]

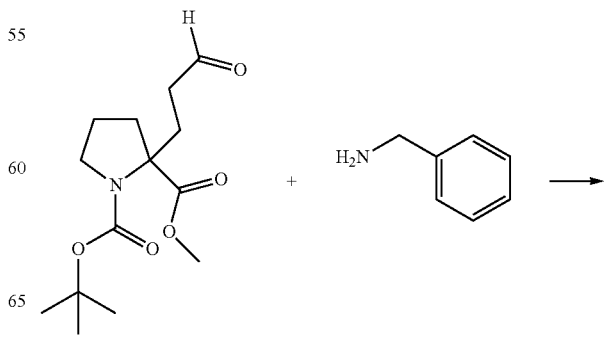

105

-continued

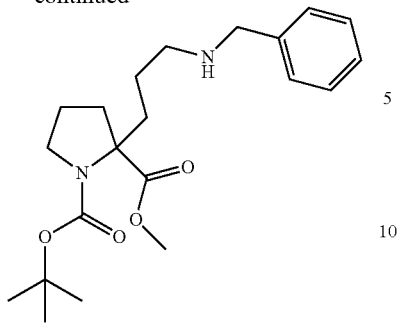

To a solution of 2-(3-oxopropyl)pyrrolidine-1,2-dicarboxylic acid 1-tert-butyl ester 2-methyl ester (5.68 g) in tetrahydrofuran (57 ml) was added benzylamine (6.53 ml) at room temperature, and the mixture was stirred for 1 hour. The mixture was cooled to 0° C., and thereto was added sodium triacetoxyborohydride (5.07 g). The mixture was stirred at room temperature for 12.5 hours. To the reaction mixture were added water (12 ml) and saturated aqueous ammonium chloride solution (200 ml), and the mixture was extracted with n-hexane/ethyl acetate (1/2, 210 ml×2, 120 ml×2) 4 times. To the combined organic layer was added n-hexane (150 ml), and the mixture was extracted with 10% aqueous potassium bisulfate solution (180 ml×3) 3 times. The combined aqueous layer was neutralized by 4M aqueous sodium hydroxide solution to pH 7 to 8, and thereto was added saturated aqueous sodium bicarbonate solution (100 ml). The mixture was extracted with ethyl acetate (200 ml). The separated aqueous layer was extracted with ethyl acetate (200 ml×2) twice, and the combined organic layer was washed with saturated aqueous sodium chloride solution (200 ml). The organic layer was dried over anhydrous sodium sulfate and concentrated under reduced pressure to give the titled compound (7.69 g).

$^1$H-NMR (CDCl$_3$) δ: 7.27-7.35 (5H, m), 3.80 (2H, s), 3.65-3.75 (0.7H, m), 3.69 (3H, s), 3.55-3.65 (0.5H, m), 3.31-3.45 (1H, m), 2.60-2.71 (2H, m), 2.25-2.35 (0.2H, m), 2.10-2.21 (0.5H, m), 2.04 (1.0H, s), 1.97-2.11 (2.4H, m), 1.74-1.93 (3.0H, m), 1.45-1.65 (1.7H, m), 1.44 (3.5H, s), 1.38 (5.5H, s)

(7) Optically-Active Compound of 2-(3-benzylaminopropyl)pyrrolidine-2-carboxylic acid methyl ester

[Chemical Formula 118]

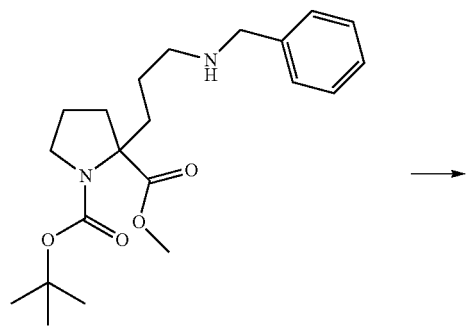

106

-continued

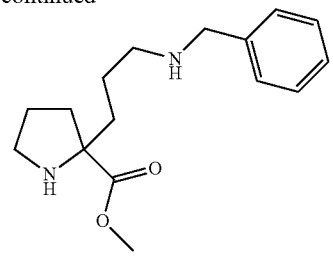

To a solution of 2-(3-benzylaminopropyl)pyrrolidine-1,2-dicarboxylic acid 1-tert-butyl ester 2-methyl ester (7.69 g) in chloroform (38 ml) cooled to 0° C. was added 4M hydrochloric acid-ethyl acetate (18 ml), and the mixture was stirred at room temperature for 3 hours. To the mixture was added additional 4M hydrochloric acidethyl acetate (20 ml), and the mixture was stirred at room temperature for 50 minutes. The reaction mixture was concentrated under reduced pressure, and then thereto was added saturated aqueous sodium bicarbonate solution (150 ml). The mixture was extracted with chloroform (100 ml×2, 75 ml×2) 4 times. The combined organic layer was dried over anhydrous sodium sulfate and concentrated under reduced pressure to give the titled compound (7.49 g).

$^1$H-NMR (CDCl$_3$) δ: 7.35-7.22 (5H, m), 3.77 (2H, s), 3.71 (3H, s), 3.02-2.92 (2H, m), 2.65-2.58 (2H, m), 2.21-2.13 (1H, m), 1.92-1.50 (8H, m), 1.43-1.31 (1H, m).

(8) Optically-Active Compound of 7-benzyl-1,7-diazaspiro[4.5]decan-6-one

[Chemical Formula 119]

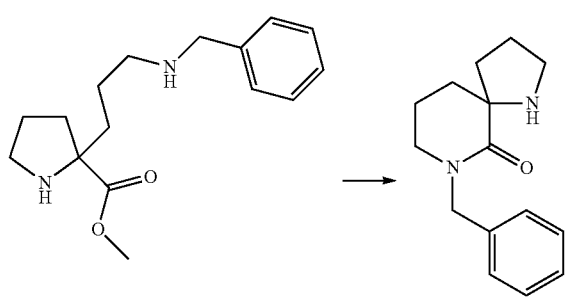

A solution of 2-(3-benzylaminopropyl)pyrrolidine-2-carboxylic acid methyl ester (133 mg) in xylene (1.5 ml) was stirred at 130° C. overnight. The mixture was cooled to room temperature, and purified by silica gel column chromatography (eluent: chloroform/methanol=10/1) to give the titled compound (90 mg).

$^1$H NMR (CDCl$_3$) δ: 7.35-7.21 (5H, m), 4.68 (1H, d, J=14.6 Hz), 4.48 (1H, d, J=14.6 Hz), 3.31-3.18 (3H, m), 2.90-2.83 (1H, m), 2.12-2.04 (1H, m), 1.99-1.80 (7H, m), 1.78-1.70 (1H, m).

(9) Optically-Active Compound of 7-benzyl-6-oxo-1,7-diazaspiro[4.5]decane-1-carboxylic acid tert-butyl ester

[Chemical Formula 120]

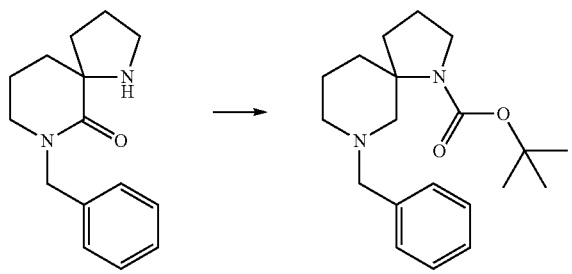

To a suspension of lithium aluminum hydride (45 mg) in tetrahydrofuran (1.5 ml) cooled to 0° C. was added concentrated sulfuric acid (31 µl), and the mixture was stirred for 50 minutes. To the mixture was added dropwise a solution of 7-benzyl-1,7-diazaspiro[4.5]decan-6-one (90 mg) in tetrahydrofuran (0.5 ml) at 0° C., and the mixture was stirred at the same temperature for 40 minutes. To the reaction mixture were sequentially added water (45 µl), 4M aqueous sodium hydroxide solution (45 µl) and water (45 µl), and the mixture was stirred for 30 minutes. To the mixture were added ethyl acetate and anhydrous magnesium sulfate, and the mixture was filtered through Celite. To the filtrate was added di-tert-butyl dicarbonate (112 mg) at room temperature, and the mixture was stirred for 100 minutes. The reaction mixture was concentrated under reduced pressure, and purified by silica gel column chromatography (eluent: n-hexane/ethyl acetate=10/1 to 5/1) to give the titled compound (76 mg).

$^1$H-NMR (DMSO-D$_6$) δ: 7.36-7.28 (4H, m), 7.25-7.20 (1H, m), 3.72-3.67 (2H, m), 3.62 (2H, s), 3.58 (1H, s), 3.56-3.45 (1H, m), 3.31-3.22 (1H, m), 2.55-2.47 (1H, m), 2.17-1.90 (3H, m), 1.83-1.72 (3H, m), 1.54-1.41 (1H, m), 1.37 (3H, s), 1.33-1.23 (1H, m), 1.29 (6H, s).

(10) Optically-Active Compound of 1,7-diazaspiro[4.5]decane-1-carboxylic acid tert-butyl ester

[Chemical Formula 121]

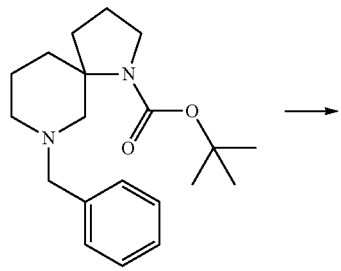

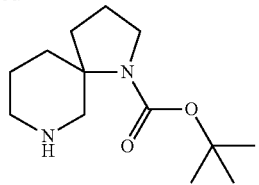

To a solution of 7-benzyl-6-oxo-1,7-diazaspiro[4.5]decane-1-carboxylic acid tert-butyl ester (76 mg) in tetrahydrofuran/methanol (1 ml/1 ml) was added 20% palladium hydroxide carbon (15 mg), and the mixture was hydrogenated under 4 atmospheres. The mixture was filtered through Celite under nitrogen, and the filtrate was concentrated under reduced pressure to give the titled compound (51 mg).

$^1$H-NMR (CDCl$_3$) δ: 3.57-3.31 (3H, m), 3.00-2.87 (1H, m), 2.78-2.39 (3H, m), 2.17-2.07 (1H, m), 1.93-1.78 (1H, m), 1.76-1.62 (3H, m), 1.53-1.42 (12H, m).

(11) Optically-Active Compound of 7-(7H-pyrrolo[2,3-d]pyrimidin-4-yl)-1,7-diazaspiro[4.5]decane-1-carboxylic acid tert-butyl ester

[Chemical Formula 122]

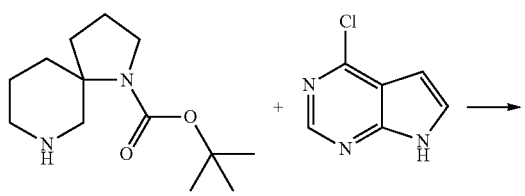

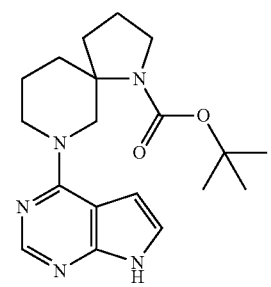

1,7-Diazaspiro[4.5]decane-1-carboxylic acid tert-butyl ester (51 mg) was mixed with 4-chloro-7H-pyrrolo[2,3-d]pyrimidine (36 mg), potassium carbonate (59 mg) and water (1 ml), and the mixture was stirred for 1.5 hours with refluxing. The mixture was cooled to room temperature, and thereto was added water. The mixture was extracted with chloroform. The organic layer was washed with saturated aqueous sodium chloride solution, dried over anhydrous sodium sulfate and concentrated under reduced pressure. The resulting residue was purified by silica gel column chromatography (eluent: n-hexane/ethyl acetate=1/1, followed by chloroform/methanol=20/1) to give the titled compound (60 mg).

$^1$H-NMR (CDCl$_3$) δ: 10.58-10.90 (1H, m), 8.30 (1H, br s), 7.07 (1H, br s), 6.48-6.56 (1H, m), 4.66-4.87 (1H, m), 4.52-4.62 (1H, m), 3.82-3.95 (0.6H, m), 3.50-3.75 (1.4H, m), 3.31-3.50 (1H, m), 3.04-3.20 (0.6H, m), 2.85-3.04 (1H, m), 2.58-2.74 (0.4H, m), 1.98-2.14 (1H, m), 1.40-1.90 (6H, m), 1.54 (3.6H, s), 1.48 (5.4H, s)

(12) Optically-Active Compound of 4-(1,7-diazaspiro[4.5]dec-7-yl)-7H-pyrrolo[2,3-d]pyrimidine

[Chemical Formula 123]

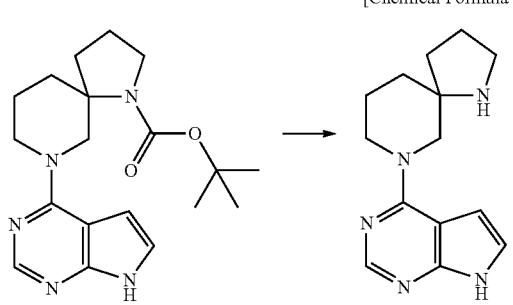

To a solution of 7-(7H-pyrrolo[2,3-d]pyrimidin-4-yl)-1,7-diazaspiro[4.5]decane-1-carboxylic acid tert-butyl ester (60 mg) in chloroform (1.0 ml) were added 4M hydrochloric acid-ethyl acetate (1.5 ml) and 2M hydrochloric acid-methanol (0.5 ml), and the mixture was stirred at room temperature for 2.5 hours. The reaction mixture was concentrated under reduced pressure, and then azeotroped with toluene. The residue was neutralized by the addition of 4M aqueous sodium hydroxide solution, and thereto was added saturated aqueous sodium chloride solution. The mixture was extracted with chloroform. The separated organic solvent was concentrated under reduced pressure to give the titled compound (30 mg).

$^1$H-NMR (CDCl$_3$) δ: 9.26 (1H, br s), 8.28 (1H, s), 7.04 (1H, d, J=3.7 Hz), 6.52 (1H, d, J=3.7 Hz), 3.92-3.86 (2H, m), 3.81 (1H, d, J=13.0 Hz), 3.72 (1H, d, J=13.0 Hz), 3.10-3.00 (2H, m), 1.94-1.80 (3H, m), 1.78-1.70 (5H, m), 1.55-1.47 (1H, m).

(13) Optically-Active Compound of 3-oxo-3-[7-(7H-pyrrolo[2.3-d]pyrimidin-4-yl)-1,7-diazaspiro[4.5]dec-1-yl)propionitrile

[Chemical Formula 124]

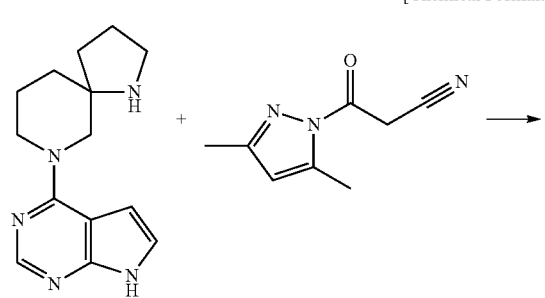

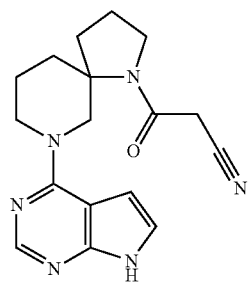

4-(1,7-Diazaspiro[4.5]dec-7-yl)-7H-pyrrolo[2,3-d]pyrimidine (30 mg) was mixed with 1-cyanoacetyl-3,5-dimethylpyrazole (38 mg), N,N-diisopropylethylamine (42 μl) and 1,4-dioxane (1 ml), and the mixture was stirred at 110° C. for 75 minutes. The mixture was cooled to room temperature, and then thereto was added saturated aqueous sodium bicarbonate solution. The mixture was extracted with ethyl acetate. The organic layer was dried over anhydrous magnesium sulfate, and concentrated under reduced pressure. The resulting residue was purified by silica gel column chromatography (eluent: chloroform/ethyl acetate=1/2, followed by chloroform/methanol=25/1 to 20/1) to give the titled compound (32 mg).

$^1$H-NMR (DMSO-D$_6$) δ: 11.69 (1H, br s), 8.09 (1H, s), 7.19-7.15 (1H, m), 6.59-6.55 (1H, m), 4.74-4.66 (1H, m), 4.55-4.47 (1H, m), 3.95 (2H, s), 3.86-3.78 (1H, m), 3.57-3.48 (1H, m), 3.45-3.37 (1H, m), 2.99-2.82 (2H, m), 1.89-1.68 (4H, m), 1.66-1.56 (2H, m), 1.55-1.47 (1H, m).

[α]D=+185.58° (25° C., c=1.04, methanol)

Preparation 8

An optical active compound of 3-[3-methyl-6-(7H-pyrrolo[2,3-d]pyrimidin-4-yl)-1,6-diazaspiro[3.4]oct-1-yl]-3-oxopropionitrile (Compound 6) was treated according to a conventional method to give 1 hydrate thereof.

$^1$H-NMR (DMSO-D$_6$) δ: 11.60 (1H, br s), 8.08 (1H, s), 7.11 (1H, s), 6.58 (1H, s), 4.16 (1H, dd, J=8.2, 8.2 Hz), 4.11-3.61 (6H, m), 3.57 (1H, dd, J=7.65, 6.26 Hz), 2.70-2.57 (2H, m), 2.24-2.10 (1H, m), 1.11 (3H, d, J=6.9 Hz).

The following Tables 1 to 3 show structural formulae and $^1$H-NMR spectral data of Compounds 1 to 95 prepared according to the above Preparations. $^1$H-NMR spectra are measured in CDCl$_3$ or DMSO-d$_6$ by using tetramethylsilane as an internal standard, and all δ values are shown in ppm. Unless otherwise specified, a 400 MHz NMR spectroscopy was used for measurement.

Symbols in Table have the following meanings.
s: singlet
d: doublet
t: triplet
q: quartet
dd: double doublet
ddd: double double doublet
brs: broad singlet
m: multiplet
J: coupling constant

TABLE 1

| No. | Structural Formula | Comments | NMR Data |
|---|---|---|---|
| 1 | | Compound 1 (Optically-active substance) | 1H-NMR (DMSO-D6) δ: 11.71 (1H, br s), 8.12 (1H, s), 7.20 (1H, dd, J = 3.5, 2.4 Hz), 6.65 (1H, dd, J = 3.6, 1.9 Hz), 4.93-4.88 (1H, m), 4.64-4.58 (1H, m), 4.24-4.18 (1H, m), 3.67 (2H, s), 3.61 (1H, d, J = 12.8 Hz), 3.46-3.41 (1H, m), 3.03-2.95 (1H, m), 2.42-2.35 (1H, m), 2.34-2.25 (1H, m), 2.15-2.08 (1H, m), 1.83-1.77 (1H, m), 1.57-1.43 (1H, m), 1.01 (3H, d, J = 7.1 Hz). |
| 2 | | Compound 2 (Optically-active substance) | 1H-NMR (DMSO-D6) δ: 11.70 (1H, br s), 8.14 (1H, s), 7.19 (1H, dd, J = 3.5, 2.4 Hz), 6.64 (1H, dd, J = 3.6, 1.9 Hz), 5.03-4.96 (1H, m), 4.66-4.59 (1H, m), 4.11-4.06 (1H, m), 3.70 (1H, d, J = 18.7 Hz), 3.65 (1H, d, J = 18.7 Hz), 3.60-3.55 (1H, m), 3.45 (1H, d, J = 13.0 Hz), 2.97-2.89 (1H, m), 2.46-2.41 (1H, m), 2.40-2.34 (1H, m), 2.00-1.94 (1H, m), 1.88-1.80 (1H, m), 1.64-1.51 (1H, m), 0.91 (3H, d, J = 7.1 Hz). |
| 3 | | Compound 3 (Optically-active substance) | 1H-NMR (DMSO-D6) δ: 11.73 (1H, br s), 8.13 (1H, s), 7.22-7.18 (1H, m), 6.67-6.63 (1H, m), 4.96 (1H, d, J = 12.6 Hz), 4.68-4.60 (1H, m), 4.11-4.03 (1H, m), 4.01-3.93 (1H, m), 3.71 (2H, s), 3.53 (1H, d, J = 12.6 Hz), 2.98-2.88 (1H, m), 2.40-2.30 (1H, m), 2.03-1.90 (3H, m), 1.83-1.75 (1H, m), 1.59-1.45 (1H, m). |
| 4 | | Compound 4 (Optically-active substance) | 1H-NMR (DMSO-D6) δ: 11.68 (1H, br s), 8.11 (1H, s), 7.17-7.14 (1H, m), 6.58 (1H, dd, J = 3.3, 1.8 Hz), 4.66-4.58 (2H, m), 4.24-4.13 (2H, m), 4.12-4.02 (1H, m), 3.89-3.78 (3H, m), 2.68-2.58 (1H, m), 2.56-2.45 (1H, m). |
| 5 | | Compound 5 (Optically-active substance) | 1H-NMR (DMSO-D6) δ: 11.74 (1H, br s), 8.15 (1H, s), 7.22-7.19 (1H, m), 6.65-6.62 (1H, m), 5.13-5.07 (1H, m), 4.69-4.46 (3H, m), 3.83 (1H, d, J = 18.8 Hz), 3.77 (1H, d, J = 19.2 Hz), 3.61-3.55 (1H, m), 2.99-2.91 (1H, m), 2.39-2.29 (1H, m), 2.26-2.19 (1H, m), 1.99-1.91 (1H, m), 1.63-1.48 (1H, m). |

TABLE 1-continued

| No. | Structural Formula | Comments | NMR Data |
|---|---|---|---|
| 6 | | Compound 6 (Optically-active substance) | 1H-NMR (DMSO-D6) δ: 11.60 (1H, br s), 8.08 (1H, s), 7.11 (1H, dd, J = 3.5, 2.4 Hz), 6.58 (1H, dd, J = 3.4, 1.9 Hz), 4.18-4.14 (1H, m), 4.09-3.93 (3H, m), 3.84-3.73 (1H, m), 3.71 (1H, d, J = 19.0 Hz), 3.66 (1H, d, J = 18.7 Hz), 3.58 (1H, dd, J = 8.2, 6.0 Hz), 2.70-2.58 (2H, m), 2.24-2.12 (1H, m), 1.12 (3H, d, J = 7.1 Hz). |
| 7 | | Compound 7 (Optically-active substance) | 1H-NMR (DMSO-D6) δ: 11.69 (1H, br s), 8.09 (1H, s), 7.19-7.15 (1H, m), 6.59-6.55 (1H, m), 4.74-4.66 (1H, m), 4.55-4.47 (1H, m), 3.95 (2H, s), 3.86-3.78 (1H, m), 3.57-3.48 (1H, m), 3.45-3.37 (1H, m), 2.99-2.82 (2H, m), 1.89-1.68 (4H, m), 1.66-1.56 (2H, m), 1.55-1.47 (1H, m). |
| 8 | | Racemate | 1H-NMR (DMSO-D6) δ: 11.66-11.52 (1.0H, m), 8.28 (0.1H, s), 8.10 (0.3H, s), 8.08-8.05 (0.6H, m), 7.15-7.06 (1.0H, m), 6.63-6.51 (1.0H, m), 4.49-4.16 (0.5H, m), 4.06-3.74 (2.0H, m), 3.66-2.72 (9.5H, m), 2.44-2.32 (0.5H, m), 2.15-1.65 (6.5H, m). |
| 9 | | Enantiomer of Compound 4 | 1H-NMR (DMSO-D6) δ: 11.68 (1H, br s), 8.11 (1H, s), 7.17-7.15 (1H, m), 6.58 (1H, dd, J = 3.2, 1.7 Hz), 4.65-4.59 (2H, m), 4.22-4.15 (2H, m), 4.13-4.01 (2H, m), 3.86 (1H, d, J = 19.0 Hz), 3.80 (1H, d, J = 19.2 Hz), 2.69-2.58 (1H, m), 2.56-2.45 (1H, m). |
| 10 | | Enantiomer of Compound 6 | 1H-NMR (DMSO-D6) δ: 11.60 (1H, br s), 8.08 (1H, s), 7.11 (1H, dd, J = 3.2, 2.5 Hz), 6.58 (1H, dd, J = 3.4, 1.9 Hz), 4.18-4.14 (1H, m), 4.09-3.93 (3H, m), 3.86-3.74 (1H, m), 3.71 (1H, d, J = 18.7 Hz), 3.66 (1H, d, J = 19.0 Hz), 3.58 (1H, dd, J = 8.2, 6.0 Hz), 2.69-2.58 (2H, m), 2.24-2.12 (1H, m), 1.12 (3H, d, J = 7.1 Hz). |

TABLE 1-continued

| No. | Structural Formula | Comments | NMR Data |
| --- | --- | --- | --- |
| 11 | | Enantiomer of Compound 2 | 1H-NMR (DMSO-D6) δ: 11.70 (1H, br s), 8.14 (1H, s), 7.19 (1H, dd, J = 3.5, 2.4 Hz), 6.64 (1H, dd, J = 3.7, 2.0 Hz), 5.02-4.97 (1H, m), 4.66-4.59 (1H, m), 4.11-4.06 (1H, m), 3.70 (1H, d, J = 18.7 Hz), 3.65 (1H, d, J = 19.0 Hz), 3.60-3.56 (1H, m), 3.45 (1H, d, J = 13.0 Hz), 2.98-2.89 (1H, m), 2.46-2.41 (1H, m), 2.39-2.34 (1H, m), 2.00-1.94 (1H, m), 1.87-1.81 (1H, m), 1.64-1.51 (1H, m), 0.91 (3H, d, J = 7.1 Hz). |
| 12 | | Enantiomer of Compound 1 | 1H-NMR (DMSO-D6) δ: 11.71 (1H, br s), 8.13 (1H, s), 7.20 (1H, dd, J = 3.5, 2.4 Hz), 6.65 (1H, dd, J = 3.5, 1.8 Hz), 4.93-4.88 (1H, m), 4.64-4.58 (1H, m), 4.24-4.18 (1H, m), 3.68 (2H, s), 3.61 (1H, d, J = 12.8 Hz), 3.45-3.41 (1H, m), 3.04-2.95 (1H, m), 2.42-2.35 (1H, m), 2.34-2.25 (1H, m), 2.15-2.08 (1H, m), 1.85-1.76 (1H, m), 1.57-1.43 (1H, m), 1.01 (3H, d, J = 7.1 Hz). |
| 13 | | Diastereomer of Compound 34 (Optically-active substance) | 1H-NMR (DMSO-D6) δ: 11.56 (1H, br s), 8.07 (1H, s), 7.12-7.08 (1H, m), 6.50-6.46 (1H, m), 4.84 (1H, q, J = 6.5 Hz), 4.05-3.98 (1H, m), 3.92 (2H, s), 3.82-3.74 (1H, m), 3.51-3.44 (2H, m), 2.68-2.59 (1H, m), 2.20-2.13 (1H, m), 1.97-1.90 (1H, m), 1.89-1.79 (3H, m), 1.26 (3H, d, J = 6.5 Hz). |
| 14 | | Diastereomer of Compound 20 (Racemate) | 1H-NMR (DMSO-D6) δ: 11.71 (1H, br s), 8.13-8.09 (1H, m), 7.21-7.16 (1H, m), 6.67-6.63 (1H, m), 4.91-4.84 (1H, m), 4.69-4.61 (1H, m), 4.51-4.44 (1H, m), 3.77 (1H, d, J = 18.6 Hz), 3.69 (1H, d, J = 18.6 Hz), 3.65 (1H, d, J = 15.3 Hz), 2.94-2.85 (1H, m), 2.38-2.29 (1H, m), 2.22-2.16 (1H, m), 1.97-1.91 (1H, m), 1.79-1.71 (1H, m), 1.58-1.48 (2H, m), 1.34 (3H, d, J = 6.3 Hz). |
| 15 | | Racemate of Compound 1 | 1H-NMR (CDCl3) δ: 9.35 (1H, br s), 8.30 (1H, s), 7.07 (1H, dd, J = 3.6, 2.3 Hz), 6.53 (1H, dd, J = 3.6, 1.9 Hz), 5.09-5.03 (1H, m), 4.65-4.59 (1H, m), 4.35-4.30 (1H, m), 3.81-3.76 (1H, m), 3.60-3.55 (1H, m), 3.21-3.13 (1H, m), 3.21 (2H, s), 2.74-2.65 (1H, m), 2.59-2.49 (1H, m), 2.23-2.17 (1H, m), 1.93-1.86 (1H, m), 1.72-1.60 (1H, m), 1.13 (3H, d, J = 7.1 Hz). |

TABLE 1-continued

| No. | Structural Formula | Comments | NMR Data |
|---|---|---|---|
| 16 | | Single diastereomer (Racemate) | 1H-NMR (DMSO-D6) δ: 11.73 (1H, br s), 8.12 (1H, s), 7.22-7.19 (1H, m), 6.65-6.62 (1H, m), 4.99-4.92 (1H, m), 4.64-4.57 (1H, m), 4.09-4.01 (1H, m), 4.00-3.92 (1H, m), 3.69 (2H, s), 3.49-3.44 (1H, m), 2.60-2.52 (1H, m), 2.08-1.90 (4H, m), 1.75-1.65 (1H, m), 0.98 (3H, d, J = 6.5 Hz). |
| 17 | | Racemate | 1H-NMR (DMSO-D6) δ: 11.61 (1H, br s), 8.08 (1H, s), 7.12 (1H, dd, J = 3.3, 2.4 Hz), 6.57 (1H, dd, J = 3.5, 1.8 Hz), 4.29-4.20 (1H, m), 4.08-3.74 (5H, m), 3.70 (2H, s), 2.69-2.58 (1H, m), 2.43-2.36 (1H, m), 2.35-2.27 (1H, m), 2.23-2.14 (1H, m). |
| 18 | | Single diastereomer (Racemate) | 1H-NMR (CDCl3) δ: 10.33 (1H, br s), 8.31 (1H, s), 7.09 (1H, dd, J = 3.5, 2.0 Hz), 6.53-6.49 (1H, m), 5.08-4.99 (1H, m), 4.97-4.88 (1H, m), 4.29-4.21 (1H, m), 4.18-4.11 (1H, m), 3.88-3.81 (1H, m), 3.25 (2H, s), 2.88-2.79 (1H, m), 2.44-2.36 (1H, m), 2.10-2.02 (1H, m), 1.92-1.79 (2H, m), 1.78-1.71 (1H, m), 1.42 (3H, d, J = 7.1 Hz). |
| 19 | | Diastereomer of Compound 6 (Racemate) | 1H-NMR (DMSO-D6) δ: 11.57 (1H, br s), 8.07 (1H, s), 7.11 (1H, dd, J = 3.6, 2.4 Hz), 6.57 (1H, dd, J = 3.4, 1.8 Hz), 4.31-4.22 (1H, m), 4.18-4.13 (1H, m), 4.09-3.94 (1H, m), 3.91-3.73 (2H, m), 3.67 (2H, s), 3.59-3.53 (1H, m), 2.80-2.71 (1H, m), 2.45-2.36 (1H, m), 2.30-2.19 (1H, m), 1.15 (3H, d, J = 6.9 Hz). |
| 20 | | Diastereomer of Compound 14 (Racemate) | 1H-NMR (CDCl3) δ: 9.04 (1H, br s), 8.32 (1H, s), 7.09-7.06 (1H, m), 6.56-6.53 (1H, m), 5.10-5.05 (1H, m), 4.72-4.66 (1H, m), 4.53-4.47 (1H, m), 3.78-3.73 (1H, m), 3.30 (1H, d, J = 17.2 Hz), 3.25 (1H, d, J = 17.6 Hz), 3.12-3.04 (1H, m), 2.77-2.69 (1H, m), 2.23-2.17 (1H, m), 1.95-1.85 (3H, m), 1.59 (4H, d, J = 6.3 Hz). |

TABLE 1-continued

| No. | Structural Formula | Comments | NMR Data |
|---|---|---|---|
| 21 | 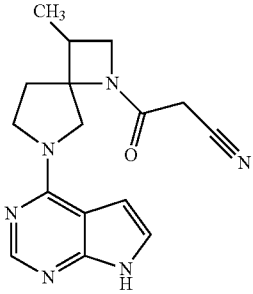 [SMILES: CC1CN(C(=O)CC#N)C12CCN(c1ncnc3[nH]ccc13)C2] | Racemate of Compound 6 | 1H-NMR (DMSO-D6) δ: 11.59 (1H, br s), 8.07 (1H, s), 7.11 (1H, dd, J = 3.2, 2.6 Hz), 6.57 (1H, dd, J = 3.4, 1.7 Hz), 4.18-4.12 (1H, m), 4.08-3.92 (3H, m), 3.84-3.72 (1H, m), 3.70 (1H, d, J = 18.8 Hz), 3.65 (1H, d, J = 18.8 Hz), 3.59-3.54 (1H, m), 2.68-2.58 (2H, m), 2.22-2.11 (1H, m), 1.11 (3H, d, J = 7.2 Hz). |
| 22 | 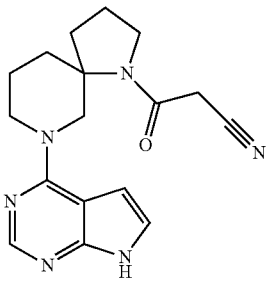 [SMILES: N#CCC(=O)N1CCCC12CCCN(c1ncnc3[nH]ccc13)C2] | Enantiomer of Compound 7 | 1H-NMR (DMSO-D6) δ: 11.69 (1H, br s), 8.09 (1H, s), 7.17 (1H, dd, J = 3.5, 2.6 Hz), 6.57 (1H, dd, J = 3.5, 1.9 Hz), 4.73-4.66 (1H, m), 4.55-4.48 (1H, m), 3.95 (2H, s), 3.85-3.78 (1H, m), 3.56-3.49 (1H, m), 3.45-3.37 (1H, m), 2.98-2.82 (2H, m), 1.89-1.69 (4H, m), 1.65-1.56 (2H, m), 1.55-1.48 (1H, m). |
| 23 | 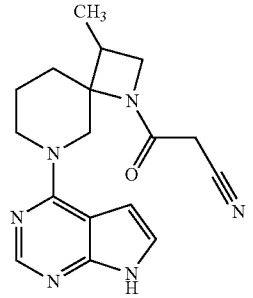 [SMILES: CC1CN(C(=O)CC#N)C12CCCN(c1ncnc3[nH]ccc13)C2] | Racemate of Compound 2 | 1H-NMR (DMSO-D6) δ: 11.70 (1H, br s), 8.14 (1H, s), 7.18 (1H, dd, J = 3.7, 2.6 Hz), 6.64 (1H, dd, J = 3.7, 1.9 Hz), 5.02-4.96 (1H, m), 4.65-4.59 (1H, m), 4.11-4.05 (1H, m), 3.70 (1H, d, J = 18.8 Hz), 3.65 (1H, d, J = 18.8 Hz), 3.59-3.54 (1H, m), 3.46-3.42 (1H, m), 2.97-2.88 (1H, m), 2.47-2.33 (2H, m), 2.00-1.93 (1H, m), 1.87-1.79 (1H, m), 1.63-1.50 (1H, m), 0.90 (3H, d, J = 7.2 Hz). |
| 24 | 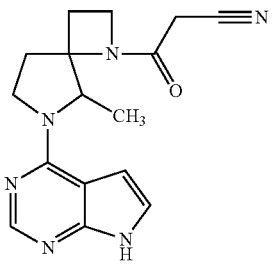 [SMILES: CC1N(c2ncnc3[nH]ccc23)CCC12CCN2C(=O)CC#N] | Single diastereomer (Racemate) | 1H-NMR (DMSO-D6) δ: 11.59 (1H, br s), 8.09 (1H, s), 7.12 (1H, dd, J = 3.2, 2.6 Hz), 6.52 (1H, dd, J = 3.5, 1.9 Hz), 4.45 (1H, q, J = 6.4 Hz), 4.08-3.99 (3H, m), 3.81 (1H, d, J = 18.8 Hz), 3.81-3.71 (1H, m), 3.75 (1H, d, J = 18.8 Hz), 3.01-2.92 (1H, m), 2.31-2.24 (1H, m), 2.20-2.12 (1H, m), 2.09-2.01 (1H, m), 1.33 (3H, d, J = 6.3 Hz). |
| 25 | 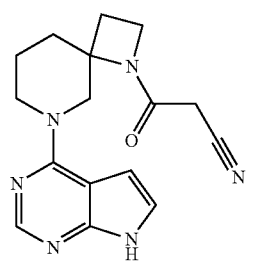 [SMILES: N#CCC(=O)N1CCC12CCCN(c1ncnc3[nH]ccc13)C2] | Enantiomer of Compound 3 | 1H-NMR (DMSO-D6) δ: 11.72 (1H, br s), 8.13 (1H, s), 7.20 (1H, dd, J = 3.5, 2.6 Hz), 6.64 (1H, dd, J = 3.6, 1.9 Hz), 4.96 (1H, d, J = 12.6 Hz), 4.68-4.59 (1H, m), 4.11-4.04 (1H, m), 4.00-3.93 (1H, m), 3.71 (2H, s), 3.53 (1H, d, J = 12.6 Hz), 2.98-2.90 (1H, m), 2.39-2.30 (1H, m), 2.01-1.93 (3H, m), 1.82-1.75 (1H, m), 1.59-1.46 (1H, m). |

TABLE 1-continued

| No. | Structural Formula | Comments | NMR Data |
|---|---|---|---|
| 26 | | Racemate of Compound 4 | 1H-NMR (DMSO-D6) δ: 11.67 (1H, br s), 8.11 (1H, s), 7.16 (1H, dd, J = 3.3, 2.4 Hz), 6.58 (1H, dd, J = 3.5, 2.0 Hz), 4.65-4.57 (2H, m), 4.23-4.14 (2H, m), 4.12-4.01 (1H, m), 3.89-3.78 (1H, m), 3.85 (1H, d, J = 19.2 Hz), 3.79 (1H, d, J = 19.0 Hz), 2.66-2.58 (1H, m), 2.56-2.46 (1H, m). |
| 27 | | Enantiomer of Compound 5 | 1H-NMR (DMSO-D6) δ: 11.74 (1H, br s), 8.15 (1H, s), 7.22-7.19 (1H, m), 6.65-6.62 (1H, m), 5.13-5.07 (1H, m), 4.70-4.46 (3H, m), 3.83 (1H, d, J = 18.8 Hz), 3.77 (1H, d, J = 19.0 Hz), 3.61-3.54 (1H, m), 2.99-2.90 (1H, m), 2.39-2.29 (1H, m), 2.26-2.19 (1H, m), 1.99-1.90 (1H, m), 1.64-1.48 (1H, m). |
| 28 | | Racemate | 1H-NMR (DMSO-D6) δ: 11.70 (1H, br s), 8.15 (1H, s), 7.19 (1H, dd, J = 3.6, 2.5 Hz), 6.65 (1H, dd, J = 3.6, 1.9 Hz), 5.11-5.03 (1H, m), 4.60-4.52 (1H, m), 3.78 (1H, d, J = 7.9 Hz), 3.70 (1H, d, J = 18.7 Hz), 3.65 (1H, d, J = 18.7 Hz), 3.52 (1H, d, J = 7.9 Hz), 3.50-3.46 (1H, m), 3.07-2.99 (1H, m), 2.34-2.25 (1H, m), 2.23-2.18 (1H, m), 1.91-1.83 (1H, m), 1.57-1.44 (1H, m), 1.23 (3H, s), 0.99 (3H, s). |
| 29 | | Racemate | 1H-NMR (CDCl3) δ: 9.43 (1H, br s), 8.28 (1H, s), 7.04 (1H, dd, J = 3.5, 2.1 Hz), 6.52 (1H, dd, J = 3.6, 1.5 Hz), 5.99-5.89 (1H, m), 5.33-5.27 (1H, m), 5.23-5.18 (1H, m), 4.75-4.68 (1H, m), 4.62-4.55 (1H, m), 4.14-4.08 (1H, m), 4.05-4.01 (2H, m), 3.81-3.76 (2H, m), 3.68-3.61 (1H, m), 3.56-3.48 (1H, m), 3.21-3.11 (2H, m), 2.66-2.54 (2H, m), 2.12-2.04 (1H, m), 1.95-1.85 (2H, m), 1.83-1.65 (3H, m), 1.58-1.51 (1H, m). |
| 30 | | Enantiomer of Compound 36. Configuration of α-carbon of carbonyl is S (derived from reagents). | 1H-NMR (CDCl3) δ: 9.54 (1H, br s), 8.29 (1H, s), 7.06 (1H, dd, J = 3.6, 1.7 Hz), 6.54-6.50 (1H, m), 4.71-4.64 (2H, m), 4.30-4.23 (1H, m), 4.06-4.00 (1H, m), 3.74 (1H, br s), 3.57-3.51 (2H, m), 3.29-3.21 (1H, m), 3.19-3.10 (1H, m), 2.11-2.04 (1H, m), 1.98-1.72 (5H, m), 1.62-1.56 (1H, m), 1.38 (3H, d, J = 6.5 Hz). |

TABLE 1-continued

| No. | Structural Formula | Comments | NMR Data |
|---|---|---|---|
| 31 | 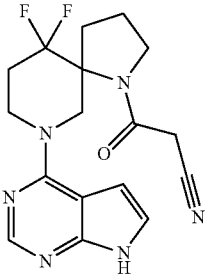 | Racemate | 1H-NMR (DMSO-D6) δ: 11.79 (1H, br s), 8.15 (1H, s), 7.23 (1H, dd, J = 3.5, 2.6 Hz), 6.66 (1H, dd, J = 3.5, 1.9 Hz), 4.83-4.76 (1H, m), 4.73-4.61 (2H, m), 4.11 (1H, d, J = 19.0 Hz), 4.00 (1H, d, J = 19.2 Hz), 3.64-3.50 (2H, m), 3.28-3.18 (1H, m), 2.35-2.26 (2H, m), 2.11-2.02 (1H, m), 1.93-1.83 (1H, m), 1.79-1.71 (2H, m). |
| 32 | 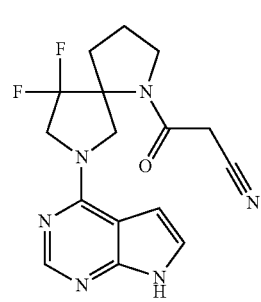 [SMILES: N#CCC(=O)N1CCCC12CN(c1ncnc3[nH]ccc13)CC2(F)F] | Racemate | 1H-NMR (DMSO-D6) δ: 11.73 (1H, s), 8.13 (1H, s), 7.19-7.16 (1H, m), 6.64-6.60 (1H, m), 4.52-3.96 (4H, m), 4.14 (1H, d, J = 19.0 Hz), 4.00 (1H, d, J = 19.2 Hz), 3.61-3.54 (2H, m), 2.46-2.42 (1H, m), 2.11-2.01 (1H, m), 1.99-1.91 (1H, m), 1.87-1.76 (1H, m). |
| 33 | 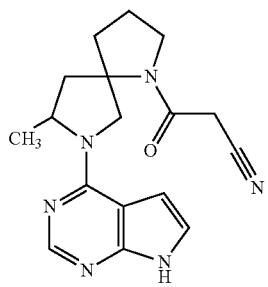 [SMILES: CC1CC2(CCCN2C(=O)CC#N)CN1c1ncnc2[nH]ccc12] | Diastereomer of Compound 42 (Optically-active substance) | 1H-NMR (DMSO-D6) δ: 11.60 (1H, br s), 8.10 (1H, s), 7.13-7.11 (1H, m), 6.45-6.43 (1H, m), 4.44-4.31 (2H, m), 4.00 (2H, s), 3.68-3.59 (1H, m), 3.52-3.39 (2H, m), 2.87-2.80 (1H, m), 1.99-1.90 (1H, m), 1.83-1.73 (4H, m), 1.36 (3H, d, J = 6.0 Hz). |
| 34 | 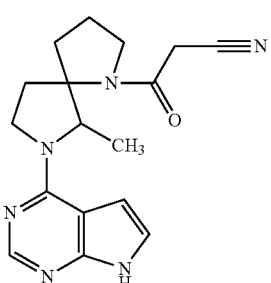 | Diastereomer of Compound 13 (Optically-active substance) | 1H-NMR (DMSO-D6) δ: 11.59 (1H, br s), 8.08 (1H, s), 7.13-7.10 (1H, m), 6.57-6.52 (1H, m), 4.24-4.16 (1H, m), 4.08 (1H, d, J = 19.0 Hz), 4.00 (1H, d, J = 19.0 Hz), 3.79-3.67 (2H, m), 3.59-3.53 (1H, m), 3.52-3.44 (1H, m), 1.91-1.65 (6H, m), 1.23 (3H, d, J = 6.7 Hz). |
| 35 | 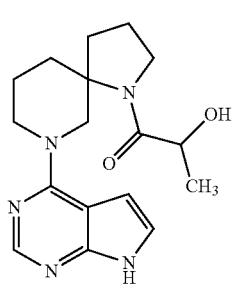 [SMILES: CC(O)C(=O)N1CCCC12CCCN(c1ncnc3[nH]ccc13)C2] | Diastereomer of Compound 36 (Optically-active substance). Configuration of α-carbon of carbonyl is S (derived from reagents). Higher polarity on TLC (chloroform/methanol = 10/1) than Compound 36. | 1H-NMR (CDCl3) δ: 9.88 (1H, br s), 8.30 (1H, s), 7.09-7.05 (1H, m), 6.54-6.51 (1H, m), 4.79-4.72 (1H, m), 4.63 (1H, d, J = 12.3 Hz), 4.33 (1H, dt, J = 6.6, 6.6 Hz), 4.10 (1H, d, J = 12.5 Hz), 3.88 (1H, br s), 3.72-3.65 (1H, m), 3.46-3.38 (1H, m), 3.24-3.16 (1H, m), 3.14-3.06 (1H, m), 2.21-2.14 (1H, m), 2.03-1.52 (6H, m), 1.34 (3H, d, J = 6.5 Hz). |

TABLE 1-continued

| No. | Structural Formula | Comments | NMR Data |
|---|---|---|---|
| 36 | | Diastereomer of Compound 35, Enantiomer of Compound 30. Configuration of α-carbon of carbonyl is R (derived from reagents). Lower polarity on TLC (chloroform/methanol = 10/1) than Compound 35. | 1H-NMR (CDC13) δ: 10.07 (1H, br s), 8.30 (1H, s), 7.10-7.06 (1H, m), 6.54-6.50 (1H, m), 4.73-4.64 (2H, m), 4.27 (1H, dt, J = 6.5, 6.5 Hz), 4.07-4.01 (1H, m), 3.77 (1H, br s), 3.60-3.51 (2H, m), 3.30-3.21 (1H, m), 3.19-3.10 (1H, m), 2.12-2.04 (1H, m), 1.98-1.57 (6H, m), 1.38 (3H, d, J = 6.5 Hz). |
| 37 | | Racemate of Compound 5 | 1H-NMR (DMSO-D6) δ: 11.73 (1H, br s), 8.15 (1H, s), 7.21 (1H, dd, J = 3.4, 2.6 Hz), 6.64 (1H, dd, J = 3.6, 2.0 Hz), 5.14-5.07 (1H, m), 4.70-4.46 (3H, m), 3.83 (1H, d, J = 18.9 Hz), 3.77 (1H, d, J = 18.9 Hz), 3.62-3.56 (1H, m), 3.00-2.91 (1H, m), 2.40-2.29 (1H, m), 2.27-2.20 (1H, m), 1.99-1.91 (1H, m), 1.63-1.49 (1H, m). |
| 38 | | Racemate | 1H-NMR (DMSO-D6) δ: 11.56 (1H, br s), 8.06 (1H, s), 7.11-7.08 (1H, m), 6.55 (1H, dd, J = 3.5, 1.9 Hz), 4.18-4.07 (2H, m), 3.97-3.85 (2H, m), 3.71 (2H, s), 3.65 (2H, s), 2.43-2.22 (2H, m), 1.24 (3H, s), 1.20 (3H, s). |
| 39 | | Racemate | 1H-NMR (CDC13) δ: 10.34 (1H, br s), 8.29 (1H, s), 7.06 (1H, d, J = 3.5 Hz), 6.52 (1H, d, J = 3.7 Hz), 4.76-4.68 (1H, m), 4.59 (1H, d, J = 13.0 Hz), 4.11 (1H, d, J = 12.8 Hz), 3.75-3.70 (2H, m), 3.66-3.60 (1H, m), 3.54-3.47 (1H, m), 3.39 (3H, s), 3.22-3.12 (2H, m), 2.64-2.51 (2H, m), 2.12-2.04 (1H, m), 1.96-1.61 (5H, m), 1.59-1.52 (1H, m). |
| 40 | | Single diastereomer (Optically-active substance) | 1H-NMR (DMSO-D6) δ: 11.73 (1H, br s), 8.14 (1H, s), 7.17 (1H, dd, J = 3.5, 2.3 Hz), 6.61 (1H, dd, J = 3.5, 1.6 Hz), 4.47-4.37 (1H, m), 4.30-4.24 (1H, m), 4.22-4.05 (2H, m), 4.12 (1H, d, J = 19.2 Hz), 4.04 (1H, d, J = 19.0 Hz), 3.65-3.60 (1H, m), 3.54-3.48 (1H, m), 2.70-2.64 (1H, m), 2.08-1.97 (1H, m), 1.71-1.63 (1H, m), 1.08 (3H, d, J = 7.0 Hz).. |

TABLE 1-continued

| No. | Structural Formula | Comments | NMR Data |
|---|---|---|---|
| 41 | (structure) | Racemate | 1H-NMR (DMSO-D6) δ: 11.57 (1H, br s), 8.07 (1H, s), 7.09 (1H, dd, J = 3.5, 2.4 Hz), 6.56 (1H, dd, J = 3.5, 2.0 Hz), 4.01-3.81 (4H, m), 3.96 (1H, d, J = 18.7 Hz), 3.90 (1H, d, J= 19.0 Hz), 3.48-3.42 (2H, m), 2.46-2.37 (1H, m), 2.16-2.06 (1H, m), 1.77-1.69 (2H, m), 1.03 (3H, s), 0.98 (3H, s). |
| 42 | (structure) | Diastereomer of Compound 33 (Optically-active substance) | 1H-NMR (DMSO-D6) δ: 11.57 (1H, br s), 8.08 (1H, s), 7.11-7.09 (1H, m), 6.50 (1H, dd, J = 3.5, 1.6 Hz), 4.73-4.65 (1H, m), 4.29-4.23 (1H, m), 3.94 (2H, s), 3.72-3.66 (1H, m), 3.51-3.44 (1H, m), 3.43-3.36 (1H, m), 3.23-3.15 (1H, m), 2.28-2.21 (1H, m), 2.13-2.05 (1H, m), 1.94-1.86 (2H, m), 1.60-1.54 (1H, m), 1.31 (3H, d, J = 6.5 Hz). |
| 43 | (structure) | Diastereomer mixture. Configuration of α-position of carbonyl of amide is S. | 1H-NMR (CDCl3) δ: 10.97-10.54 (1H, m), 8.30 (1H, s), 7.11-7.08 (1H, m), 6.51 (1H, d, J = 3.2 Hz), 4.80-4.59 (2H, m), 4.36-4.24 (1H, m), 4.12-4.01 (1H, m), 3.89 (1H, br s), 3.71-3.65 (0.5H, m), 3.58-3.51 (1H, m), 3.45-3.37 (0.5H, m), 3.29-3.05 (2H, m), 2.21-2.14 (0.5H, m), 2.11-2.04 (0.5H, m), 2.02-1.70 (5H, m), 1.66-1.53 (1H, m), 1.39-1.32 (3H, m). |
| 44 | (structure) | Racemate | 1H-NMR (CDCl3) δ: 10.67-10.25 (1H, m), 8.30 (1H, s), 7.11-7.07 (1H, m), 6.52 (1H, d, J = 3.2 Hz), 4.78-4.71 (1H, m), 4.70-4.64 (1H, m), 4.09 (1H, d, J = 15.3 Hz), 4.04-3.98 (1H, m), 4.03 (1H, d, J = 15.3 Hz), 3.67 (1H, br s), 3.50-3.42 (1H, m), 3.41-3.32 (1H, m), 3.26-3.17 (1H, m), 3.17-3.08 (1H, m), 2.18-2.10 (1H, m), 2.04-1.58 (6H, m). |
| 45 | (structure) | Diastereomer mixture. Configuration of α-position of carbonyl of amide is S (derived from (S)-(−)-2-methoxypropionic acid). | 1H-NMR (CDCl3) δ: 10.62 (1H, br s), 8.30 (1H, s), 7.08 (1H, d, J = 3.5 Hz), 6.54-6.50 (1H, m), 4.75-4.57 (2H, m), 4.20-4.12 (1H, m), 4.05-3.99 (1H, m), 3.85-3.78 (0.5H, m), 3.67-3.62 (1H, m), 3.54-3.46 (0.5H, m), 3.37-3.35 (3H, m), 3.27-3.12 (2H, m), 2.13-2.04 (1H, m), 1.99-1.49 (6H, m), 1.41-1.36 (3H, m). |

TABLE 1-continued

| No. | Structural Formula | Comments | NMR Data |
|---|---|---|---|
| 46 | | Diastereomer mixture. Configuration of α-position of carbonyl of amide is R (derived from (R)-(+)-2-methoxypropionic acid). | 1H-NMR (CDCl3) δ: 10.98 (1H, br s), 8.30 (1H, s), 7.09 (1H, d, J = 3.5 Hz), 6.53-6.50 (1H, m), 4.74-4.58 (2H, m), 4.20-4.12 (1H, m), 4.05-3.99 (1H, m), 3.85-3.78 (0.5H, m), 3.68-3.62 (1H, m), 3.53-3.46 (0.5H, m), 3.37-3.35 (3H, m), 3.27-3.14 (2H, m), 2.13-2.04 (1H, m), 1.99-1.48 (6H, m), 1.40-1.36 (3H, m). |
| 47 | | Diastereomer mixture. Configuration of α-position of carbonyl of amide is S (derived from (S)-(−)-2-acetoxypropionyl chloride). | 1H-NMR (DMSO-D6) δ: 11.67 (1H, br s), 8.11 (0.5H, s), 8.10 (0.5H, s), 7.18-7.16 (1H, m), 6.58 (0.5H, dd, J = 3.5, 1.8 Hz), 6.51 (0.5H, dd, J = 3.7, 1.8 Hz), 5.10-5.03 (1H, m), 4.70-4.60 (1H, m), 4.52-4.45 (1H, m), 3.88-3.79 (1H, m), 3.77-3.70 (0.5H, m), 3.61-3.51 (1H, m), 3.49-3.41 (0.5H, m), 3.01-2.82 (2H, m), 2.05 (1.5H, s), 2.04 (1.5H, s), 1.91-1.72 (4H, m), 1.66-1.56 (2H, m), 1.50-1.43 (1H, m), 1.35 (1.5H, d, J = 6.8 Hz), 1.31 (1.5H, d, J = 6.8 Hz). |
| 48 | | Racemate | 1H-NMR (DMSO-D6) δ: 11.67 (1H, br s), 8.08 (1H, s), 7.15 (1H, dd, J = 3.5, 2.3 Hz), 6.56 (1H, dd, J = 3.6, 1.7 Hz), 4.72-4.66 (1H, m), 4.48 (1H, d, J = 12.5 Hz), 3.98 (1H, d, J = 14.6 Hz), 3.94 (1H, d, J = 14.8 Hz), 3.89 (1H, d, J = 13.0 Hz), 3.53-3.46 (1H, m), 3.39-3.34 (1H, m), 3.30 (3H, s), 2.99-2.89 (2H, m), 1.85-1.66 (4H, m), 1.62-1.52 (2H, m), 1.51-1.45 (1H, m). |
| 49 | | Racemate | 1H-NMR (DMSO-D6) δ: 11.64 (1H, br s), 8.08 (1H, s), 7.13 (1H, dd, J = 3.5, 2.6 Hz), 6.54 (1H, dd, J = 3.6, 1.7 Hz), 5.97 (1H, t, J = 5.6 Hz), 4.72-4.64 (1H, m), 4.40 (1H, d, J = 12.5 Hz), 3.87 (1H, d, J = 12.5 Hz), 3.39-3.29 (1H, m), 3.28-3.21 (1H, m), 3.07-3.00 (2H, m), 2.96-2.84 (2H, m), 1.83-1.65 (4H, m), 1.62-1.47 (2H, m), 1.44-1.37 (1H, m), 1.02 (3H, t, J = 7.1 Hz). |
| 50 | | Racemate | 1H-NMR (CDCl3) δ: 10.68 (1H, br s), 8.28 (1H, s), 7.07 (1H, d, J = 3.2 Hz), 6.51 (1H, d, J = 3.7 Hz), 4.75-4.68 (1H, m), 4.67-4.61 (1H, m), 4.64 (1H, d, J = 14.6 Hz), 4.60 (1H, d, J = 14.8 Hz), 4.06-4.01 (1H, m), 3.58-3.51 (1H, m), 3.49-3.42 (1H, m), 3.21-3.07 (2H, m), 2.21 (3H, s), 2.13-2.05 (1H, m), 2.03-1.81 (3H, m), 1.79-1.55 (3H, m). |

TABLE 1-continued

| No. | Structural Formula | Comments | NMR Data |
|---|---|---|---|
| 51 | | Racemate | 1H-NMR (CDCl3) δ: 9.34 (1H, br s), 8.28 (1H, s), 7.00-6.97 (1H, m), 6.58-6.54 (1H, m), 4.19-3.95 (2H, m), 3.84-3.45 (6H, m), 3.24-3.08 (2H, m), 2.28-2.14 (2H, m), 2.07-1.90 (5H, m), 1.85-1.61 (2H, m). |
| 52 | | Racemate | 1H-NMR (DMSO-D6) δ: 11.68 (1H, br s), 8.10 (1H, s), 7.16 (1H, dd, J = 3.5, 2.6 Hz), 6.82 (1H, t, J = 5.6 Hz), 6.59 (1H, dd, J = 3.7, 1.9 Hz), 4.75-4.67 (1H, m), 4.51-4.45 (1H, m), 4.03 (2H, d, J = 5.8 Hz), 3.86-3.81 (1H, m), 3.44-3.37 (1H, m), 3.32-3.25 (1H, m), 2.97-2.85 (2H, m), 1.88-1.69 (4H, m), 1.66-1.52 (2H, m), 1.52-1.45 (1H, m). |
| 53 | | Racemate | 1H-NMR (CDCl3) δ: 10.30-10.10 (1H, m), 8.33 (1H, s), 7.06 (1H, d, J = 2.8 Hz), 6.60 (1H, d, J = 3.0 Hz), 4.10-4.03 (1H, 8.10 (1H, m), 3.87-3.62 (3H, m), 2.53 (2H, t, J = 6.7 Hz), 2.22-2.08 (1H, m), 1.99-1.85 (6H, m) |
| 54 | | Single diastereomer (Optically-active substance) | 1H-NMR (DMSO-D6) δ: 12.75 (1H, br s), 8.32 (1H, s), 7.49-7.45 (1H, m), 6.98-6.93 (1H, m), 4.26-3.78 (5H, m), 3.97 (2H, s), 3.58-3.23 (2H, m), 2.83-2.73 (1H, m), 2.28-2.20 (1H, m), 2.17-1.96 (2H, m), 1.70-1.49 (1H, m), 1.02 (3H, d, J = 6.7 Hz). |
| 55 | | Racemate | 1H-NMR (DMSO-D6) δ: 11.70 (1H, br s), 8.14 (1H, s), 7.18 (1H, dd, J = 3.5, 2.3 Hz), 6.63 (1H, dd, J = 3.5, 1.9 Hz), 4.22-4.01 (5H, m), 3.96-3.82 (1H, m), 3.72-3.60 (2H, m), 2.86-2.77 (1H, m), 2.72-2.51 (2H, m), 2.41-2.30 (1H, m). |

TABLE 1-continued

| No. | Structural Formula | Comments | NMR Data |
|---|---|---|---|
| 56 | 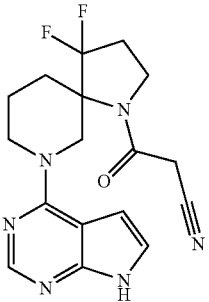 | Racemate | 1H-NMR (DMSO-D6) δ: 11.67 (1H, br s), 8.11 (1H, s), 7.17 (1H, dd, J = 3.5, 2.6 Hz), 6.61 (1H, dd, J = 3.7, 1.9 Hz), 4.90-4.84 (1H, m), 4.63-4.56 (1H, m), 4.06 (1H, d, J = 19.0 Hz), 3.99 (1H, d, J = 19.0 Hz), 3.94-3.88 (1H, m), 3.67-3.60 (1H, m), 3.56-3.49 (1H, m), 3.16-3.08 (1H, m), 2.81-2.71 (1H, m), 2.48-2.37 (2H, m), 2.00-1.90 (2H, m), 1.85-1.72 (1H, m). |
| 57 | 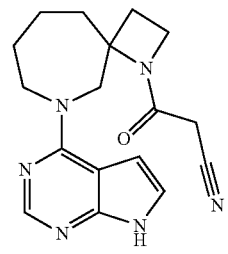 [SMILES: N#CCC(=O)N1CCC12CCCCN(c1ncnc3[nH]ccc13)C2] | Racemate | 1H-NMR (DMSO-D6) δ: 11.59 (1H, br s), 8.08 (1H, s), 7.13-7.10 (1H, m), 6.55 (1H, dd, J = 3.2, 1.6 Hz), 4.33-4.28 (1H, m), 4.08 (2H, s), 3.97-3.54 (3H, m), 3.48-3.29 (2H, m), 2.61-2.53 (1H, m), 2.30-2.06 (1H, m), 1.82-1.47 (6H, m). |
| 58 | 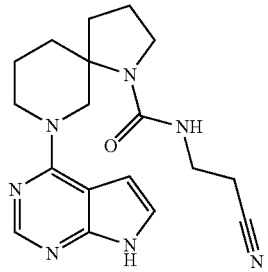 [SMILES: N#CCCNC(=O)N1CCCC12CCCN(c1ncnc3[nH]ccc13)C2] | Racemate | 1H-NMR (DMSO-D6) δ: 11.67 (1H, br s), 8.10 (1H, s), 7.16 (1H, dd, J = 3.5, 2.6 Hz), 6.56 (1H, dd, J = 3.6, 1.7 Hz), 6.46 (1H, t, J = 5.6 Hz), 4.74-4.67 (1H, m), 4.45 (1H, d, J = 12.5 Hz), 3.87 (1H, d, J = 12.8 Hz), 3.43-3.36 (1H, m), 3.30-3.24 (3H, m), 2.96-2.87 (2H, m), 2.66 (2H, t, J = 6.6 Hz), 1.87-1.68 (4H, m), 1.65-1.51 (2H, m), 1.49-1.42 (1H, m). |
| 59 | 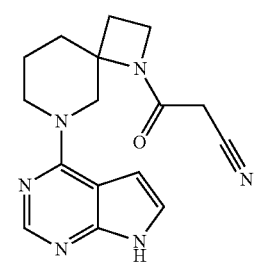 [SMILES: N#CCC(=O)N1CCC12CCCN(c1ncnc3[nH]ccc13)C2] | Racemate of Compound 3 | 1H-NMR (DMSO-D6) δ: 11.71 (1H, br s), 8.13 (1H, s), 7.20 (1H, dd, J = 3.5, 2.4 Hz), 6.64 (1H, dd, J = 3.6, 1.9 Hz), 4.96 (1H, d, J = 12.6 Hz), 4.67-4.60 (1H, m), 4.11-4.04 (1H, m), 4.00-3.93 (1H, m), 3.70 (2H, s), 3.53 (1H, d, J = 12.6 Hz), 2.98-2.90 (1H, m), 2.39-2.31 (1H, m), 2.01-1.93 (3H, m), 1.83-1.75 (1H, m), 1.58-1.46 (1H, m). |
| 60 | 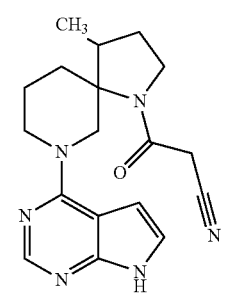 | Single diastereomer (Optically-active substance) | 1H-NMR (DMSO-D6) δ: 11.67 (1H, br s), 8.12 (1H, s), 7.16 (1H, dd, J = 3.5, 2.6 Hz), 6.61 (1H, dd, J = 3.7, 1.9 Hz), 4.60 (1H, d, J = 13.2 Hz), 4.38-4.30 (1H, m), 3.98 (1H, d, J = 18.8 Hz), 3.92 (1H, d, J = 19.0 Hz), 3.75 (1H, d, J = 13.2 Hz), 3.54-3.47 (1H, m), 3.46-3.35 (1H, m), 3.28-3.20 (1H, m), 2.54-2.46 (1H, m), 2.18-2.07 (2H, m), 2.01-1.92 (1H, m), 1.87-1.76 (1H, m), 1.66-1.58 (1H, m), 1.56-1.47 (1H, m), 0.82 (3H, d, J = 7.0 Hz). |

TABLE 1-continued

| No. | Structural Formula | Comments | NMR Data |
|---|---|---|---|
| 61 | | Racemate | 1H-NMR (CDCl3) δ: 10.99-10.59 (1H, m), 8.31 (1H, s), 7.08-7.01 (1H, m), 6.55 (1H, d, J = 3.0 Hz), 4.63-4.03 (2H, m), 3.84-3.44 (4H, m), 3.70 (3H, s), 3.31-3.12 (0.7H, m), 3.00-2.81 (0.3H, m), 2.16-1.71 (5H, m). |
| 62 | | Racemate | 1H-NMR (DMSO-D6) δ: 11.56 (1H, br s), 8.07 (1H, s), 7.09 (1H, dd, J = 3.2, 2.6 Hz), 6.92 (1H, t, J = 5.7 Hz), 6.55 (1H, dd, J = 3.2, 1.9 Hz), 4.37-4.12 (1H, m), 4.05-3.93 (1H, m), 4.02 (2H, d, J = 5.6 Hz), 3.79-3.49 (2H, m), 3.40-3.27 (2H, m), 3.07-2.94 (1H, m), 1.98-1.83 (4H, m), 1.76-1.67 (1H, m). |
| 63 | | Racemate | 1H-NMR (CDCl3) δ: 9.13 (1H, br s), 8.29 (1H, s), 7.00-6.97 (1H, m), 6.58-6.54 (1H, m), 4.18-4.09 (1H, m), 4.06-3.93 (2H, m), 3.88-3.72 (1H, m), 3.68-3.61 (1H, m), 3.59-3.53 (2H, m), 3.22-3.09 (1H, m), 2.98 (3H, s), 2.07-1.92 (5H, m), 1.87-1.69 (1H, m). |
| 64 | | Racemate | 1H-NMR (CDCl3) δ: 9.33-9.10 (1H, m), 8.32 (1H, s), 7.79 (1H, s), 7.76-7.70 (2H, m), 7.58-7.52 (1H, m), 7.03-7.00 (1H, m), 6.61-6.57 (1H, m), 4.75-4.55 (1H, m), 4.27-4.18 (1H, m), 3.97-3.81 (1H, m), 3.79-3.72 (1H, m), 3.57-3.40 (3H, m), 2.23-2.15 (1H, m), 2.12-2.03 (1H, m), 1.98-1.85 (3H, m). |
| 65 | | Racemate | 1H-NMR (CDCl3) δ: 9.44 (1H, br s), 8.32 (1H, s), 7.73 (2H, d, J = 8.3 Hz), 7.58 (2H, d, J = 8.1 Hz), 7.02 (1H, dd, J = 3.6, 2.2 Hz), 6.59 (1H, dd, J = 3.2, 1.9 Hz), 4.75-4.52 (1H, m), 4.29-4.17 (1H, m), 3.97-3.82 (1H, m), 3.78-3.73 (1H, m), 3.53-3.41 (3H, m), 2.22-2.15 (1H, m), 2.11-2.03 (1H, m), 1.97-1.87 (3H, m). |

TABLE 1-continued

| No. | Structural Formula | Comments | NMR Data |
|---|---|---|---|
| 66 | | Single diastereomer (Optically-active substance) | 1H-NMR (DMSO-D6) δ: 11.60 (1H, br s), 8.08 (1H, s), 7.11 (1H, dd, J = 3.5, 2.6 Hz), 6.58 (1H, dd, J = 3.5, 1.9 Hz), 3.99 (1H, d, J = 19.0 Hz), 3.98-3.78 (4H, m), 3.92 (1H, d, J = 19.2 Hz), 3.54-3.47 (1H, m), 3.44-3.38 (1H, m), 3.05-2.95 (1H, m), 2.21-2.11 (1H, m), 1.98-1.87 (2H, m), 1.63-1.52 (1H, m), 0.93 (3H, d, J = 6.7 Hz). |
| 67 | | Racemate | 1H-NMR (DMSO-D6) δ: 11.55 (1H, br s), 8.05 (1H, s), 7.08 (1H, dd, J = 3.2, 2.6 Hz), 6.58-6.51 (2H, m), 4.35-4.16 (1H, m), 4.00-3.92 (1H, m), 3.72-3.50 (2H, m), 3.39-3.27 (2H, m), 3.26-3.21 (2H, m), 3.08-2.95 (1H, m), 2.62 (2H, t, J = 6.6 Hz), 1.94-1.82 (4H, m), 1.71-1.63 (1H, m). |
| 68 | | Racemate | 1H-NMR (DMSO-D6) δ: 11.55 (1H, s), 8.06 (1H, s), 7.08 (1H, dd, J = 3.4, 2.4 Hz), 6.55-6.52 (1H, m), 6.10 (1H, t, J = 5.6 Hz), 4.37-4.15 (1H, m), 4.01-3.90 (1H, m), 3.69-3.55 (1H, m), 3.54-3.49 (1H, m), 3.37-3.28 (2H, m), 3.09-3.01 (1H, m), 2.99-2.93 (2H, m), 1.93-1.80 (4H, m), 1.68-1.62 (1H, m), 1.46-1.37 (2H, m), 0.83 (3H, t, J = 7.4 Hz). |
| 69 | | Racemate | 1H-NMR (DMSO-D6) δ: 11.58 (1H, br s), 8.06 (1H, s), 7.10-7.07 (1H, m), 6.55-6.49 (1H, m), 4.39-4.10 (1H, m), 4.04-3.92 (1H, m), 3.83-3.62 (1H, m), 3.62-3.49 (3H, m), 3.56 (3H, s), 3.07-2.91 (1H, m), 2.60-2.53 (2H, m), 2.51-2.45 (2H, m), 1.99-1.93 (2H, m), 1.91-1.82 (2H, m), 1.75-1.65 (1H, m). |
| 70 | | Racemate | 1H-NMR (CDCl3) δ: 10.81 (1H, br s), 8.29 (1H, s), 7.02 (1H, d, J = 3.7 Hz), 6.52 (1H, d, J = 3.5 Hz), 4.64 (2H, s), 4.55-4.39 (1H, m), 4.18-4.07 (1H, m), 3.85-3.74 (1H, m), 3.72-3.64 (1H, m), 3.59-3.48 (2H, m), 3.37-3.26 (1H, m), 2.19 (3H, s), 2.14-1.91 (4H, m), 1.83-1.72 (1H, m). |

TABLE 1-continued

| No. | Structural Formula | Comments | NMR Data |
|---|---|---|---|
| 71 | 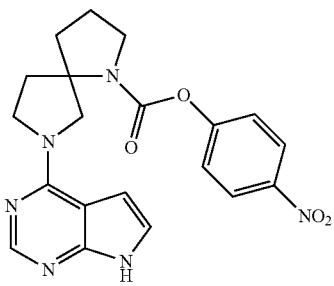 [SMILES: O=C(Oc1ccc([N+](=O)[O-])cc1)N1CCCC12CCN(c1ncnc3[nH]ccc13)C2] | Racemate | 1H-NMR (DMSO-D6) δ: 11.58 (1H, br s), 8.27 (2H, d, J = 9.0 Hz), 8.07 (1H, s), 7.46 (2H, d, J = 9.3 Hz), 7.12-7.09 (1H, m), 6.60-6.57 (1H, m), 4.29-4.15 (1H, m), 4.05-3.95 (1H, m), 3.78-3.65 (4H, m), 2.98-2.82 (1H, m), 2.15-2.03 (2H, m), 1.97-1.86 (3H, m). |
| 72 | 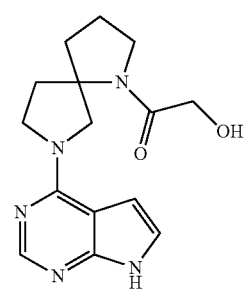 [SMILES: O=C(CO)N1CCCC12CCN(c1ncnc3[nH]ccc13)C2] | Racemate | 1H-NMR (DMSO-D6) δ: 11.57 (1H, br s), 8.07 (1H, s), 7.10-7.08 (1H, m), 6.56-6.52 (1H, m), 4.46 (1H, t, J = 5.6 Hz), 4.39-4.21 (1H, m) 4.06-3.96 (3H, m), 3.74-3.55 (2H, m), 3.45-3.39 (2H, m), 3.09-2.97 (1H, m), 1.97-1.92 (2H, m), 1.90-1.84 (2H, m), 1.78-1.71 (1H, m). |
| 73 | 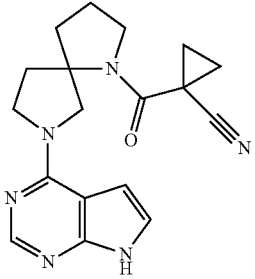 [SMILES: N#CC1(C(=O)N2CCCC23CCN(c2ncnc4[nH]ccc24)C3)CC1] | Racemate | 1H-NMR (DMSO-D6) δ: 11.58 (1H, br s), 8.06 (1H, s), 7.10 (1H, dd, J = 3.4, 2.4 Hz), 6.57 (1H, dd, J = 3.5, 2.1 Hz), 4.30-4.09 (1H, m), 4.04-3.94 (1H, m), 3.92-3.82 (2H, m), 3.77-3.52 (2H, m), 2.97-2.84 (1H, m), 2.07-1.92 (4H, m), 1.85-1.76 (1H, m), 1.63-1.49 (4H, m). |
| 74 | 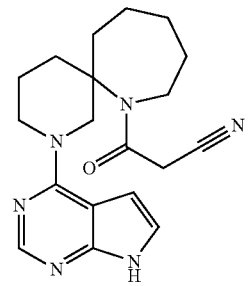 [SMILES: N#CCC(=O)N1CCCCCC12CCCN(c1ncnc3[nH]ccc13)C2] | Racemate | 1H-NMR (DMSO-D6) δ: 11.63 (1H, s), 8.09 (1H, s), 7.15 (1H, dd, J = 3.5, 2.6 Hz), 6.64 (1H, dd, J = 3.6, 2.0 Hz), 4.53 (1H, d, J = 13.2 Hz), 4.38-4.29 (1H, m), 4.18 (1H, d, J = 13.0 Hz), 4.02 (2H, s), 3.35-3.31 (3H, m), 2.63-2.55 (1H, m), 1.88-1.77 (2H, m), 1.74-1.50 (6H, m), 1.47-1.34 (3H, m). |
| 75 | 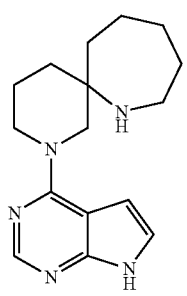 [SMILES: c1nc(N2CCCC3(CCCCCN3)C2)c2cc[nH]c2n1] | Racemate | 1H-NMR (DMSO-D6) δ: 11.59 (1H, br s), 8.08 (1H, s), 7.13 (1H, dd, J = 3.5, 2.6 Hz), 6.57 (1H, dd, J = 3.6, 1.7 Hz), 3.90-3.83 (1H, m), 3.70-3.62 (1H, m), 3.69 (1H, d, J = 12.8 Hz), 3.53 (1H, d, J = 12.8 Hz), 2.67-2.57 (1H, m), 2.54-2.45 (1H, m), 1.76-1.63 (2H, m), 1.60-1.36 (10H, m). |

TABLE 1-continued

| No. | Structural Formula | Comments | NMR Data |
|---|---|---|---|
| 76 | | Racemate | 1H-NMR (DMSO-D6) δ: 11.67 (1H, br s), 8.08 (1H, s), 7.18-7.14 (1H, m), 6.69-6.63 (1H, m), 4.53-4.45 (1H, m), 4.33-4.24 (1H, m), 4.14-4.07 (1H, m), 3.45-3.25 (3H, m), 2.52-2.39 (1H, m), 1.85-1.47 (11H, m), 1.40 (9H, s). |
| 77 | | Racemate | 1H-NMR (DMSO-D6) δ: 11.60 (1H, br s), 8.08 (1H, s), 7.13-7.10 (1H, m), 6.57-6.51 (1H, m), 4.32-4.26 (1H, m), 4.07 (2H, s), 4.00-3.50 (3H, m), 3.48-3.32 (2H, m), 2.60-2.52 (1H, m), 2.30-2.08 (1H, m), 1.82-1.44 (6H, m). |
| 78 | | Racemate | 1H-NMR (DMSO-D6) δ: 11.59 (1H, br s), 8.08 (1H, s), 7.13-7.11 (1H, m), 6.55-6.52 (1H, m), 4.39-4.33 (1H, m), 3.92-3.74 (2H, m), 3.64-3.51 (2H, m), 3.42-3.36 (1H, m), 2.65-2.56 (1H, m), 2.24-1.97 (1H, m), 2.06 (3H, s), 1.87-1.73 (1H, m), 1.71-1.56 (4H, m), 1.52-1.40 (1H, m). |
| 79 | | Racemate | 1H-NMR (DMSO-D6) δ: 11.53 (1H, br s), 8.05 (1H, s), 7.08 (1H, d, J = 3.5 Hz), 6.55 (1H, t, J = 4.4 Hz), 3.91-3.67 (3H, m), 3.61-3.40 (1H, m), 2.76-2.62 (2H, m), 2.04-1.91 (2H, m), 1.88-1.79 (1H, m), 1.64-1.46 (4H, m), 1.45-1.37 (2H, m). |
| 80 | | Racemate | 1H-NMR (DMSO-D6) δ: 11.58 (1H, br s), 8.07 (1H, s), 7.12-7.10 (1H, m), 6.55 (1H, dd, J = 3.2, 1.9 Hz), 4.31-4.21 (1H, m), 4.00-3.47 (4H, m), 3.33-3.22 (1H, m), 2.59-2.44 (1H, m), 2.24-2.04 (1H, m), 1.82-1.71 (1H, m), 1.69-1.56 (3H, m), 1.53-1.45 (1H, m), 1.45-1.36 (1H, m), 1.42 (9H, s). |

TABLE 1-continued

| No. | Structural Formula | Comments | NMR Data |
|---|---|---|---|
| 81 | 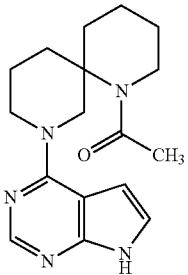 | Racemate | 1H-NMR (DMSO-D6) δ: 12.02 (1H, br s), 8.17 (1H, s), 7.27-7.23 (1H, m), 6.75-6.69 (1H, m), 4.57-4.35 (3H, m), 3.46-3.33 (3H, m), 2.78-2.68 (1H, m), 2.02 (3H, s), 1.87-1.78 (1H, m), 1.75-1.40 (8H, m). |
| 82 | 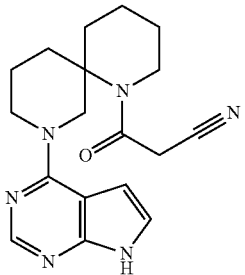 [SMILES: N#CCC(=O)N1CCCCC12CCCN(c1ncnc3[nH]ccc13)C2] | Racemate | 1H-NMR (DMSO-D6) δ: 11.68 (1H, br s), 8.10 (1H, s), 7.17 (1H, dd, J = 3.5, 2.6 Hz), 6.59 (1H, dd, J = 3.7, 1.9 Hz), 4.64-4.59 (1H, m), 4.51-4.44 (1H, m), 4.26-4.21 (1H, m), 4.07 (1H, d, J = 18.8 Hz), 4.01 (1H, d, J = 18.6 Hz), 3.31-3.13 (2H, m), 2.77-2.67 (1H, m), 1.86-1.37 (10H, m). |
| 83 | 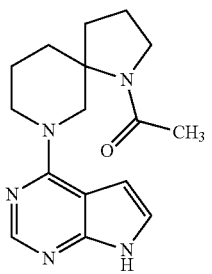 [SMILES: CC(=O)N1CCCC12CCCN(c1ncnc3[nH]ccc13)C2] | Racemate | 1H-NMR (DMSO-D6) δ: 11.65 (1H, br s), 8.09 (1H, s), 7.15 (1H, dd, J = 3.4, 2.5 Hz), 6.57 (1H, dd, J = 3.6, 1.9 Hz), 4.73-4.65 (1H, m), 4.47 (1H, d, J = 12.1 Hz), 3.90 (1H, d, J = 12.4 Hz), 3.62-3.54 (1H, m), 3.48-3.41 (1H, m), 3.00-2.88 (2H, m), 1.97 (3H, s), 1.88-1.67 (4H, m), 1.65-1.53 (2H, m), 1.50-1.43 (1H, m). |
| 84 | 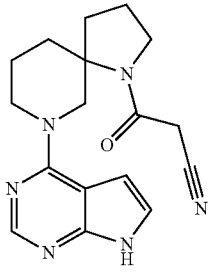 | Racemate of Compound 7 | 1H-NMR (DMSO-D6) δ: 11.64 (1H, br s), 8.10 (1H, s), 7.16 (1H, dd, J = 3.4, 2.6 Hz), 6.57 (1H, dd, J = 3.6, 1.6 Hz), 4.73-4.66 (1H, m), 4.52 (1H, d, J = 12.5 Hz), 3.93 (2H, s), 3.83 (1H, d, J = 12.9 Hz), 3.58-3.51 (1H, m), 3.46-3.39 (1H, m), 2.99-2.84 (2H, m), 1.90-1.70 (4H, m), 1.67-1.57 (2H, m), 1.56-1.49 (1H, m). |
| 85 | 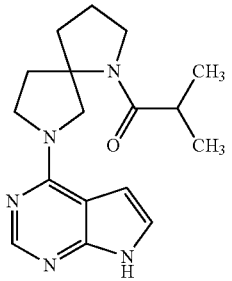 [SMILES: CC(C)C(=O)N1CCCC12CCN(c1ncnc3[nH]ccc13)C2] | Racemate | 1H-NMR (CDCl3) δ: 9.05 (1H, br s), 8.27 (1H, s), 6.96 (1H, d, J = 3.7 Hz), 6.55 (1H, d, J = 3.5 Hz), 4.19-4.10 (1H, m), 3.90-3.75 (1H, m), 3.70-3.56 (3H, m), 3.39-3.28 (1H, m), 2.70-2.60 (1H, m), 2.12-2.03 (1H, m), 1.99-1.91 (4H, m), 1.79-1.69 (1H, m), 1.16-1.08 (6H, m). |

TABLE 1-continued

| No. | Structural Formula | Comments | NMR Data |
|---|---|---|---|
| 86 | | Racemate | 1H-NMR (DMSO-D6) δ: 11.56 (1H, br s), 8.07 (1H, s), 7.10-7.07 (1H, m), 6.56-6.51 (1H, m), 4.36-4.22 (1H, m), 4.04-3.94 (1H, m), 3.72-3.59 (1H, m), 3.56-3.49 (3H, m), 3.11-2.97 (1H, m), 2.29 (2H, q, J = 7.5 Hz), 1.97-1.93 (2H, m), 1.90-1.82 (2H, m), 1.74-1.66 (1H, m), 0.97 (3H, t, J = 7.4 Hz). |
| 87 | | Racemate | 1H-NMR (DMSO-D6) δ: 11.58 (1H, br s), 8.07 (1H, s), 7.11-7.08 (1H, m), 6.57-6.52 (1H, m), 4.38-4.24 (1H, m), 4.03-3.94 (1H, m), 3.75-3.60 (1H, m), 3.59-3.48 (3H, m), 3.13-2.99 (1H, m), 1.99 (3H, s), 1.98-1.93 (2H, m), 1.90-1.82 (2H, m), 1.74-1.66 (1H, m). |
| 88 | | Racemate | 1H-NMR (DMSO-D6) δ: 11.59 (1H, br s), 8.08 (1H, s), 7.10 (1H, dd, J = 3.4, 2.4 Hz), 6.56-6.52 (1H, m), 4.36-4.17 (1H, m), 4.10-3.94 (1H, m), 3.99 (2H, s), 3.76-3.19 (4H, m), 3.05-2.92 (1H, m), 2.01-1.94 (2H, m), 1.93-1.83 (2H, m), 1.81-1.72 (1H, m). |
| 89 | | Racemate | 1H-NMR (CDCl3) δ: 11.52 (1H, s), 8.05 (1H, s), 7.08 (1H, dd, J = 3.2, 1.9 Hz), 6.55 (1H, d, J = 2.3 Hz), 3.87-3.71 (2H, m), 3.67-3.53 (2H, m), 2.91-2.81 (2H, m), 2.31 (1H, br s), 1.99-1.84 (2H, m), 1.81-1.63 (4H, m). |
| 90 | | Racemate | 1H-NMR (DMSO-D6) δ: 11.56 (1H, br s), 8.07 (1H, s), 7.35-7.27 (4H, m), 7.22-7.18 (1H, m), 7.11-7.09 (1H, m), 6.62-6.58 (1H, m), 4.04-3.91 (1H, m), 3.80-3.56 (5H, m), 2.68-2.55 (2H, m), 2.29-2.19 (1H, m), 1.91-1.71 (5H, m). |

TABLE 2

| No. | Structural Formula | Comments | NMR Data |
|---|---|---|---|
| 91 | | Racemate | 1H-NMR (DMSO-D6) δ: 13.60 (1H, br s), 8.24 (1H, s), 8.17 (1H, s), 4.02-3.98 (1H, m), 3.93 (2H, s), 3.81-3.75 (1H, m), 3.51-3.38 (2H, m), 3.27-3.05 (2H, m), 2.94-2.84 (1H, m), 2.37-2.28 (1H, m), 1.85-1.69 (5H, m), 1.57-1.50 (1H, m). |
| 92 | | Racemate | 1H-NMR (DMSO-D6) δ: 13.32 (1H, br s), 8.18 (1H, s), 8.01 (1H, s), 4.66-4.62 (1H, m), 4.09-4.00 (2H, m), 3.99 (2H, s), 3.60-3.56 (1H, m), 3.53-3.42 (2H, m), 3.06-2.97 (1H, m), 2.03-1.81 (4H, m), 1.77-1.71 (1H, m). |
| 93 | | Racemate | 1H-NMR (DMSO-D6) δ: 13.32 (1H, br s), 8.13 (1H, d, J = 1.4 Hz), 8.02 (1H, s), 4.39 (1H, d, J = 10.9 Hz), 4.28 (1H, d, J = 10.7 Hz), 4.09 (2H, s), 4.08-4.01 (1H, m), 3.88-3.82 (1H, m), 3.50-3.43 (1H, m), 3.38-3.27 (1H, m), 2.61-2.54 (1H, m), 2.16-2.06 (1H, m), 1.84-1.45 (6H, m). |

TABLE 3

| No. | Structural Formula | Comments | NMR Data |
|---|---|---|---|
| 94 | | Racemate | 1H-NMR (DMSO-D6) δ: 13.02 (1H, br s), 8.17 (1H, s), 8.11 (1H, s), 5.72-4.95 (1H, m), 4.05 (1H, d, J = 19.2 Hz), 3.94 (1H, d, J = 19.0 Hz), 3.89-3.78 (1H, m), 3.60-3.52 (1H, m), 3.46-3.39 (1H, m), 2.97-2.73 (2H, m), 1.94-1.84 (2H, m), 1.82-1.49 (6H, m). |
| 95 | | Racemate | 1H-NMR (DMSO-D6) δ: 12.92 (1H, br s), 8.17 (1H, s), 8.07 (1H, s), 4.95-4.78 (1H, m), 4.34-4.09 (1H, m), 4.06 (2H, s), 3.99-3.67 (1H, m), 3.60-3.50 (1H, m), 3.43-3.28 (2H, m), 2.58-2.41 (1H, m), 2.30-2.11 (1H, m), 1.81-1.48 (6H, m). |

The following Table 4 shows chemical structures of compounds of which absolute configurations have been specified among the above optically-active compounds.

TABLE 4

| No. | Structural Formula |
|---|---|
| 3 | |

TABLE 4-continued

| No. | Structural Formula |
|---|---|
| 4 | (structure) |
| 9 | (structure) |
| 25 | (structure) |

[Test 1]

JAK3 activity inhibitory effects of test compounds were evaluated by the following kinase reactions.

In the kinase reactions, fused proteins (6His tag-fused hJAK3 kinase domain (aa781-end)) which were coexpressed in Sf21 cells and purified by Ni2+/NTA agarose were used. The kinase reactions were initiated by the addition of the following solutions of (a) to (c) to 96-well half-area white plates (plates, Corning Incorporated 3642).

(a) 5 µmol/L TK substrate-biotin (cisbio) diluted by kinase buffer (50 mmol/L 4-(2-hydroxyethyl)-1-piperazineethanesulfonic acid (pH 7.0)), 0.02% sodium azide, 0.1 mmol/L sodium vanadate, 5 mmol/L magnesium chloride, 1 mmol/L dithiothreitol, 0.01% bovine serum albumin), 25 µmol/L ATP, 250 nmol/L Supplement Enzymatic buffer (cisbio) solution: 10 µL/well (b) Test-article solution prepared by using kinase buffer containing 5% dimethylsulfoxide: 10 µL/well (c) 33 ng/mL hJAK3 enzyme diluted by kinase buffer: 30 µL/well A well in which ATP was not added was set out as a blank well.

Plates were let stand at room temperature for 10 minutes from starting reactions.

To the plates were added 50 µL/well of a buffer for detection containing TK-Antibody-Cryptate (5 tests/50 µL) and streptoavidine-addition XL665 (62.5 nmol/L) reagent (50 mmol/L 4-(2-hydroxyethyl)-1-piperazineethanesulfonic acid (pH 7.0), 20 mM EDTA, 800 mmol/L potassium fluoride, 0.1% bovine serum albumin).

One hour after the addition of the buffer for detection, fluorescence counts of each well were measured by a fluorescence microplate reader. Specifically, fluorescence counts in 620 nm excited in 337 nm, and fluorescence counts in 665 nm excited by fluorescence in 620 nm were measured.

Ratio of each well was calculated from measured fluorescence counts (fluorescence counts in 665 nm/fluorescence counts in 620 nm×10000).

Data were obtained by deducting the average Ratio of a blank well from Ratio of each well. IC50 values of test articles were calculated from % of control values of 2 doses before as well as after 50% in 100% as % of a control value of a solvent control. % Inhibition of either 0.1 µmol/L or 1 µmol/L (100-% of control values) was also calculated.

[Test 2]

JAK2 activity inhibitory effects of test compounds were evaluated by the following kinase reactions.

In the kinase reactions, fused proteins (6His tag-fused hJAK2 kinase domain (aa808-end)) which were coexpressed in Sf21 cells and purified by Ni2+/NTA agarose were used. The kinase reactions were initiated by the addition of the following solutions of (a) to (c) to 96-well half-area white plates (plates, Corning Incorporated 3642).

(a) 5 µmol/L TK substrate-biotin (cisbio) diluted by kinase buffer (50 mmol/L 4-(2-hydroxyethyl)-1-piperazineethanesulfonic acid (pH 7.0)), 0.02% sodium azide, 0.1 mmol/L sodium vanadate, 5 mmol/L magnesium chloride, 1 mmol/L dithiothreitol, 0.01% bovine serum albumin), 100 µmol/L ATP, 250 nmol/L Supplement Enzymatic buffer (cisbio) solution: 10 µL/well (b) Test-article solution prepared by using kinase buffer containing 5% dimethylsulfoxide: 10 µL/well (c) 7 ng/mL hJAK2 enzyme diluted by kinase buffer: 30 µL/well A well in which ATP was not added was set out as a blank well.

Plates were let stand at room temperature for 10 minutes from starting reactions.

To the plates were added 50 µL/well of a buffer for detection containing TK-Antibody-Cryptate (5 tests/50 µL) and streptoavidine-addition XL665 (62.5 nmol/L) reagent (50 mmol/L 4-(2-hydroxyethyl)-1-piperazineethanesulfonic acid (pH 7.0), 20 mM EDTA, 800 mmol/L potassium fluoride, 0.1% bovine serum albumin).

One hour after the addition of the buffer for detection, fluorescence counts of each well were measured by a fluorescence microplate reader. Specifically, fluorescence counts in 620 nm excited in 337 nm, and fluorescence counts in 665 nm excited by fluorescence in 620 nm were measured.

Ratio of each well was calculated from measured fluorescence counts (fluorescence counts in 665 nm/fluorescence counts in 620 nm×10000).

Data were obtained by deducting the average Ratio of a blank well from Ratio of each well. IC50 values of test articles were calculated from % of control values of 2 doses before as well as after 50% in 100% as % of a control value of a solvent control.

The following Tables 5 to 7 show JAK3 activity inhibition data or % inhibition data of Compounds 1 to 95.

TABLE 5

| Compound No. | JAK3 IC50 (uM) | % Inhibition |
|---|---|---|
| 1 | 0.0034 | |
| 2 | 0.0047 | |
| 3 | 0.010 | |
| 4 | 0.0051 | |
| 5 | 0.0040 | |
| 6 | 0.0071 | |
| 7 | 0.0058 | |
| 8 | 0.73 | |
| 9 | | 24 (0.1 uM) |
| 10 | | 28 (0.1 uM) |
| 11 | | 38 (0.1 uM) |
| 12 | | 46 (0.1 uM) |
| 13 | | 26 (1 uM) |
| 14 | 0.041 | |
| 15 | 0.0071 | |
| 16 | 0.058 | |
| 17 | 0.087 | |
| 18 | 0.41 | |
| 19 | 0.40 | |
| 20 | 0.10 | |
| 21 | 0.021 | |
| 22 | | 30 (1 uM) |
| 23 | 0.014 | |
| 24 | 0.13 | |
| 25 | 0.23 | |
| 26 | 0.012 | |
| 27 | 0.088 | |
| 28 | 0.13 | |
| 29 | 0.047 | |
| 30 | 0.58 | |
| 31 | 0.046 | |
| 32 | 0.49 | |
| 33 | 0.48 | |
| 34 | 0.036 | |
| 35 | 0.53 | |
| 36 | 0.15 | |
| 37 | 0.0033 | |
| 38 | 0.15 | |
| 39 | 0.12 | |
| 40 | 0.14 | |
| 41 | 0.090 | |
| 42 | 0.10 | |
| 43 | 0.040 | |
| 44 | 0.067 | |
| 45 | 0.27 | |
| 46 | 0.27 | |
| 47 | 0.11 | |
| 48 | 0.17 | |
| 49 | 0.092 | |
| 50 | 0.23 | |
| 51 | | 41 (1 uM) |
| 52 | 0.010 | |
| 53 | 0.056 | |
| 54 | 0.0059 | |
| 55 | 0.0066 | |
| 56 | 0.0068 | |
| 57 | 0.037 | |
| 58 | 0.031 | |
| 59 | 0.038 | |
| 60 | 0.014 | |
| 61 | 0.65 | |
| 62 | 0.13 | |
| 63 | 0.24 | |
| 64 | 0.18 | |
| 65 | 0.19 | |
| 66 | 0.011 | |
| 67 | 0.24 | |
| 68 | 0.28 | |
| 69 | 0.32 | |
| 70 | 0.30 | |

TABLE 5-continued

| Compound No. | JAK3 IC50 (uM) | % Inhibition |
|---|---|---|
| 71 | 0.25 | |
| 72 | 0.15 | |
| 73 | 0.073 | |
| 74 | 0.18 | |
| 75 | | 1 (1 uM) |
| 76 | 0.76 | |
| 77 | 0.048 | |
| 78 | 0.15 | |
| 79 | | 38 (1 uM) |
| 80 | 0.10 | |
| 81 | 0.46 | |
| 82 | 0.013 | |
| 83 | 0.25 | |
| 84 | 0.014 | |
| 85 | 0.57 | |
| 86 | 0.45 | |
| 87 | | 39 (1 uM) |
| 88 | 0.032 | |
| 89 | 8.6 | |
| 90 | 0.55 | |

TABLE 6

| Compound No. | JAK3 IC50 (uM) | % Inhibition |
|---|---|---|
| 91 | | 42 (1 uM) |
| 92 | 0.33 | |
| 93 | 0.11 | |

TABLE 7

| Compound No. | JAK3 IC50 (uM) | % Inhibition |
|---|---|---|
| 94 | 0.35 | |
| 95 | 0.078 | |

The following Table 8 shows JAK2 activity inhibition data or % inhibition data of Compounds 1 to 7.

TABLE 8

| Compound No. | JAK2 IC50 (uM) | % Inhibition |
|---|---|---|
| 1 | 0.0010 | |
| 2 | 0.0017 | |
| 3 | 0.0022 | |
| 4 | 0.0017 | |
| 5 | 0.0019 | |
| 6 | 0.0021 | |
| 7 | 0.0047 | |

[Formulations]

The formulation examples of the present invention include the following formulations. However, the present invention is not intended to be limited thereto.

Formulation 1 (Preparation of Capsule)

| | |
|---|---|
| 1) Compound 1 | 30 mg |
| 2) Microcrystalline cellulose | 10 mg |

-continued

|  |  |
|---|---|
| 3) Lactose | 19 mg |
| 4) Magnesium stearate | 1 mg |

1), 2), 3) and 4) are mixed to fill in a gelatin capsule.

Formulation 2 (Preparation of Tablet)

|  |  |
|---|---|
| 1) Compound 1 | 10 g |
| 2) Lactose | 50 g |
| 3) Cornstarch | 15 g |
| 4) Carmellose calcium | 44 g |
| 5) Magnesium stearate | 1 g |

The whole amount of 1), 2) and 3) and 30 g of 4) are combined with water, dried in vacuo, and then granulated. The resulting granules are mixed with 14 g of 4) and 1 g of 5), and tableted by a tableting machine. Then, 1000 tablets wherein Compound 1 (10 mg) is comprised in each tablet are obtained.

INDUSTRIAL APPLICABILITY

The present invention is useful for the treatment or prevention of:

(a) organ transplant rejection, graft versus host reaction after transplantation;

(b) autoimmune diseases including rheumatoid arthritis, psoriasis, psoriatic arthritis, multiple sclerosis, ulcerative colitis, Crohn's disease, systemic lupus erythematosus, type I diabetes, myasthenia gravis, Castleman's disease, juvenile idiopathic arthritis, dry eye; and (c) allergic diseases including asthma, atopic dermatitis, rhinitis, etc. The present invention is also useful for the treatment or prevention of chronic myeloproliferative diseases including polycythemia vera, primary myelofibrosis, essential thrombocythemia, etc.

The invention claimed is:

1. A compound of formula [I]:

[Chemical Formula 1]

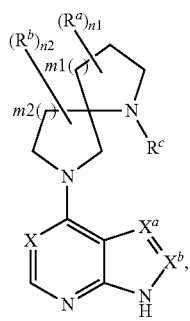

[I]

wherein $R^a$ is the same or different and each is:
(1) $C_{1-6}$ alkyl, or
(2) halogen atom,
n1 is an integer selected from 0 to 4, $R^b$ is the same or different and each is:
(1) $C_{1-6}$ alkyl, or
(2) halogen atom,
n2 is an integer selected from 0 to 4,
m1 is an integer selected from 0 to 3,
m2 is an integer selected from 1 to 4,
$X^a=X^b$ is
CH=CH,
X is
a nitrogen atom,
$R^c$ is a group selected from the following (1) to (6):
(1) hydrogen atom,
(2) $C_{1-6}$ alkyl optionally substituted by the same or different 1 to 5 substituents selected from the following Group A,
(3) —C(=O)—$R^{c1}$,
(4) —C(=O)—O—$R^{c2}$,
(5) —C(=O)—N$R^{c3}R^{c4}$
in which $R^{c1}$, $R^{c2}$, $R^{c3}$ and $R^{c4}$ are the same or different and each is:
(i) hydrogen atom, or
(ii) $C_{1-6}$ alkyl optionally substituted by the same or different 1 to 5 substituents selected from the following Group A, and
(6) a group of formula:

[Chemical Formula 2]

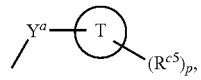

in which $Y^a$ is a group selected from the following (i) to (iii):
(i) $C_{1-6}$ alkylene,
(ii) —C(=O)—, and
(iii) —C(=O)—O—,
Ring T is:
(i) $C_{6-10}$ aryl,
(ii) $C_{3-10}$ cycloalkyl, or
(iii) saturated monoheterocyclyl wherein the saturated monoheterocyclyl comprises 1 to 4 heteroatoms selected from nitrogen atom, oxygen atom or sulfur atom as well as carbon atoms and the number of the constituent ring atoms is 3 to 7,
$R^{c5}$ is the same or different and each is:
(i) cyano, or
(ii) nitro,
p is an integer selected from 0 to 4,
Group A is selected from the group consisting of:
(a) hydroxyl,
(b) $C_{1-6}$ alkoxy,
(c) cyano,
(d) $C_{1-6}$ alkoxycarbonyl,
(e) $C_{1-6}$ alkylcarbonyloxy, and
(f) $C_{2-6}$ alkenyloxy,
or a pharmaceutically acceptable salt thereof, or a solvate of the compound or salt thereof.

2. The compound as claimed in claim 1, wherein n1 is an integer selected from 0 to 2,
n2 is an integer selected from 0 to 2,
m1 is an integer selected from 0 to 3,
m2 is an integer selected from 1 to 3,
X is
a nitrogen atom, $R^c$ is a group selected from the following (1) to (6):

(1) hydrogen atom, (2) $C_{1-6}$ alkyl substituted by one substituent selected from the following Group A, (3) —C(=O)—$R^{c1}$, (4) —C(=O)—O—$R^{c2}$, (5) —C(=O)—$NR^{c3}R^{c4}$ in which $R^{c1}$ is $C_{1-6}$ alkyl optionally substituted by one substituent selected from the following Group A, $R^{c2}$ is $C_{1-6}$ alkyl, $R^{c3}$ is $C_{1-6}$ alkyl optionally substituted by one substituent selected from the following Group A, $R^{c4}$ is (i) hydrogen atom, or (ii) $C_{1-6}$ alkyl, and (6) a group of formula:

[Chemical Formula 3]

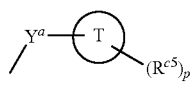

in which $Y^a$ is a group selected from the following (i) to (iii):

(i) $C_{1-6}$ alkylene, (ii) —C(=O)—, and (iii) —C(=O)—O—,

Ring T is:

(i) phenyl, (ii) $C_{3-6}$ cycloalkyl, or (iii) pyrrolidinyl, $R^{c5}$ is (i) cyano, or (ii) nitro, p is an integer selected from 0 or 1, Group A is selected from the group consisting of:

(a) hydroxyl, (b) $C_{1-6}$ alkoxy, (c) cyano, (d) $C_{1-6}$ alkoxycarbonyl, (e) $C_{1-6}$ alkylcarbonyloxy, and (f) $C_{2-6}$ alkenyloxy, or a pharmaceutically acceptable salt thereof, or a solvate of the compound or salt thereof.

3. The compound as claimed in claim 1, wherein m1 is an integer of 0 or 1 and m2 is an integer of 1 or 2, or a pharmaceutically acceptable salt thereof, or a solvate of the compound or salt thereof.

4. The compound as claimed in claim 3, wherein m1 is 1 and m2 is 2, which is a compound of formula [II]:

[Chemical Formula 4]

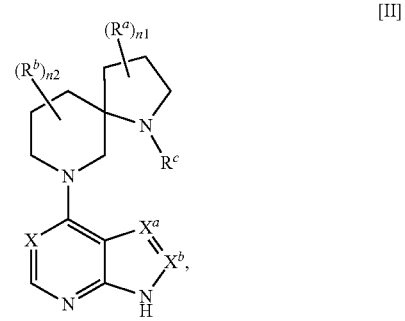

wherein each symbol has the same meaning as defined in claim 1, or a pharmaceutically acceptable salt thereof, or a solvate of the compound or salt thereof.

5. The compound as claimed in claim 3, wherein m1 is 0 and m2 is 2, which is a compound of formula [III]:

[Chemical Formula 5]

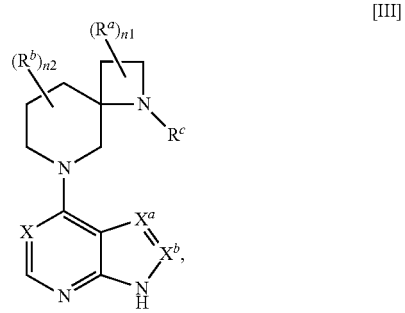

wherein each symbol has the same meaning as defined in claim 1, or a pharmaceutically acceptable salt thereof, or a solvate of the compound or salt thereof.

6. The compound as claimed in claim 3, wherein m1 is 0 and m2 is 1, which is a compound of formula [IV]:

[Chemical Formula 6]

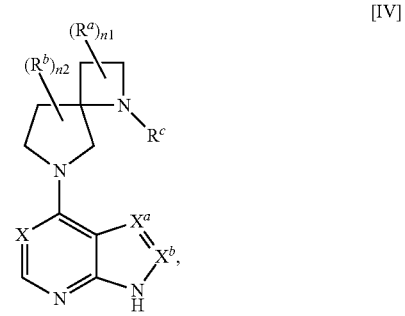

wherein each symbol has the same meaning as defined in claim 1, or a pharmaceutically acceptable salt thereof, or a solvate of the compound or salt thereof.

7. The compound as claimed in claim 1, wherein m1 is 0 and m2 is 3, or m1 is 2 and m2 is 1, or m1 is 2 and m2 is 2, or m1 is 3 and m2 is 2, or a pharmaceutically acceptable salt thereof, or a solvate of the compound or salt thereof.

8. The compound as claimed in claim 1, wherein n1 is 0 and n2 is 0, or a pharmaceutically acceptable salt thereof, or a solvate of the compound or salt thereof.

9. The compound as claimed in claim 1, wherein n1 is 1 and n2 is 0, or a pharmaceutically acceptable salt thereof, or a solvate of the compound or salt thereof.

10. The compound as claimed in claim 1, wherein n1 is 0 and n2 is 1, or a pharmaceutically acceptable salt thereof, or a solvate of the compound or salt thereof.

11. The compound as claimed in claim 1, wherein n1 is 2 and n2 is 0, or a pharmaceutically acceptable salt thereof, or a solvate of the compound or salt thereof.

12. The compound as claimed in claim 1, wherein n1 is 0 and n2 is 2, or a pharmaceutically acceptable salt thereof, or a solvate of the compound or salt thereof.

13. The compound as claimed in claim 9, wherein $R^a$ is methyl or fluorine atom, or a pharmaceutically acceptable salt thereof, or a solvate of the compound or salt thereof.

14. The compound as claimed in claim 1, wherein $R^c$ is —C(=O)—$R^{c1}$, or a pharmaceutically acceptable salt thereof, or a solvate of the compound or salt thereof.

15. The compound as claimed in claim 14, wherein $R^{c1}$ is $C_{1-6}$ alkyl substituted by one hydroxyl or cyano group, or a pharmaceutically acceptable salt thereof, or a solvate of the compound or salt thereof.

16. The compound as claimed in claim 1, wherein $R^c$ is —C(=O)—$NR^{c3}R^{c4}$, or a pharmaceutically acceptable salt thereof, or a solvate of the compound or salt thereof.

17. The compound as claimed in claim 16, wherein $R^{c3}$ is $C_{1-6}$ alkyl substituted by one cyano group, and $R^{c4}$ is hydrogen, or a pharmaceutically acceptable salt thereof, or a solvate of the compound or salt thereof.

18. The compound as claimed in claim 1 selected from the following chemical structural formula:

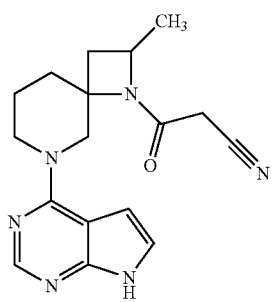

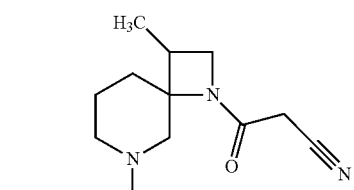

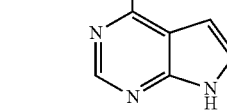

-continued

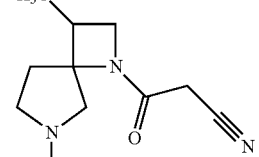

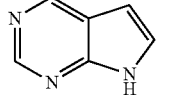

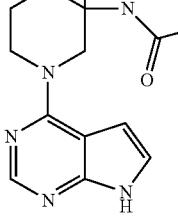

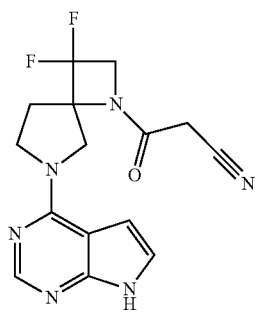

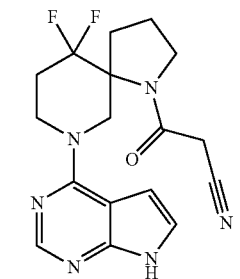

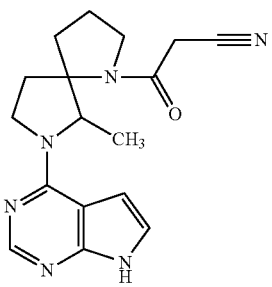

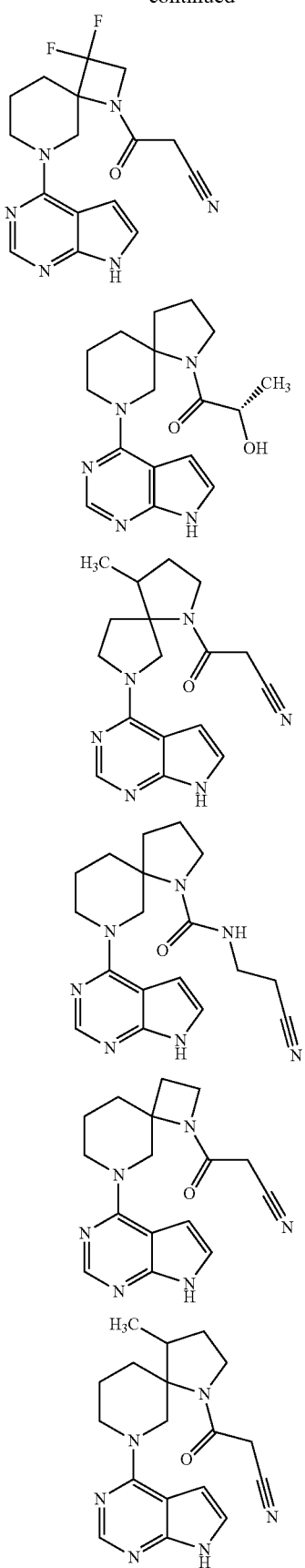

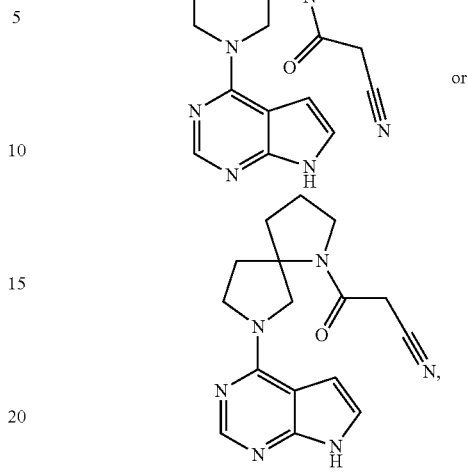

or a pharmaceutically acceptable salt thereof, or a solvate of the compound or salt thereof.

19. A pharmaceutical composition, comprising the compound as claimed in claim 1 or a pharmaceutically acceptable salt thereof, or a solvate of the compound or salt thereof, and a pharmaceutically acceptable carrier.

20. A method for inhibiting Janus kinase 2 or Janus kinase 3, comprising administering to a mammal in need thereof a pharmaceutically effective amount of the compound as claimed in claim 1 or a pharmaceutically acceptable salt thereof, or a solvate of the compound or salt thereof.

21. The method as claimed in claim 20, wherein the Janus kinase is Janus kinase 3.

22. The method as claimed in claim 20, wherein the Janus kinase is Janus kinase 2.

23. A method for treating or preventing a disease selected from the group consisting of organ transplant rejection and graft versus host reaction after transplantation, comprising administering to a mammal in need thereof a pharmaceutically effective amount of the compound as claimed in claim 1 or a pharmaceutically acceptable salt thereof, or a solvate of the compound or salt thereof.

24. A method for treating rheumatoid arthritis, comprising administering to a mammal in need thereof a pharmaceutically effective amount of the compound as claimed in claim 1 or a pharmaceutically acceptable salt thereof, or a solvate of the compound or salt thereof.

25. A method for treating psoriasis, comprising administering to a mammal in need thereof a pharmaceutically effective amount of the compound as claimed in claim 1 or a pharmaceutically acceptable salt thereof, or a solvate of the compound or salt thereof.

26. A method for treating dry eye, comprising administering to a mammal in need thereof a pharmaceutically effective amount of the compound as claimed in claim 1 or a pharmaceutically acceptable salt thereof, or a solvate of the compound or salt thereof.

27. A method for treating or preventing atopic dermatitis, comprising administering to a mammal in need thereof a pharmaceutically effective amount of the compound as claimed in claim 1 or a pharmaceutically acceptable salt thereof, or a solvate of the compound or salt thereof.

28. The method of claim 20, wherein said mammal is human.

29. The method of claim 23, wherein said mammal is human.

30. The method of claim 24, wherein said mammal is human.

31. The method of claim 25, wherein said mammal is human.

32. The method of claim 26, wherein said mammal is human.

33. The method of claim 27, wherein said mammal is human.

34. The compound as claimed in claim 1 which is represented by the following formula:

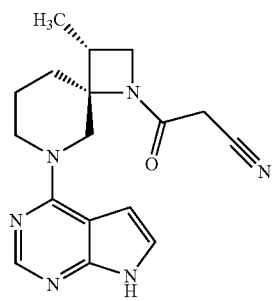 [SMILES: C[C@@H]1CN(C(=O)CC#N)[C@]12CCCN(c1ncnc3[nH]ccc13)C2]

or a pharmaceutically acceptable salt thereof, or a solvate of the compound or salt thereof.

35. The compound as claimed in claim 1 which is represented by the following formula:

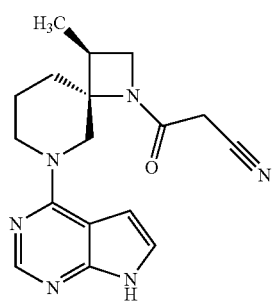 [SMILES: C[C@H]1CN(C(=O)CC#N)[C@]12CCCN(c1ncnc3[nH]ccc13)C2]

or a pharmaceutically acceptable salt thereof, or a solvate of the compound or salt thereof.

36. The compound as claimed in claim 1 which is represented by the following formula:

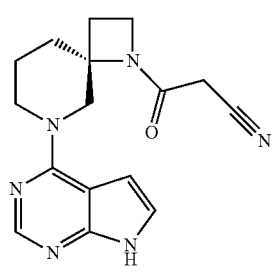 [SMILES: N#CCC(=O)N1CC[C@@]12CCCN(c1ncnc3[nH]ccc13)C2]

or a pharmaceutically acceptable salt thereof, or a solvate of the compound or salt thereof.

37. The compound as claimed in claim 1 which is represented by the following formula:

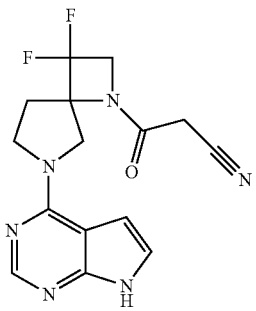

or a pharmaceutically acceptable salt thereof, or a solvate of the compound or salt thereof.

38. The compound as claimed in claim 1 which is represented by the following formula:

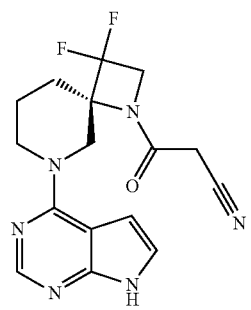 [SMILES: N#CCC(=O)N1CC(F)(F)[C@@]12CCCN(c1ncnc3[nH]ccc13)C2]

or a pharmaceutically acceptable salt thereof, or a solvate of the compound or salt thereof.

39. The compound as claimed in claim 1 which is represented by the following formula:

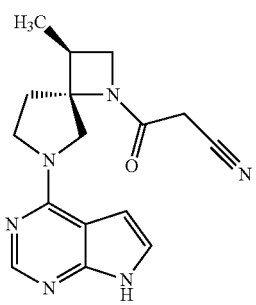 [SMILES: C[C@H]1CN(C(=O)CC#N)[C@]12CCN(c1ncnc3[nH]ccc13)C2]

or a pharmaceutically acceptable salt thereof, or a solvate of the compound or salt thereof.

40. The compound as claimed in claim 1 which is represented by the following formula:

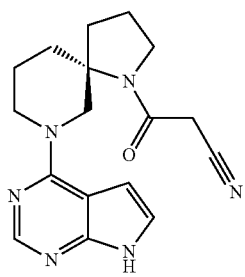 [SMILES: N#CCC(=O)N1CCC[C@@]12CCCN(c1ncnc3[nH]ccc13)C2]

or a pharmaceutically acceptable salt thereof, or a solvate of the compound or salt thereof.

41. The compound as claimed in claim 1 which is represented by the following formula:

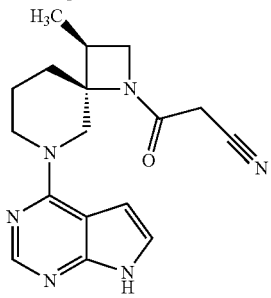 [SMILES: C[C@H]1CN(C(=O)CC#N)[C@@]12CCCN(c1ncnc3[nH]ccc13)C2]

or a pharmaceutically acceptable salt thereof, or a solvate of the compound or salt thereof.

42. The compound as claimed in claim 1 which is represented by the following formula:

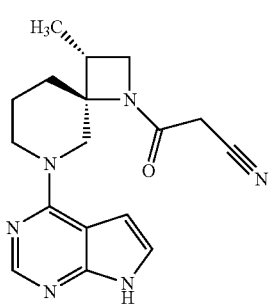 [SMILES: C[C@@H]1CN(C(=O)CC#N)[C@@]12CCCN(c1ncnc3[nH]ccc13)C2]

or a pharmaceutically acceptable salt thereof, or a solvate of the compound or salt thereof.

43. The compound as claimed in claim 1 which is represented by the following formula:

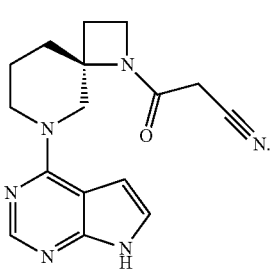 [SMILES: N#CCC(=O)N1CC[C@]12CCCN(c1ncnc3[nH]ccc13)C2]

or a pharmaceutically acceptable salt thereof, or a solvate of the compound or salt thereof.

44. The compound as claimed in claim 1 which is represented by the following formula:

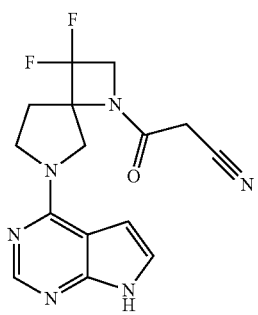 [SMILES: N#CCC(=O)N1CC(F)(F)C12CCN(c1ncnc3[nH]ccc13)C2]

or a pharmaceutically acceptable salt thereof, or a solvate of the compound or salt thereof.

45. The compound as claimed in claim 1 which is represented by the following formula:

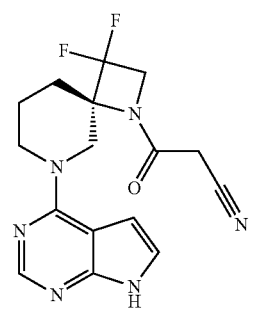 [SMILES: N#CCC(=O)N1CC(F)(F)[C@]12CCCN(c1ncnc3[nH]ccc13)C2]

or a pharmaceutically acceptable salt thereof, or a solvate of the compound or salt thereof.

46. The compound as claimed in claim 1 which is represented by the following formula:

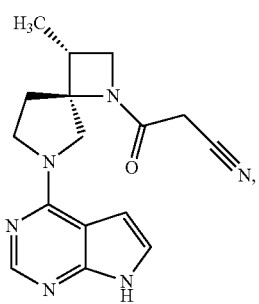 [SMILES: C[C@@H]1CN(C(=O)CC#N)[C@@]12CCN(c1ncnc3[nH]ccc13)C2]

or a pharmaceutically acceptable salt thereof, or a solvate of the compound or salt thereof.

47. The compound as claimed in claim 1 which is represented by the following formula:

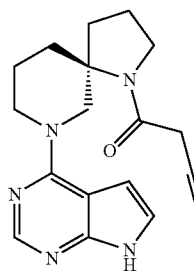

or a pharmaceutically acceptable salt thereof, or a solvate of the compound or salt thereof.

48. The compound as claimed in claim 1 which is represented by the following formula:

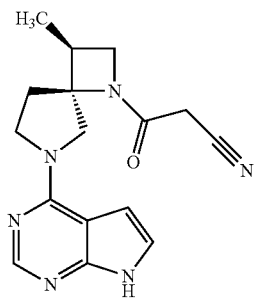 [SMILES: C[C@H]1CN(C(=O)CC#N)[C@@]12CCN(c1ncnc3[nH]ccc13)C2]

or a pharmaceutically acceptable salt thereof, or a solvate of the compound or salt thereof.

49. The compound as claimed in claim 1 which is represented by the following formula:

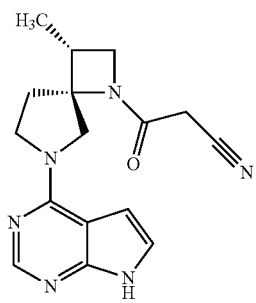 [SMILES: C[C@@H]1CN(C(=O)CC#N)[C@]12CCN(c1ncnc3[nH]ccc13)C2]

or a pharmaceutically acceptable salt thereof, or a solvate of the compound or salt thereof.

50. A pharmaceutical composition, comprising the compound as claimed in any one of claims 34 to 49, or a pharmaceutically acceptable salt thereof, or a solvate of the compound or salt thereof, and a pharmaceutically acceptable carrier.

51. A method for inhibiting Janus kinase 2 or Janus kinase 3, comprising administering to a mammal in need thereof a pharmaceutically effective amount of the compound as claimed in any one of claims 34 to 49, or a pharmaceutically acceptable salt thereof, or a solvate of the compound or salt thereof.

52. The method of claim 51, wherein said mammal is human.

53. The method as claimed in claim 51, wherein the Janus kinase is Janus kinase 3.

54. The method as claimed in claim 51, wherein the Janus kinase is Janus kinase 2.

55. A method for treating or preventing a disease selected from the group consisting of organ transplant rejection and graft versus host reaction after transplantation, comprising administering to a mammal in need thereof a pharmaceutically effective amount of the compound as claimed in any one of claims 34 to 49, or a pharmaceutically acceptable salt thereof, or a solvate of the compound or salt thereof.

56. The method of claim 55, wherein said mammal is human.

57. A method for treating rheumatoid arthritis, comprising administering to a mammal in need thereof a pharmaceutically effective amount of the compound as claimed in any one of claims 34 to 49, or a pharmaceutically acceptable salt thereof, or a solvate of the compound or salt thereof.

58. The method of claim 57, wherein said mammal is human.

59. A method for treating psoriasis, comprising administering to a mammal in need thereof a pharmaceutically effective amount of the compound as claimed in any one of claims 34 to 49, or a pharmaceutically acceptable salt thereof, or a solvate of the compound or salt thereof.

60. The method of claim 59, wherein said mammal is human.

61. A method for treating dry eye, comprising administering to a mammal in need thereof a pharmaceutically effective amount of the compound as claimed in any one of claims 34 to 49, or a pharmaceutically acceptable salt thereof, or a solvate of the compound or salt thereof.

62. The method of claim 61, wherein said mammal is human.

63. A method for treating atopic dermatitis, comprising administering to a mammal in need thereof a pharmaceutically effective amount of the compound as claimed in any one of claims 34 to 49, or a pharmaceutically acceptable salt thereof, or a solvate of the compound or salt thereof.

64. The method of claim 63, wherein said mammal is human.

65. The compound as claimed in claim 1 which is represented by the following formula:

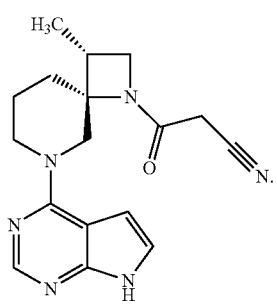 [SMILES: C[C@@H]1CN(C(=O)CC#N)[C@]12CCCN(c1ncnc3[nH]ccc13)C2]

66. The compound as claimed in claim 1 which is represented by the following formula:

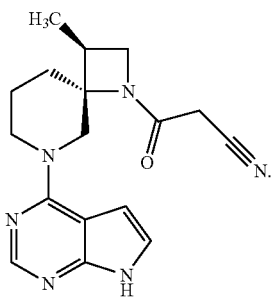 [SMILES: C[C@H]1CN(C(=O)CC#N)[C@]12CCCN(c1ncnc3[nH]ccc13)C2]

67. The compound as claimed in claim 1 which is represented by the following formula:

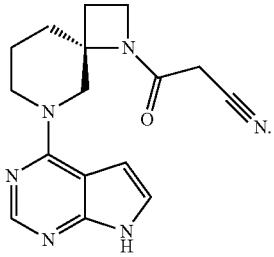 [SMILES: N#CCC(=O)N1CC[C@@]12CCCN(c1ncnc3[nH]ccc13)C2]

68. The compound as claimed in claim 1 which is represented by the following formula:

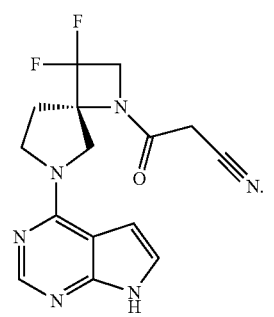 [SMILES: N#CCC(=O)N1CC(F)(F)[C@@]12CCN(c1ncnc3[nH]ccc13)C2]

69. The compound as claimed in claim 1 which is represented by the following formula:

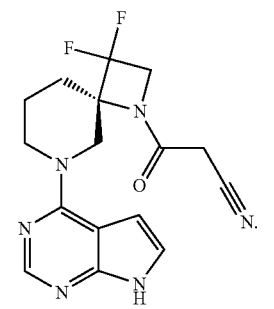 [SMILES: N#CCC(=O)N1CC(F)(F)[C@@]12CCCN(c1ncnc3[nH]ccc13)C2]

70. The compound as claimed in claim 1 which is represented by the following formula:

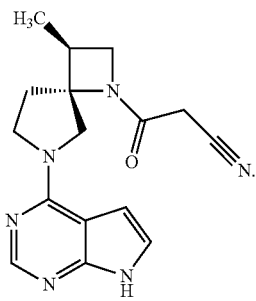 [SMILES: C[C@H]1CN(C(=O)CC#N)[C@]12CCN(c1ncnc3[nH]ccc13)C2]

71. The compound as claimed in claim 1 which is represented by the following formula:

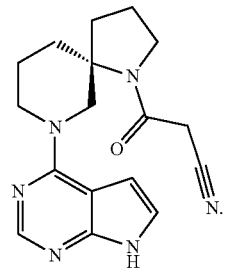 [SMILES: N#CCC(=O)N1CCC[C@@]12CCCN(c1ncnc3[nH]ccc13)C2]

72. The compound as claimed in claim 1 which is represented by the following formula:

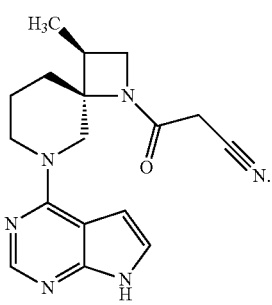 [SMILES: C[C@H]1CN(C(=O)CC#N)[C@@]12CCCN(c1ncnc3[nH]ccc13)C2]

73. The compound as claimed in claim 1 which is represented by the following formula:

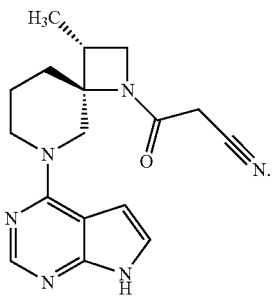 [SMILES: C[C@@H]1CN(C(=O)CC#N)[C@@]12CCCN(c1ncnc3[nH]ccc13)C2]

74. The compound as claimed in claim 1 which is represented by the following formula:

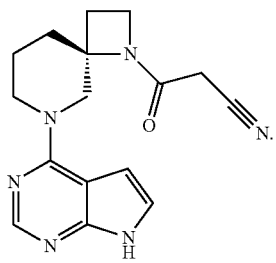 [SMILES: N#CCC(=O)N1CC[C@]12CCCN(c1ncnc3[nH]ccc13)C2]

75. The compound as claimed in claim 1 which is represented by the following formula:

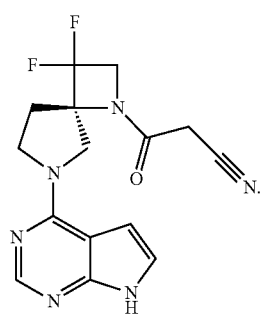 [SMILES: N#CCC(=O)N1CC(F)(F)[C@]12CCN(c1ncnc3[nH]ccc13)C2]

76. The compound as claimed in claim 1 which is represented by the following formula:

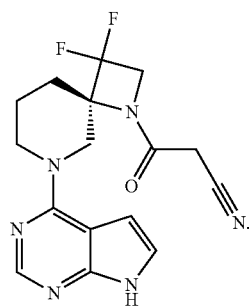 [SMILES: N#CCC(=O)N1CC(F)(F)[C@]12CCCN(c1ncnc3[nH]ccc13)C2]

77. The compound as claimed in claim 1 which is represented by the following formula:

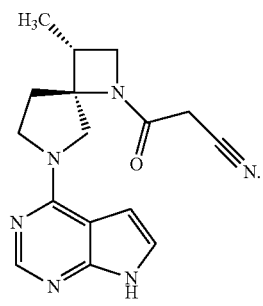 [SMILES: C[C@@H]1CN(C(=O)CC#N)[C@@]12CCN(c1ncnc3[nH]ccc13)C2]

78. The compound as claimed in claim 1 which is represented by the following formula:

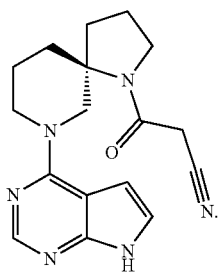 [SMILES: N#CCC(=O)N1CCC[C@]12CCCN(c1ncnc3[nH]ccc13)C2]

79. The compound as claimed in claim 1 which is represented by the following formula:

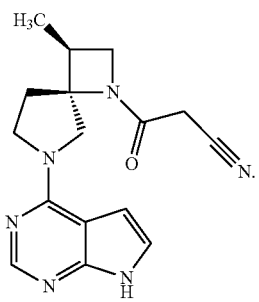 [SMILES: C[C@H]1CN(C(=O)CC#N)[C@@]12CCN(c1ncnc3[nH]ccc13)C2]

80. The compound as claimed in claim 1 which is represented by the following formula:

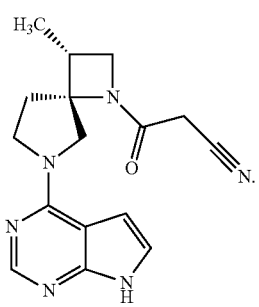 [SMILES: C[C@@H]1CN(C(=O)CC#N)[C@]12CCN(c1ncnc3[nH]ccc13)C2]

81. A pharmaceutical composition, comprising the compound as claimed in any one of claims 65 to 80 and a pharmaceutically acceptable carrier.

82. A method for inhibiting Janus kinase 2 or Janus kinase 3, comprising administering to a mammal in need thereof a pharmaceutically effective amount of the compound as claimed in any one of claims 65 to 80.

83. The method of claim 82, wherein said mammal is human.

84. The method as claimed in claim 82, wherein the Janus kinase is Janus kinase 3.

85. The method as claimed in claim 82, wherein the Janus kinase is Janus kinase 2.

86. A method for treating or preventing a disease selected from the group consisting of organ transplant rejection and graft versus host reaction after transplantation, comprising administering to a mammal in need thereof a pharmaceutically effective amount of the compound as claimed in any one of claims 65 to 80.

87. The method of claim 86, wherein said mammal is human.

88. A method for treating rheumatoid arthritis, comprising administering to a mammal in need thereof a pharmaceutically effective amount of the compound as claimed in any one of claims 65 to 80.

89. The method of claim 88, wherein said mammal is human.

90. A method for treating psoriasis, comprising administering to a mammal in need thereof a pharmaceutically effective amount of the compound as claimed in any one of claims 65 to 80.

91. The method of claim 90, wherein said mammal is human.

92. A method for treating dry eye, comprising administering to a mammal in need thereof a pharmaceutically effective amount of the compound as claimed in any one of claims 65 to 80.

93. The method of claim 92, wherein said mammal is human.

94. A method for treating atopic dermatitis, comprising administering to a mammal in need thereof a pharmaceutically effective amount of the compound as claimed in any one of claims 65 to 80.

95. The method of claim 94, wherein said mammal is human.

* * * * *

UNITED STATES PATENT AND TRADEMARK OFFICE
CERTIFICATE OF CORRECTION

PATENT NO. : 8,609,647 B2
APPLICATION NO. : 12/847025
DATED : December 17, 2013
INVENTOR(S) : Satoru Noji et al.

It is certified that error appears in the above-identified patent and that said Letters Patent is hereby corrected as shown below:

In the Claims

Column 162

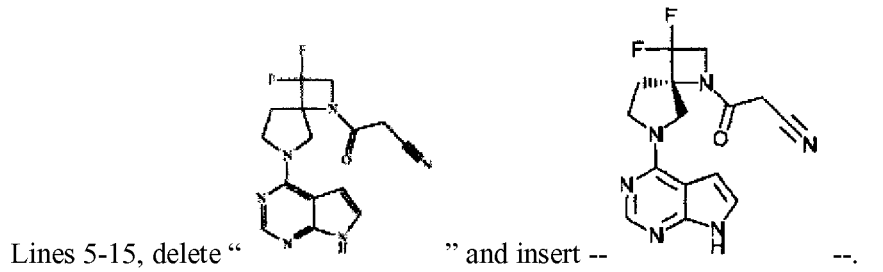

Lines 5-15, delete " " and insert -- --.

Column 163

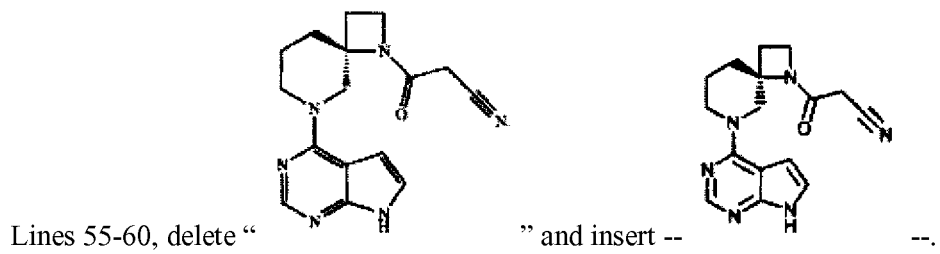

Lines 55-60, delete " " and insert -- --.

Column 164

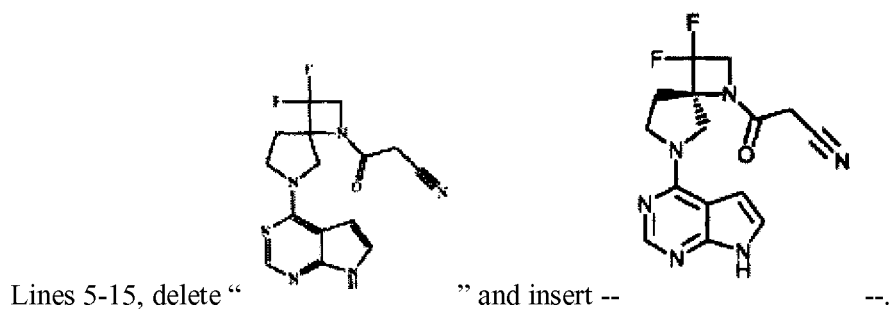

Lines 5-15, delete " " and insert -- --.

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,609,647 B2

Column 164

Lines 50-60, delete " 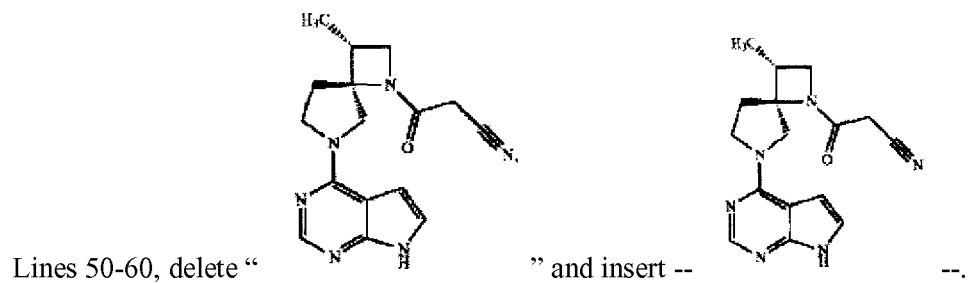 " and insert -- -- .